United States Patent
Canales et al.

(10) Patent No.: US 8,536,187 B2
(45) Date of Patent: *Sep. 17, 2013

(54) 2,4,6-TRISUBSTITUTED PYRIDO(3,2-D)PYRIMIDINES USEFUL FOR TREATING VIRAL INFECTIONS

(75) Inventors: Eda Canales, San Mateo, CA (US); Lee S. Chong, Newark, CA (US); Michael O' Neil Hanrahan Clarke, Redwood City, CA (US); Scott E. Lazerwith, San Francisco, CA (US); Willard Lew, San Mateo, CA (US); Qi Liu, Foster City, CA (US); Michael L. Mitchell, Hayward, CA (US); William J. Watkins, Saratoga, CA (US); Jennifer R. Zhang, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/996,110

(22) PCT Filed: Jul. 1, 2009

(86) PCT No.: PCT/US2009/049412
§ 371 (c)(1),
(2), (4) Date: Jan. 11, 2011

(87) PCT Pub. No.: WO2010/002998
PCT Pub. Date: Jan. 7, 2010

(65) Prior Publication Data
US 2011/0123493 A1      May 26, 2011

Related U.S. Application Data

(60) Provisional application No. 61/078,185, filed on Jul. 3, 2008, provisional application No. 61/084,254, filed on Jul. 28, 2008.

(51) Int. Cl.
*A01N 43/90* (2006.01)
*A61K 31/519* (2006.01)
*C07D 487/00* (2006.01)

(52) U.S. Cl.
USPC ..................... 514/264.11; 544/279

(58) Field of Classification Search
None
See application file for complete search history.

(56) References Cited

U.S. PATENT DOCUMENTS

| | | | |
|---|---|---|---|
| 2,924,599 A | 2/1960 | Oakes et al. | |
| 4,460,591 A | 7/1984 | DeGraw et al. | |
| 5,167,963 A | 12/1992 | DeGraw et al. | |
| 5,508,281 A | 4/1996 | Gangjee | |
| 5,521,190 A | 5/1996 | Henrie, II et al. | |
| 5,654,307 A | 8/1997 | Bridges et al. | |
| 6,476,031 B1 | 11/2002 | Chakravarty et al. | |
| 6,713,484 B2 | 3/2004 | Bridges et al. | |
| 6,723,726 B1 | 4/2004 | Cockerill et al. | |
| 6,730,682 B2 | 5/2004 | Schnute et al. | |
| 2002/0049207 A1 | 4/2002 | McCarthy | |
| 2003/0186987 A1 | 10/2003 | Bridges et al. | |
| 2003/0199526 A1 | 10/2003 | Choquette et al. | |
| 2004/0039000 A1 | 2/2004 | Gangjee | |
| 2004/0106616 A1 | 6/2004 | Bakthavatchalam et al. | |
| 2008/0182870 A1* | 7/2008 | Bondy et al. ................. | 514/303 |

FOREIGN PATENT DOCUMENTS

| | | |
|---|---|---|
| WO | WO-94/27439 A1 | 12/1994 |
| WO | WO-99/43681 A1 | 9/1999 |
| WO | WO-99/43682 A1 | 9/1999 |
| WO | WO-00/12497 A2 | 3/2000 |
| WO | WO-02/00623 A2 | 1/2002 |
| WO | WO-02/22602 A2 | 3/2002 |
| WO | WO-02/22607 A1 | 3/2002 |
| WO | WO-03/062209 A2 | 7/2003 |
| WO | WO-03/097615 A1 | 11/2003 |
| WO | WO-2004/010929 A2 | 2/2004 |
| WO | WO-2005/065691 A1 | 7/2005 |
| WO | WO-2006/039718 A2 | 4/2006 |
| WO | WO-2006/069805 A2 | 7/2006 |
| WO | WO-2007/076092 A2 | 7/2007 |
| WO | WO-2007/117394 A2 | 10/2007 |
| WO | WO-2008/077651 A1 | 7/2008 |

OTHER PUBLICATIONS

International Search Report mailed Nov. 5, 2009 for PCT/US2009/049412, filed Jul. 1, 2009.
Written Opinion mailed Nov. 5, 2009 for PCT/US2009/049412, filed Jul. 1, 2009.

* cited by examiner

Primary Examiner — Jeffrey Murray

(57) ABSTRACT

Pyrido(3,2-d)pyrimidine derivatives represented by the structural formula (Ia): wherein, $R_1$, $R_2$ and $R_3$ are defined herein, pharmaceutical acceptable addition salts, stereochemical isomeric forms, N-oxides, solvates and pro-drugs thereof, for use in the treatment of hepatitis C.

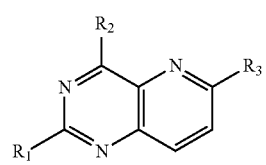

(Ia)

23 Claims, 4 Drawing Sheets

2,4,6-TRISUBSTITUTED PYRIDO(3,2-D)PYRIMIDINES USEFUL FOR TREATING VIRAL INFECTIONS

CROSS-REFERENCE RELATED APPLICATIONS

The present application is a National Phase filing under 35 U.S.C. §371 of International Application No. PCT/US2009/049412 filed on 1 Jul. 2009, which claims priority to U.S. Provisional Patent Application No. 61/078,185, filed on 3 Jul. 2008 and U.S. Provisional Patent Application No. 61/084,254, filed on 28 Jul. 2008, the content of each of which is incorporated herein by reference in its entirety.

The present invention relates to a class of novel 2,4,6-trisubstituted pyrido(3,2-d)pyrimidine derivatives. This invention also relates to pharmaceutical compositions comprising said 2,4,6-trisubstituted pyrido(3,2-d)pyrimidine derivatives and one or more pharmaceutically acceptable excipients. The present invention further relates to methods of prevention or treatment of infections by a virus of the Flaviridae family, e.g., by inhibiting replication of hepatitis C virus, by the administration of a therapeutically effective amount of such a 2,4,6-trisubstituted pyrido(3,2-d)pyrimidine derivative optionally together with one or more other anti-viral agents.

BACKGROUND OF THE INVENTION

Many substituted pyrido(3,2-d)pyrimidine derivatives are known in the art. For instance, pyrido(3,2-d)pyrimidine derivatives with various substituents on positions 2, 4 and 6 (using the standard atom numbering for the pyrido(3,2-d)pyrimidine moiety) are known with biological activities such as competitive inhibition of pteroylglutamic acid, inhibition of thrombocyte aggregation and adhesiveness, antineoplastic activity, inhibition of dihydrofolate reductase and thymidylate synthase, e.g., from U.S. Pat. Nos. 2,924,599, 3,939,268, 4,460,591, 5,167,963 and 5,508,281.

Pyrido(3,2-d)pyrimidine derivatives with various substituents on positions 2, 4, 6 and 7 (using the standard atom numbering for the pyrido(3,2-d)pyrimidine moiety), some of them with biological activities, are also known e.g., from U.S. Pat. No. 5,521,190, U.S. patent application publication No. 2002/0049207, U.S. patent application publication No. 2003/0186987, U.S. patent application publication No. 2003/0199526, U.S. patent application publication No. 2004/0039000, U.S. patent application publication No. 2004/0106616, U.S. Pat. Nos. 6,713,484, 6,730,682 and 6,723,726.

U.S. Pat. No. 5,654,307 discloses pyrido(3,2-d)pyrimidine derivatives substituted on position 4 with monoarylamino or monobenzylamino, and on positions 6 and 7 with substituents each independently selected from the group consisting of lower alkyl, amino, lower alkoxy, mono- or dialkylamino, halogen and hydroxy. WO 01/083456 discloses pyrido(3,2-d)pyrimidine derivatives substituted on position 4 with morpholinyl and on position 2 with hydroxyphenyl or morpholinoethoxyphenyl, having PI3K and cancer inhibiting activity. U.S. Pat. No. 6,476,031 discloses substituted quinazoline derivatives, including (in reaction scheme 5) a series of pyrido(3,2-d)pyrimidine derivatives which are substituted on position 4 with hydroxy, chloro or an aryl, heteroaryl (including pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl), cycloaliphatic or cycloheteroaliphatic group being optionally spaced from the pyrido(3,2-d)pyrimidine ring by a linker such as NH.

WO 02/22602 and WO 02/22607 disclose pyrazole and triazole compounds, including 2-(1-trifluoromethylphenyl)-4-fluorobenzopyrazolyl-pyrido(3,2-d)pyrimidine and 2-(1-tri-fluoromethylphenyl)-4-methyltriazolyl-pyrido(3,2-d)pyrimidine being useful as protein kinase inhibitors. WO 03/062209 discloses pyrido(3,2-d)pyrimidine derivatives substituted on position 7 with aryl or heteroaryl and on position 4 with monoarylamino or monoheteroarylamino and which may further be substituted on positions 2 and/or 6, being useful as capsaicin receptor modulators.

WO 2006/069805 discloses pyrido(3,2-d)pyrimidine derivatives substituted on position 6 with aryl or heteroaryl and on both positions 2 and 4 with monoalkylamino, monocycloalkylamino, monoarylamino or monoarylalkylamino, and which may further be substituted on position 7, being useful in the treatment of a disease mediated by phosphodiesterase-4 activity. WO 2006/135993 discloses di- and tri-substituted pyrido(3,2-d)pyrimidine derivatives being highly active and virus-specific anti-flaviridae agents which are especially useful in the treatment of hepatitis C.

More recently, novel pyrido(3,2-d)pyrimidine derivatives have been disclosed in WO2008/009078, WO2008/009076, WO2008/009079, WO2008/009077, WO2008/043149, PCT/EP2007/011494, PCT/EP2007/011495 and PCT/EP2007/011496.

Notwithstanding the discoveries of new compounds disclosed in the above patent applications, there remains a continuous need in the art for specific and highly therapeutically active compounds for preventing or treating infections due to Flaviridae and pathologic conditions associated therewith, especially hepatitis C. In particular, there is a need in the art to provide drugs which are active against hepatitis C in order to replace existing drugs having significant side effects and to decrease treatment costs.

Hepatitis is an inflammation of the liver that is most often caused by infection with one of three viruses known as hepatitis A, B or C. HCV is a representative and highly significant member of the Flaviviridae family, a family of positive-strand RNA viruses. Current standard of care for HCV treatment is a combination of (pegylated) interferon alpha and the antiviral drug ribavirin for a period of 24 or 48 weeks, depending upon the viral genotype.

Best results have been achieved with the combination of weekly subcutaneous injections of long-acting peginterferon alpha and oral ribavirin daily. Interferons are substances naturally released by cells in the body after viral invasion. Interferon alfa-2b and peginterferon alfa-2b are synthetic versions of these substances. The protein product is manufactured by recombinant DNA-technology. Second generation interferons are further derivatized by binding to inert polyethylene glycol, thereby altering the pharmacokinetic properties. Ribavirin is a nucleoside analogue, which disrupts viral replication of hepatitis C virus (HCV).

The most common side effects of HCV treatment with (pegylated) interferon include: a decrease in white blood cells and platelets, anemia, nausea, diarrhea, fever, chills, muscle and joint pain, difficulty in concentrating, thyroid dysfunction, hair loss, sleeplessness, irritability, mild to serious depression, and rarely, suicidal thoughts. Other serious adverse events include bone marrow toxicity, cardiovascular disorders, hypersensitivity, endocrine disorders, pulmonary disorders, colitis, pancreatitis, and ophthalmologic disorders (eye and vision problems). (Pegylated) interferon may also cause or make worse fatal or life-threatening neuropsychiatric, autoimmune, ischemic, and infectious disorders. Patients with persistently severe or worsening signs or symptoms of these conditions are advised to stop therapy.

The most common side effect of HCV treatment with ribavirin is anaemia, which can be treated with erythropoietin. Other side effects include mood swings, irritability, anxiety, insomnia, abdominal pain, nervousness, breathlessness, rash, hair loss, dry skin, nausea, diarrhoea, loss of appetite, dizziness and weight loss. Ribavirin can also cause birth defects. Ribavirin should not be taken in combination with certain HIV drugs such as, but not limited to, didanosine, since lactic acidosis with fatal hepatic steatosis (fatty liver) may occur. Special attention should be taken for treatment with HIV co-infection.

There is a strong need in the art to improve, or to provide alternatives to, the existing prophylactic or therapeutic solutions to infections by a virus of the Flaviridae family, more specifically HCV infection. In particular there is still a need in the art for providing alternative synthetic molecules having significant HCV replication inhibiting activity and improved druggable properties, particularly, there is a need to provide improved pyrido(3,2-d)pyrimidines. There is also a need in the art for providing effective inhibiting molecules which are free from the significant drawbacks of current drugs, like pegylated interferon and ribavirin. Meeting these various needs in the art constitutes a main goal of the present invention.

SUMMARY OF THE INVENTION

The present invention is based on the unexpected finding that certain specific substituents on position 4 of the pyrido (3,2-d)pyrimidine core structure (using the atom numbering resulting from standard nomenclature), together with a suitable selection of substituents on positions 2 and 6 of said pyrido(3,2-d)pyrimidine core, which are not suggested by the prior art, are however able to meet one or more of the needs recited herein above, in particular to achieve derivatives having desirable pharmacological properties such as a high activity and selectivity against infections by a virus of the Flaviridae family, more particularly a significant HCV replication inhibiting activity.

Based on this finding, the present invention relates, in a first embodiment, to a class of pyrido(3,2-d)pyrimidine derivative represented by the structural formula (Ia):

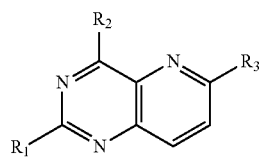

(Ia)

wherein:
  $R_1$ is —NH—$CHR_5R_6$ or —NH—$R_8$;
  $R_5$ and $R_6$ are each independently selected from the group consisting of hydrogen, $C_{1-6}$ alkyl, $C_{3-10}$ cycloalkyl, aryl and heterocyclyl, wherein said aryl is substituted with one or more substituents independently selected from the group consisting of halogen, hydroxy, nitro, cyano, trifluoromethyl, trifluoromethoxy, $C_{1-4}$ alkyl, $C_{1-4}$ alkoxy, carboxamido, sulfamoyl, carbamoyl, sulfonamido, heterocyclyl, —CON($R_{13}$)$_2$, —COR$_{10}$, —NR$_{12}$COR$_{10}$, —NR$_{11}$R$_{11}$, —SO$_2$R$_9$, —NHSO$_2$R$_9$ and phenoxy, and wherein said $C_{1-6}$ alkyl or heterocyclyl is optionally substituted with one or more substituents independently selected from the group consisting of halogen, —CON($R_{13}$)$_2$, —SO$_2$R$_9$, hydroxy, $C_{1-4}$ alkoxy and —NR$_{11}$R$_{11}$;

$R_8$ is selected from the group consisting of $C_{3-10}$ cycloalkyl, heteroaryl and aryl, wherein said heteroaryl or aryl is optionally substituted with one or more substituents independently selected from the group consisting of halogen and $C_{1-4}$ alkyl, and wherein said $C_{3-10}$ cycloalkyl is optionally substituted at the carbon position adjacent to the N atom of $R_1$ with aryl or heteroaryl, wherein said aryl is optionally substituted with halogen;
  $R_2$ is —NHR$_4$ or XR$_7$ or is selected from the group consisting of N-morpholinyl, N-thiomorpholinyl and N-thiomorpholinyl dioxide;
  X is selected from the group consisting of O, S, NR$_{13}$ and CH$_2$;
  $R_7$ is selected from the group consisting of $C_{1-20}$ alkyl, $C_{3-10}$ cycloalkyl, aryl, heterocyclyl and aryl-$C_{1-4}$ alkyl; wherein said heterocyclyl is optionally substituted with $C_{1-4}$ alkyl when X is NH; and wherein said $C_{1-20}$ alkyl is optionally substituted with methylsulfonyl, heterocyclyl, one to six halogen atoms or $C_{1-4}$ alkoxy when X is NR$_{13}$ or said $C_{1-20}$ alkyl is optionally substituted with $C_{1-4}$ alkoxy, halo-$C_{1-4}$ alkoxy or heterocyclyl-oxy $C_{1-4}$ alkoxy when X is O; wherein said $C_{3-10}$ cycloalkyl is optionally substituted with one or more substituents independently selected from the group consisting of halogen, hydroxy, nitro, cyano, $C_{1-4}$ alkyl optionally substituted with one or more halogen, $C_{1-4}$ alkoxy optionally substituted with one or more halogen, mono-$C_{1-4}$ alkylamino, di-$C_{1-4}$ alkylamino, carboxamido, sulfamoyl, carbamoyl, sulfonamido, —CON($R_{13}$)$_2$, —NR$_{12}$COR$_{10}$, —SO$_2$R$_9$, —NHSO$_2$R$_9$ and phenoxy;
  $R_4$ is $C_{3-10}$ cycloalkyl substituted with one or more substituents independently selected from the group consisting of halogen, hydroxy, nitro, $C_{1-4}$ alkyl optionally substituted with one or more halogen, $C_{1-4}$ alkoxy optionally substituted with one or more halogen, mono-$C_{1-4}$ alkylamino, di-$C_{1-4}$ alkylamino, carboxamido, sulfamoyl, carbamoyl, sulfonamido, —CON($R_{13}$)$_2$, —NR$_{12}$COR$_{10}$, —SO$_2$R$_9$, —NHSO$_2$R$_9$ and phenoxy;
    wherein when $R_2$ is —NHR$_4$, $R_3$ is selected from the group consisting of optionally substituted $C_{1-6}$ alkynyl, optionally substituted $C_{1-6}$ alkenyl, mono-substituted or di-substituted aryl, mono-substituted or di-substituted heteroaryl and mono-substituted or di-substituted heterocyclyl; wherein the substituents of said aryl, heteroaryl or heterocyclyl are independently selected from the group consisting of oxo, halogen, hydroxy, cyano, —CON($R_{13}$)$_2$, —NR$_{12}$COR$_{10}$, —NR$_{11}$R$_{11}$, —SO$_2$R$_9$, —NHSO$_2$R$_9$, $C_{3-6}$ cycloalkyl, phenoxy, $C_{1-6}$ alkoxy and $C_{1-6}$ alkyl wherein said $C_{1-6}$ alkoxy and $C_{1-6}$ alkyl is optionally substituted with one or more substituents selected from halogen, hydroxy, alkoxy, cyano, amino, di-$C_{1-4}$ alkylamino, mono-alkylamino and heterocyclyl; or
    wherein when $R_2$ is XR$_7$ or is selected from the group consisting of N-morpholinyl, N-thiomorpholinyl and N-thiomorpholinyl dioxide; $R_3$ is selected from:
      optionally substituted $C_{2-6}$ alkynyl or optionally substituted $C_{2-6}$ alkenyl;
      an at least para-substituted phenyl group wherein the para-substituent of said phenyl group is $C_{1-6}$ alkoxy optionally substituted with 1-6 halogens;
      a pyridin-3-yl or pyrimidin-5-yl group wherein the 6-position of said pyridin-3-yl or 2-position of said pyrimidin-5-yl group is substituted with a $C_{2-6}$ alkoxy group optionally substituted with 2-5 deuteriums; a $C_1$ alkoxy group substituted with 1-3 halogens; or a $C_{3-7}$ cycloalkoxy group; or a mono-substituted or di-substituted phenyl or heteroaryl, wherein at least one substituent of said phenyl or heteroaryl is —SO$_2$(C$_{1-3}$ alkyl) wherein said C$_{1-3}$ alkyl is optionally substituted with one to three halogens; —SO$_2$(C$_{3-6}$ cycloalkyl) or —SO$_2$(CH$_2$OCH$_3$) and the remaining substituents of said phenyl or heteroaryl are independently selected from the group consisting of H, halogen, hydroxyl, cyano, —CON(R$_{13}$)$_2$, —NR$_{12}$COR$_{10}$, —NR$_{11}$R$_{11}$, —SO$_2$R$_9$, —NHSO$_2$R$_9$, C$_{3-6}$ cycloalkyl, phenoxy, C$_{1-6}$ alkoxy and C$_{1-6}$ alkyl wherein said C$_{1-6}$ alkyl or C$_{1-6}$ alkoxy is optionally substituted with one or more substituents selected from halogen, hydroxyl, C$_{1-4}$ alkoxy, cyano, amino, di-C$_{1-4}$ alkylamino, mono-C$_{1-4}$ alkylamino or heterocyclyl;

R$_9$ is selected from the group consisting of C$_{1-6}$ alkyl, C$_{3-6}$ cycloalkyl and —NR$_{11}$R$_{11}$;

each R$_{11}$ is independently selected from the group consisting of hydrogen, C$_{1-6}$ alkyl, C$_{3-6}$ cycloalkyl, —COR$_{10}$, heterocyclyl, aryl and heteroaryl; or each R$_{11}$, together with the nitrogen atom to which they are attached, form a 5-7 membered heterocyclyl or heteroaryl ring;

R$_{10}$ is selected from the group consisting of C$_{1-6}$ alkyl optionally substituted with one or more substituents independently selected from the group consisting of amino, cyano, halogen and hydroxy; hydroxy, C$_{1-6}$ alkoxy optionally substituted with one or more substituents independently selected from the group consisting of amino, mono-C$_{1-4}$ alkylamino, di-C$_{1-4}$ alkylamino, cyano, halogen, and heterocyclyl; heterocyclyl optionally substituted with one or more substituents independently selected from the group consisting of C$_{1-6}$ alkyl, acylamino and oxo; C$_{3-10}$ cycloalkyl optionally substituted with one or more substituents independently selected from the group consisting of halogen, hydroxy, nitro, C$_{1-4}$ alkyl optionally substituted with one or more halogen, C$_{1-4}$ alkoxy optionally substituted with one or more halogen, mono-C$_{1-4}$ alkylamino, di-C$_{1-4}$ alkylamino, carboxamido, sulfamoyl, carbamoyl, sulfonamido, CON(R$_{13}$)$_2$, —SO$_2$R$_9$, and —NHSO$_2$R$_9$; and amino optionally substituted with one or more substituents independently selected from the group consisting of C$_{1-6}$ alkyl, wherein said C$_{1-6}$ alkyl is optionally substituted with one or more substituents independently selected from the group consisting of amino, mono-C$_{1-4}$ alkylamino, di-C$_{1-4}$ alkylamino, cyano, halogen and heterocyclyl;

R$_{12}$ is selected from the group consisting of hydrogen and C$_{1-6}$ alkyl, wherein said C$_{1-6}$ alkyl is optionally substituted with one or more substituents independently selected from the group consisting of cyano, halogen and hydroxy;

each R$_{13}$ is independently selected from the group consisting of hydrogen, C$_{1-20}$ alkyl or C$_{3-10}$ cycloalkyl optionally substituted with one or more substituents independently selected from the group consisting of halogen, hydroxy, nitro, C$_{1-4}$ alkyl optionally substituted with one or more halogen, C$_{1-4}$ alkoxy optionally substituted with one or more halogen, mono-C$_{1-4}$ alkylamino, di-C$_{1-4}$ alkylamino, carboxamido, sulfamoyl, carbamoyl, sulfonamido, —SO$_2$R$_9$, and —NHSO$_2$R$_9$;

wherein the substituents of said optionally substituted C$_{2-6}$ alkynyl or optionally substituted C$_{2-6}$ alkenyl are independently selected from the group consisting of oxo, halogen, hydroxyl, cyano, —CON(R$_{13}$)$_2$, —NR$_{12}$COR$_{10}$, —NR$_{11}$R$_{11}$, —SO$_2$R$_9$, —NHSO$_2$R$_9$, C$_{3-6}$ cycloalkyl, optionally substituted phenyl, optionally substituted heteroaryl, C$_{1-6}$ alkoxy and C$_{1-6}$ alkyl wherein said C$_{1-6}$ alkoxy and C$_{1-6}$ alkyl is optionally substituted with one or more substituents selected from halogen, hydroxyl, alkoxy, cyano, amino, di-C$_{1-4}$ alkylamino, mono-C$_{1-4}$ alkylamino or heterocyclyl;

or a pharmaceutical acceptable addition salt or a stereochemical isomeric form thereof or a N-oxide thereof or a solvate thereof or a prodrug thereof.

In another embodiment, the present invention relates to the unexpected finding that desirable pharmacological properties such as a high and specific antiviral activity, especially against infections by a virus of the Flaviridae family, more specifically the ability to inhibit hepatitis C virus (HCV) replication, is present in the classes of compounds represented by the structural formulae (I), (Ia), (Ib), (II), (III) and (IV).

As a consequence, the invention relates to pharmaceutical compositions comprising one or more pharmaceutically acceptable carriers and, as a biologically active principle, a therapeutically effective amount of at least one pyrido(3,2-d)pyrimidine derivative represented by the above structural formulae (I), (Ia), (Ib), (II), (III) and (IV), and/or a pharmaceutically acceptable addition salt thereof and/or a stereochemical isomeric form thereof and/or a N-oxide thereof and/or a solvate thereof and/or a pro-drug thereof.

The pyrido(3,2-d)pyrimidine compounds represented by the above structural formulae (I), (Ia), (Ib), (II), (III) and (IV), are highly active anti-flaviridae agents, especially anti-HCV agents which, together with one or more pharmaceutically acceptable carriers, may be formulated into pharmaceutical compositions for the prevention or treatment of pathologic conditions such as, but not limited to, hepatitis C infection. It has furthermore been surprisingly found that their activity is virus-specific.

In a further embodiment, the present invention relates to combined preparations containing at least one pyrido(3,2-d)pyrimidine compound represented by the above structural formulae (I), (Ia), (Ib), (II), (III) and (IV), and one or more other antiviral agents, especially one or more other anti-flaviridae agents. In a further embodiment, the present invention relates to the prevention or treatment of the above-cited pathologic conditions or infections by administering to the patient in need thereof a therapeutically effective amount of at least one above-defined pyrido(3,2-d)pyrimidine compound optionally in the form of a pharmaceutical composition or a combined preparation with one or more other suitable drugs, in particular antiviral agents.

In another embodiment, the present invention relates to various processes and methods for making the novel above-defined pyrido(3,2-d)pyrimidine derivatives as well as their pharmaceutically acceptable salts, N-oxides, solvates, pro-drugs and/or stereochemical isomeric forms, e.g., via one or more groups of tri-substituted pyrido(3,2-d)pyrimidine intermediates.

DEFINITIONS

Figure 1:
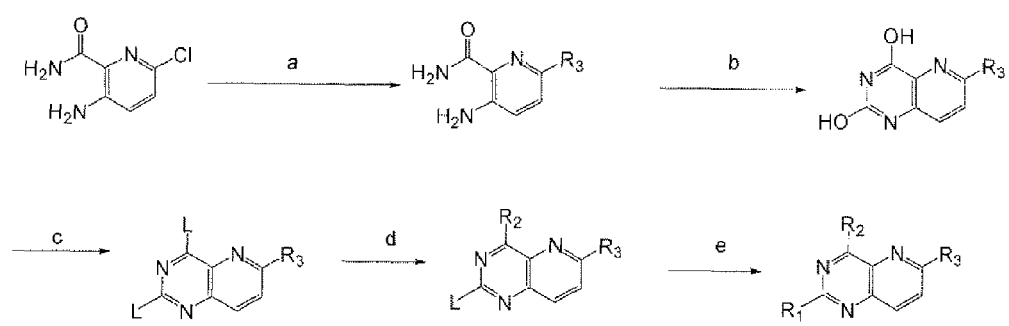
FIG. 1 schematically shows a first method for making certain 2,4,6-tri-substituted pyrido(3,2-d)pyrimidine derivatives of the invention.

Unless otherwise stated herein, the term "tri-substituted" means that three of the carbon atoms being in positions 2, 4 and 6 of the pyrido(3,2-d)pyrimidine core structure (according to standard atom numbering for the pyrido(3,2-d)pyrimidine moiety) are substituted with an atom or group of atoms other than hydrogen.

As used herein with respect to a substituting radical, and unless otherwise stated, the term "$C_{1-6}$ alkyl" means straight and branched chain saturated acyclic hydrocarbon monovalent radicals having from 1 to 6 carbon atoms such as, for example, methyl, ethyl, propyl, n-butyl, 1-methylethyl (isopropyl), 2-methylpropyl (isobutyl), 1,1-dimethylethyl (tert-butyl), 2-methylbutyl, n-pentyl, dimethylpropyl, n-hexyl, 2-methylpentyl, 3-methylpentyl, and the like. By analogy, the term "$C_{1-4}$ alkyl" refers to such radicals having from 1 to 4 carbon atoms, and the term "$C_{1-20}$ alkyl" refers to such radicals having from 1 to 20 carbon atoms, including n-octyl, n-decyl, n-dodecyl, n-hexadecyl and the like.

As used herein with respect to a substituting radical, and unless otherwise stated, the term "acyl" broadly refers to a substituent derived from an acid such as an organic monocarboxylic acid, a carbonic acid, a carbamic acid (resulting into a carbamoyl substituent) or the thioacid or imidic acid (resulting into a carbamidoyl substituent) corresponding to said acids, and the term "sulfonyl" refers to a substituent derived from an organic sulfonic acid, wherein said acids comprise an aliphatic, aromatic or heterocyclic group in the molecule. A more specific kind of "acyl" group within the scope of the above definition refers to a carbonyl (oxo) group adjacent to a $C_{1-7}$ alkyl, a $C_{3-10}$ cycloalkyl, an aryl, an arylalkyl or a heterocyclic group, all of them being such as herein defined. Suitable examples of acyl groups are to be found below.

Acyl and sulfonyl groups originating from aliphatic or cycloaliphatic monocarboxylic acids or sulphonic acids, are designated herein as aliphatic or cycloaliphatic acyl and sulfonyl groups and include, but are not limited to, the following:

- alkanoyl (for example formyl, acetyl, propionyl, butyryl, isobutyryl, valeryl, isovaleryl, pivaloyl and the like);
- cycloalkanoyl (for example cyclobutanecarbonyl, cyclopentanecarbonyl, cyclo-hexanecarbonyl, 1-adamantanecarbonyl and the like);
- cycloalkyl-alkanoyl (for example cyclohexylacetyl, cyclopentylacetyl and the like);
- alkenoyl (for example acryloyl, methacryloyl, crotonoyl and the like);
- alkylthioalkanoyl (for example methylthioacetyl, ethylthioacetyl and the like);
- alkanesulfonyl (for example mesyl, ethanesulfonyl, propanesulfonyl and the like);
- alkoxycarbonyl (for example methoxycarbonyl, ethoxycarbonyl, propoxycarbonyl, isopropoxycarbonyl, butoxycarbonyl, isobutoxycarbonyl and the like);
- alkylcarbamoyl (for example methylcarbamoyl and the like);
- (N-alkyl)-thiocarbamoyl (for example (N-methyl)-thiocarbamoyl and the like);
- alkylcarbamidoyl (for example methylcarbamidoyl and the like); and
- alkoxyalkyl (for example methoxyalkyl, ethoxyalkyl, propoxyalkyl and the like);

Acyl and sulfonyl groups may also originate from aromatic monocarboxylic acids or sulphonic acids, and include, but are not limited to, the following:

- aroyl (for example benzoyl, toluoyl, xyloyl, 1-naphthoyl, 2-naphthoyl and the like);
- arylakanoyl (for example phenylacetyl and the like);
- arylalkenoyl (for example cinnamoyl and the like);
- aryloxyalkanoyl (for example phenoxyacetyl and the like);
- arylthioalkanoyl (for example phenylthioacetyl and the like);
- arylaminoalkanoyl (for example N-phenylglycyl, and the like);
- arylsulfonyl (for example benzenesulfonyl, toluenesulfonyl, naphthalene sulfonyl and the like);
- aryloxycarbonyl (for example phenoxycarbonyl, naphthyloxycarbonyl and the like);
- arylalkoxycarbonyl (for example benzyloxycarbonyl and the like);
- arylcarbamoyl (for example phenylcarbamoyl, naphthylcarbamoyl and the like);
- arylglyoxyloyl (for example phenylglyoxyloyl and the like).
- arylthiocarbamoyl (for example phenylthiocarbamoyl and the like); and
- arylcarbamidoyl (for example phenylcarbamidoyl and the like).

Acyl groups may also originate from an heterocyclic monocarboxylic acids or sulphonic acids, and include, but are not limited to, the following:

- heterocyclic-carbonyl, in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiophenoyl, furoyl, pyrrolecarbonyl, nicotinoyl and the like); and
- heterocyclic-alkanoyl in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiopheneacetyl, furylacetyl, imidazolylpropionyl, tetrazolylacetyl, 2-(2-amino-4-thiazolyl)-2-methoxyiminoacetyl and the like).

As used herein with respect to a substituting radical, and unless otherwise stated, the term "$C_{3-10}$ cycloalkyl" means a mono- or polycyclic saturated hydrocarbon monovalent radical having from 3 to 10 carbon atoms, such as for instance cyclo-propyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl. In certain embodiments, the cycloalkyl group is optionally substituted, that is, one or more of the hydrogens of the cycloalkyl hydrocarbon may be replaced by a substituent. The optional substituents may be at any position on the cycloalkyl hydrocarbon including the position of attachment of the cycloalkyl radical. In a non-limiting example, $R_4$ of $NHR_4$ may be optionally substituted cyclopropyl wherein the 1 position of the cyclopropyl group is substituented with trifluoromethyl, i.e.,

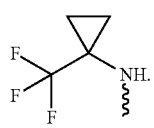

1-(trifluoromethyl)cyclopropylamino

In such an example, the trifluoromethyl group is said to be geminal to the attachment of the cyclopropyl group.

As used herein with respect to a substituting radical, and unless otherwise stated, the term "aryl" designates any mono- or polycyclic aromatic monovalent hydrocarbon radical having from 6 up to 30 carbon atoms such as but not limited to phenyl, naphthyl, anthracenyl, phenanthracyl, fluoranthenyl, chrysenyl, pyrenyl, biphenyyl, terphenyl, picenyl, indenyl, biphenyl, indacenyl, benzocyclobutenyl, benzocyclooctenyl and the like, including fused benzo-$C_{4-8}$ cycloalkyl radicals (the latter being as defined above) such as, for instance, indenyl, tetrahydronaphthyl, fluorenyl and the like, all of the said radicals being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein with respect to a substituting radical (including the combination of substituents in certain positions of the pyrido(3,2-d)pyrimidine ring together with the carbon atoms in the same positions of said ring), and unless otherwise stated, the term "heterocyclyl" refers to a mono- or polycyclic, saturated or mono-unsaturated or polyunsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphtho-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxathiinyl, benzodioxinyl, benzodithiinyl, benzoxazepinyl, benzothiazepinyl, benzodiazepinyl, benzodioxepinyl, benzodithiepinyl, benzoxazocinyl, benzo-thiazocinyl, benzodiazocinyl, benzoxathiocinyl, benzodioxocinyl, benzotrioxepinyl, benzoxathiazepinyl, benzoxadiazepinyl, benzothia-diazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypo-xanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzo-carbazolyl, dibenzoacridinyl, dibenzophenazinyl, dibenzothiepinyl, dibenzoxepinyl, dibenzopyranonyl, dibenzoquinoxalinyl, dibenzothiazepinyl, dibenzisoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphthindazolyl, naphthindolyl, naphthothiazolyl, naphthothioxolyl, naphthoxindoiyl, naphthotriazolyl, naphthopyranyl, oxabicycloheptyl, azabenzimidazolyl, azacycloheptyl, azacyclooctyl, azacyclononyl, azabicyclononyl, tetrahydrofuryl, tetrahydropyranyl, tetrahydropyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphtothienyl, thianthrenyl, pyronyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimi-dazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, pheno-metoxazinyl, phenoparoxazinyl, phentriazinyl, thiodiazinyl, thiodiazoiyl, indoxyl, thioindoxyl, benzodiazinyl (e.g. phthalazinyl), phthalidyl, phthalimidinyl, phthalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof; depending upon the number of unsaturations in the 3 to 10 atoms ring, heterocyclic radicals are conventionally sub-divided into heteroaromatic (or "heteroaryl") radicals and non-aromatic heterocyclic radicals.

Particularly useful, but non-limiting, optionally substituted heteroaromatic radicals include 2-pyridinyl, 3-pyridinyl, 4-pyridinyl, 2-pyrimidinyl, 4-pyrimidinyl and 5-pyrimidinyl radicals. Non-limiting examples of an optionally substituted 3-pyridinyl radical or optimally substituted 5-pyrimidinyl radical are the 6-alkoxy-pyridin-3-yl radical and the 2-alkoxy-pyrimidin-5-yl radical, respectively, shown below.

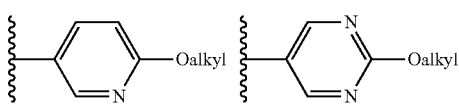

As used herein with respect to a substituting radical, and unless otherwise stated, the terms "$C_{1-6}$ alkoxy", "$C_{3-10}$ cycloalkoxy" and "heterocyclyloxy" refer to substituents wherein a carbon atom of a $C_{1-6}$ alkyl, $C_{3-10}$ cycloalkyl or heterocyclyl radical (each of them such as defined herein), is attached to an oxygen atom through a single bond such as, but not limited to, methoxy, ethoxy, propoxy, butoxy, pentoxy, isopropoxy, sec-butoxy, tert-butoxy, isopentoxy, cyclopropoxy, cyclobutoxy, cyclopentoxy, cyclohexyloxy, cycloheptyloxy, cyclooctyloxy, and various isomers of piperidinoxy, methylpiperidinoxy, pyrrolidinoxy, pyridinoxy, tetrahydrofuranyloxy, and the like.

As used herein with respect to a substituting atom, and unless otherwise stated, the term halogen means any atom selected from the group consisting of fluorine, chlorine, bromine and iodine.

As used herein with respect to a substituting radical, and unless otherwise stated, the term "arylalkyl" refers to an aliphatic saturated hydrocarbon monovalent radical (preferably a $C_{1-6}$ alkyl or $C_{1-4}$ alkyl radical such as defined above) onto which an aryl radical (such as defined above) is attached via a carbon atom, and wherein the said aliphatic radical and/or the said aryl radical may be optionally substituted with one or more substituents independently selected from the group consisting of halogen, amino, hydroxyl, trifluoromethyl and nitro, such as but not limited to benzyl, 4-chlorobenzyl, 4-fluorobenzyl, 2-fluorobenzyl, 3,4-dichlorobenzyl, 2,6-dichlorobenzyl, 3-methylbenzyl, 4-methylbenzyl, 4-tert-butylbenzyl, phenylpropyl, 1-naphthylmethyl, phenylethyl, 1-amino-2-phenylethyl, 1-amino-2-[4-hydroxy-phenyl]ethyl, and the like.

As used herein with respect to a substituting radical, and unless otherwise stated, the term "alkylamino" means that one (thus monosubstituted amino or monoalkylamino) or respectively two (thus disubstituted amino or dialkylamino) $C_{1-6}$ alkyl or $C_{1-4}$ alkyl radical(s) (as defined herein, respectively, is/are attached to a nitrogen atom through a single bond such as, but not limited to, methylamino, dimethylamino, ethylamino, diethylamino, isopropylamino, n-butylamino, tert-butylamino, dibutylamino.

As used herein with respect to a substituting radical, and unless otherwise stated, the term "carboxamido" refers to a substituting radical having the structural formula —$NR_{12}COR_{10}$ wherein $R_{10}$ and $R_{12}$ are as defined herein.

As used herein with respect to a substituting radical, and unless otherwise stated, the term "sulfonamido" refers to a substituting radical having the structural formula —$NR_{12}SO_2R_{11}$ wherein $R_{11}$ and $R_{12}$ are as defined herein.

As used herein with respect to a substituent of a phenyl group at position 6 of the pyrido(3,2-d)pyrimidine core, and unless otherwise stated, the term "meta substituent" refers to the meta substituting position with respect to the point of attachment of said phenyl onto the pyrido(3,2-d)pyrimidine core.

As used herein and unless otherwise stated, the term "stereochemical isomeric form" refers to all possible different isomeric as well as conformational forms which the compounds of this invention, e.g. derivatives represented by the structural formula (Ia) or the structural formula (Ib), may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a pyrido(3,2-d)pyrimidine derivative of this invention with a suitable inorganic solvent (e.g. hydrates) or organic solvent, such as but not limited to alcohols, ketones, esters, ethers, nitriles and the like.

DETAILED DESCRIPTION OF THE INVENTION

In a one embodiment of the present invention, the novel trisubstituted pyrido(3,2-d)pyrimidine derivatives are as defined in the structural formula (Ia), wherein the substituents independently correspond to any of the definitions given above, in particular with any of the individual meanings (such as illustrated above) of generic terms used for substituting groups such as, but not limited to, "$C_{1-20}$ alkyl", "$C_{3-10}$ cycloalkyl", "aryl", "heterocyclic", "halogen", "arylalkyl", "monoalkylamino", "dialkylamino", "$C_{1-4}$ alkoxy", "$C_{1-4}$ alkylthio" and the like.

In one embodiment of the pyrido(3,2-d)pyrimidine derivatives of structural formula (Ia), $R_2$ is —$NHR_4$. In one aspect of this embodiment, $R_4$ is $C_{3-6}$ cycloalkyl substituted with one or more substituents independently selected from the group consisting of halogen, hydroxy, nitro, $C_{1-4}$ alkyl optionally substituted with one or more halogen, $C_{1-4}$ alkoxy optionally substituted with one or more halogens, mono-$C_{1-4}$ alkylamino, di-$C_{1-4}$ alkylamino, carboxamido, sulfamoyl, carbamoyl, sulfonamido, —$CON(R_{13})_2$, —$NR_{12}COR_{10}$, —$SO_2R_9$, —$NHSO_2R_9$ and phenoxy. In another aspect of this embodiment, $R_4$ is $C_{3-6}$ cycloalkyl substituted with one or more substituents independently selected from $C_{1-4}$ alkyl optionally substituted with one or more halogens, or —$CON(R_{13})_2$. In another aspect of this embodiment, $R_4$ is cyclopropyl substituted with one or more substituents independently selected from $C_{1-4}$ alkyl optionally substituted with one or more halogens, or —$CON(R_{13})_2$. In a preferred aspect of this embodiment, $R_4$ is cyclopropyl substituted with one or more substituents independently selected from $C_{1-4}$ alkyl optionally substituted with one or more fluorines. In another preferred aspect of this embodiment, $R_4$ is cyclopropyl substituted with one or more trifluoromethyl groups. In a particularly preferred aspect of this embodiment, —$NHR_4$ is:

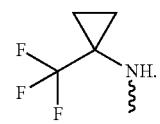

1-(trifluoromethyl)cyclopropylamino

In one embodiment of the pyrido(3,2-d)pyrimidine derivatives of structural formula (Ia), $R_2$ is —$NHR_4$ wherein $R_4$ is $C_{3-6}$ cycloalkyl substituted with one or more substituents independently selected from $C_{1-4}$ alkyl optionally substituted with one or more halogens and $R_1$ is —NH—$CH_2R_6$, —NHCH($CH_3$)$R_6$ or NH—CH($CH_2CH_3$)$R_6$. In another aspect of this embodiment, $R_4$ is $C_{3-6}$ cycloalkyl substituted with one or more substituents independently selected from $C_{1-4}$ alkyl substituted with one to six fluorines. In another aspect of this embodiment, —$NHR_4$ is 1-(trifluoromethyl) cyclopropylamino. In another aspect of this embodiment, $R_6$ is aryl or heterocyclyl wherein said aryl is substituted with one or more substituents independently selected from the group consisting of halogen, hydroxy, nitro, cyano, trifluoromethyl, trifluoromethoxy, $C_{1-4}$ alkyl, $C_{1-4}$ alkoxy, carboxamido, sulfamoyl, carbamoyl, sulfonamide, heterocyclyl, —CON($R_{13}$)$_2$, —COR$_{10}$, —NR$_{12}$COR$_{10}$, —NR$_{11}$R$_{11}$, SO$_2$R$_9$, —NHSO$_2$R$_9$ and phenoxy, and wherein said heterocyclyl is optionally substituted with one or more substituents independently selected from the group consisting of halogen, —CON($R_{13}$)$_2$, —SO$_2$R$_9$, hydroxy, $C_{1-4}$ alkoxy and —NR$_{11}$R$_{11}$. In another aspect of this embodiment, $R_6$ is phenyl substituted with one or more substituents independently selected from the group consisting of chloro, fluoro, cyano, trifluoromethyl, trifluoromethoxy, $C_{1-4}$ alkyl, $C_{1-4}$ alkoxy, carboxamido, sulfamoyl, carbamoyl, sulfonamido, heterocyclyl, —CON($R_{13}$)$_2$, —COR$_{10}$, —NR$_{12}$COR$_{10}$, —NR$_{11}$R$_{11}$, —SO$_2$R$_9$, and —NHSO$_2$R$_9$. In another aspect of this embodiment, —$NHR_4$ is 1-(trifluoromethyl)cyclopropylamino and $R_6$ is phenyl substituted with one or more substituents independently selected from the group consisting of chloro, fluoro, cyano, trifluoromethyl, trifluoromethoxy, $C_{1-4}$ alkyl, $C_{1-4}$ alkoxy, carboxamido, sulfamoyl, carbamoyl, sulfonamido, heterocyclyl, —CON($R_{13}$)$_2$, —COR$_{10}$, —NR$_{12}$COR$_{10}$, —NR$_{11}$R$_{11}$, —SO$_2$R$_9$, and —NHSO$_2$R$_9$. In another aspect of this embodiment, —$NHR_4$ is 1-(trifluoromethyl)cyclopropylamino and $R_6$ is heterocyclyl wherein heterocyclyl is optionally substituted with one or more substituents independently selected from the group consisting of halogen, —CON($R_{13}$)$_2$, —SO$_2$R$_9$, hydroxy, $C_{1-4}$ alkoxy and —NR$_{11}$R$_{11}$.

In another embodiment of the pyrido(3,2-d)pyrimidine derivatives of structural formula (Ia), $R_2$ is —$NHR_4$ wherein $R_4$ is $C_{3-6}$ cycloalkyl substituted with one or more substituents independently selected from $C_{1-4}$ alkyl optionally substituted with one or more halogens; $R_1$ is —NH—$CH_2R_6$, —NHCH($CH_3$)$R_6$ or NH—CH($CH_2CH_3$)$R_6$; and $R_3$ is selected from the group consisting of optionally substituted $C_{1-6}$ alkynyl, optionally substituted $C_{1-6}$ alkenyl, mono-substituted or di-substituted aryl, mono-substituted or di-substituted heteroaryl and mono-substituted or di-substituted heterocyclyl; wherein the substituents of said aryl, heteroaryl or heterocyclyl are independently selected from the group consisting of oxo, halogen, hydroxy, cyano, —CON($R_{13}$)$_2$, —NR$_{12}$COR$_{10}$, —NR$_{11}$R$_{11}$, —SO$_2$R$_9$, —NHSO$_2$R$_9$, $C_{3-6}$ cycloalkyl, phenoxy, $C_{1-6}$ alkoxy and $C_{1-6}$ alkyl wherein said $C_{1-6}$ alkoxy and $C_{1-6}$ alkyl is optionally substituted with one or more substituents selected from halogen, hydroxy, alkoxy, cyano, amino, di-$C_{1-4}$ alkylamino, mono-$C_{1-4}$ alkylamino and heterocyclyl. In another aspect of this embodiment, $R_3$ is mono-substituted or disubstituted phenyl. In another aspect of this embodiment, $R_3$ is mono-substituted or di-substituted heteroaryl. In another aspect of this embodiment, $R_3$ is mono-substituted or di-substituted pyridyl. In another aspect of this embodiment, —$NHR_4$ is 1-(trifluoromethyl)cyclopropylamino.

In another embodiment of the pyrido(3,2-d)pyrimidine derivatives of structural formula (Ia), $R_2$ is —$NHR_4$ wherein —$NHR_4$ is 1-(trifluoromethyl)cyclopropylamino, 1-(trifluoromethyl)cyclobutylamino, 1-(trifluoromethyl)cyclopentylamino or 1-(trifluoromethyl(cyclohexyl); $R_1$ is —NH—$CH_2R_6$, —NHCH($CH_3$)$R_6$ or NH—CH($CH_2CH_3$)$R_6$; and $R_3$ is selected from the group consisting of optionally substituted $C_{1-6}$ alkynyl, optionally substituted $C_{1-6}$ alkenyl, mono-substituted or di-substituted aryl, mono-substituted or di-substituted heteroaryl and mono-substituted or di-substituted heterocyclyl; wherein the substituents of said aryl, heteroaryl or heterocyclyl are independently selected from the group consisting of oxo, halogen, hydroxy, cyano, —CON($R_{13}$)$_2$, —NR$_{12}$COR$_{10}$, —NR$_{11}$R$_{11}$, —SO$_2$R$_9$, —NHSO$_2$R$_9$, $C_{3-6}$ cycloalkyl, phenoxy, $C_{1-6}$ alkoxy and $C_{1-6}$ alkyl wherein said $C_{1-6}$ alkoxy and $C_{1-6}$ alkyl is optionally substituted with one or more substituents selected from halogen, hydroxy, alkoxy, cyano, amino, di-$C_{1-4}$ alkylamino, mono-$C_{1-4}$ alkylamino and heterocyclyl. In another aspect of this embodiment, $R_3$ is optionally substituted $C_{1-6}$ alkynyl. In another aspect of this embodiment, $R_3$ is optionally substituted $C_{1-6}$ alkynyl where the substitutents of said optionally substituted $C_{1-6}$ alkynyl are $C_{3-6}$ cycloalkyl or $C_{1-6}$ alkyl. In another aspect of this embodiment, $R_3$ is mono-substituted or di-substituted phenyl. In another aspect of this embodiment, $R_3$ is a mono-substituted or di-substituted phenyl wherein the substituents of said mono-substituted or di-substituted phenyl are independently selected from the group consisting of fluoro, chloro, difluoromethoxy, methoxy, —SO$_2$CH$_3$, —SO$_2$NH$_2$, trifluoromethyl, NR$_{11}$R$_{11}$, methyl, cyano, CONH$_2$, NHCOR$_{10}$, and —CONR$_{13}$R$_{13}$. In another aspect of this embodiment, $R_3$ is mono-substituted or di-substituted heteroaryl. In another aspect of this embodiment, $R_3$ is mono-substituted or di-substituted pyridyl. In another aspect of this embodiment, $R_3$ is mono-substituted or di-substituted pyridyl wherein the substitutents of said mono-substituted or di-substituted pyridyl are independently selected from methoxy, ethoxy, —NR$_{11}$R$_{11}$, or fluoro.

In another embodiment of the pyrido(3,2-d)pyrimidine derivatives of structural formula (Ia), $R_2$ is XR$_7$ or is selected from the group consisting of N-morpholinyl, N-thiomorpholinyl and N-thiomorpholinyl dioxide. In another aspect of this embodiment, $R_2$ is OR$_7$. In another aspect of this embodiment, $R_2$ is SR$_7$. In another aspect of this embodiment, $R_2$ is NR$_{13}$R$_7$. In another aspect of this embodiment, $R_2$ is selected from the group consisting of N-morpholinyl, N-thiomorpholinyl and N-thiomorpholinyl dioxide.

In another embodiment of the pyrido(3,2-d)pyrimidine derivatives of structural formula (Ia), $R_2$ is XR$_7$ or is selected from the group consisting of N-morpholinyl, N-thiomorpholinyl and N-thiomorpholinyl dioxide and $R_3$ is selected from optionally substituted $C_{2-6}$ alkynyl or optionally substituted $C_{2-6}$ alkenyl. In another aspect of this embodiment, $R_2$ is OR$_7$. In another aspect of this embodiment, $R_2$ is SR$_7$. In another aspect of this embodiment, $R_2$ is NR$_{13}$R$_7$. In another aspect of this embodiment, $R_2$ is selected from the group consisting of N-morpholinyl, N-thiomorpholinyl and N-thiomorpholinyl dioxide. In another aspect of this embodiment, $R_3$ is optionally substituted $C_{2-6}$ alkynyl. In another aspect of this embodiment, $R_3$ is optionally substituted $C_{2-6}$ alkynyl wherein the substitutents of said optionally substituted $C_{2-6}$ alkynyl are selected from the group consisting of hydroxyl, optionally substituted phenyl, optionally substituted heteroaryl, alkoxy, $C_{1-6}$ alkyl, and $C_{3-6}$ cycloalkyl. In another aspect of this embodiment, $R_3$ is ethynyl optionally substituted with methoxymethyl, 2-methyl-2-propyl, cyclopropyl, methyl, thiazoyl, or imidazoyl.

In another embodiment of the pyrido(3,2-d)pyrimidine derivatives of structural formula (Ia), $R_2$ is OR$_7$ and $R_3$ is selected from optionally substituted $C_{2-6}$ alkynyl or optionally substituted $C_{2-6}$ alkenyl. In another aspect of this embodiment, $R_3$ is optionally substituted $C_{2-6}$ alkynyl. In another aspect of this embodiment, $R_3$ is optionally substituted $C_{2-6}$ alkenyl. In another aspect of this embodiment, $R_3$ is optionally substituted $C_{2-6}$ alkynyl wherein the substitutents of said optionally substituted $C_{2-6}$ alkynyl are independently selected from the group consisting of oxo, halogen, hydroxyl, cyano, —CON($R_{13}$)$_2$, —NR$_{12}$COR$_{10}$, —NR$_{11}$R$_{11}$, —SO$_2$R$_9$, —NHSO$_2$R$_9$, $C_{3-6}$ cycloalkyl, optionally substituted phenyl, optionally substituted heteroaryl, $C_{1-6}$ alkoxy and $C_{1-6}$ alkyl wherein said $C_{1-6}$ alkoxy and $C_{1-6}$ alkyl is optionally substituted with one or more substituents selected from halogen, hydroxyl, alkoxy, cyano, amino, di-$C_{1-4}$ alkylamino, mono-$C_{1-4}$ alkylamino or heterocyclyl. In another aspect of this embodiment, $R_3$ is optionally substituted $C_{2-6}$ alkynyl wherein the substitutents of said optionally substituted $C_{2-6}$ alkynyl are independently selected from the group consisting of hydroxyl, optionally substituted phenyl, optionally substituted heteroaryl, $C_{1-4}$ alkoxy, $C_{1-6}$ alkyl, and $C_{3-6}$ cycloalkyl. In another aspect of this embodiment, $R_3$ is optionally substituted ethynyl wherein the substitutents of said optionally substituted ethynyl are independently selected from the group consisting of optionally substituted phenyl, optionally substituted heteroaryl, $C_{1-6}$ alkoxy, $C_{1-6}$ alkyl, and $C_{3-6}$ cycloalkyl. In another aspect of this embodiment, $R_3$ is ethynyl optionally substituted with methoxymethyl, 2-methyl-2-propyl, cyclopropyl, methyl, thiazoyl, or imidazoyl. In another aspect of this embodiment, $R_7$ is selected from the group consisting of $C_{1-20}$ alkyl, $C_{3-10}$ cycloalkyl, aryl, heterocyclyl and aryl-$C_{1-4}$ alkyl; wherein said $C_{3-20}$ alkyl is optionally substituted with $C_{1-4}$ alkoxy, halo-$C_{1-4}$ alkoxy or heterocyclyl-oxy $C_{1-4}$ alkoxy and wherein said $C_{3-10}$ cycloalkyl is optionally substituted with one or more substituents independently selected from the group consisting of halogen, hydroxy, nitro, cyano, $C_{1-4}$ alkyl optionally substituted with one or more halogen, $C_{1-4}$ alkoxy optionally substituted with one or more halogen, mono-$C_{1-4}$ alkylamino, alkylamino, carboxamido, sulfamoyl, carbamoyl, sulfonamido, CON($R_{13}$)$_2$, —NR$_{12}$COR$_{10}$, —SO$_2$R$_9$, —NHSO$_2$R$_9$ and phenoxy.

In another embodiment of the pyrido(3,2-d)pyrimidine derivatives of structural formula (Ia), $R_2$ is OR$_7$ wherein R$_7$ is $C_{1-6}$ alkyl or $C_{3-6}$ cycloalkyl, wherein said $C_{3-6}$ cycloalkyl is optionally substituted with one or more substituents independently selected from $C_{1-4}$ alkyl optionally substituted with one or more halogen or $C_{1-4}$ alkoxy optionally substituted with one or more halogen and $R_3$ is selected from optionally substituted $C_{2-6}$ alkynyl or optionally substituted $C_{2-6}$ alkenyl. In another aspect of this embodiment, $R_3$ is optionally substituted $C_{2-6}$ alkynyl. In another aspect of this embodiment, $R_3$ is optionally substituted $C_{2-6}$ alkenyl. In another aspect of this embodiment, $R_3$ is optionally substituted $C_{2-6}$ alkynyl wherein the substitutents of said optionally substituted $C_{2-6}$ alkynyl are independently selected from the group consisting of oxo, halogen, hydroxyl, cyano, —CON($R_{13}$)$_2$, —NR$_{12}$COR$_{10}$, —NR$_{11}$R$_{11}$, —SO$_2$R$_9$, —NHSO$_2$R$_9$, $C_{3-6}$ cycloalkyl, optionally substituted phenyl, optionally substituted heteroaryl, $C_{1-6}$ alkoxy and $C_{1-6}$ alkyl wherein said $C_{1-6}$ alkoxy and $C_{1-6}$ alkyl is optionally substituted with one or more substituents selected from halogen, hydroxyl, alkoxy, cyano, amino, di-$C_{1-4}$ alkylamino, mono-$C_{1-4}$ alkylamino or heterocyclyl. In another aspect of this embodiment, $R_3$ is optionally substituted $C_{2-6}$ alkynyl wherein the substitutents of said optionally substituted $C_{2-6}$ alkynyl are independently selected from the group consisting of hydroxyl, optionally substituted phenyl, optionally substituted heteroaryl, $C_{1-6}$ alkoxy, $C_{1-6}$ alkyl, and $C_{3-6}$ cycloalkyl. In another aspect of this embodiment, $R_3$ is ethynyl optionally substituted with methoxymethyl, 2-methyl-2-propyl, cyclopropyl, methyl, thiazoyl, or imidazoyl. In another aspect of this embodiment, $R_7$ is $C_{3-6}$ cycloalkyl wherein said $C_{3-6}$ cycloalkyl is optionally substituted with one or more substituents independently selected from $C_{1-4}$ alkyl and $R_3$ is optionally substituted ethynyl wherein the substitutents of said optionally substituted ethynyl are independently selected from the group consisting of optionally substituted phenyl, optionally substituted heteroaryl, $C_{1-6}$ alkoxy, $C_{1-6}$ alkyl, and $C_{3-6}$ cycloalkyl. In another aspect of this embodiment, $R_7$ is $C_{3-6}$ cycloalkyl wherein said $C_{3-6}$ cycloalkyl is optionally substituted with one or more substituents independently selected from $C_{1-4}$ alkyl and $R_3$ is ethynyl optionally substituted with methoxymethyl, 2-methyl-2-propyl, cyclopropyl, methyl, thiazoyl, or imidazoyl.

In another embodiment of the pyrido(3,2-d)pyrimidine derivatives of structural formula (Ia), $R_2$ is NR$_{13}$R$_7$ and $R_3$ is selected from optionally substituted $C_{2-6}$ alkynyl or optionally substituted $C_{2-6}$ alkenyl. In another aspect of this embodiment, $R_3$ is optionally substituted $C_{2-6}$ alkynyl. In another aspect of this embodiment, $R_3$ is optionally substituted $C_{2-6}$ alkenyl. In another aspect of this embodiment, $R_3$ is optionally substituted $C_{2-6}$ alkynyl wherein the substitutents of said optionally substituted $C_{2-6}$ alkynyl are independently selected from the group consisting of oxo, halogen, hydroxyl, cyano, —CON($R_{13}$)$_2$, —NR$_{12}$COR$_{10}$, —NR$_{11}$R$_{11}$, —SO$_2$R$_9$, —NHSO$_2$R$_9$, $C_{3-6}$ cycloalkyl, optionally substituted phenyl, optionally substituted heteroaryl, $C_{1-6}$ alkoxy and $C_{1-6}$ alkyl wherein said $C_{1-6}$ alkoxy and $C_{1-6}$ alkyl is optionally substituted with one or more substituents selected from halogen, hydroxyl, alkoxy, cyano, amino, di-$C_{1-4}$ alkylamino, mono-$C_{1-4}$ alkylamino or heterocyclyl. In another aspect of this embodiment, $R_3$ is optionally substituted $C_{2-6}$ alkynyl wherein the substitutents of said optionally substituted $C_{2-6}$ alkynyl are independently selected from the group consisting of hydroxyl, optionally substituted phenyl, optionally substituted heteroaryl, $C_{1-6}$ alkoxy, $C_{1-6}$ alkyl, and $C_{3-6}$ cycloalkyl. In another aspect of this embodiment, $R_3$ is optionally substituted ethynyl wherein the substitutents of said optionally substituted ethynyl are independently selected from the group consisting of optionally substituted phenyl, optionally substituted heteroaryl, alkoxy, $C_{1-6}$ alkyl, and $C_{3-6}$ cycloalkyl. In another aspect of this embodiment, $R_3$ is ethynyl optionally substituted with methoxymethyl, 2-methyl-2-propyl, cyclopropyl, methyl, thiazoyl, or imidazoyl. In another aspect of this embodiment, $R_{13}$ is H and $R_7$ is selected from the group consisting of $C_{1-6}$ alkyl, $C_{3-6}$ cycloalkyl, aryl, heterocyclyl and aryl-$C_{1-4}$ alkyl; wherein said heterocyclyl is optionally substituted with $C_{1-4}$ alkyl; and wherein said $C_{1-6}$ alkyl is optionally substituted with methylsulfonyl, heterocyclyl, one to six halogen atoms or $C_{1-4}$ alkoxy; and wherein said $C_{3-10}$ cycloalkyl is optionally substituted with one or more substituents independently selected from the group consisting of halogen, hydroxy, nitro, cyano, $C_{1-4}$ alkyl optionally substituted with one or more halogen, $C_{1-4}$ alkoxy optionally substituted with one or more halogen, mono-$C_{1-4}$ alkylamino, alkylamino, carboxamido, sulfamoyl, carbamoyl, sulfonamido, —CON($R_{13}$)$_2$, —NR$_{12}$COR$_{10}$, —SO$_2$R$_9$, —NHSO$_2$R$_9$ and phenoxy. In another aspect of this embodiment $R_7$ is 2,2,2-trifluoroethyl.

In another embodiment of the pyrido(3,2-d)pyrimidine derivatives of structural formula (Ia), $R_2$ is NHR$_7$ wherein $R_7$ is $C_{1-6}$ alkyl wherein said $C_{1-6}$ alkyl is optionally substituted with one to six fluorine atoms and $R_3$ is selected from optionally substituted $C_{2-6}$ alkynyl or optionally substituted $C_{2-6}$ alkenyl. In another aspect of this embodiment, $R_3$ is optionally substituted $C_{2-6}$ alkynyl. In another aspect of this embodiment, $R_3$ is optionally substituted $C_{2-6}$ alkenyl. In another aspect of this embodiment, $R_3$ is optionally substituted $C_{2-6}$ alkynyl wherein the substituents of said optionally substituted $C_{2-6}$ alkynyl are independently selected from the group consisting of oxo, halogen, hydroxyl, cyano, —CON$(R_{13})_2$, —NR$_{12}$COR$_{10}$, —, —NR$_{11}$R$_{11}$, —SO$_2$R$_9$, —NHSO$_2$R$_9$, $C_{3-6}$ cycloalkyl, optionally substituted phenyl, optionally substituted heteroaryl, $C_{1-6}$ alkoxy and $C_{1-6}$ alkyl wherein said $C_{1-6}$ alkoxy and $C_{1-6}$ alkyl is optionally substituted with one or more substituents selected from halogen, hydroxyl, alkoxy, cyano, amino, alkylamino, mono-$C_{1-4}$ alkylamino or heterocyclyl. In another aspect of this embodiment, $R_3$ is optionally substituted $C_{2-6}$ alkynyl wherein the substitutents of said optionally substituted $C_{2-6}$ alkynyl are independently selected from the group consisting of hydroxyl, optionally substituted phenyl, optionally substituted heteroaryl, $C_{1-6}$ alkoxy, $C_{1-6}$ alkyl, and $C_{3-6}$ cycloalkyl. In another aspect of this embodiment, $R_3$ is optionally substituted ethynyl wherein the substitutents of said optionally substituted ethynyl are independently selected from the group consisting of optionally substituted phenyl, optionally substituted heteroaryl, alkoxy, $C_{1-6}$ alkyl, and $C_{3-6}$ cycloalkyl. In another aspect of this embodiment, $R_3$ is ethynyl optionally substituted with methoxymethyl, 2-methyl-2-propyl, cyclopropyl, methyl, thiazoyl, or imidazoyl. In another aspect of this embodiment, $R_7$ is 2,2,2-trifluoroethyl. In another aspect of this embodiment, $R_7$ is 2,2,2-trifluoroethyl and $R_3$ is optionally substituted ethynyl wherein the substitutents of said optionally substituted ethynyl are independently selected from the group consisting of optionally substituted phenyl, optionally substituted heteroaryl, $C_{1-6}$ alkoxy, $C_{1-6}$ alkyl, and $C_{3-6}$ cycloalkyl. In another aspect of this embodiment, $R_7$ is 2,2,2-trifluoroethyl and $R_3$ is ethynyl optionally substituted with methoxymethyl, 2-methyl-2-propyl, cyclopropyl, methyl, thiazoyl, or imidazoyl.

In another embodiment of the pyrido(3,2-d)pyrimidine derivatives of structural formula (Ia), $R_2$ is $XR_7$ or is selected from the group consisting of N-morpholinyl, N-thiomorpholinyl and N-thiomorpholinyl dioxide and $R_3$ is an at least para-substituted phenyl group wherein the para-substituent of said phenyl group is $C_{1-6}$ alkoxy optionally substituted with 1-6 halogens; or a pyridin-3-yl or pyrimidin-5-yl group wherein the 6-position of said pyridin-3-yl or 2-position of said pyrimidin-5-yl group is substituted with a $C_{2-6}$ alkoxy group optionally substituted with 2-5 deuteriums; a $C_i$ alkoxy group substituted with 1-3 halogens; or a $C_{3-7}$ cycloalkoxy group. In another aspect of this embodiment, $R_2$ is OR$_7$, in another aspect of this embodiment, $R_2$ is SR$_7$. In another aspect of this embodiment, $R_2$ is NR$_{13}$R$_7$. In another aspect of this embodiment, $R_2$ is selected from the group consisting of N-morpholinyl, N-thiomorpholinyl and N-thiomorpholinyl dioxide. In another aspect of this embodiment, $R_3$ is an at least para-substituted phenyl group wherein the para-substituent of said phenyl group is $C_{1-6}$ alkoxy optionally substituted with 1-6 halogens. In another aspect of this embodiment, $R_3$ is a pyridin-3-yl or pyrimidin-5-yl group wherein the 6-position of said pyridin-3-yl or 2-position of said pyrimidin-5-yl group is substituted with a $C_{2-6}$ alkoxy group optionally substituted with 2-5 deuteriums; a $C_1$ alkoxy group substituted with 1-3 halogens; or a $C_{3-7}$ cycloalkoxy group.

In another embodiment of the pyrido(3,2-d)pyrimidine derivatives of structural formula (Ia), $R_2$ is OR$_7$ and $R_3$ is an at least para-substituted phenyl group wherein the para-substituent of said phenyl group is $C_{1-6}$ alkoxy optionally substituted with 1-6 halogens; or a pyridin-3-yl or pyrimidin-5-yl group wherein the 6-position of said pyridin-3-yl or 2-position of said pyrimidin-5-yl group is substituted with a $C_{2-6}$ alkoxy group optionally substituted with 2-5 deuteriums; a $C_1$ alkoxy group substituted with 1-3 halogens; or a $C_{3-7}$ cycloalkoxy group. In another aspect of this embodiment, $R_3$ is an at least para-substituted phenyl group wherein the para-substituent of said phenyl group is $C_{1-6}$ alkoxy optionally substituted with 1-6 halogens. In another aspect of this embodiment, $R_3$ is a pyridin-3-yl or pyrimidin-5-yl group wherein the 6-position of said pyridin-3-yl or 2-position of said pyrimidin-5-yl group is substituted with a $C_{2-6}$ alkoxy group optionally substituted with 2-5 deuteriums; a $C_1$ alkoxy group substituted with 1-3 halogens; or a $C_{3-7}$ cycloalkoxy group. In another aspect of this embodiment, $R_7$ is selected from the group consisting of $C_{1-20}$ alkyl, $C_{3-10}$ cycloalkyl, aryl, heterocyclyl and aryl-$C_{1-4}$ alkyl; wherein said $C_{1-20}$ alkyl is optionally substituted with $C_{1-4}$ alkoxy, halo-$C_{1-4}$ alkoxy or heterocyclyl-oxy $C_{1-4}$ alkoxy and wherein said $C_{3-10}$ cycloalkyl is optionally substituted with one or more substituents independently selected from the group consisting of halogen, hydroxy, nitro, cyano, $C_{1-4}$ alkyl optionally substituted with one or more halogen, $C_{1-4}$ alkoxy optionally substituted with one or more halogen, mono-$C_{1-4}$ alkylamino, di-$C_{1-4}$ alkylamino, carboxamido, sulfamoyl, carbamoyl, sulfonamido, —CON(R$_{13}$)$_2$, —NR$_{12}$COR$_{10}$, —SO$_2$R$_9$, —NHSO$_2$R$_9$ and phenoxy. In another aspect of this embodiment, $R_7$ is $C_{3-6}$ cycloalkyl optionally substituted with one or more substituents independently selected from the group consisting of halogen, hydroxy, cyano, $C_{1-4}$ alkyl optionally substituted with one or more halogen, $C_{1-4}$ alkoxy optionally substituted with one or more halogen, mono-$C_{1-4}$ alkylamino, di-$C_{1-4}$ alkylamino, carboxamido, sulfamoyl, carbamoyl, sulfonamido, —CON(R$_{13}$)$_2$, —NR$_{12}$COR$_{10}$, —SO$_2$R$_9$, and —NHSO$_2$R$_9$. In another aspect of this embodiment, $R_7$ is cyclopropyl optionally substituted with one or more halogen, hydroxy, cyano, $C_{1-4}$ alkyl optionally substituted with one or more halogen, alkoxy optionally substituted with one or more halogen, mono-$C_{1-4}$ alkylamino, alkylamino, carboxamido, sulfamoyl, carbamoyl, sulfonamido, —CON(R$_{13}$)$_2$, —NR$_{12}$COR$_{10}$, —SO$_2$R$_9$, and —NHSO$_2$R$_9$. In another aspect of this embodiment, $R_7$ is cyclopropyl optionally substituted with $C_{1-4}$ alkyl.

In another embodiment of the pyrido(3,2-d)pyrimidine derivatives of structural formula (Ia), $R_2$ is OR$_7$; $R_7$ is $C_{3-6}$ cycloalkyl optionally substituted with one or more substituents independently selected from the group consisting of halogen, hydroxy, cyano, $C_{1-4}$ alkyl optionally substituted with one or more halogen, $C_{1-4}$ alkoxy optionally substituted with one or more halogen, mono-$C_{1-4}$ alkylamino, di-$C_{1-4}$ alkylamino, carboxamido, sulfamoyl, carbamoyl, sulfonamido, —CON(R$_{13}$)$_2$, NR$_{12}$COR$_{10}$, —SO$_2$R$_9$, and —NHSO$_2$R$_9$; and $R_3$ is an at least para-substituted phenyl group wherein the para-substituent of said phenyl group is $C_{1-6}$ alkoxy optionally substituted with 1-6 halogens; or a pyridin-3-yl or pyrimidin-5-yl group wherein the 6-position of said pyridin-3-yl or 2-position of said pyrimidin-5-yl group is substituted with a $C_{2-6}$ alkoxy group optionally substituted with 2-5 deuteriums; a $C_1$ alkoxy group substituted with 1-3 halogens; or a $C_{3-7}$ cycloalkoxy group. In another aspect of this embodiment, $R_3$ is an at least para-substituted phenyl group wherein the para-substituent of said phenyl group is $C_{1-6}$ alkoxy optionally substituted with 1-6 halogens. In another aspect of this embodiment, $R_3$ is a pyridin-3-yl or pyrimidin-5-yl group wherein the 6-position of said pyridin-3-yl or 2-position of said pyrimidin-5-yl group is substituted with a $C_{2-6}$ alkoxy group optionally substituted with 2-5 deuteriums; a $C_1$ alkoxy group substituted with 1-3 halogens; or a $C_{3-7}$ cycloalkoxy group. In another aspect of this embodiment, $R_7$ is cyclopropyl optionally substituted with one or more halogen, hydroxy, cyano, $C_{1-4}$ alkyl optionally substituted with one or more halogen, $C_{1-4}$ alkoxy optionally substituted with one or more halogen, mono-$C_{1-4}$ alkylamino, alkylamino, carboxamido, sulfamoyl, carbamoyl, sulfonamido, —CON($R_{13}$)$_2$, —NR$_{12}$COR$_{10}$, —SO$_2$R$_9$, and —NHSO$_2$R$_9$. In another aspect of this embodiment, $R_7$ is cyclopropyl optionally substituted with $C_{1-4}$ alkyl. In another aspect of this embodiment, $R_3$ is a pyridin-3-yl or pyrimidin-5-yl group wherein the 6-position of said pyridin-3-yl or 2-position of said pyrimidin-5-yl group is substituted with ethoxy, cyclopropoxy, or cyclobutoxy.

In another embodiment of the pyrido(3,2-d)pyrimidine derivatives of structural formula (Ia), $R_2$ is NR$_{13}$R$_7$ and $R_3$ is an at least para-substituted phenyl group wherein the para-substituent of said phenyl group is $C_{1-6}$ alkoxy optionally substituted with 1-6 halogens; or a pyridin-3-yl or pyrimidin-5-yl group wherein the 6-position of said pyridin-3-yl or 2-position of said pyrimidin-5-yl group is substituted with a $C_{2-6}$ alkoxy group optionally substituted with 2-5 deuteriums; a $C_1$ alkoxy group substituted with 1-3 halogens; or a $C_{3-7}$ cycloalkoxy group. In another aspect of this embodiment, $R_3$ is an at least para-substituted phenyl group wherein the para-substituent of said phenyl group is $C_{1-6}$ alkoxy optionally substituted with 1-6 halogens. In another aspect of this embodiment, $R_3$ is a pyridin-3-yl or pyrimidin-5-yl group wherein the 6-position of said pyridin-3-yl or 2-position of said pyrimidin-5-yl group is substituted with a $C_{2-6}$ alkoxy group optionally substituted with 2-5 deuteriums; a $C_1$ alkoxy group substituted with 1-3 halogens; or a $C_{3-7}$ cycloalkoxy group. In another aspect of this embodiment, $R_{13}$ is H and $R_7$ is selected from the group consisting of $C_{1-6}$ alkyl, $C_{3-6}$ cycloalkyl, aryl, heterocyclyl and aryl-$C_{1-4}$ alkyl; wherein said heterocyclyl is optionally substituted with $C_{1-4}$ alkyl; and wherein said $C_{1-6}$ alkyl is optionally substituted with methylsulfonyl, heterocyclyl, one to six halogen atoms or $C_{1-4}$ alkoxy; and wherein said $C_{3-10}$ cycloalkyl is optionally substituted with one or more substituents independently selected from the group consisting of halogen, hydroxy, nitro, cyano, $C_{1-4}$ alkyl optionally substituted with one or more halogen, $C_{1-4}$ alkoxy optionally substituted with one or more halogen, mono-$C_{1-4}$ alkylamino, di-$C_{1-4}$ alkylamino, carboxamido, sulfamoyl, carbamoyl, sulfonamido, —CON($R_{13}$)$_2$, —NR$_{12}$COR$_{10}$, —SO$_2$R$_9$, —NHSO$_2$R$_9$ and phenoxy. In another aspect of this embodiment $R_7$ is 2,2,2-trifluoroethyl.

In another embodiment of the pyrido(3,2-d)pyrimidine derivatives of structural formula (Ia), $R_2$ is NHR$_7$ wherein $R_7$ is $C_{1-6}$ alkyl wherein said $C_{1-6}$ alkyl is optionally substituted one to six fluorine or chlorine atoms and $R_3$ is an at least para-substituted phenyl group wherein the para-substituent of said phenyl group is $C_{1-6}$ alkoxy optionally substituted with 1-6 halogens; or a pyridin-3-yl or pyrimidin-5-yl group wherein the 6-position of said pyridin-3-yl or 2-position of said pyrimidin-5-yl group is substituted with a $C_{2-6}$ alkoxy group optionally substituted with 2-5 deuteriums; a $C_1$ alkoxy group substituted with 1-3 halogens; or a $C_{3-7}$ cycloalkoxy group. In another aspect of this embodiment, $R_3$ is an at least para-substituted phenyl group wherein the para-substituent of said phenyl group is $C_{1-6}$ alkoxy optionally substituted with 1-6 halogens. In another aspect of this embodiment, $R_3$ is a pyridin-3-yl or pyrimidin-5-yl group wherein the 6-position of said pyridin-3-yl or 2-position of said pyrimidin-5-yl group is substituted with a $C_{2-6}$ alkoxy group optionally substituted with 2-5 deuteriums; a $C_1$ alkoxy group substituted with 1-3 halogens; or a $C_{3-7}$ cycloalkoxy group. In another aspect of this embodiment, $R_7$ is 2,2,2-trifluoroethyl and $R_3$ is an at least para-substituted phenyl group wherein the para-substituent of said phenyl group is $C_{1-6}$ alkoxy optionally substituted with 1-6 halogens. In another aspect of this embodiment, $R_7$ is 2,2,2-trifluoroethyl and $R_3$ is a pyridin-3-yl or pyrimidin-5-yl group wherein the 6-position of said pyridin-3-yl or 2-position of said pyrimidin-5-yl group is substituted with a $C_{2-6}$ alkoxy group optionally substituted with 2-5 deuteriums; a $C_1$ alkoxy group substituted with 1-3 halogens; or a $C_{3-7}$ cycloalkoxy group. In another aspect of this embodiment, $R_3$ is an at least para-substituted phenyl group wherein the para-substituent of said phenyl group is methoxy, difluoromethoxy, trifluoromethoxy, or ethoxy. In another aspect of this embodiment, $R_3$ is a pyridin-3-yl or pyrimidin-5-yl group wherein the 6-position of said pyridin-3-yl or 2-position of said pyrimidin-5-yl group is substituted with an ethoxy or 2-propoxy group optionally substituted with 2-5 deuteriums; difluoromethoxy; cyclopropoxy; or cyclobutoxy.

In another embodiment of the pyrido(3,2-d)pyrimidine derivatives of structural formula (Ia), $R_2$ is XR$_7$ or is selected from the group consisting of N-morpholinyl, N-thiomorpholinyl and N-thiomorpholinyl dioxide and $R_3$ is a mono-substituted or di-substituted phenyl or heteroaryl, wherein at least one substituent of said phenyl or heteroaryl is —SO$_2$(C$_{1-3}$ alkyl) wherein said $C_{1-3}$ alkyl is optionally substituted with one to three halogens; —SO$_2$(C$_{3-6}$ cycloalkyl) or —SO$_2$(CH$_2$OCH$_3$) and the remaining substituents of said phenyl or heteroaryl are independently selected from the group consisting of H, halogen, hydroxyl, cyano, —CON(R$_{13}$)$_2$, —NR$_{12}$COR$_{10}$, —NR$_{11}$R$_{11}$, —SO$_2$R$_9$, —NHSO$_2$R$_9$, $C_{3-6}$ cycloalkyl, phenoxy, $C_{1-6}$ alkoxy and $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, mono-$C_{1-4}$ alkylamino or heterocyclyl. In another aspect of this embodiment, $R_2$ is OR$_7$. In another aspect of this embodiment, $R_2$ is SR$_7$. In another aspect of this embodiment, $R_2$ is NR$_{13}$R$_7$. In another aspect of this embodiment, $R_2$ is selected from the group consisting of N-morpholinyl, N-thiomorpholinyl and N-thiomorpholinyl dioxide.

In another embodiment of the pyrido(3,2-d)pyrimidine derivatives of structural formula (Ia), $R_2$ is OR$_7$ and $R_3$ is a mono-substituted or di-substituted phenyl or heteroaryl, wherein at least one substituent of said phenyl or heteroaryl is —SO$_2$(C$_{1-3}$ alkyl) wherein said $C_{1-3}$ alkyl is optionally substituted with one to three halogens; —SO$_2$(C$_{3-6}$ cycloalkyl) or —SO$_2$(CH$_2$OCH$_3$) and the remaining substituents of said phenyl or heteroaryl are independently selected from the group consisting of H, halogen, hydroxyl, cyano, —CON(R$_{13}$)$_2$, —NR$_{12}$COR$_{10}$, —NR$_{11}$R$_{11}$, —SO$_2$R$_9$, —NHSO$_2$R$_9$, $C_{3-6}$ cycloalkyl, phenoxy, alkoxy and $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, mono-$C_{1-4}$ alkylamino or heterocyclyl. In another aspect of this embodiment, $R_7$ is selected from the group consisting of $C_{1-6}$ alkyl, $C_{3-6}$ cycloalkyl, aryl, heterocyclyl and aryl-$C_{1-4}$ alkyl; wherein said $C_{1-6}$ alkyl is optionally substituted with $C_{1-4}$ alkoxy, halo-$C_{1-4}$ alkoxy or heterocyclyl-oxy $C_{1-4}$ alkoxy and wherein said $C_{3-6}$ cycloalkyl is optionally substituted with one or more substituents independently selected from the group consisting of halogen, hydroxy, nitro, cyano, $C_{1-4}$ alkyl optionally substituted with one or more halogen, $C_{1-4}$ alkoxy optionally substituted with one or more halogen, mono-$C_{1-4}$ alkylamino, di-$C_{1-4}$ alkylamino, carboxamido, sulfamoyl, carbamoyl, sulfonamido, —CON($R_{13}$)$_2$, —NR$_{12}$COR$_{10}$, —SO$_2$R$_9$, —NHSO$_2$R$_9$ and phenoxy. In another aspect of this embodiment, $R_7$ is $C_{1-6}$ alkyl or $C_{3-6}$ cycloalkyl, wherein said $C_{3-6}$ cycloalkyl is optionally substituted with one or more substituents independently selected from $C_{1-4}$ alkyl optionally substituted with one or more halogen or $C_{1-4}$ alkoxy optionally substituted with one or more halogen. In another aspect of this embodiment, $R_3$ is a mono-substituted or di-substituted phenyl wherein at least one substituent of said phenyl is —SO$_2$($C_{1-3}$ alkyl) wherein said $C_{1-3}$ alkyl is optionally substituted with one to three halogens; —SO$_2$($C_{3-6}$ cycloalkyl) or —SO$_2$(CH$_2$OCH$_3$) and the remaining substituents of said phenyl are independently selected from the group consisting of H, halogen, hydroxyl, cyano, —CON($R_{13}$)$_2$, —NR$_{12}$COR$_{10}$, —NR$_{11}$R$_{11}$, —SO$_2$R$_9$, —NHSO$_2$R$_9$, $C_{3-6}$ cycloalkyl, phenoxy, $C_{1-6}$ alkoxy and $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, alkylamino or heterocyclyl. In another aspect of this embodiment, $R_3$ is a mono-substituted or di-substituted phenyl wherein at least one substituent of said phenyl is —SO$_2$($C_{1-3}$ alkyl) wherein said $C_{1-3}$ alkyl is optionally substituted with one to three halogens; —SO$_2$($C_{3-6}$ cycloalkyl) or —SO$_2$(CH$_2$OCH$_3$) and the remaining substituents of said phenyl are independently selected from H, $C_{1-6}$ alkoxy or $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, or mono-$C_{1-4}$ alkylamino. In another aspect of this embodiment, $R_3$ is a mono-substituted or di-substituted phenyl wherein at least one substituent of said phenyl is meta-SO$_2$($C_{1-3}$ alkyl) wherein said $C_{1-3}$ alkyl is optionally substituted with one to three halogens; meta-SO$_2$($C_{3-6}$ cycloalkyl) or meta-SO$_2$(CH$_2$OCH$_3$) and the remaining substituents of said phenyl are independently selected from H, halogen, $C_{1-6}$ alkoxy or $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, or mono-$C_{1-4}$ alkylamino.

In another embodiment of the pyrido(3,2-d)pyrimidine derivatives of structural formula (Ia), $R_2$ is OR$_7$ wherein R$_7$ is $C_{1-6}$ alkyl or $C_{3-6}$ cycloalkyl, wherein said $C_{3-6}$ cycloalkyl is optionally substituted with one or more substituents independently selected from $C_{1-4}$ alkyl optionally substituted with one or more halogen or $C_{1-4}$ alkoxy optionally substituted with one or more halogen and $R_3$ is a mono-substituted or di-substituted phenyl or heteroaryl, wherein at least one substituent of said phenyl or heteroaryl is —SO$_2$($C_{1-3}$ alkyl) wherein said $C_{1-3}$ alkyl is optionally substituted with one to three halogens; —SO$_2$($C_{3-6}$ cycloalkyl) or —SO$_2$(CH$_2$OCH$_3$) and the remaining substituents of said phenyl or heteroaryl are independently selected from the group consisting of H, halogen, hydroxyl, cyano, —CON($R_{13}$)$_2$, —NR$_{12}$COR$_{10}$, —NR$_{11}$R$_{11}$, —SO$_2$R$_9$, —NHSO$_2$R$_6$, $C_{3-6}$ cycloalkyl, phenoxy, $C_{1-6}$ alkoxy and $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, mono-$C_{1-4}$ alkylamino or heterocyclyl. In another aspect of this embodiment. In another aspect of this embodiment, $R_3$ is a mono-substituted or di-substituted phenyl wherein at least one substituent of said phenyl is —SO$_2$($C_{1-3}$ alkyl) wherein said $C_{1-3}$ alkyl is optionally substituted with one to three halogens; —SO$_2$($C_{3-6}$ cycloalkyl) or —SO$_2$(CH$_2$OCH$_3$) and the remaining substituents of said phenyl are independently selected from H, halogen, $C_{1-6}$ alkoxy or $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, or mono-$C_{1-4}$ alkylamino. In another aspect of this embodiment, $R_3$ is a mono-substituted or di-substituted phenyl wherein at least one substituent of said phenyl is meta-SO$_2$($C_{1-3}$ alkyl) wherein said $C_{1-3}$ alkyl is optionally substituted with one to three halogens; meta-SO$_2$($C_{3-6}$ cycloalkyl) or meta-SO$_2$(CH$_2$OCH$_3$) and the remaining substituents of said phenyl are independently selected from H, halogen, $C_{1-6}$ alkoxy or $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, or mono-$C_{1-4}$ alkylamino. In another aspect of this embodiment, $R_3$ is a mono-substituted or di-substituted phenyl wherein at least one substituent of said phenyl is meta-SO$_2$CH$_3$, meta-SO$_2$CH$_2$CH$_3$, meta-SO$_2$(cyclopropyl), or meta-SO$_2$CF$_3$ and the remaining substituents of said phenyl are independently selected from H, halogen, $C_{1-6}$ alkoxy or $C_{1-6}$ alkyl wherein said $C_{1-6}$ alkyl or $C_{1-6}$ alkoxy is optionally substituted with one or more halogens.

In another embodiment of the pyrido(3,2-d)pyrimidine derivatives of structural formula (Ia), $R_2$ is NR$_{13}$R$_7$ and $R_3$ is a mono-substituted or di-substituted phenyl or heteroaryl, wherein at least one substituent of said phenyl or heteroaryl is —SO$_2$($C_{1-3}$ alkyl) wherein said $C_{1-3}$ alkyl is optionally substituted with one to three halogens; —SO$_2$($C_{3-6}$ cycloalkyl) or —SO$_2$(CH$_2$OCH$_3$) and the remaining substituents of said phenyl or heteroaryl are independently selected from the group consisting of H, halogen, hydroxyl, cyano, —CON($R_{13}$)$_2$, —NR$_{12}$COR$_{10}$, —NR$_{11}$R$_{11}$, —SO$_2$R$_9$, —NHSO$_2$R$_9$, $C_{3-6}$ cycloalkyl, phenoxy, $C_{1-6}$ alkoxy and $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, mono-$C_{1-4}$ alkylamino or heterocyclyl. In another aspect of this embodiment, $R_7$ is $C_{1-6}$ alkyl wherein said $C_{1-6}$ alkyl is optionally substituted one to six fluorine or chlorine atoms or $C_{3-6}$ cycloalkyl, wherein said $C_{3-6}$ cycloalkyl is optionally substituted with one or more substituents independently selected from $C_{1-4}$ alkyl optionally substituted with one or more halogen or $C_{1-4}$ alkoxy optionally substituted with one or more halogen. In another aspect of this embodiment, $R_3$ is a mono-substituted or di-substituted phenyl wherein at least one substituent of said phenyl is —SO$_2$($C_{1-3}$ alkyl) wherein said $C_{1-3}$ alkyl is optionally substituted with one to three halogens; —SO$_2$($C_{3-6}$ cycloalkyl) or —SO$_2$(CH$_2$OCH$_3$) and the remaining substituents of said phenyl are independently selected from the group consisting of H, halogen, hydroxyl, cyano, —CON($R_{13}$)$_2$, —NR$_{12}$COR$_{10}$, —NR$_{11}$R$_{11}$, —SO$_2$R$_9$, —NHSO$_2$R$_9$, $C_{3-6}$ cycloalkyl, phenoxy, $C_{1-6}$ alkoxy and $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, mono-$C_{1-4}$ alkylamino or heterocyclyl. In another aspect of this embodiment, $R_3$ is a mono-substituted or di-substituted phenyl wherein at least one substituent of said phenyl is —SO$_2$($C_{1-3}$ alkyl) wherein said $C_{1-3}$ alkyl is optionally substituted with one to three halogens; —SO$_2$($C_{3-6}$ cycloalkyl) or —SO$_2$(CH$_2$OCH$_3$) and the remaining substituents of said phenyl are independently selected from H, halogen, $C_{1-6}$ alkoxy or $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, or mono-$C_{1-4}$ alkylamino. In another aspect of this embodiment, $R_3$ is a mono-substituted or di-substituted phenyl wherein at least one substituent of said phenyl is meta-$SO_2(C_{1-3}$ alkyl) wherein said $C_{1-3}$ alkyl is optionally substituted with one to three halogens; meta-$SO_2$ ($C_{3-6}$ cycloalkyl) or meta-$SO_2(CH_2OCH_3)$ and the remaining substituents of said phenyl are independently selected from H, halogen, $C_{1-6}$ alkoxy or $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, or mono-$C_{1-4}$ alkylamino.

In another embodiment of the pyrido(3,2-d)pyrimidine derivatives of structural formula (Ia), $R_2$ is $NHR_7$ wherein $R_7$ is $C_{1-6}$ alkyl optionally substituted with one to six fluorine or chlorine atoms or $C_{3-6}$ cycloalkyl optionally substituted with one or more substituents independently selected from $C_{1-4}$ alkyl optionally substituted with one or more halogen or $C_{1-4}$ alkoxy optionally substituted with one or more halogen and $R_3$ is a mono-substituted or di-substituted phenyl or heteroaryl, wherein at least one substituent of said phenyl or heteroaryl is —$SO_2(C_{1-3}$ alkyl) wherein said $C_{1-3}$ alkyl is optionally substituted with one to three halogens; —$SO_2(C_{3-6}$ cycloalkyl) or —$SO_2(CH$-$2OCH_3)$ and the remaining substituents of said phenyl or heteroaryl are independently selected from H, halogen, $C_{1-6}$ alkoxy or $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, or mono-$C_{1-4}$ alkylamino. In another aspect of this embodiment, $R_3$ is a mono-substituted or di-substituted phenyl wherein at least one substituent of said phenyl is —$SO_2(C_{1-3}$ alkyl) wherein said $C_{1-3}$ alkyl is optionally substituted with one to three halogens; —$SO_2(C_{3-6}$ cycloalkyl) or —$SO_2(CH_2OCH_3)$ and the remaining substituents of said phenyl are independently selected from H, halogen, $C_{1-6}$ alkoxy or $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, or mono-$C_{1-4}$ alkylamino. In another aspect of this embodiment, $R_3$ is a mono-substituted or di-substituted phenyl wherein at least one substituent of said phenyl is meta-$SO_2(C_{1-3}$ alkyl) wherein said $C_{1-3}$ alkyl is optionally substituted with one to three halogens; meta-$SO_2(C_{3-6}$ cycloalkyl) or meta-$SO_2$ ($CH_2OCH_3$) and the remaining substituents of said phenyl are independently selected from H, halogen, $C_{1-6}$ alkoxy or $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, or mono-$C_{1-4}$ alkylamino, in another aspect of this embodiment, $R_7$ is 2,2,2-trifluoroethyl. In another aspect of this embodiment, $R_7$ is 1-(trifluoromethyl)cyclopropyl. In another aspect of this embodiment, $R_3$ is a mono-substituted or di-substituted phenyl wherein at least one substituent of said phenyl is —$SO_2CH_3$, —$SO_2CH_2CH_3$, —$SO_2$(cyclopropyl), or —$SO_2CF_3$ and the remaining substituents of said phenyl are independently selected from H, halogen, $C_{1-6}$ alkoxy or $C_{1-6}$ alkyl wherein said $C_{1-6}$ alkyl or $C_{1-6}$ alkoxy is optionally substituted with one or more halogens.

In another embodiment of the pyrido(3,2-d)pyrimidine derivatives of structural formula (Ia), $R_2$ is $NHR_7$ wherein $R_7$ is 2,2,2-trifluoroethyl and $R_3$ is a mono-substituted or di-substituted phenyl or heteroaryl, wherein at least one substituent of said phenyl or heteroaryl is —$SO_2(C_{1-3}$ alkyl) wherein said $C_{1-3}$ alkyl is optionally substituted with one to three halogens; —$SO_2(C_{3-6}$ cycloalkyl) or —$SO_2$ ($CH_2OCH_3$) and the remaining substituents of said phenyl or heteroaryl are independently selected from H, halogen, $C_{1-6}$ alkoxy or $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, or mono-$C_{1-4}$ alkylamino. In another aspect of this embodiment, $R_3$ is a mono-substituted or di-substituted phenyl wherein at least one substituent of said phenyl is —$SO_2(C_{1-3}$ alkyl) wherein said $C_{1-3}$ alkyl is optionally substituted with one to three halogens; —$SO_2(C_{3-6}$ cycloalkyl) or —$SO_2(CH_2OCH_3)$ and the remaining substituents of said phenyl are independently selected from H, halogen, $C_{1-6}$ alkoxy or $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, or mono-$C_{1-4}$ alkylamino. In another aspect of this embodiment, $R_3$ is a mono-substituted or di-substituted phenyl wherein at least one substituent of said phenyl is meta-$SO_2(C_{1-3}$ alkyl) wherein said $C_{1-3}$ alkyl is optionally substituted with one to three halogens; meta-$SO_2(C_{3-6}$ cycloalkyl) or meta-$SO_2(CH_2OCH_3)$ and the remaining substituents of said phenyl are independently selected from H, halogen, $C_{1-6}$ alkoxy or $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, or mono-$C_{1-4}$ alkylamino. In another aspect of this embodiment, $R_3$ is a mono-substituted or di-substituted phenyl wherein at least one substituent of said phenyl is —$SO_2CH_3$, —$SO_2CH_2CH_3$, —$SO_2$(cyclopropyl), or —$SO_2CF_3$ and the remaining substituents of said phenyl are independently selected from H, halogen, $C_{1-6}$ alkoxy or $C_{1-6}$ alkyl wherein said $C_{1-6}$ alkyl or $C_{1-6}$ alkoxy is optionally substituted with one or more halogens.

In a another embodiment, the present invention relates to a class of pyrido(3,2-d)pyrimidine derivatives represented by the structural formula (Ib):

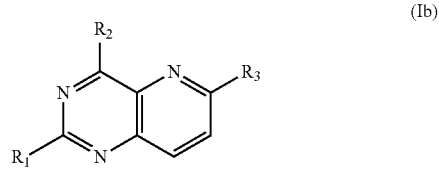

(Ib)

wherein:

$R_1$ is —NH—$CH_2R_6$ or —NH—$CH(CH_3)R_6$;

$R_6$ is phenyl substituted with one or two substituents independently selected from the group consisting of chloro, fluoro, methyl, trifluoromethyl, triazolyl and —$SO_2NH_2$.

$R_2$ is —$NHR_4$;

$R_4$ is $C_{3-6}$ cycloalkyl substituted with one or two $C_{1-4}$ alkyl groups, wherein at least one of the $C_{1-4}$ alkyl groups is substituted with one or more fluorine.

$R_3$ is di-substituted phenyl, wherein the first substituent of said di-substituted phenyl is —$SO_2R_9$ located at the meta position of said di-substituted phenyl, and wherein the second substituent of said di-substituted phenyl is selected from the group consisting of fluoro, chloro, methoxy and ethoxy, and is located at the para position of said di-substituted phenyl; and $R_9$ is selected from the group consisting of $C_{1-6}$ alkyl and $C_{3-6}$ cycloalkyl; or a pharmaceutical acceptable addition salt or a stereochemical isomeric form thereof or a N-oxide thereof or a solvate thereof or a prodrug thereof.

In another embodiment of the present invention, the novel trisubstituted pyrido(3,2-d)pyrimidine derivatives are as defined in the structural formula (Ib), wherein the substituents independently correspond to any of the definitions given above, in particular with any of the individual meanings (such as illustrated above) of generic terms used for substituting groups such as, but not limited to, "$C_{1-20}$ alkyl", "$C_{3-10}$ cycloalkyl", "aryl", "heterocyclic", "halogen", "arylalkyl", "monoalkylamino", "dialkylamino", "$C_{1-4}$ alkoxy", "alkylthio" and the like.

In another embodiment, the present invention relates to a class of pyrido(3,2-d)pyrimidine derivatives represented by the structural formula (I):

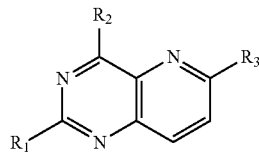

wherein:
- $R_1$ is —NH—CHR$_5$R$_6$ or —NH—R$_8$,
- $R_5$ and $R_6$ are independently selected from the group consisting of hydrogen, $C_{1-6}$ alkyl, $C_{3-10}$ cycloalkyl, aryl and heterocyclyl, wherein said aryl is substituted with one or more substituents independently selected from the group consisting of halogen, hydroxy, amino, nitro, cyano, trifluoromethyl, trifluoromethoxy, $C_{1-4}$ alkyl, $C_{1-4}$ alkoxy, di-$C_{1-4}$alkylamino, mono-$C_{1-4}$alkylamino, carboxamido, sulfamoyl, carbamoyl, sulfonamido, —SO$_2$NHR$_{13}$, —CON(R$_{13}$)$_2$, —NR$_{12}$COR$_{10}$, —SO$_2$R$_{13}$, NHSO$_2$R$_{13}$ and phenoxy, and wherein said $C_{1-6}$ alkyl is optionally substituted with one or more substituents independently selected from the group consisting of halogen and $C_{1-4}$ alkoxy, and
- $R_8$ is selected from the group consisting of $C_{3-10}$ cycloalkyl, heteroaryl and aryl wherein said heteroaryl or aryl is optionally substituted with one or more substituents independently selected from the group consisting of halogen and $C_{1-4}$ alkyl and wherein said $C_{3-10}$ cycloalkyl is optionally substituted at the carbon position adjacent to the N atom of $R_1$ with aryl or heteroaryl wherein said aryl is optionally substituted with halogen;
- $R_2$ is XR$_7$ or is selected from the group consisting of N-morpholinyl, N-thiomorpholinyl and N-thiomorpholinyl dioxide;
- X is selected from the group consisting of O, S, NR$_{13}$ and CH$_2$;
- $R_7$ is selected from the group consisting of $C_{1-20}$ alkyl, $C_{3-10}$ cycloalkyl, aryl, heterocyclyl and aryl-$C_{1-4}$ alkyl; wherein said heterocyclyl is optionally substituted with $C_{1-4}$ alkyl when X is NH; and wherein said $C_{1-20}$ alkyl is optionally substituted with methylsulfonyl, heterocyclyl, one to three halogen atoms or $C_{1-4}$ alkoxy when X is NR$_{13}$ or said $C_{1-20}$ alkyl is optionally substituted with $C_{1-4}$ alkoxy, halo-$C_{1-4}$ alkoxy or heterocyclyl-oxy $C_{1-4}$ alkoxy when X is O;
- $R_3$ is a mono-substituted or di-substituted phenyl, wherein at least one substituent of said phenyl is —SO$_2$R$_9$;
- $R_9$ is selected from the group consisting of $C_{1-3}$ alkyl and methoxymethyl;
- $R_{10}$ is selected from the group consisting of $C_{1-6}$ alkyl optionally substituted with one or more substituents independently selected from the group consisting of amino, cyano, halogen and hydroxy; $C_{1-6}$ alkoxy optionally substituted with one or more substituents independently selected from the group consisting of amino, alkylamino, cyano, dialkylamino, halogen, and heterocyclyl; heterocyclyl optionally substituted with one or more substituents independently selected from the group consisting of $C_{1-6}$ alkyl, acylamino and oxo; $C_{3-10}$ cycloalkyl optionally substituted with one or more substituents independently selected from the group consisting of amino or hydroxy; and amino optionally substituted with one or more substituents independently selected from the group consisting of $C_{1-6}$ alkyl wherein said $C_{1-6}$ alkyl is optionally substituted with one or more substituents independently selected from the group consisting of amino, alkylamino, cyano, dialkylamino, halogen and heterocyclyl;
- $R_{12}$ is selected from the group consisting of hydrogen and $C_{1-6}$ alkyl, wherein said $C_{1-6}$ alkyl is optionally substituted with one or more substituents independently selected from the group consisting of cyano, halogen and hydroxy;
- each $R_{13}$ is independently selected from the group consisting of hydrogen and $C_{1-20}$ alkyl;
or a pharmaceutical acceptable addition salt or a stereochemical isomeric form thereof or a N-oxide thereof or a solvate thereof or a prodrug thereof.

Trisubstituted pyrido(3,2-d)pyrimidine derivatives are as defined in the structural formula (I), wherein X and each of the substituents $R_1$, $R_2$, $R_3$, $R_5$, $R_6$, $R_7$, $R_8$, $R_9$, $R_{10}$, $R_{12}$, and/or $R_{13}$ may independently correspond to any of the definitions given above, in particular with any of the individual meanings (such as illustrated above) of generic terms used for substituting groups such as, but not limited to, "$C_{1-20}$ alkyl", "$C_{3-10}$ cycloalkyl", "aryl", "heterocyclic", "halogen", "arylalkyl", "monoalkylamino", "dialkylamino", "$C_{1-4}$ alkoxy", "$C_{1-4}$ alkylthio" and the like.

In one embodiment of the trisubstituted pyrido(3,2-d)pyrimidine derivatives represented by structural formula (I), the SO$_2$R$_9$ substituent is a meta-substituent of said mono-substituted or di-substituted phenyl.

In another embodiment of the trisubstituted pyrido(3,2-d)pyrimidine derivatives represented by structural formula (I), $R_3$ is a disubstituted phenyl wherein the second substituent of said phenyl is selected from the group consisting of halogen and $C_{1-6}$ alkoxy.

In another embodiment of the trisubstituted pyrido(3,2-d)pyrimidine derivatives represented by structural formula (I), $R_3$ is a disubstituted phenyl wherein the second substituent of said phenyl is selected from the group consisting of fluoro, chloro, methoxy and ethoxy.

In another embodiment of the trisubstituted pyrido(3,2-d)pyrimidine derivatives represented by structural formula (I), $R_3$ is a disubstituted phenyl, wherein said SO$_2$R$_9$ substituent is a meta-substituent of said di-substituted phenyl and wherein the second substituent of said di-substituted phenyl is selected from the group consisting of halogen and $C_{1-6}$ alkoxy. In another aspect of this embodiment, the second substituent of said di-substituted phenyl is selected from the group consisting of fluoro, chloro, methoxy and ethoxy.

In another embodiment of the trisubstituted pyrido(3,2-d)pyrimidine derivatives represented by structural formula (I), $R_2$ is NR$_7$R$_{13}$; $R_{13}$ is hydrogen or methyl; and $R_7$ is selected from the group consisting of $C_{1-6}$ alkyl, $C_{3-8}$ cycloalkyl, aryl, heterocyclyl and benzyl; wherein said $C_{1-6}$ alkyl is optionally substituted with methylsulfonyl, heterocyclyl, chloro, fluoro or $C_{1-4}$ alkoxy.

In another embodiment of the trisubstituted pyrido(3,2-d)pyrimidine derivatives represented by structural formula (I), $R_2$ is selected from the group consisting of methylamino, ethylamino, n-propylamino, isopropylamino, n-butylamino, isobutylamino, tert-butylamino, N-methylisopropylamino, N-methyl-n-butylamino, N-methylisobutylamino, N-methyl-tert-butylamino, 3-chloropropylamino, 3-fluoropropylamino, 2-fluoroethylamino, 2-chloroethylamino, 2,2,2-trifluoroethylamino, methyl-(2,2,2-trifluoroethyl)-amino, 2,2-difluoroethylamino, 3,3,3-trifluoropropylamino, cyclopropylamino, cyclobutylamino, cyclopentylamino, cyclohexylamino, cycloheptylamino, cyclooctylamino, N-methylcyclobutylamino, N-methylcyclopentylamino, N-methylcyclohexylamino, benzylamino, anilino, pyridin-3-ylmethylamino, 1-pyridin-2-ylethylamino, 1-pyridin-3-ylethylamino, 1-pyridin-4-ylethylamino, 2-pyridin-4-ylethylamino, 2-morpholin-4-ylethylamino, 2-morpholin-4-ylpropylamino, 3-morpholin-4-ylpropylamino, 2-methoxyethylamino and 3-methoxypropylamino.

In another embodiment of the trisubstituted pyrido(3,2-d)pyrimidine derivatives represented by structural formula (I), $R_2$ is $OR_7$ and $R_7$ is selected from the group consisting of $C_{1-6}$ alkyl, $C_{3-8}$ cycloalkyl, phenyl, heterocyclyl and benzyl.

In another embodiment of the trisubstituted pyrido(3,2-d)pyrimidine derivatives represented by structural formula (I), $R_2$ is selected from the group consisting of cyclopropyloxy, cyclobutoxy, cyclopentoxy, cyclohexyloxy, cycloheptyloxy, cyclooctyloxy, tetrahydrofuranyloxy, methoxy, ethoxy, propyloxy, n-butoxy, isopropyloxy, isobutoxy, tert-butoxy, pentoxy, hexyloxy, heptyloxy, octyloxy and benzyloxy.

In another embodiment of the trisubstituted pyrido(3,2-d)pyrimidine derivatives represented by structural formula (I), the $SO_2R_9$ substituent is a meta-substituent of said mono-substituted or di-substituted phenyl and $R_2$ is selected from the group consisting of methylamino, ethylamino, n-propylamino, isopropylamino, n-butylamino, isobutylamino, tert-butylamino, N-methylisopropylamino, N-methyl-n-butylamino, N-methylisobutylamino, N-methyl-tert-butylamino, 3-chloropropylamino, 3-fluoropropylamino, 2-fluoroethylamino, 2-chloroethylamino, 2,2,2-trifluoroethylamino, methyl-(2,2,2-trifluoroethyl)-amino, 2,2-difluoroethylamino, 3,3,3-trifluoropropylamino, cyclopropylamino, cyclobutylamino, cyclopentylamino, cyclohexylamino, cycloheptylamino, cyclooctylamino, N-methylcyclobutylamino, N-methylcyclopentylamino, N-methylcyclohexylamino, benzylamino, anilino, pyridin-3-ylmethylamino, 1-pyridin-2-ylethylamino, 1-pyridin-3-ylethylamino, 1-pyridin-4-ylethylamino, 2-pyridin-4-ylethylamino, 2-morpholin-4-ylethylamino, 2-morpholin-4-ylpropylamino, 3-morpholin-4-ylpropylamino, 2-methoxyethylamino and 3-methoxypropylamino.

In another embodiment of the trisubstituted pyrido(3,2-d)pyrimidine derivatives represented by structural formula (I), the $SO_2R_9$ substituent is a meta-substituent of said mono-substituted or di-substituted phenyl, and $R_2$ is selected from the group consisting of cyclopropyloxy, cyclobutoxy, cyclopentoxy, cyclohexyloxy, cycloheptyloxy, cyclooctyloxy, tetrahydrofuranyloxy, methoxy, ethoxy, propyloxy, n-butoxy, isopropyloxy, isobutoxy, tert-butoxy, pentoxy, hexyloxy, heptyloxy, octyloxy and benzyloxy.

In another embodiment of the trisubstituted pyrido(3,2-d)pyrimidine derivatives represented by structural formula (I), $R_1$ is —NH—$CH_2R_6$ and $R_6$ is phenyl substituted with one or two substituents independently selected from the group consisting of halogen, trifluoromethyl, triazolyl and —$SO_2NH_2$.

In another embodiment of the trisubstituted pyrido(3,2-d)pyrimidine derivatives represented by structural formula (I), the $SO_2R_9$ substituent is a meta-substituent of said mono-substituted or di-substituted phenyl; $R_1$ is —NH—$CH_2R_6$; and $R_6$ is phenyl substituted with one or two substituents independently selected from the group consisting of halogen, trifluoromethyl, triazolyl and —$SO_2NH_2$.

The present invention also relates, in another embodiment, to a class of pyrido(3,2-d)pyrimidine derivatives represented by the structural formula (II):

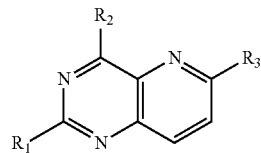

wherein:
$R_1$ is —NH—$CHR_5R_6$ or —NH—$R_8$,
$R_5$ and $R_6$ are independently selected from the group consisting of hydrogen, $C_{1-6}$ alkyl, $C_{3-10}$ cycloalkyl, aryl and heterocyclyl, wherein said aryl is substituted with one or more substituents selected from the group consisting of halogen, hydroxy, amino, nitro, cyano, trifluoromethyl, trifluoromethoxy, $C_{1-4}$ alkyl, $C_{1-4}$ alkoxy, di-$C_{1-4}$ alkylamino, mono-$C_{1-4}$ alkylamino, carboxamido, sulfamoyl, carbamoyl, sulfonamido, —$SO_2NHR_{13}$, —$CON(R_{13})_2$, —$NR_{12}COR_{10}$, —$SO_2R_{13}$, —$NHSO_2R_{13}$ and phenoxy, and wherein said $C_{1-6}$ alkyl is optionally substituted with one or more substituents selected from the group consisting of halogen and $C_{1-4}$ alkoxy, and
$R_8$ is selected from the group consisting of $C_{3-10}$ cycloalkyl, heteroaryl and aryl wherein said heteroaryl or aryl is optionally substituted with one or more substituents selected from the group consisting of halogen and $C_{1-4}$ alkyl and wherein said $C_{3-10}$ cycloalkyl is optionally substituted at the carbon position adjacent to the N atom of $R_1$ with aryl or heteroaryl wherein said aryl is optionally substituted with halogen;
$R_2$ is $XR_7$ or is selected from the group consisting of N-morpholinyl, N-thiomorpholinyl and N-thiomorpholinyl dioxide;
X is selected from the group consisting of O, S, $NR_{13}$ and $CH_2$;
$R_7$ is selected from the group consisting of $C_{1-20}$ alkyl, $C_{3-10}$ cycloalkyl, aryl, heterocyclyl and aryl-$C_{1-4}$ alkyl; wherein said heterocyclyl is optionally substituted with $C_{1-4}$ alkyl when X is NH; and wherein said $C_{1-20}$ alkyl is optionally substituted with methylsulfonyl, heterocyclyl, one to three halogen atoms or $C_{1-4}$ alkoxy when X is $NR_{13}$ or said $C_{1-20}$ alkyl is optionally substituted with $C_{1-4}$ alkoxy, halo-$C_{1-4}$ alkoxy or heterocyclyl-oxy $C_{1-4}$ alkoxy when X is O;
$R_3$ is an at least para-substituted phenyl group, wherein the para-substituent of said phenyl group is $C_{1-6}$ alkoxy;
$R_{10}$ is selected from the group consisting of $C_{1-6}$ alkyl optionally substituted with one or more substituents selected from the group consisting of amino, cyano, halogen and hydroxy; $C_{1-6}$ alkoxy optionally substituted with one or more substituents selected from the group consisting of amino, alkylamino, cyano, dialkylamino, halogen, and heterocyclyl; heterocyclyl optionally substituted with one or more substituents selected from the group consisting of $C_{1-6}$ alkyl, acylamino and oxo; $C_{3-10}$ cycloalkyl optionally substituted with one or more substituents selected from the group consisting of amino or hydroxy; and amino optionally substituted with one or more substituents selected from the group consisting of $C_{1-6}$ alkyl wherein said $C_{1-6}$ alkyl is optionally substituted with one or more substituents selected from the group consisting of amino, alkylamino, cyano, dialkylamino, halogen and heterocyclyl;
$R_{12}$ is selected from the group consisting of hydrogen and $C_{1-6}$ alkyl, wherein said $C_{1-6}$ alkyl is optionally substituted with one or more substituents selected from the group consisting of cyano, halogen and hydroxy;

each $R_{13}$ is independently selected from the group consisting of hydrogen and $C_{1-20}$ alkyl;

or a pharmaceutical acceptable addition salt or a stereochemical isomeric form thereof or a N-oxide thereof or a solvate thereof or a pro-drug thereof.

The present invention also relates, to another embodiment of formula II, to a group of pyrido(3,2-d)pyrimidine species having in common a 4-fluorophenyl group on position 6 of said pyrido(3,2-d)pyrimidine core.

Trisubstituted pyrido(3,2-d)pyrimidine derivatives are as defined in the structural formula (II), wherein X and each of the substituents $R_1$, $R_2$, $R_3$, $R_5$, $R_6$, $R_7$, $R_8$, $R_{10}$, $R_{12}$, and/or $R_{13}$ may independently correspond to any of the definitions given above, in particular with any of the individual meanings (such as illustrated above) of generic terms used for substituting groups such as, but not limited to, "$C_{1-20}$ alkyl", "$C_{3-10}$ cycloalkyl", "aryl", "heterocyclic", "halogen", "arylalkyl", "monoalkylamino", "dialkylamino", "$C_{1-4}$ alkoxy", "$C_{1-4}$ alkylthio" and the like.

In another embodiment of the trisubstituted pyrido(3,2-d)pyrimidine derivatives represented by structural formula (II), the para-substituent of said $R_3$ phenyl group is selected from the group consisting of methoxy or ethoxy, propoxy or isopropoxy.

In another embodiment of the trisubstituted pyrido(3,2-d)pyrimidine derivatives represented by structural formula (II), the at least para-substituted $R_3$ phenyl group is further substituted with a second meta-$SO_2R_9$ substituent wherein $R_9$ is selected from the group consisting of $C_{1-3}$ alkyl and methoxymethyl.

In another embodiment of the trisubstituted pyrido(3,2-d)pyrimidine derivatives represented by structural formula (II), $R_2$ is $NR_7R_{13}$, $R_{13}$ is hydrogen or methyl; and $R_7$ is selected from the group consisting of $C_{1-6}$ alkyl, $C_{3-8}$ cycloalkyl, aryl, heterocyclyl and benzyl; wherein said $C_{1-6}$ alkyl is optionally substituted with methylsulfonyl, heterocyclyl, chloro, fluoro or $C_{1-4}$ alkoxy.

In another embodiment of the trisubstituted pyrido(3,2-d)pyrimidine derivatives represented by structural formula (II), $R_2$ is selected from the group consisting of methylamino, ethylamino, n-propylamino, isopropylamino, n-butylamino, isobutylamino, Pert-butylamino, N-methylisopropylamino, N-methyl-n-butylamino, N-methylisobutylamino, N-methyl-tert-butylamino, 3-chloropropylamino, 3-fluoropropylamino, 2-fluoroethylamino, 2-chloroethylamino, 2,2,2-trifluoroethylamino, methyl-(2,2,2-trifluoroethyl)-amino, 2,2-difluoroethylamino, 3,3,3-trifluoropropylamino, cyclopropylamino, cyclobutylamino, cyclopentylamino, cyclohexylamino, cycloheptylamino, cyclooctylamino, N-methylcyclobutylamino, N-methylcyclopentylamino, N-methylcyclohexylamino, benzylamino, anilino, pyridin-3-ylmethylamino, 1-pyridin-2-ylethylamino, 1-pyridin-3-ylethylamino, 1-pyridin-4-ylethylamino, 2-pyridin-4-ylethylamino, 2-morpholin-4-ylethylamino, 2-morpholin-4-ylpropylamino, 3-morpholin-4-ylpropylamino, 2-methoxyethylamino and 3-methoxypropylamino.

In another embodiment of the trisubstituted pyrido(3,2-d)pyrimidine derivatives represented by structural formula (II), $R_2$ is $OR_7$ and $R_7$ is selected from the group consisting of $C_{1-6}$ alkyl, $C_{3-8}$ cycloalkyl, phenyl, heterocyclyl and benzyl.

In another embodiment of the trisubstituted pyrido(3,2-d)pyrimidine derivatives represented by structural formula (II), $R_2$ is selected from the group consisting of cyclopropyloxy, cyclobutoxy, cyclopentoxy, cyclohexyloxy, cycloheptyloxy, cyclooctyloxy, tetrahydrofuranyloxy, methoxy, ethoxy, propyloxy, n-butoxy, isopropyloxy, isobutoxy, tert-butoxy, pentoxy, hexyloxy, heptyloxy, octyloxy and benzyloxy.

In another embodiment of the trisubstituted pyrido(3,2-d)pyrimidine derivatives represented by structural formula (II), $R_1$ is —NH—$CH_2R_6$ wherein $R_6$ is phenyl substituted with one or two substituents independently selected from the group consisting of halogen, trifluoromethyl, triazolyl and —$SO_2NH_2$.

In another embodiment of the trisubstituted pyrido(3,2-d)pyrimidine derivatives represented by structural formula (II), the at least para-substituted $R_3$ phenyl group is further substituted with a second meta-$SO_2R_9$ substituent wherein $R_9$ is selected from the group consisting of $C_{1-3}$ alkyl and methoxymethyl; and $R_1$ is —NH—$CH_2R_6$ wherein $R_6$ is phenyl substituted with one or two substituents independently selected from the group consisting of halogen, trifluoromethyl, triazolyl and —$SO_2NH_2$.

Within the broad class of trisubstituted pyrido(3,2-d)pyrimidine derivatives represented by the above structural formula (I) or the structural formula (II), a useful sub-group of compounds is one wherein $R_2$ is selected from the group consisting of mono-$C_{2-20}$ alkyl-amino, mono-$C_{3-10}$ cycloalkyl-amino, benzylamino, $C_{1-4}$ alkoxy and $C_{1-4}$ alkylthio.

Within the broad class of trisubstituted pyrido(3,2-d)pyrimidine derivatives represented by the above structural formula (I) or the structural formula (II), a useful sub-group of compounds is one wherein both $R_5$ and $R_6$ are hydrogen atoms.

Within the broad class of trisubstituted pyrido(3,2-d)pyrimidine derivatives represented by the above structural formula (I) or the structural formula (II), a useful sub-group of compounds is one wherein $R_8$ is selected from the group consisting of phenyl, pyridazinyl and pyrazolyl and wherein said $R_8$ is optionally substituted with a substituent selected from the group consisting of halogen and methyl.

Within the broad class of trisubstituted pyrido(3,2-d)pyrimidine derivatives represented by the above structural formula (I) or the structural formula (II), a useful sub-group of compounds is one wherein $R_5$ is hydrogen and $R_6$ is selected from the group consisting of trifluoromethyl, naphthyl, imidazol-2-yl and thien-2-yl.

Within the broad class of trisubstituted pyrido(3,2-d)pyrimidine derivatives represented by the above structural formula (I) or the structural formula (II), a useful sub-group of compounds is one wherein $R_5$ is hydrogen and $R_6$ is selected from the group consisting of $C_{1-4}$ alkyl, $C_{3-10}$ cycloalkyl, heterocyclic and phenyl, wherein said phenyl is optionally substituted with one or more substituents selected from the group consisting of halogen, hydroxy, amino, nitro, cyano, trifluoromethyl, trifluoromethoxy, $C_{1-4}$ alkyl, $C_{1-4}$ alkoxy, dimethylamino, diethylamino and phenoxy.

The present invention also relates, in another embodiment, to a group of pyrido(3,2-d)pyrimidine derivatives represented by the structural formula (III):

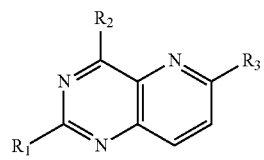

wherein:
R₁ is —NH—CHR₅R₆ or —NH—R₈,
R₅ and R₆ are independently selected from the group consisting of hydrogen, $C_{1-6}$ alkyl, $C_{3-10}$ cycloalkyl, aryl and heterocyclyl, wherein said aryl is substituted with one or more substituents selected from the group consisting of halogen, hydroxy, amino, nitro, cyano, trifluoromethyl, trifluoromethoxy, $C_{1-4}$ alkyl, $C_{1-4}$ alkoxy, di-$C_{1-4}$ alkylamino, mono-$C_{1-4}$ alkylamino, carboxamido, sulfamoyl, carbamoyl, sulfonamido, —SO₂NHR₁₃, —CON(R₁₃)₂, —NR₁₂COR₁₀, —SO₂R₁₃, —NHSO₂R₁₃ and phenoxy, and wherein said $C_{1-6}$ alkyl is optionally substituted with one or more substituents selected from the group consisting of halogen and $C_{1-4}$ alkoxy, and
R₈ is selected from the group consisting of $C_{3-10}$ cycloalkyl, heteroaryl and aryl wherein said heteroaryl or aryl is optionally substituted with one or more substituents selected from the group consisting of halogen and $C_{1-4}$ alkyl and wherein said $C_{3-10}$ cycloalkyl is optionally substituted at the carbon position adjacent to the N atom of R₁ with aryl or heteroaryl wherein said aryl is optionally substituted with halogen;
R₂ is NR₇R₁₃;
R₇ is selected from the group consisting of heterocyclyl substituted with $C_{1-4}$ alkyl; and $C_{1-20}$ alkyl optionally substituted with heterocyclyl;
R₃ is selected from the group consisting of optionally mono-substituted or disubstituted aryl and heterocyclyl, wherein at least one substituent of said aryl or heterocyclyl is selected from the group consisting of halogen, hydroxyl, amino, $C_{1-6}$ alkyl, $C_{1-6}$ alkoxy, —CONHR₉, —NR₁₂COR₁₀, —NR₁₂SO₂R₁₁, —SO₂NH₂, heterocyclyl and heterocyclyl substituted with one or more substituents independently selected from the group consisting of hydroxy, oxo, halogen, amino, $C_{1-6}$ alkyl and $C_{1-6}$ alkoxy;
R₉ is selected from the group consisting of H, $C_{3-10}$ cycloalkyl optionally substituted with one more substituents selected from the group consisting of cyano, halogen, hydroxy, amino, $C_{1-6}$ alkyl and $C_{1-6}$ alkoxy; $C_{1-6}$ alkyl optionally substituted with one or more substituents selected from the group consisting of amino, alkylamino, cyano, dialkylamino, halogen, and heterocyclyl; $C_{1-6}$ alkoxy; heterocyclyl optionally substituted with $C_{1-6}$ alkyl; and phenyl optionally substituted with one or more halogens;
R₁₀ and R₁₁ are each independently selected from the group consisting of $C_{1-6}$ alkyl optionally substituted with one or more substituents selected from the group consisting of amino, cyano, halogen and hydroxy; $C_{1-6}$ alkoxy optionally substituted with one or more substituents selected from the group consisting of amino, alkylamino, cyano, dialkylamino, halogen, and heterocyclyl; heterocyclyl optionally substituted with one or more substituents selected from the group consisting of $C_{1-6}$ alkyl, acylamino and oxo; $C_{3-10}$ cycloalkyl optionally substituted with one or more substituents selected from the group consisting of amino or hydroxy; and amino optionally substituted with one or more substituents selected from the group consisting of $C_{1-6}$ alkyl wherein said $C_{1-6}$ alkyl is optionally substituted with one or more substituents selected from the group consisting of amino, alkylamino, cyano, dialkylamino, halogen and heterocyclyl;
R₁₂ is selected from the group consisting of hydrogen and $C_{1-6}$ alkyl, wherein said $C_{1-6}$ alkyl is optionally substituted with one or more substituents selected from the group consisting of cyano, halogen and hydroxy;
each R₁₃ is independently selected from the group consisting of hydrogen and $C_{1-20}$ alkyl;
or a pharmaceutical acceptable addition salt or a stereochemical isomeric form thereof or a N-oxide thereof or a solvate thereof or a prodrug thereof,
provided that said pyrido(3,2-d)pyrimidine derivative is not N2-(4-fluorobenzyl)-6-(4-fluorophenyl)-N4-(pyridin-3-ylmethyl)-pyrido(3,2-d)pyrimidine-2,4-diamine, N2-(4-fluorobenzyl)-6-(4-fluorophenyl)-N4-(1-isopropyl-piperidin-4-yl)-pyrido(3,2-d)pyrimidine-2,4-diamine, or N2-(4-fluorobenzyl)-6-(4-fluorophenyl)-N4-(2-morpholin-4-ylethyl)-pyrido(3,2-d)pyrimidine-2,4-diamine.

The present invention also relates, in another embodiment, to a group of pyrido(3,2-d)pyrimidine derivatives represented by the structural formula (IV):

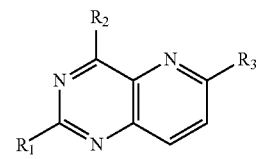

wherein:
R₁ is —NH—CHR₅R₆ or —NH—R₈,
R₅ and R₆ are independently selected from the group consisting of hydrogen, $C_{1-6}$ alkyl, $C_{3-10}$ cycloalkyl, aryl and heterocyclyl, wherein said aryl is substituted with one or more substituents selected from the group consisting of halogen, hydroxy, amino, nitro, cyano, trifluoromethyl, trifluoromethoxy, $C_{1-4}$ alkyl, $C_{1-4}$ alkoxy, di-$C_{1-4}$ alkylamino, mono-$C_{1-4}$ alkylamino, carboxamido, sulfamoyl, carbamoyl, sulfonamido, —SO₂NHR₁₃, —CON(R₁₃)₂, —NR₁₂COR₁₀, —SO₂R₁₃, —NHSO₂R₁₃ and phenoxy, and wherein said $C_{1-6}$ alkyl is optionally substituted with one or more substituents selected from the group consisting of halogen and $C_{1-4}$ alkoxy, and
R₈ is selected from the group consisting of $C_{3-10}$ cycloalkyl, heteroaryl and aryl wherein said heteroaryl or aryl is optionally substituted with one or more substituents selected from the group consisting of halogen and $C_{1-4}$ alkyl and wherein said $C_{3-10}$ cycloalkyl is optionally substituted at the carbon position adjacent to the N atom of R₁ with aryl or heteroaryl wherein said aryl is optionally substituted with halogen;
R₂ is $C_{3-8}$ cycloalkoxy;
R₃ is 4-fluorophenyl;
R₁₀ is selected from the group consisting of $C_{1-6}$ alkyl optionally substituted with one or more substituents selected from the group consisting of amino, cyano, halogen and hydroxy; $C_{1-6}$ alkoxy optionally substituted with one or more substituents selected from the group consisting of amino, alkylamino, cyano, dialkylamino, halogen, and heterocyclyl; heterocyclyl optionally substituted with one or more substituents selected from the group consisting of $C_{1-6}$ alkyl, acylamino and oxo; $C_{3-10}$ cycloalkyl optionally substituted with one or more substituents selected from the group consisting of amino or hydroxy; and amino optionally substituted with one or more substituents selected from the group consisting of $C_{1-6}$ alkyl wherein said $C_{1-6}$ alkyl is optionally substituted with one or more substituents selected from the group consisting of amino, alkylamino, cyano, dialkylamino, halogen and heterocyclyl;

$R_{12}$ is selected from the group consisting of hydrogen and $C_{1-6}$ alkyl, wherein said $C_{1-6}$ alkyl is optionally substituted with one or more substituents selected from the group consisting of cyano, halogen and hydroxy;

each $R_{13}$ is independently selected from the group consisting of hydrogen and $C_{1-20}$ alkyl;

or a pharmaceutical acceptable addition salt or a stereochemical isomeric form thereof or a N-oxide thereof or a solvate thereof or a prodrug thereof, provided that said derivative is not 4-((4-cyclopropoxy-6-(4-fluorophenyl)-pyrido(3,2-d)pyrimidin-2-ylamino)-methyl)benzenesulfonamide, 4-((4-cyclopentoxy-6-(4-fluoro-phenyl)-pyrido(3,2-d)pyrimidin-2-ylamino)-methyl) benzenesulfonamide, 4-((4-cyclo-butoxy-6-(4-fluorophenyl)-pyrido(3,2-d)pyrimidin-2-ylamino)-methyl) benzene-sulfonamide, (4-fluorobenzyl)-(6-(4-fluorophenyl)-4-(tetrahydrofuran-3-yloxy)-pyrido(3,2-d)pyrimidin-2-yl)amine, 4-{[6-(4-fluorophenyl)-4-(1-methyl-cyclopropoxy)-pyrido(3,2-d)pyrimidin-2-ylamino]-methyl}benzene-sulfonamide or (6-(4-fluorophenyl)-4-(tetrahydrofuran-3-yloxy)-pyrido(3,2-d)pyrimidin-2-yl)-(2,2,2-trifluoroethyl)amine.

In one embodiment of the invention of formula (I), (Ia), (Ib), (II), (III), or (IV), $R_6$ is substituted aryl, such as substituted phenyl. In another embodiment, $R_6$ is substituted phenyl, with one or two substituents selected from halogen, $C_{1-4}$ alkyl, $C_{1-4}$ alkoxy, triazolyl and —$SO_2NH_2$, wherein said $C_{1-4}$ alkyl substituents and $C_{1-4}$ alkoxy substituents are each independently optionally substituted with one or more halogen.

In another embodiment, $R_6$ is phenyl substituted with one or two substituents independently selected from the group consisting of chloro, fluoro, methyl, trifluoromethyl, triazolyl and —$SO_2NH_2$.

In one embodiment of the invention of formula (Ib), $R_3$ is mono-substituted or di-substituted phenyl. In another embodiment, at least one substituent of said mono-substituted or di-substituted phenyl is selected from the group consisting of halogen, $C_{1-6}$ alkyl, $C_{1-6}$ alkoxy, —$NHR_7$ and —$SO_2R_9$, wherein $R_7$ and $R_9$ are each defined the same as in the summary of the invention. In another embodiment, the —$SO_2R_9$ substituent is located at the meta position of the mono-substituted or di-substituted phenyl. In another embodiment, the halogen substituent is located at the para position of said mono-substituted or di-substituted phenyl. In another embodiment, phenyl is di-substituted with the —$SO_2R_9$ substituent located at the meta position and the halogen (e.g., fluorine) substituent located at the para position. In another embodiment, the di-substituted phenyl group is substituted with fluoro, chloro, methyl, ethyl, methoxy or ethoxy.

In one embodiment of the invention of formula (Ia) or (Ib), $R_4$ is $C_{3-6}$ cycloalkyl substituted with any of the substituents defined above in the summary of the invention. In another embodiment, $R_4$ is $C_{3-6}$ cycloalkyl substituted with one or more substituents independently selected from the group consisting of halogen, $C_{1-4}$ alkyl optionally substituted with one or more halogen (e.g., fluorine), $C_{1-4}$ alkoxy optionally substituted with one or more halogen, di-$C_{1-4}$ alkylamino and mono-$C_{1-4}$ alkylamino. In another embodiment, $R_4$ is cyclopropyl substituted as defined above in the summary of the invention. In another embodiment, $R_4$ is $C_{3-6}$ cycloalkyl (e.g., cyclopropyl) substituted with a haloalkyl group (e.g., trifluoromethyl, trifluoroethyl, and the like). In another embodiment, the substituent (e.g., haloalkyl) on the $C_{3-6}$ cycloalkyl (e.g., cyclopropyl) group is positioned at the carbon atom adjacent to the nitrogen atom of —$NHR_4$.

The present invention further provides various processes and methods for making the novel pyrido(3,2-d)pyrimidine derivatives represented by the structural formulae (I), (Ia), (Ib), (II), (III), or (IV) as well as pyrido(3,2-d)pyrimidine species having in common a 4-fluorophenyl group on position 6 of said pyrido(3,2-d)pyrimidine core. As a general rule, the preparation of these compounds is based on the principle that, starting from a suitable precursor such as 3-amino-6-chloro-pyridine-2-carboxylic acid amide (e.g. methods shown in FIGS. 1 and 2), each of the desirable substituents $R_2$ and $R_3$ may be introduced separately without adversely influencing the presence of one or more substituents already introduced at other positions on the pyrido(3,2-d)pyrimidine moiety or the capacity to introduce further substituents later on.

Methods of manufacture have been developed by the present inventors which may be used alternatively to, or may be combined with, the methods of synthesis already known in the art of pyrido(3,2-d)pyrimidine derivatives (depending upon the targeted final compound). For instance, the synthesis of mono- and di-N-oxides of the pyrido(3,2-d)pyrimidine derivatives of this invention can easily be achieved by treating the said derivatives with an oxidizing agent such as, but not limited to, hydrogen peroxide (e.g. in the presence of acetic acid) or a peracid such as chloroperbenzoic acid. The methods for making the pyrido(3,2-d)pyrimidine derivatives of the present invention will now be explained in more details by reference to the appended FIGS. 1 and 2 wherein, unless otherwise stated hereinafter, each of the substituting groups or atoms $R_1$, $R_2$ and $R_3$ is as defined in the structural formulae (I) and (II) of the summary of the invention and, more specifically, may correspond to any of the individual meanings disclosed herein.

In the description of the reaction steps involved in each figure, reference is made to the use of certain catalysts and/or certain types of solvents. It should be understood that each catalyst mentioned should be used in a catalytic amount well known to the skilled person with respect to the type of reaction involved. Solvents that may be used in the following reaction steps include various kinds of organic solvents such as protic solvents, polar aprotic solvents and non-polar solvents as well as aqueous solvents which are inert under the relevant reaction conditions. More specific examples include aromatic hydrocarbons, chlorinated hydrocarbons, ethers, aliphatic hydrocarbons, alcohols, esters, ketones, amides, water or mixtures thereof, as well as supercritical solvents such as carbon dioxide (while performing the reaction under supercritical conditions). The suitable reaction temperature and pressure conditions applicable to each kind of reaction step will not be detailed herein but do not depart from the relevant conditions already known to the skilled person with respect to the type of reaction involved and the type of solvent used (in particular its boiling point).

Most of the present methods make use of a boronic acid, or a pinacol ester thereof, for introducing substituent $R_3$ onto the core structure. In the following methods, suitable substituted phenyl-boronic acids are well known to those skilled in the art are and are usually commercially available.

FIG. 1 schematically shows a method for making certain 2,4,6-tri-substituted pyrido(3,2-d)pyrimidine derivatives of this invention. In step (a), 6-chloro-3-amino-2-pyridylcarboxamide is subjected to a palladium-catalyzed coupling reaction such as, but not limited to, a Stifle coupling reaction (i.e. a palladium catalysed coupling reaction with a substituted phenyltin reagent, optionally in the additional presence of lithium chloride) or a Suzuki reaction with a substituted phenylboronic acid, or ester thereof, wherein the phenyl group is substituted with alkylsulfonyl or methoxymethylsulfonyl (derivatives represented by the structural formula I), para $C_{1-6}$ alkoxy (derivatives represented by the structural formula II) or para fluoro (the remaining individual derivatives) to yield the corresponding 6-(substituted phenyl)-3-amino-2-pyridylcarboxamide. In step (b), a ring closure reaction leading to the formation of the pyrido[3,2-d]pyrimidine scaffold occurs by treatment with a ring closure reagent such as, but not limited to, phosgene, triphosgene or dicyclohexyl carbodiimide.

In step (c), a leaving group L, such as a chloro or 1,2,4-triazol-1-yl, is introduced at the 2- and 4-positions of the pyrido(3,2-d)pyrimidine ring. The chloro derivatives can be obtained by treating the product obtained from step (b) with a reagent such as, but not limited to, thionyl chloride or phosphorus oxychloride. The triazolyl derivatives can be obtained by treating the product obtained from step (b) with a reagent system such as, but is not limited to, thionyl chloride or phosphorus oxychloride in combination with 1,2,4-triazole, optionally in the presence of a base such as trialkylamine or 1,8-diazabicyclo[5.4.0]undec-7-ene DBU). Nucleophilic displacement of the triazolyl group or chloro atom L at the 4 position occurs in step (d) by reacting the intermediate obtained in step (c) with an appropriate nucleophile $R_2H$ (e.g. morpholine, thiomorpholine, thiomorpholine dioxide, a $R_7$-containing amine, a $R_7$-containing alkali alkoxide, or a $R_7$-containing thiol) in a polar aprotic solvent. In step (e), the leaving group L at the 2 position of the pyrido(3,2-d)pyrimidine ring is then displaced by reacting the intermediate obtained in step (d) with a suitable $R_1$-containing amine nucleophile.

Figure 2:
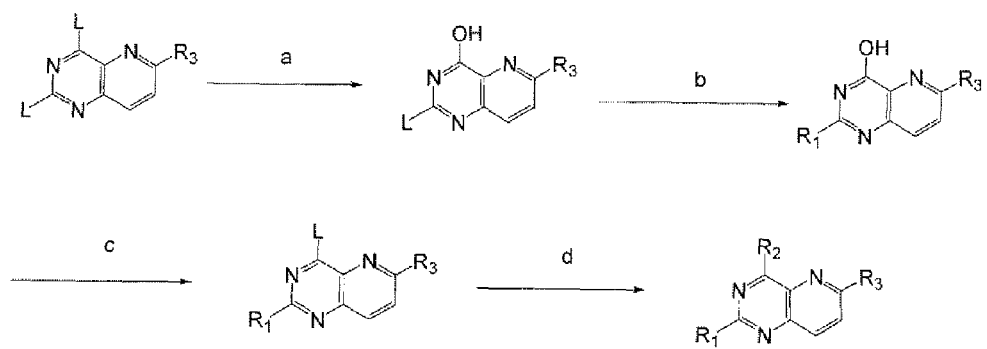
FIG. 2 schematically shows an alternative method for making 2,4,6-tri-substituted pyrido(3,2-d)pyrimidine derivatives in which the substituent at position 4 is introduced in the final step.

FIG. 2 schematically shows an alternative method for making 2,4,6-tri-substituted pyrido(3,2-d)pyrimidine derivatives in which the substituent at position 4 is introduced in the final step. In this variant, the intermediate generated in step (c) of FIG. 1 is first treated in step (a) with an aqueous solution of an alkali metal hydroxide such as sodium hydroxide or potassium hydroxide, thereby hydrolysing the leaving group L at position 4. The desired $R_1$-containing amino substituent is then introduced in step (b) in a manner analogous to step (e) in FIG. 1 such as, for example, heating with the requisite amine in a dipolar aprotic solvent in the presence of a base such as diisopropylethylamine. If a sulphonamide introduced as part of the amine nucleophile bears a protecting group such as, for example, a ten-butyl group, it is convenient to remove it, for example by treatment with a strong acid such as trifluoroacetic acid, prior to step (c), in which the hydroxyl substituent at position 4 of the pyrido(3,2-d)pyrimidine scaffold is converted to a leaving group L such as, but not limited to, benzotriazolyloxy, triazolyl or halo by treatment with, for example, benzotriazol-1-yl-oxy-tris-(dimethylamino)-phosphonium hexafluorophosphate. Nucleophilic displacement of the leaving group L occurs in the final step (d) by reacting the intermediate obtained in step (c) with an appropriate nucleophile $R_2H$ (e.g. morpholine, thiomorpholine, thiomorpholine dioxide, a $R_7$-containing amine, a $R_7$-containing alkali alkoxide, or a $R_7$-containing thiol) in a polar aprotic solvent. Examples of suitable nucleophiles include lithium, sodium, potassium or cesium $R_7$-containing alkoxides, and $R_7$-containing primary amines.

Figure 3:
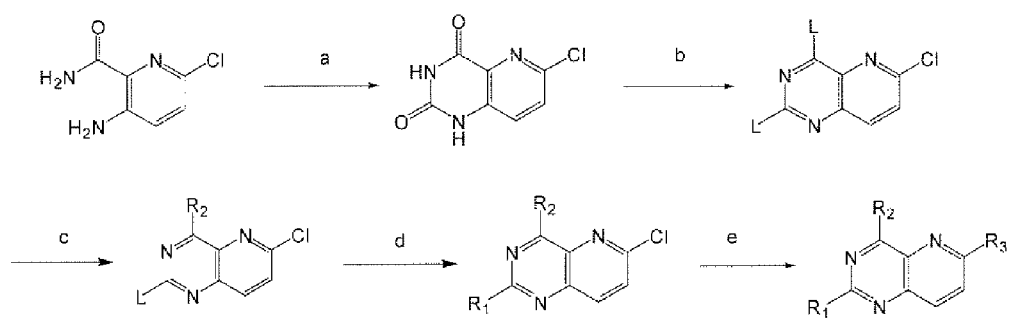
FIG. 3 schematically shows an alternative method for making the 2,4,6-trisubstituted 8-deazapteridines of this invention.

FIG. 3 schematically shows an alternative method for making the 2,4,6-trisubstituted 8-deazapteridines of this invention. In step (a), treatment of a 3-amino-6-chloro-pyridine-2-carboxylic acid amide either with phosgene or a phosgene derivative in an aprotic solvent provides 2,4-dioxo-6-chloro-8-deazapteridine. In step (b), the tautomeric hydroxyl groups at position 2 and 4 are both converted to a suitable leaving group L, such as chloro, e.g. by treatment with phosphorus oxychloride. In step (c), the leaving group L at position 4 is selectively displaced by reaction with an appropriate nucleophile $R_2H$ (e.g. morpholine, thiomorpholine, thiomorpholine dioxide, a $R_7$-containing amine, a $R_7$-containing alkali alkoxide, or a $R_7$-containing thiol) in a polar aprotic solvent. Examples of suitable nucleophiles include lithium, sodium, potassium or cesium $R_7$-containing alkoxides, and $R_7$-containing primary amines. In step (d), an amine nucleophile $R_1H$ is reacted with the intermediate obtained in step (c). A palladium-mediated cross-coupling reaction (Suzuki type) occurs in step (e) by treatment with a suitably substituted phenylboronic acid, or a pinacol ester thereof, wherein the phenyl group is substituted with alkylsulfonyl or methoxymethylsulfonyl (derivatives represented by the structural formula I), para $C_{1-6}$ alkoxy (derivatives represented by the structural formula II) or para fluoro (the remaining individual derivatives) to yield the desired derivative in the presence of aqueous base and a palladium(0) catalyst such as, but not limited to, $Pd(PPh_3)_4$.

Figure 4:
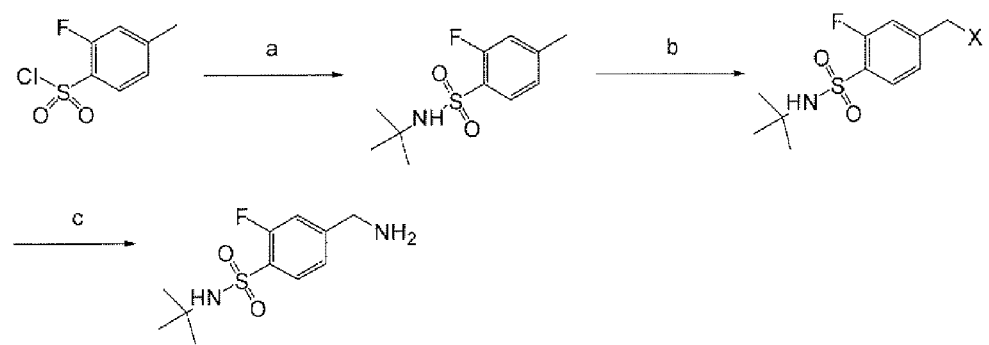
FIG. 4 schematically shows a method for making 4-aminomethyl-N-tert-butyl-2-fluorobenzenesulfonamide.

FIG. 4 schematically shows a method for making 4-aminomethyl-N-tert-butyl-2-fluorobenzenesulfonamide. In step (a), 2-fluoro-4-methylbenzene-1-sulfonyl chloride is treated with tert-butylamine in an apolar solvent. In step (b), a leaving group X such as a halogen atom, is introduced onto the benzylic methyl group by treatment with a reagent such as, but not limited to, N-bromosuccinimide under conditions that catalyze the formation of halogen radicals such as, for example, heating with benzoyl peroxide and light, or heating in the presence of azobisisobutyronitrile. In step (c) the leaving group X is displaced e.g. by treatment with aqueous ammonium hydroxide.

Figure 5:
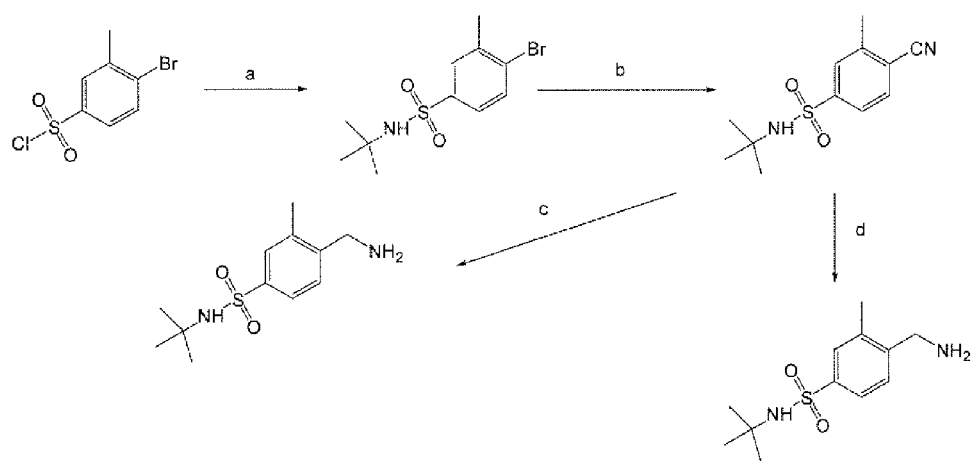
FIG. 5 schematically shows a method for making 4-aminomethyl-N-tert-butyl-3-methyl-benzenesulfonamide.

FIG. 5 schematically shows a method for making 4-aminomethyl-N-tert-butyl-3-methyl-benzenesulfonamide. In step (a), 4-bromo-3-methylbenzene-1-sulfonyl chloride is treated with tert-butylamine in an apolar solvent. In step (b), the phenyl bromide is converted to the corresponding phenyl cyanide by palladium-catalysed reaction with zinc cyanide in the presence of one or more suitable ligands such as, for example, triphenylphoshine and/or 1,1-bis(diphenylphosphino)ferrocene. In step (c), the benzonitrile formed is reduced by hydrogenation, e.g. with hydrogen gas in an alcoholic solvent over a catalyst such as palladium adsorbed on charcoal, preferably in the presence of an acid such as hydrochloric acid, to produce the desired aminomethyl derivative. Alternatively in step (d) the benzonitrile formed in step (b) may be treated with an organometallic reagent such as methylmagnesium bromide in a aprotic solvent to generate an imine, which is then reduced to the desired aminoethyl derivative by treatment with a reducing agent such as, but not limited to, sodium borohydride in a protic solvent (e.g. an alcohol).

Figure 6:
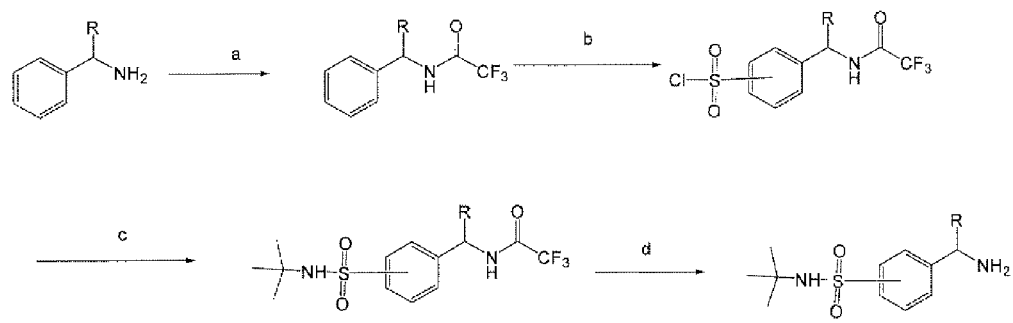
FIG. 6 schematically shows a method for making N-tert-butyl-benzenesulfonamides bearing aminoalkyl substituents.

FIG. 6 schematically shows a method for making N-tert-butyl-benzenesulfonamides bearing branched aminoalkyl substituents. In step (a) an appropriate benzylamine wherein the carbon atom adjacent to the phenyl ring bears a substituent R (e.g. R is methyl) is masked with a protecting group such as, but not limited to, trifluoroacetyl by treatment with a suitable carboxylic acid anhydride or carboxylic acid chloride in the presence of a base such as, for example, pyridine. In step (b) a chlorosulphonyl group is introduced onto the phenyl ring by treatment with chlorosulphonic acid, thereby often producing a mixture of isomers that can be separated if necessary. In step (c), the intermediate(s) from step (b) is treated with tert-butylamine in an apolar solvent. Finally in step (d), the trifluoroacetyl-protected amino group is deprotected by treatment with a base such as potassium carbonate in an alcoholic solvent such as methanol. The isomers produced may also conveniently be separated by chromatography at this stage.

Figure 7:
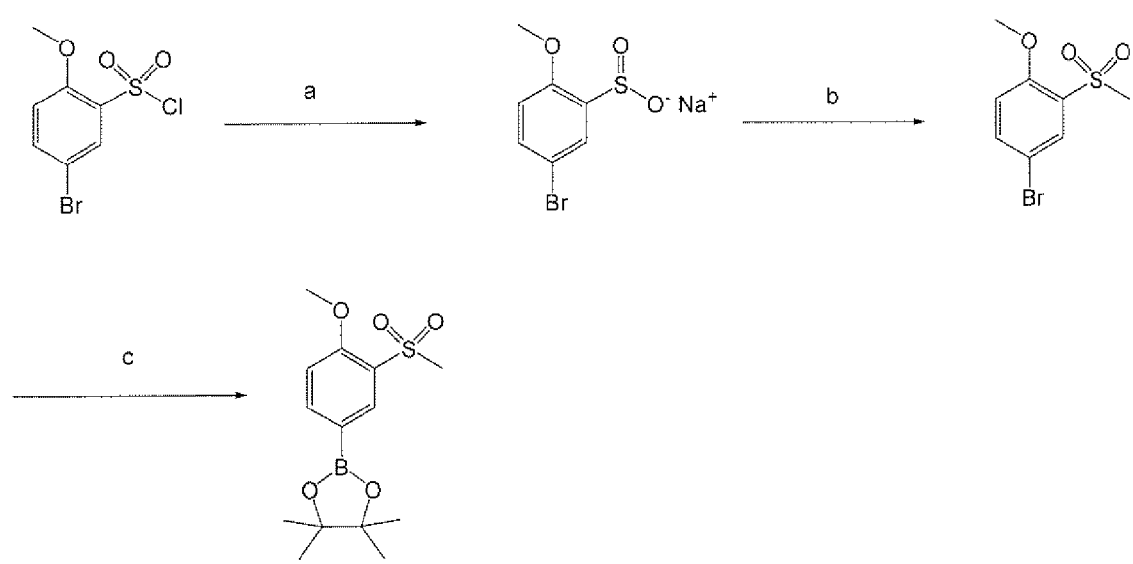
FIG. 7 schematically shows a method for making a boronic reagent suitable for a Suzuki-type cross-coupling reaction.

FIG. 7 schematically shows a method for generating a specific phenylboronic reagent suitable for palladium-catalysed cross-coupling reactions, e.g. to introduce a 3-methanesulfonyl-4-methoxyphenyl substituent at the 6-position of the 2,4,6-1.0 trisubstituted 8-deazapteridines of this invention. In step (a), 5-bromo-2-methoxybenzene-1-sulfonyl chloride is reduced to the corresponding sulphinic acid by treatment with a reducing agent such as sodium sulphite in a weakly alkaline aqueous solution. In step (b) the corresponding methylsulphone is generated through treatment with a methylating agent such as methyl iodide in a dipolar aprotic solvent. Finally in step (c) the aryl bromide is converted into a boronic acid, or an ester derivative thereof (for example the pinacol ester), suitable for participation in a Suzuki coupling through treatment with a reagent such as, but not limited to, bis(pinacolato)diboron in the presence of a suitable palladium catalyst such as tris(dibenzylideneacetone)dipalladium(0), a ligand such as 2-dicyclohexylphosphino-2',4',6'-triisopropylbiphenyl) and a buffer such as potassium.

The present invention encompasses compounds containing each substituent as defined herein, and any combination of substituents thereof, including compounds containing a combination of substituents not specifically exemplified in the actual and prophetic examples disclosed herein. One skilled in the art can readily envisage the compounds of the invention without having to conduct any undue experimentation.

The present invention further provides various processes and methods for making the novel pyrido(3,2-d)pyrimidine derivatives represented by the structural formulae (Ia) or (Ib). As a general rule, the preparation of these compounds is based on the principle that, starting from a suitable precursor, each of the desirable substituents may be introduced separately without adversely influencing the presence of one or more substituents already introduced at other positions on the pyrido(3,2-d)pyrimidine moiety or the capacity to introduce further substituents later on.

Methods of manufacture have been developed by the present inventors which may be used alternatively to, or may be combined with, the methods of synthesis already known in the art of pyrido(3,2-d)pyrimidine derivatives (depending upon the targeted final compound).

In the description of the reaction steps involved in the experimentals, reference is made to the use of certain catalysts and/or certain types of solvents. It should be understood that each catalyst mentioned should be used in a catalytic amount well known to the skilled person with respect to the type of reaction involved. Solvents that may be used in the following reaction steps include various kinds of organic solvents such as protic solvents, polar aprotic solvents and non-polar solvents as well as aqueous solvents which are inert under the relevant reaction conditions. More specific examples include aromatic hydrocarbons, chlorinated hydrocarbons, ethers, aliphatic hydrocarbons, alcohols, esters, ketones, amides, water or mixtures thereof, as well as supercritical solvents such as carbon dioxide (while performing the reaction under supercritical conditions). The suitable reaction temperature and pressure conditions applicable to each kind of reaction step will not be detailed herein but do not depart from the relevant conditions already known to the skilled person with respect to the type of reaction involved and the type of solvent used (in particular its boiling point).

Most of the present methods make use of a boronic acid, or a pinacol ester thereof, for introducing substituent onto the core structure. In the following methods, suitable substituted phenyl-boronic acids are well known to those skilled in the art are and are usually commercially available.

The present invention includes the below disclosed prophetic examples. A skilled artisan can prepare the compounds of the prophetic examples by following the methods of making and processes shown in the below experimentals, and modifying steps where appropriate to provide the desired final compound. A skilled artisan could also use and modify the methods and processes taught in the art to make compounds of the prophetic examples, such as by modifying the those methods and processes taught in WO2008/009078, WO2008/009076, WO2008/009079, WO2008/009077, WO2008/043149, PCT/EP2007/011494, PCT/EP2007/011495 and PCT/EP2007/011496, each of which is herein incorporated by reference in its entirety. In particular, PCT/EP2007/011494 teaches specifically how to make a cyano substituted cyclopropyl amino substituent at the 4-position of a pyrido(3,2-d)pyrimidine in the experimental for making 4-{[4-(1-cyano-cyclopropyl amino)-6-(4-fluoro-phenyl)-pyrido[3,-d]pyrimidin-2-ylamino]-methyl}-benzenesulfonamide. See Example 303, of the specification. One skilled in the art can modify that process, along with other processes known in the art, and the processes taught herein, to prepare a prophetic compound or any other compound covered by structural formulae (Ia) and (Ib).

PROPHETIC EXAMPLES

2-, 4- and 6-Substituents

2-Substituents

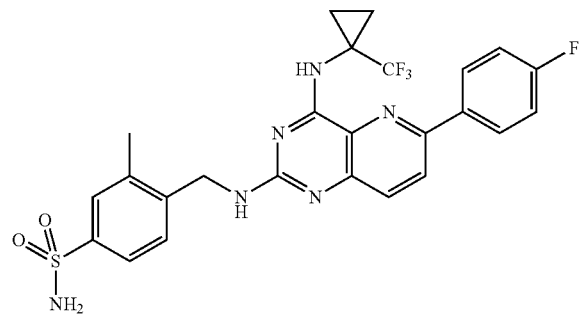

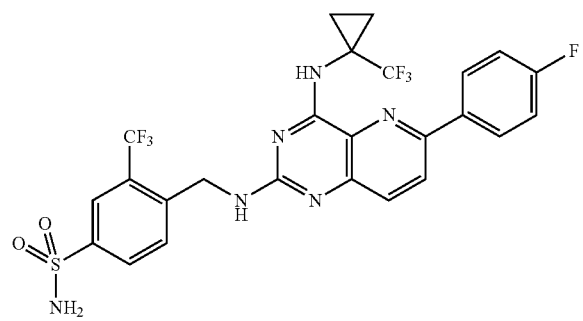

-continued
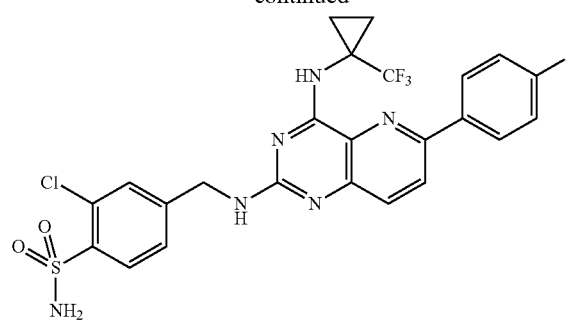
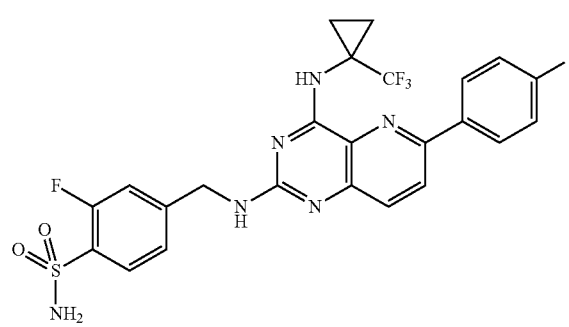
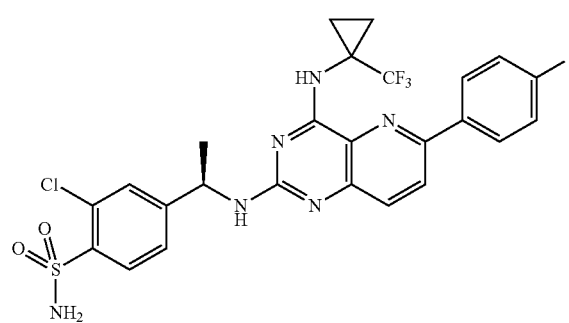
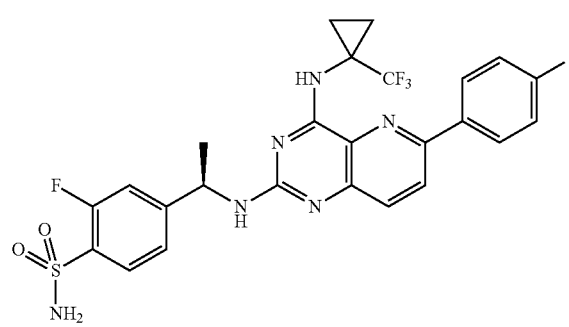
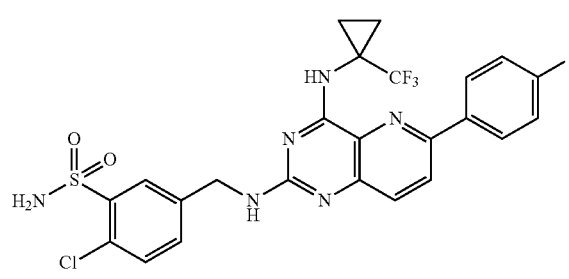
-continued
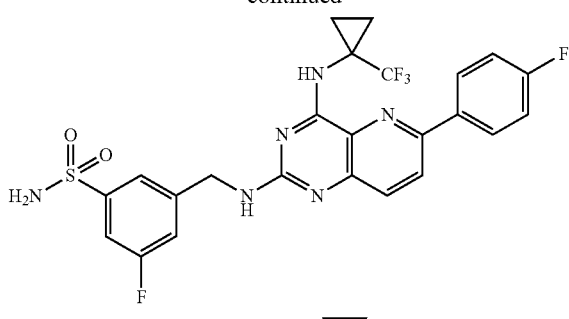
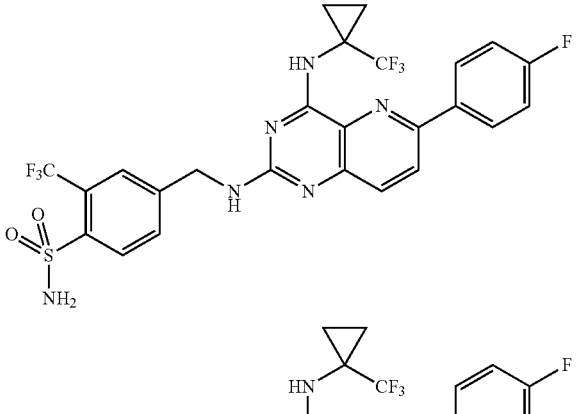
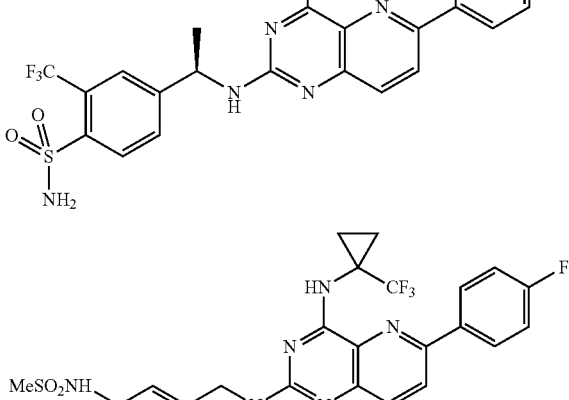
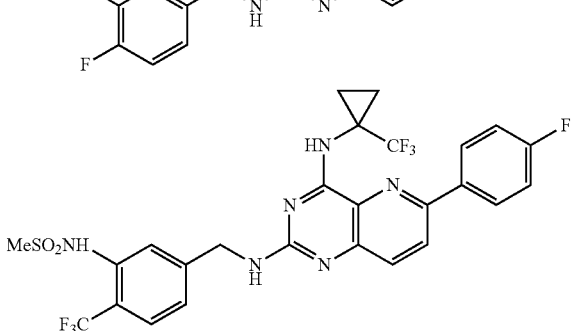
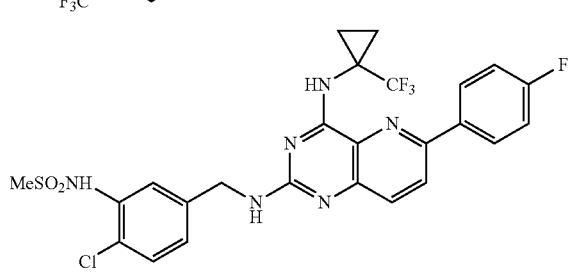

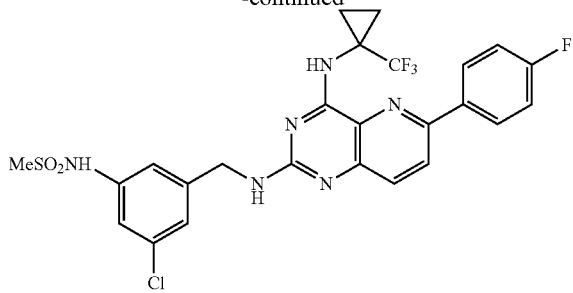

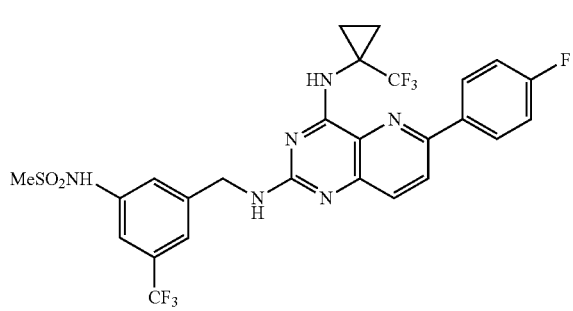

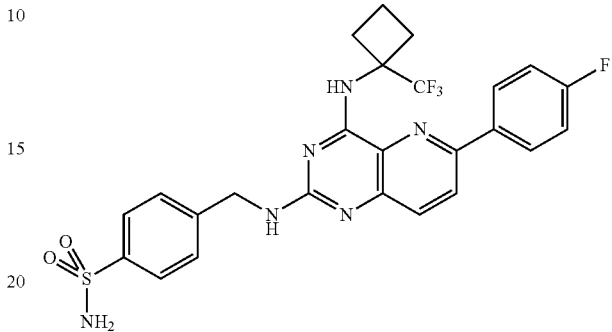

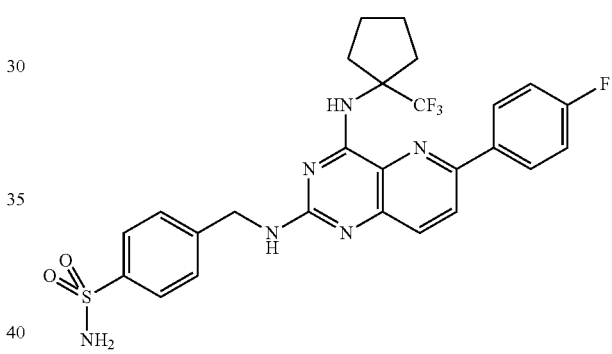

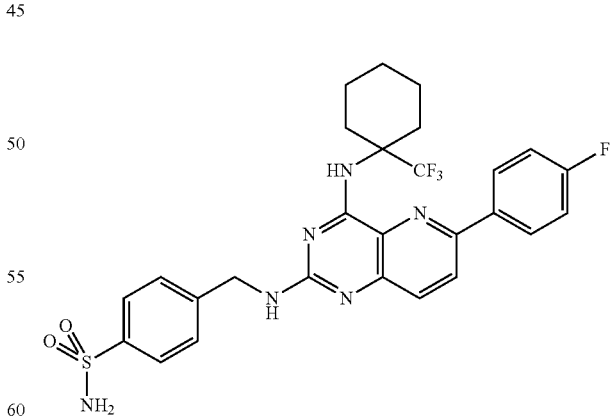

trifluoromethyl-cyclopropylamino)-pyrido[3,2-d]pyrimidin-2-ylamino]-methyl}-5-trifluoromethyl-phenyl)-methanesulfonamide.

4-Substituents

4-{[6-(4-Fluoro-phenyl)-4-(1-trifluoromethyl-cyclopropylamino)-pyrido[3,2-d]pyrimidin-2-ylamino]-methyl}-3-methyl-benzenesulfonamide; 4-{[6-(4-Fluoro-phenyl)-4-(1-trifluoromethyl-cyclopropylamino)-pyrido[3,2-d]pyrimidin-2-ylamino]-methyl}-3-trifluoromethyl-benzenesulfonamide; 2-Chloro-4-{[6-(4-fluoro-phenyl)-4-(1-trifluoromethyl-cyclopropylamino)-pyrido[3,2-d]pyrimidin-2-ylamino]-methyl}-benzenesulfonamide; 2-Fluoro-4-{[6-(4-fluoro-phenyl)-4-(1-trifluoromethyl-cyclopropylamino)-pyrido[3,2-d]pyrimidin-2-ylamino]-methyl}-benzenesulfonamide; 2-Chloro-4-{1-[6-(4-fluoro-phenyl)-4-(1-trifluoromethyl-cyclopropylamino)-pyrido[3,2-d]pyrimidin-2-ylamino]-ethyl}-benzenesulfonamide; 2-Fluoro-4-{[6-(4-fluoro-phenyl)-4-(1-trifluoromethyl-cyclopropylamino)-pyrido[3,2-d]pyrimidin-2-ylamino]-ethyl}-benzenesulfonamide; 2-Chloro-5-{[6-(4-fluoro-phenyl)-4-(1-trifluoromethyl-cyclopropylamino)-pyrido[3,2-d]pyrimidin-2-ylamino]-methyl}-benzenesulfonamide; 3-Fluoro-5-{[6-(4-fluoro-phenyl)-4-(1-trifluoromethyl-cyclopropylamino)-pyrido[3,2-d]pyrimidin-2-ylamino]-methyl}-benzenesulfonamide; 4-{[6-(4-Fluoro-phenyl)-4-(1-trifluoromethyl-cyclopropylamino)-pyrido[3,2-d]pyrimidin-2-ylamino]-methyl}-2-trifluoromethyl-benzenesulfonamide; 4-{[6-(4-Fluoro-phenyl)-4-(1-trifluoromethyl-cyclopropylamino)-pyrido[3,2-d]pyrimidin-2-ylamino]-ethyl}-2-trifluoromethyl-benzenesulfonamide; N-(2-Fluoro-5-{[6-(4-fluoro-phenyl)-4-(1-trifluoromethyl-cyclopropylamino)-pyrido[3,2-d]pyrimidin-2-ylamino]-methyl}-phenyl)-methanesulfonamide, N-(5-{[6-(4-Fluoro-phenyl)-4-(1-trifluoromethyl-cyclopropylamino)-pyrido[3,2-d]pyrimidin-2-ylamino]-methyl}-2-trifluoromethyl-phenyl)-methanesulfonamide; N-(2-Chloro-5-{[6-(4-fluoro-phenyl)-4-(1-trifluoromethyl-cyclopropylamino)-pyrido[3,2-d]pyrimidin-2-ylamino]-methyl}-phenyl)-methanesulfonamide; N-(3-Chloro-5-{[6-(4-fluoro-phenyl)-4-(1-trifluoromethyl-cyclopropylamino)-pyrido[3,2-d]pyrimidin-2-ylamino]-methyl}-phenyl)-methanesulfonamide; N-(3-{[6-(4-Fluoro-phenyl)-4-(1-

4-{[6-(4-Fluoro-phenyl)-4-(1-trifluoromethyl-cyclobutylamino)-pyrido[3,2-d]pyrimidin-2-ylamino]-methyl}-benzenesulfonamide; 4-{[6-(4-Fluoro-phenyl)-4-(1-trifluoromethyl-cyclopentylamino)-pyrido[3,2-d]pyrimidin-2-ylamino]-methyl}-benzenesulfonamide; 4-{[6-(4-Fluorophenyl)-4-(1-trifluoromethyl-cyclohexylamino)-pyrido[3,2-d]pyrimidin-2-ylamino]-methyl}-benzenesulfonamide.

6-Substituents

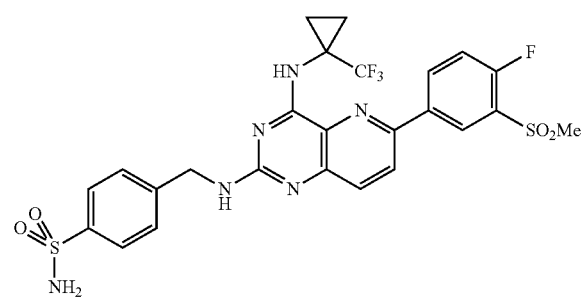

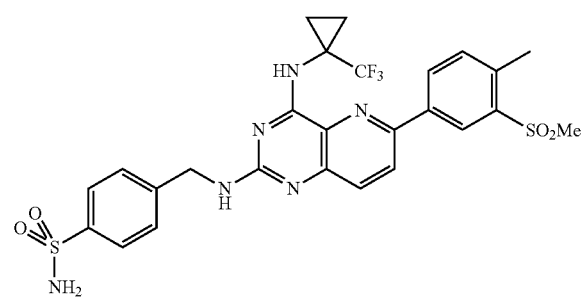

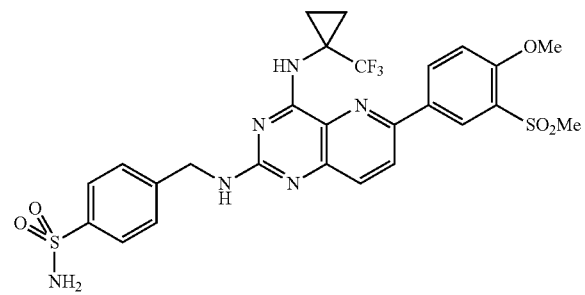

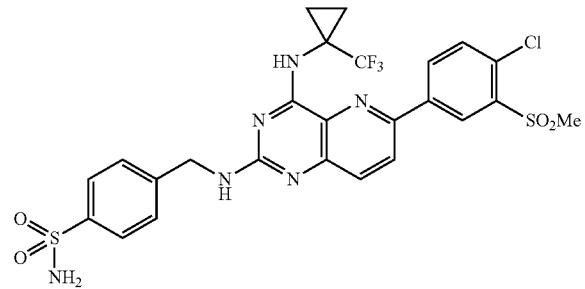

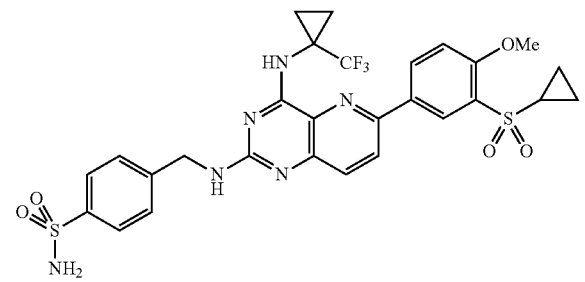

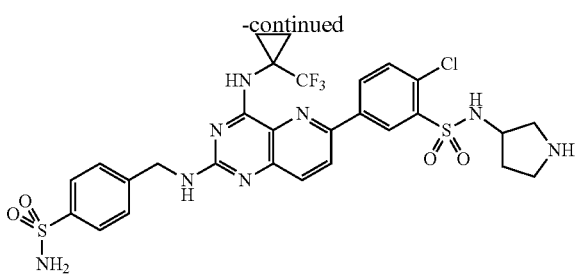

4-{[6-(4-Fluoro-3-methanesulfonyl-phenyl)-4-(1-trifluoromethyl-cyclopropylamino)-pyrido[3,2-d]pyrimidin-2-ylamino]-methyl}-benzenesulfonamide; 4-{[6-(3-Methanesulfonyl-4-methyl-phenyl)-4-(1-trifluoromethyl-cyclopropylamino)-pyrido[3,2-d]pyrimidin-2-ylamino]-methyl}-benzenesulfonamide; 4-{[6-(3-Methanesulfonyl-4-methoxy-phenyl)-4-(1-trifluoromethyl-cyclopropylamino)-pyrido[3,2-d]pyrimidin-2-ylamino]-methyl}-benzenesulfonamide; 4-{[6-(4-Chloro-3-methanesulfonyl-phenyl)-4-(1-trifluoromethyl-cyclopropylamino)-pyrido[3,2-d]pyrimidin-2-ylamino]-methyl}-benzenesulfonamide; 4-{[6-(3-Cyclopropanesulfonyl-4-methoxy-phenyl)-4-(1-trifluoromethyl-cyclopropylamino)-pyrido[3,2-d]pyrimidin-2-ylamino]-methyl}-benzenesulfonamide; 6-(3-Methanesulfonyl-4-methoxy-phenyl)-N2-[1-(4-[1,2,4]triazol-1-yl-phenyl)-ethyl]-N4-(1-trifluoromethyl-cyclopropyl)-pyrido[3,2-d]pyrimidine-2,4-diamine In another particular embodiment, the invention relates to a group of trisubstituted pyrido(3,2-d)pyrimidine derivatives, as well as pharmaceutical compositions comprising such pyrido(3,2-d)pyrimidine derivatives as active principle, represented by the above structural formulae (I), (Ia), (Ib), (II), (III), or (IV) and being in the form of a pharmaceutically acceptable salt. The latter include any therapeutically active non-toxic addition salt which compounds represented by the structural formulae (I), (Ia), (Ib), (II), (III), or (IV) are able to form with a salt-forming agent. Such addition salts may conveniently be obtained by treating the trisubstituted pyrido(3,2-d)pyrimidine derivatives of the invention with an appropriate salt-forming acid or base. For instance, pyrido(3,2-d)pyrimidine derivatives having basic properties may be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as, but not limited to, hydrohalides (e.g. hydrochloride and hydrobromide), sulfate, nitrate, phosphate, diphosphate, carbonate, bicarbonate, and the like; and organic mono- or di-acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzenesulfonate, p-toluene-sulfonate, salicylate, p-aminosalicylate, pamoate, bitartrate, camphorsulfonate, edetate, 1,2-ethanedisulfonate, fumarate, glucoheptonate, gluconate, glutamate, hexylresorcinate, hydroxynaphthoate, hydroxyethanesulfonate, mandelate, methylsulfate, pantothenate, stearate, as well as salts derived from ethanedioic, propanedioic, butanedioic, (Z)-2-butenedioic, (E)2-butenedioic, 2-hydroxybutanedioic, 2,3-dihydroxybutane-dioic, 2-hydroxy-1,2,3-propanetricarboxylic and cyclohexane-sulfamic acids and the like.

Trisubstituted pyrido(3,2-d)pyrimidine derivatives of the structural formulae (I), (Ia), (Ib), (II), (III), or (IV) and having acidic properties may be converted in a similar manner into the corresponding therapeutically active, non-toxic base addition salt form. Examples of appropriate salt-forming bases include, for instance, inorganic bases like metallic hydroxides such as, but not limited to, those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzylethylenediamine, chloroprocaine, choline, diethanolamine, ethylene-diamine, N-methylglucamine, procaine and the like.

Reaction conditions for treating the trisubstituted pyrido (3,2-d)pyrimidine derivatives having the structural formulae (I), (Ia), (Ib), (II), (III), or (IV) of this invention with an appropriate salt-forming acid or base are similar to standard conditions involving the same acid or base but different organic compounds with basic or acidic properties, respectively. Preferably, in view of its use in a pharmaceutical composition or in the manufacture of a medicament for treating specific diseases, the pharmaceutically acceptable salt will be designed, i.e. the salt-forming acid or base will be selected so as to impart greater water solubility, lower toxicity, greater stability and/or slower dissolution rate to the pyrido(3,2-d) pyrimidine derivative of this invention.

The present invention further provides the use of a trisubstituted pyrido(3,2-d)pyrimidine derivative represented by the structural formulae (I), (Ia), (Ib), (II), (III), or (IV), or a pharmaceutically acceptable salt or a solvate thereof, as a biologically-active ingredient, i.e. active principle, especially as a medicine or for the manufacture of a medicament for the treatment of a Flaviridae viral infection such as, but not limited to, hepatitis C.

In another embodiment, the present invention provides methods of treating a Flaviridae infection, especially hepatitis C, in a patient, comprising administering to the patient a therapeutically effective amount of a trisubstituted pyrido(3, 2-d)pyrimidine derivative represented by the structural formulae (I), (Ia), (Ib), (II), (III), or (IV), or a pharmaceutically acceptable salt, solvate, and/or ester thereof, optionally in combination with at least one additional biologically active agent, e.g. an anti-viral agent.

In another embodiment, the present invention provides methods of treating HCV in a patient, comprising: administering to the patient a therapeutically effective amount of a trisubstituted pyrido(3,2-d)pyrimidine derivative represented by the structural formulae (I), (Ia), (Ib), (II), (III), or (IV), or a pharmaceutically acceptable salt, solvate, and/or ester thereof, and/or pro-drug thereof.

In another embodiment, the present application provides for methods of treating HCV in a patient, comprising: administering to the patient a therapeutically effective amount of a trisubstituted pyrido(3,2-d)pyrimidine derivative represented by the structural formulae (I), (Ia), (Ib), (II), (III), or (IV), or a pharmaceutically acceptable salt, solvate, and/or ester thereof and/or pro-drug thereof, and at least one additional active agent, whereby HCV polymerase is inhibited.

In another embodiment, the present invention provides methods of treating HCV in a patient, comprising: administering to the patient a therapeutically effective amount of a trisubstituted pyrido(3,2-d)pyrimidine derivative represented by the structural formulae (I), (Ia), (Ib), (II), (III), or (IV), or a pharmaceutically acceptable salt, solvate, and/or ester thereof, and/or pro-drug thereof and at least one additional active agent selected from the group consisting of interferons, ribavirin analogs, HCV NS3 protease inhibitors, alpha-glucosidase 1 inhibitors, hepato-protectants, non-nucleoside inhibitors of HCV, and other drugs for treating HCV, or mixtures thereof.

In another embodiment, the present invention provides the use of a trisubstituted pyrido(3,2-d)pyrimidine derivative represented by the structural formulae (I), (Ia), (Ib), (II), (III), or (IV), or a pharmaceutically acceptable salt, solvate, and/or ester thereof, and/or pro-drug thereof, for the preparation of a medicament for treating a viral infection, e.g., an HBV/HCV infection.

In yet another embodiment, the present application provides a method for treating or preventing a viral infection comprising co-administering, to a patient in need thereof, a therapeutically effective amount of at least one a trisubstituted pyrido(3,2-d)pyrimidine derivative represented by the structural formulae (I), (Ia), (Ib), (II), (III), or (IV), and at least one additional bioactive agent selected from the group consisting of interferons, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta; ribavirin analogs, e.g., rebetol, copegus, and viramidine (taribavirin); NS5b polymerase inhibitors, e.g., NM-283, valopicitabine, R1626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-950 (telaprevir), BILN-2065, BMS-605339, and ITMN-191; alpha-glucosidase 1 inhibitors, e.g., MX-3253 (celgosivir) and UT-2318; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

The invention further relates to a pharmaceutical composition comprising:
(a) one or more pyrido(3,2-d)pyrimidine derivatives represented by the structural formulae (I), (Ia), (Ib), (II), (III), or (IV), and
(b) one or more pharmaceutically acceptable carriers.

In another embodiment, the compounds of the present invention are used in combination with other active therapeutic ingredients or agents. Combinations of the trisubstituted pyrido(3,2-d)pyrimidine derivatives represented by the structural formulae (I), (Ia), (Ib), (II), (III), or (IV), and additional bioactive agents may be selected to treat patients with a viral infection, e.g., HBV, HCV, or HIV infection. In this embodiment, the invention further provides combinations, preferably synergistic combinations, of one or more pyrido(3,2-d)pyrimidine derivatives represented by the general formulae (I), (Ia), (Ib), (II), (III), or (IV), with one or more antiviral agents. As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively. As will be explained in more detail herein below, this principle may be applied to a number of biologically desirable effects such as, but not limited to, an anti-viral activity against a Flaviridae virus, e.g. HCV.

Preferably, the other active therapeutic ingredients or agents are interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

In another embodiment, non-limiting examples of suitable combinations include combinations of one or more compounds of the present invention with one or more interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV.

More specifically, one or more compounds of the present invention may be combined with one or more compounds selected from the group consisting of:

1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha-2b XL, BLX-883 (Locteron), DA-3021, glycosylated interferon alpha-2b (AVI-005), PEG-Infergen, PEGylated interferon lambda-1 (PEGylated IL-29), and belerofon,
2) ribavirin and its analogs, e.g., ribavirin (Rebetol, Copegus), and taribavirin (Viramidine),
3) HCV NS3 protease inhibitors, e.g., boceprevir (SCH-503034, SCH-7), telaprevir (VX-950), TMC435350, BI-1335, BI-1230, MK-7009, VBY-376, VX-500, BMS-790052, BMS-605339, PHX-1766, AS-101, YH-5258, YH5530, YH5531, and ITMN-191,
4) alpha-glucosidase 1 inhibitors, e.g., celgosivir (MX-3253), Miglitol, and UT-231B,
5) hepatoprotectants, e.g., IDN-6556, ME 3738, LB-84451, silibilin, and MitoQ,
6) nucleoside or nucleotide inhibitors of HCV NS5B polymerase, e.g., R1626, R7128 (R4048), IDX184, IDX-102, BCX-4678, valopicitabine (NM-283), and MK-0608,
7) non-nucleoside inhibitors of HCV NS5B polymerase, e.g., PF-868554, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190,
8) HCV NS5A inhibitors, e.g., AZD-2836 (A-831), and A-689,
9) TLR-7 agonists, e.g., ANA-975, and SM-360320
10) cyclophillin inhibitors, e.g., DEBIO-025, SCY-635, and NIM811,
11) HCV IRES inhibitors, e.g., MCI-067,
12) pharmacokinetic enhancers, e.g., BAS-100, SPI-452, PF-4194477, TMC-41629, GS-9350 and roxythromycin,
13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, and VX-497 (merimepodib).

Combinations of the trisubstituted pyrido(3,2-d)pyrimidine derivatives represented by the structural formulae I, (Ia), (Ib), II, III, or IV are typically selected based on the condition to be treated, cross-reactivities of ingredients and pharmaco-properties of the combination. For example, when treating an infection (e.g., HCV), the compositions of the invention are combined with other active agents (such as those described herein).

It is also possible to combine any compound of the invention with one or more other active agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Co-administration includes administration of unit dosages of the compounds of the invention before or after administration of unit dosages of one or more other active agents, for example, administration of the compounds of the invention within seconds, minutes, or hours of the administration of one or more other active agents. For example, a unit dose of a compound of the invention can be administered first, followed within seconds or minutes by administration of a unit dose of one or more other active agents. Alternatively, a unit dose of one or more other active agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active agents. In other cases, it may be desirable to administer a unit dose of one or more other active agents first, followed, after a period of hours (e.g. from about 1 hour to about 12 hours), by administration of a unit dose of the compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1)

co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In an embodiment, the present invention discloses pharmaceutical compositions comprising one or more compounds of the present invention, e.g. trisubstituted pyrido(3,2-d)pyrimidine derivatives represented by the structural formulae I, (Ia), (Ib), II, III, or IV, or a pharmaceutically acceptable salt, solvate, and/or ester thereof, in combination with at least one additional active agent, and a pharmaceutically acceptable carrier or excipient.

According to the present invention, the active agent used in combination with the compound of the present invention can be any agent having a therapeutic effect when used in combination with the compound of the present invention. For example, the active agent used in combination with the compound of the present invention can be interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

In particular, the invention further relates to a pharmaceutical composition or combined preparation having synergistic effects against a hepatitis C infection and containing:
(a) one or more anti-viral agents, and
(b) at least one pyrido(3,2-d)pyrimidine derivative represented by the structural formulae I, (Ia), (Ib), II, III, or IV, and
(c) optionally one or more pharmaceutical excipients or pharmaceutically acceptable carriers,
for simultaneous, separate or sequential use in the treatment of HCV infection.

Alternatively, the present invention provides a pharmaceutical composition comprising:
a) a first pharmaceutical composition comprising a compound of the present invention, or a pharmaceutically acceptable salt, solvate, or ester thereof; and
b) a second pharmaceutical composition comprising at least one additional active agent selected from the group consisting of interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

In certain embodiments of the invention, suitable anti-viral agents for inclusion into the synergistic antiviral compositions or combined preparations of this invention include, for instance, ribavirin, (pegylated)interferon, and retroviral enzyme inhibitors belonging to categories well known in the art, such as HIV-1 IN inhibitors, nucleoside reverse transcriptase inhibitors (e.g. zidovudine, lamivudine, didanosine, stavudine, zalcitabine and the like), non-nucleoside reverse transcriptase inhibitors (e.g. nevirapine, delavirdine and the like), other reverse transcriptase inhibitors (e.g. foscamet sodium and the like), and HIV-1 protease inhibitors (e.g. saquinavir, ritonavir, indinavir, nelfinavir and the like). Other suitable antiviral agents include for instance acemannan, acyclovir, adefovir, alovudine, alvircept, amantadine, aranotin, arildone, atevirdine, pyridine, cidofovir, cipamfylline, cytarabine, desciclovir, disoxaril, edoxudine, enviradene, enviroxime, famciclovir, famotine, fiacitabine, fialuridine, floxuridine, fosarilate, fosfonet, ganciclovir, idoxuridine, kethoxal, lobucavir, memotine, methisazone, penciclovir, pirodavir, somantadine, sorivudine, tilorone, trifluridine, valaciclovir, vidarabine, viroxime, zinviroxime, moroxydine, podophyllotoxin, ribavirine, rimantadine, stallimycine, statolon, tromantadine and xenazoic acid, and their pharmaceutically acceptable salts.

In particular embodiments of the invention, suitable active agents or ingredients which can be combined with the new compounds of the present invention, especially pyrido(3,2-d) pyrimidine derivatives represented by the structural formulae I, (Ia), (Ib), II, III, or IV, can include interferons, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen actimmune, IFN-omega with DUROS, albuferon, locteron, Albuferon, Rebif, Oral interferon alpha, IFNalpha-2b XL, AVI-005, PEG-Infergen, and Pegylated IFN-beta; ribavirin analogs, e.g., rebetol, copegus, and viramidine (taribavirin); NS5b polymerase inhibitors, e.g., NM-283, valopicitabine, 81626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-950 (telaprevir), BILN-2065, BMS-605339, and ITMN-191; alpha-glucosidase 1 inhibitors, e.g., MX-3253 (celgosivir) and UT-231 B; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

Especially relevant to this aspect of the invention is the inhibition of the replication of viruses selected from the group consisting of picorna-, toga-, bunya, orthomyxo-, paramyxo-, rhabdo-, retro-, arena-, hepatitis B-, hepatitis C-, hepatitis D-, adeno-, vaccinia-, papilloma-, herpes-, corona-, varicella- and zoster-virus, in particular human immunodeficiency virus (HIV). Synergistic activity of the pharmaceutical compositions or combined preparations of this invention against viral infection may be readily determined by means of one or more tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration (hereinafter referred as FIC). When the minimum FIC index corresponding to the FIC of combined compounds (e.g., $FIC_x+FIC_y$) is equal to 1.0, the combination is said to be additive; when it is between 1.0 and 0.5, the combination is defined as sub-synergistic, and when it is lower than 0.5, the combination is by defined as synergistic. When the minimum FIC index is between 1.0 and 2.0, the combination is defined as subantagonistic and, when it is higher than 2.0, the combination is defined as antagonistic.

The pharmaceutical compositions or combined preparations with synergistic activity against viral infection according to this invention may contain the trisubstituted pyrido(3, 2-d)pyrimidine derivative represented by the structural formulae (I), (Ia), (Ib), (II), (III), or (IV) over a broad content range depending on the contemplated use and the expected effect of the preparation. The pyrido(3,2-d)pyrimidine derivative content of the combined preparation may be within a range of from about 1 to about 99% by weight, preferably from about 5 to about 95% by weight, more preferably from about 20 to 80% by weight.

The pharmaceutical compositions and combined preparations according to this invention may be administered orally or in any other suitable fashion. Oral administration is preferred and the preparation may have the form of a tablet, aqueous dispersion, dispersable powder or granule, emulsion, hard or soft capsule, syrup, elixir or gel. The dosing forms may be prepared using any method known in the art for manufacturing these pharmaceutical compositions and may comprise as additives sweeteners, flavoring agents, coloring agents, preservatives and the like. Carrier materials and excipients are detailed hereinbelow and may include, inter alia, calcium carbonate, sodium carbonate, lactose, calcium phosphate or sodium phosphate; granulating and disintegrating agents, binding agents and the like. The pharmaceutical composition or combined preparation of this invention may be included in a gelatin capsule mixed with any inert solid diluent or carrier material, or has the form of a soft gelatin capsule, in which the ingredient is mixed with a water or oil medium. Aqueous dispersions may comprise the biologically active composition or combined preparation in combination with a suspending agent, dispersing agent or wetting agent. Oil dispersions may comprise suspending agents such as a vegetable oil. Rectal administration is also applicable, for instance in the form of suppositories or gels. Injection (e.g. intramuscularly or intraperitoneously) is also applicable as a mode of administration, for instance in the form of injectable solutions or dispersions, depending upon the disorder to be treated and the condition of the patient.

The term "pharmaceutically acceptable carrier or excipient" as used herein in relation to pharmaceutical compositions and combined preparations means any material or substance with which the active principle, i.e. the pyrido(3,2-d) pyrimidine derivative represented by the general formulae (I), (Ia), (Ib), (II), (III), or (IV), and optionally the additional one or more antiviral agents, may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the pyrido(3,2-d)pyrimidine derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents. The compositions may also be prepared by micronisation, for instance in view to obtain them in the form of microspheres usually having a diameter of about 1 to 10 pm, namely for the manufacture of microcapsules for controlled or sustained release of the biologically active ingredient(s).

Suitable surface-active agents to be used in the pharmaceutical compositions of the present invention are non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphthalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidyiglycerine, lysolecithin, cardiolipin, dioctanyl-phosphatidylcholine, dipalmitoylphoshatidylcholine and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with polypropylene glycol, ethylenediamino-polypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having four hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-$C_{1-4}$ alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional ingredients may be included in order to control the duration of action of the biologically-active ingredient in the compositions and combined preparations of the invention. Control release compositions may thus be achieved by selecting appropriate polymer carriers such as for example polyesters, polyamino-acids, polyvinyl-pyrrolidone, ethylene-vinyl acetate copolymers, methylcellulose, carboxy-methylcellulose, protamine sulfate and the like. The rate of drug release and duration of action may also be controlled by incorporating the active ingredient into particles, e.g. microcapsules, of a polymeric substance such as hydrogels, polylactic acid, hydroxymethyl-cellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

Other modes of local drug administration can also be used. For example, the selected active agent may be administered topically, in an ointment, gel or the like, or transdermally, using a conventional transdermal drug delivery system.

Since, in the case of combined preparations including a pyrido(3,2-d)pyrimidine derivative of this invention and an additional active agent, in particular an antiviral agent, both ingredients do not necessarily bring out their synergistic therapeutic effect against the pathologic condition (viral infection) directly at the same time in the patient to be treated, the said combined preparation may be in the form of a medical kit or package containing the two ingredients in separate but adjacent form. In the latter context, each ingredient may therefore be formulated in a way suitable for an administration route different from that of the other ingredient, e.g. one of them may be in the form of an oral or parenteral formulation whereas the other is in the form of an ampoule for intravenous injection or an aerosol.

The present invention further relates to a method for treating hepatitis C in a patient, preferably a mammal, more preferably a human being. The method of this invention consists of administering to the patient in need thereof an effective amount of a trisubstituted pyrido(3,2-d)pyrimidine derivative having the general formula (Ia), wherein $R_3$ is not halogen, optionally together with an effective amount of an antiviral agent, or a pharmaceutical composition comprising the same, such as disclosed above in extensive details. The effective amount is usually in the range of about 0.01 mg to 20 mg, preferably about 0.1 mg to 5 mg, per day per kg bodyweight for humans. Depending upon the pathologic condition to be treated and the patient's condition, the said effective amount may be divided into several sub-units per day or may be administered at more than one day intervals. The patient to be treated may be any warm-blooded animal, preferably a mammal, more preferably a human being, suffering from said pathologic condition.

In certain embodiments, preferred compounds of the present invention are non-sedating. In other words, a dose of such compounds that is twice the minimum dose sufficient to provide analgesia in an animal model for determining pain relief causes only transient (i.e. lasting for no more than half the time that pain relief lasts) or preferably no statistically significant sedation in an animal model assay of sedation (using the method described by Fitzgerald et al. in *Toxicology* (1988) 49:433-9). Preferably, a dose that is five times the minimum dose sufficient to provide analgesia does not produce statistically significant sedation. More preferably, a compound provided herein does not produce sedation at intravenous doses of less than 10 mg/kg per day or at oral doses of less than 30 mg/kg per day. If desired, compounds provided herein may be evaluated for toxicity (a preferred compound is non-toxic when an antiviral amount is administered to a subject) and/or side effects (a preferred compound produces side effects comparable to placebo when a therapeutically effective amount of the compound is administered to a subject). Toxicity and side effects may be assessed using any standard method. In general, the term "non-toxic" as used herein shall be understood as referring to any substance that, in keeping with established criteria, is susceptible to approval by the United States Federal Drug Administration for administration to mammals, preferably humans. Toxicity may be also evaluated using assays including bacterial reverse mutation assays, such as an Ames test, as well as standard teratogenicity and tumorogenicity assays. Preferably, administration of compounds provided herein within the therapeutic dose ranges disclosed hereinabove does not result in prolongation of heart QT intervals (e.g. as determined by electrocardiography in guinea pigs, minipigs or dogs). When administered daily, such doses also do not cause liver enlargement resulting in an increase of liver to body weight ratio of more than 50% over matched controls in laboratory rodents (e.g. mice or rats). Such doses also preferably do not cause liver enlargement resulting in an increase of liver to body weight ratio of more than 10% over matched untreated controls in dogs or other non-rodent mammals.

Another embodiment of this invention includes the various precursors or "pro-drug" forms of the trisubstituted pyrido(3,2-d)pyrimidine derivatives having the general formula (Ia), wherein $R_3$ is not halogen, or formula (Ib) of the present invention. It may be desirable, under specific circumstances, to formulate the compounds of the present invention in the form of a chemical species which itself is not significantly biologically-active, but which when delivered to the body of a human being or higher mammal will undergo a chemical reaction catalyzed by the normal function of the body, inter alia, enzymes present in the stomach or in blood serum, said chemical reaction having the effect of releasing a compound as defined herein. The term "pro-drug" thus relates to these species which are converted in vivo into the active pharmaceutical ingredient.

The pro-drugs of the present invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used.

For the purpose of the present invention the term "therapeutically suitable pro-drug" is defined herein as a compound modified in such a way as to be transformed in vivo to the therapeutically active form, whether by way of a single or by multiple biological transformations, when in contact with the tissues of humans or mammals to which the pro-drug has been administered, and without undue toxicity, irritation, or allergic response, and achieving the intended therapeutic outcome.

In another embodiment, the present invention provides methods of inhibiting a viral polymerase in a cell, in particular HCV polymerase. The method comprises the step of contacting a cell infected with a virus, in particular HCV, with an effective amount of a compound of the present invention as described herein, e.g. trisubstituted pyrido(3,2-d)pyrimidine derivative represented by the structural formula (Ia) or the structural formula (Ib), or a pharmaceutically acceptable salt, solvate, and/or ester thereof, and/or pro-drug thereof, whereby HCV polymerase is inhibited.

In another embodiment, the present invention provides methods of inhibiting a viral polymerase in a cell, in particular HCV polymerase, comprising contacting a cell infected with a virus, in particular HCV with an effective amount of a trisubstituted pyrido(3,2-d)pyrimidine derivative represented by the structural formulae I, (Ia), (Ib), II, III, or IV, or a pharmaceutically acceptable salt, solvate, and/or ester thereof, and at least one additional active agent, whereby HCV polymerase is inhibited.

In a particular embodiment, the present application provides for methods of inhibiting HCV polymerase in a cell, comprising: contacting a cell infected with HCV with an effective amount of a trisubstituted pyrido(3,2-d)pyrimidine derivative represented by the structural formulae I, (Ia), (Ib), II, III, or IV, or a pharmaceutically acceptable salt, solvate, and/or ester thereof, and at least one additional active agent selected from the group consisting of interferons, ribavirin analogs, HCV NS3 protease inhibitors, alpha-glucosidase 1 inhibitors, hepatoprotectants, non-nucleoside inhibitors of HCV, and other drugs for treating HCV.

The present invention will be further described with reference to certain more specific embodiments, detailed schemes and examples, but the present invention is not limited thereto but only by the attached claims. The following examples are given by way of illustration only.

EXAMPLE 1

Synthesis of 6-(4-Fluoro-phenyl)-N2-(3-[1,2,4]-triazol-1-yl-benzyl)-N4-(2,2,2-trifluoro-ethyl)-pyrido[3,2-d]pyrimidine-2,4-diamine

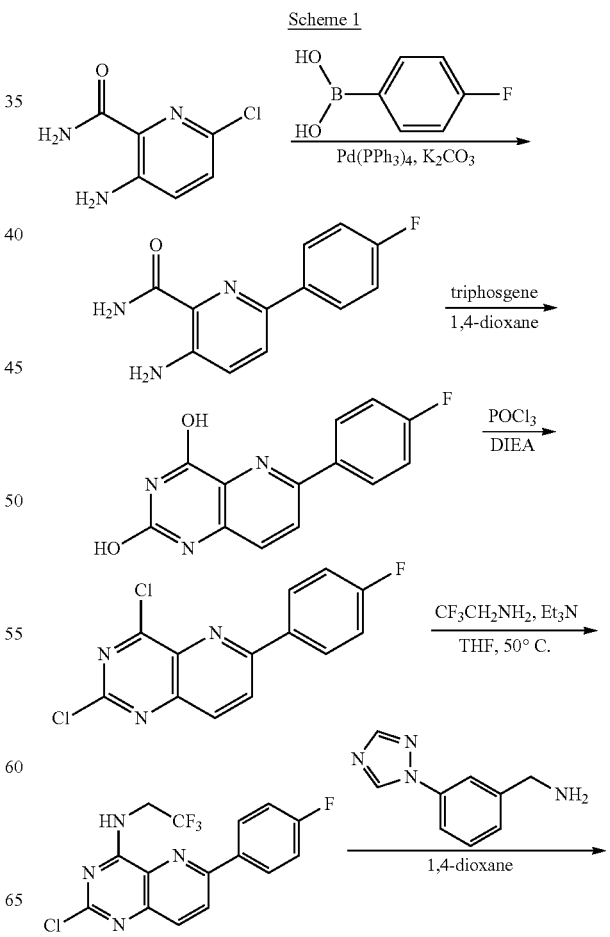

Scheme 1

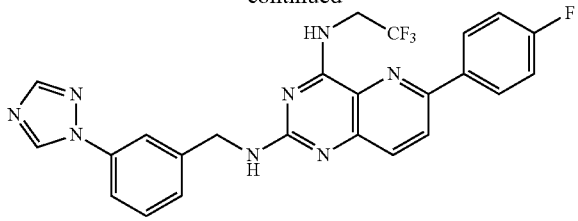

A mixture of 3-amino-6-chloro-pyridine-2-carboxylic acid amide (2 g), potassium carbonate (3.2 g), tetrakis(triphenylphosphine) palladium (0.674 g) and 4-fluorophenylboronic acid (1.79 g) in DMF (50 mL) and water (10 mL) was heated to 120° C. for 16 hours. Solvents were removed and 1N HCl (30 ml) was added to the mixture. The resulting solid was filtered to provide 2.48 g of 3-amino-6-(4-fluorophenyl)picolinamide which was characterized by its mass spectrum as follows: MS (m/z) 232 [M+H]+.

A solution of 3-amino-6-(4-fluorophenyl)picolinamide (2.48 g) and triphosgene in 1,4-dioxane (50 mL) was heated to 100° C. for 1 hour. Cooling and filtration provided 2.2 g of 6-(4-fluorophenyl)pyrido[3,2-c]pyrimidine-2,4-diol which was characterized by its mass spectrum as follows: MS (m/z) 258 [M+H]+.

A solution of 6-(4-fluorophenyl)pyrido[3,2-d]pyrimidine-2,4-diol (1 g), POCl$_3$ (20 ml) and DIEA (2.0 ml) was heated to reflux for 16 hours. POCl$_3$ was removed and the residue was dissolved in ethyl acetate. The organic layer was extracted with brine three times. It was dried and concentrated to provide 0.97 g of 2,4-dichloro-6-(4-fluorophenyl) pyrido[3,2-d]pyrimidine which was characterized by its mass spectrum as follows: MS (m/z) 294 [M+H]+.

2,4-Dichloro-6-(4-fluoro-phenyl)-pyrido[3,2-d]pyrimidine (5.00 g, 17.00 mmol, see Scheme 1 above) was suspended in THF (50 mL) and treated with triethylamine (3.60 ml, 25.5 mmol) followed by 2,2,2-trifluoro-ethylamine (2.01 mL, 25.5 mmol) and stirred at ambient temperature. After 2 hours, water (approx, 75 mL) was added resulting in an oily biphasic mixture. THF was added until the mixture became homogenous. The THF was removed by evaporation resulting in an orange precipitate. A small amount of THF (10-15 mL) was added and the mixture was stirred 2-3 h. The light orange solid was filtered, washed with water, and dried to 5.45 g (90%). This material was used without further purification in the next step.

A mixture of [2-Chloro-6-(4-fluoro-phenyl)-pyrido[3,2-d] pyrimidin-4-yl]-(2,2,2-trifluoro-ethyl)-amine (108 mg) and 3-[1,2,4]Triazol-1-yl-benzylamine (124 mg) was dissolved in NMP (1.9 mL) and treated with diisopropylethylamine (0.060 mL). The reaction mixture was sealed and heated by microwave to 160° C. for 1 h. After cooling, the reaction mixture was added dropwise to a stirred solution of water: acetonitrile (1:1). The resulting precipitate was filtered and purified by silica gel chromatography (0-10% EtOH (containing 11% NH4OH sat aq):DCM) to afford 89 mg (60% yield) of the title compound, which was characterized by its NMR and mass spectrum as follows: $^1$H NMR (d$_6$-DMSO): d 4.29-4.41 (m, 2H), 4.63-4.66 (m, 2H), 7.29-7.35 (m, 2H), 7.40-7.51 (m, 2H), 7.70-7.75 (m, 3H), 7.87 (s, 1H), 8.19-8.22 (m, 2H), 8.36-8.39 (m, 2H), 8.61-8.64 (m, 1H), 9.25 (s, 1H); MS (m/z): 495.3 ([M+H]+, 100).

EXAMPLE 2

Synthesis of 6-(4-Fluoro-phenyl)-N2-(3-pyrazol-1-yl-benzyl)-N4-(2,2,2-trifluoro-ethyl)-pyrido[3,2-d] pyrimidine-2,4-diamine

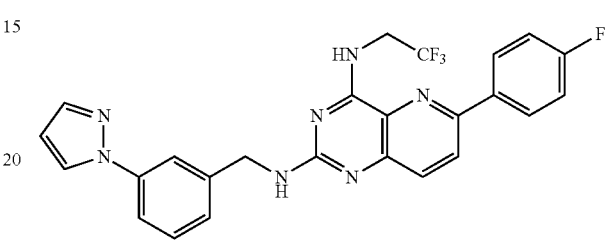

The title compound was synthesized in a manner analogous to Example 1, using 3-Pyrazol-1-yl-benzylamine in place of 3-[1,2,4]Triazol-1-yl-benzylamine, and was characterized by its NMR and mass spectrum as follows: $^1$H NMR (d$_6$-DMSO): d 4.28-4.42 (m, 2H), 4.63 (d, 2H), 6.51-6.53 (m, 1H), 7.29-7.43 (m, 4H), 7.65-7.74 (m, 4H), 7.86 (s, 1H), 8.19 (d, 1H), 8.35-8.44 (m, 3H), 8.61-8.63 (m, 1H); MS (m/z): 494.2 ([M+H]+, 100).

EXAMPLE 3

Synthesis of 2-Fluoro-4-{[6-(4-fluoro-phenyl)-4-(2, 2,2-trifluoro-ethylamino)-pyrido[3,2-d]pyrimidin-2-ylamino]-methyl}-benzenesulfonamide

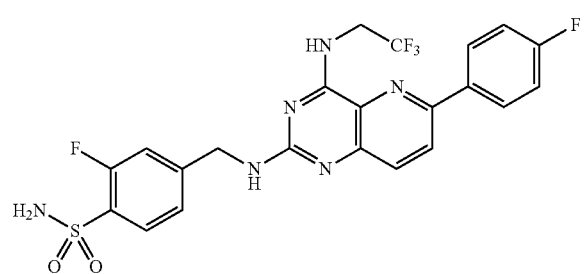 [SMILES: NS(=O)(=O)c1ccc(CNc2nc(NCC(F)(F)F)c3nc(-c4ccc(F)cc4)ccc3n2)cc1F]

The title compound was synthesized in a manner analogous to Example 1, using 4-Aminomethyl-N-tert-butyl-2-fluoro-benzenesulfonamide in place of 3-[1,2,4]Triazol-1-yl-benzylamine and removal of the t-butyl protecting group in a final step by stirring in trifluoroacetic acid at room temperature, and was characterized by its NMR and mass spectrum as follows: $^1$H NMR (d$_6$-DMSO): d 4.32-4.36 (m, 2H), 4.59 (d, 2H), 7.17-7.35 (m, 6H), 7.69-7.74 (m, 3H), 8.20 (d, 1H), 8.35-8.40 (m, 2H), 8.65 (s, 1H); MS (m/z): 525.1 ([M+H]+, 100).

4-Aminomethyl-N-tert-butyl-2-fluoro-benzenesulfonamide was synthesized as follows:

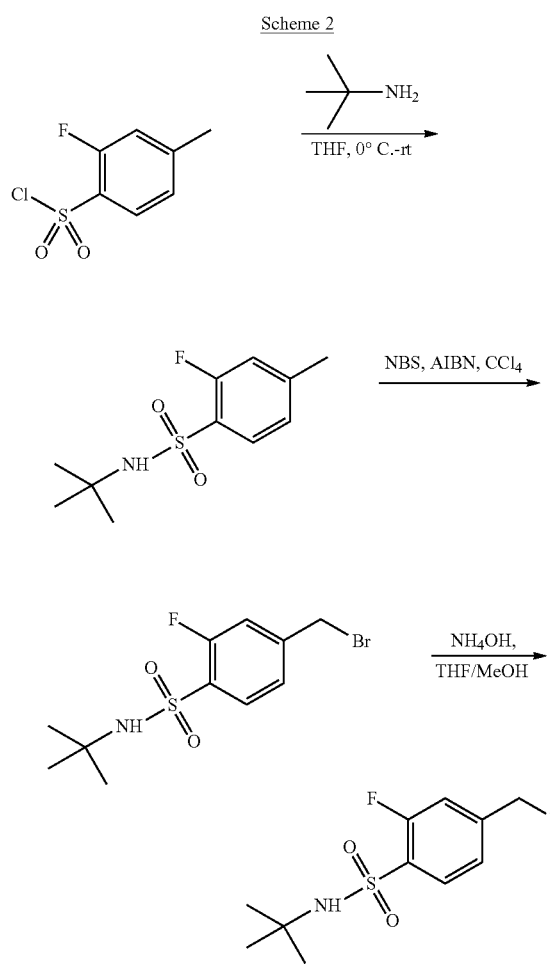

Scheme 2

EXAMPLE 4

Synthesis of 4-{[6-(4-Fluoro-phenyl)-4-(2,2,2-trifluoro-ethylamino)-pyrido[3,2-d]pyrimidin-2-ylamino]-methyl}-3-methyl-benzenesulfonamide

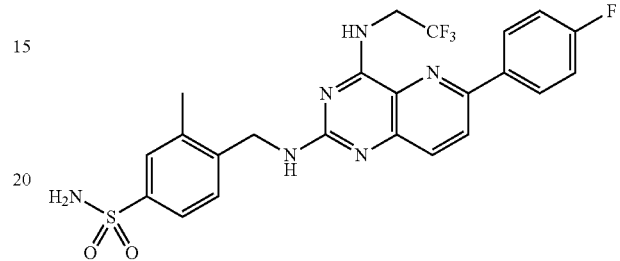

The title compound was synthesized in a manner analogous to Example 1, using 4-Aminomethyl-N-tert-butyl-3-methyl-benzenesulfonamide in place of 3-[1,2,4]Triazol-1-yl-benzylamine and removal of the t-butyl protecting group in a final step by stirring in trifluoroacetic acid at room temperature, and was characterized by its NMR and mass spectrum as follows: $^1$H NMR ($d_6$-DMSO): d 2.38 (s, 3H), 4.33-4.36 (m, 2H), 4.60-4.73 (m, 2H), 7.24 (s, 2H), 7.31-7.44 (m, 3H), 7.53-7.61 (m, 2H), 7.95 (d, 1H), 8.37-8.45 (m, 3H), 9.06 (bs, 1H), 9.92 (bs, 1H); MS (m/z): 521.1 ([M+H]$^+$, 100).

4-Aminomethyl-N-tert-butyl-3-methyl-benzenesulfonamide was synthesized as follows:

To an ice cooled solution of tert-butylamine (12.55 ml) in THF (60 ml) was added a solution of 2-fluoro-4-methylbenzene-1-sulfonyl chloride (5 g) in THF (25 ml), dropwise. After stirring for 15 min at 0° C., the reaction mixture was allowed to warm and stirred at room temperature for 2 hours. The HCl salt was removed by filtration and the filtrate was concentrated to give a yellow residue, which was triturated with Et$_2$O and Hexanes to give 5.10 g N-tert-butyl-2-fluoro-4-methylbenzenesulfonamide as an off-white granular solid.

A mixture of N-tert-butyl-2-fluoro-4-methylbenzenesulfonamide (2 g), NBS (1.16 g) and AIBN (40 mg) in CCl$_4$ (25 ml) was refluxed for 3 hours. The reaction mixture was cooled, filtered and concentrated to give a viscous syrup, which was purified by silica gel column chromatography to give 1.68 g 4-(bromomethyl)-N-tert-butyl-2-fluorobenzenesulfonamide as a colorless crystal solid.

To a solution of 4-(bromomethyl)-N-tert-butyl-2-fluorobenzenesulfonamide (500 mg) in THF/MeOH (1:1, 15 ml) was added NH$_4$OH (4.5 ml). The mixture was stirred at room temperature overnight. The reaction mixture was concentrated and partitioned between EtOAc/H$_2$O and the aq phase was extracted by EtOAc (3×). The organic phase was then combined, washed with brine, dried over Na$_2$SO$_4$ and concentrated to give 4-(aminomethyl)-N-tert-butyl-2-fluorobenzenesulfonamide as a viscous oil, which was used in the next step without further purification.

Scheme 3

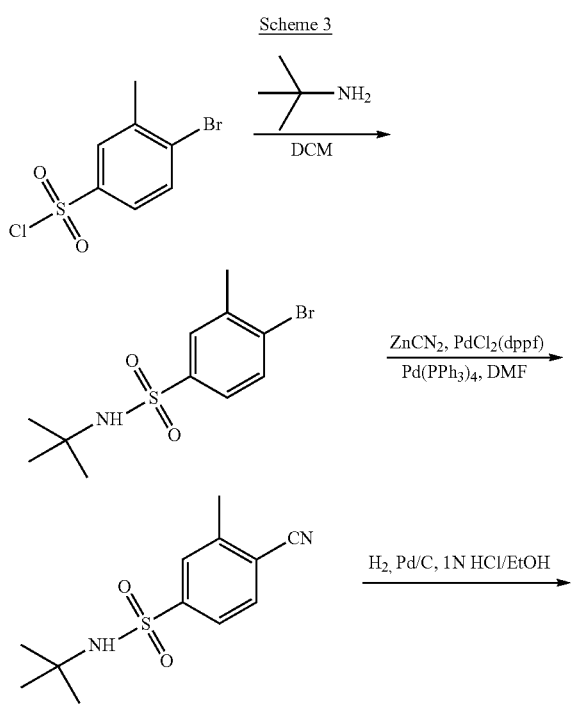

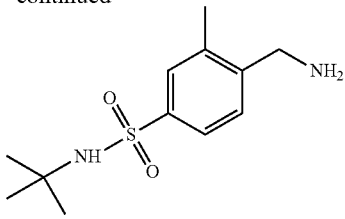

To a solution of 4-bromo-3-methylbenzene-1-sulfonyl chloride (1.50 g) in dichloromethane (10 ml) at 0° C. was added tert-butylamine (1.5 ml). The reaction mixture was allowed to warm to and stirred at room temperature overnight. The reaction mixture was diluted with dichloromethane, washed with 1N HCl and with sat. aq. NaHCO$_3$ solution. The organic layer was dried (MgSO$_4$) and concentrated to give 1.20 g 4-bromo-N-tert-butyl-3-methylbenzenesulfonamide as a white solid.

A mixture of 4-bromo-N-tert-butyl-3-methylbenzene-sulfonamide (1.207 g) and zinc cyanide (0.976 g) in DMF (8 ml) was purged with N$_2$ for 20 min. Then PdCl$_2$(dppf) was added. The reaction mixture was heated at 120° C. for 4 hours and showed no reaction. Pd(PPh$_3$)$_4$ was added and the reaction mixture was stirred at 120° C. over the weekend. The reaction mixture was diluted with EtOAc and washed with 5% LiCl solution (2×). The combined organic layers were dried (MgSO$_4$), concentrated and purified by silica gel column chromatography to give 1.227 g N-tert-butyl-4-cyano-3-methylbenzenesulfonamide as a white solid.

The reaction mixture of N-tert-butyl-4-cyano-3-methyl-benzenesulfonamide (0.7176 g) and Pd/C (0.97 g) in 1N HCl/EtOH (1.5 ml 1N HCl in 15 ml EtOH) was stirred under H$_2$ for 2 hours. Then 1N HCl (3 ml) was added to improve the reaction progress and it was stirred overnight. The reaction mixture was filtered through a pad of diatomaceous earth, washed with MeOH and concentrated to about 3 ml. The residue was diluted with H$_2$O and lyophilized to give 0.8275 g 4-(aminomethyl)-N-tert-butyl-3-methylbenzenesulfonamide as white powder.

EXAMPLE 5

Synthesis of 2-Chloro-4-{[6-(4-fluoro-phenyl)-4-(2,2,2-trifluoro-ethylamino)-pyrido[-3,2-d]pyrimidin-2-ylamino]-methyl}-benzenesulfonamide

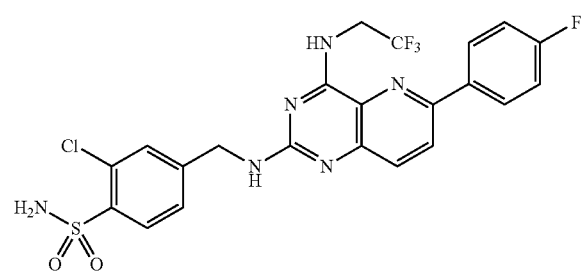

The title compound was synthesized in a manner analogous to Example 1, using 4-Aminomethyl-N-tert-butyl-2-chloro-benzenesulfonamide in place of 3-[1,2,4]Triazol-1-yl-benzylamine and removal of the t-butyl protecting group in a final step by stirring in trifluoroacetic acid at room temperature, and was characterized by its NMR and mass spectrum as follows: $^1$H NMR (d$_6$-DMSO): d 4.40-4.46 (m, 2H), 4.72-4.79 (m, 2H), 7.36-7.65 (m, 6H), 7.91-7.99 (m, 2H), 8.38-8.48 (m, 3H), 9.07 (bs, 1H), 9.97 (bs, 1H); MS (m/z): 541.1 ([M+H]$^+$, 100).

4-Aminomethyl-N-tert-butyl-2-chloro-benzenesulfonamide was synthesized in a manner analogous to 4-Aminomethyl-N-tert-butyl-3-methyl-benzenesulfonamide in Example 4, using 4-bromo-2-chlorobenzene-1-sulfonyl chloride in place of 4-bromo-3-methylbenzene-1-sulfonyl chloride. In the second step NMP was used as the solvent, Pd(dppf)Cl$_2$ alone was used as catalyst and the reaction mixture was stirred at 150° C. for 30 min, then heated at 120° C. overnight. Reduction of the cyano group to aminomethyl group in the last step was achieved by stirring with lithium aluminium hydride from 0° C. to room temperature in THF.

EXAMPLE 6

Synthesis of 5-{[6-(4-Fluoro-phenyl)-4-(2,2,2-trifluoro-ethylamino pyrido[3,2-d]pyrimidin-2-ylamino]-methyl}-2-methoxy-benzenesulfonamide

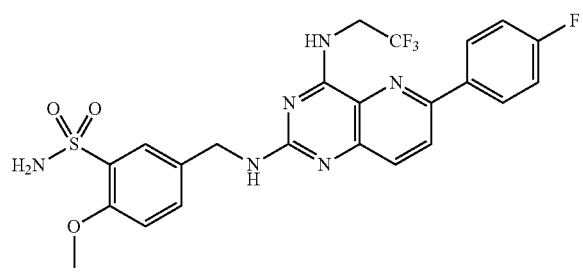 [SMILES: COc1ccc(CNc2nc(NCC(F)(F)F)c3nc(-c4ccc(F)cc4)ccc3n2)cc1S(N)(=O)=O]

The title compound was synthesized in a manner analogous to Example 1, using 5-Aminomethyl-N-tert-butyl-2-methoxy-benzenesulfonamide in place of 3-[1,2,4]Triazol-1-yl-benzylamine and removal of the t-butyl protecting group in a final step by stirring in trifluoroacetic acid at room temperature, and was characterized by its NMR and mass spectrum as follows: $^1$H NMR (d$_6$-DMSO): d 3.88 (s, 3H), 4.41-4.49 (m, 2H), 4.63-4.69 (m, 2H), 7.04 (s, 2H), 7.14-7.18 (m, 1H), 7.36-7.40 (m, 2H), 7.58-7.61 (m, 1H), 7.82 (d, 1H), 7.94-7.98 (m, 1H), 8.42-8.46 (m, 3H); MS (m/z): 537.1 ([M+H]$^+$, 100).

5-Aminomethyl-N-tert-butyl-2-methoxy-benzenesulfonamide was synthesized in a manner analogous to 4-Aminomethyl-N-tert-butyl-2-chloro-benzenesulfonamide in Example 5, using 5-bromo-2-methoxybenzene-1-sulfonyl chloride in place of 4-bromo-3-methylbenzene-1-sulfonyl chloride.

EXAMPLE 7

Synthesis of 2-Fluoro-5-{[6-(4-fluoro-phenyl)-4-(2,2,2-trifluoro-ethylamino)-pyrido[3,2-d]pyrimidin-2-ylamino]-methyl}-benzenesulfonamide

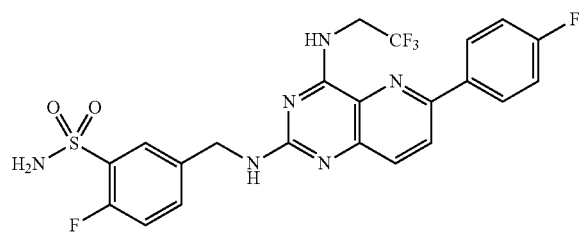 [SMILES: NS(=O)(=O)c1cc(CNc2nc(NCC(F)(F)F)c3nc(-c4ccc(F)cc4)ccc3n2)ccc1F]

The title compound was synthesized in a manner analogous to Example 1, using 5-Aminomethyl-N-tert-butyl-2-fluoro-benzenesulfonamide in place of 3-[1,2,4]Triazol-1-yl-benzylamine and removal of the t-butyl protecting group in a final step by stirring in trifluoroacetic acid at room temperature, and was characterized by its NMR and mass spectrum as follows: $^1$H NMR (d$_6$-DMSO): d 4.40-4.47 (m, 2H), 4.68-4.76 (m, 2H), 7.35-7.41 (m, 3H), 7.65-7.70 (m, 3H), 7.84 (d, 1H), 7.97 (d, 1H), 8.40-8.48 (m, 3H), 9.12 (bs, 1H), 9.99 (bs, 1H); MS (m/z): 525.2 ([M+H]$^+$, 100).

5-Aminomethyl-N-tert-butyl-2-fluoro-benzenesulfonamide was synthesized in a manner analogous to 4-Aminomethyl-N-tert-butyl-3-methyl-benzenesulfonamide in Example 4, using 5-chloro-2-fluorobenzene-1-sulfonyl chloride in place of 4-bromo-3-methylbenzene-1-sulfonyl chloride. In the second step NMP was used as the solvent, Pd(dppf)Cl$_2$ alone was used as catalyst and the reaction mixture was stirred at 120° C. for 15 hours.

EXAMPLE 8

Synthesis of 3-{[6-(4-Fluoro-phenyl)-4-(2,2,2-trifluoro-ethylamino)-pyrido[3,2-d]pyrimidin-2-ylamino]-methyl}-5-trifluoromethyl-benzenesulfonamide

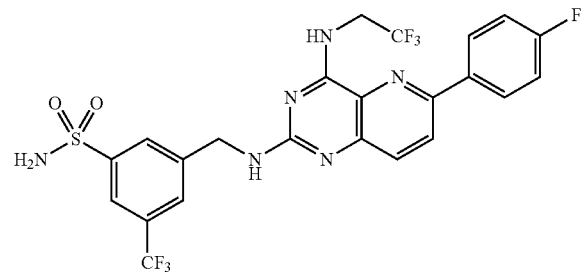 [SMILES: NS(=O)(=O)c1cc(CNc2nc(NCC(F)(F)F)c3nc(-c4ccc(F)cc4)ccc3n2)cc(C(F)(F)F)c1]

The title compound was synthesized in a manner analogous to Example 1, using 3-Aminomethyl-N-tert-butyl-5-trifluoromethyl-benzenesulfonamide in place of 3-[1,2,4]Triazol-1-yl-benzylamine and removal of the t-butyl protecting group in a final step by stirring in trifluoroacetic acid at room temperature, and was characterized by its NMR and mass spectrum as follows: $^1$H NMR (d$_6$-DMSO): d 4.37-4.44 (m, 2H), 4.84-4.90 (m, 2H), 7.35-7.41 (m, 2H), 7.59 (s, 2H), 7.97-8.12 (m, 4H), 8.41-8.50 (m, 3H), 9.34 (bs, 1H), 9.98 (bs, 1H); MS (m/z): 575.3 ([M+H]$^+$, 100).

3-Aminomethyl-N-tert-butyl-5-trifluoromethyl-benzenesulfonamide was synthesized in a manner analogous to 4-Aminomethyl-N-tert-butyl-3-methyl-benzenesulfonamide in Example 4, using 3-bromo-5-(trifluoromethyl)benzene-1-sulfonyl chloride in place of 4-bromo-3-methylbenzene-1-sulfonyl chloride. In the second step NMP was used as the solvent, Pd(dppf)Cl$_2$ alone was used as catalyst and the reaction mixture was stirred at 150° C. for 30 min.

EXAMPLE 9

Synthesis of 4-{[6-(4-Fluoro-phenyl)-4-(2,2,2-trifluoro-ethylamino)-pyrido[3,2-d]pyrimidin-2-ylamino]-methyl}-2-trifluoromethyl-benzenesulfonamide

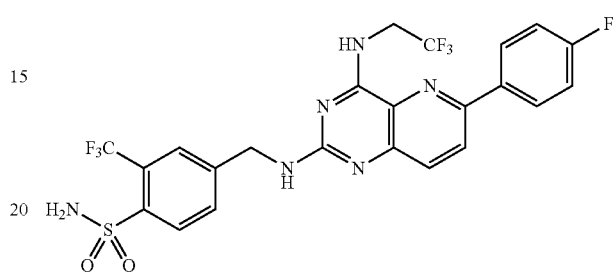

The title compound was synthesized in a manner analogous to Example 1, using 4-Aminomethyl-N-tert-butyl-2-trifluoromethyl-benzenesulfonamide in place of 3-[1,2,4]Triazol-1-yl-benzylamine and removal of the t-butyl protecting group in a final step by stirring in trifluoroacetic acid at room temperature, and was characterized by its NMR and mass spectrum as follows: $^1$H NMR (d$_6$-DMSO): d 4.38-4.46 (m, 2H), 4.79-4.88 (m, 2H), 7.35-7.41 (m, 2H), 7.69 (s, 2H), 7.85 (d, 1H), 7.95-7.98 (m, 2H), 8.11 (d, 1H), 8.41-8.49 (m, 3H), 9.24 (bs, 1H), 9.94 (bs, 1H); MS (m/z): 575.3 ([M+H]$^+$, 100).

4-Aminomethyl-N-tert-butyl-2-trifluoromethyl-benzenesulfonamide was synthesized in a manner analogous to 4-Aminomethyl-N-tert-butyl-3-methyl-benzenesulfonamide in Example 4, using 4-bromo-2-(trifluoromethyl)benzene-1-sulfonyl chloride in place of 4-bromo-3-methylbenzene-1-sulfonyl chloride. In the second step, K$_4$-[Fe(CN)$_6$].3H$_2$O was used in place of Zn(CN)$_2$, Pd(OAc)$_2$/dppf was used as the catalyst, Na$_2$CO$_3$ was used as base and the reaction mixture was stirred at 110° C. with microwave irradiation for one hour.

EXAMPLE 10

Synthesis of 4-{1-[6-(4-Fluoro-phenyl)-4-(2,2,2-trifluoro-ethylamino)-pyrido[3,2-d]pyrimidin-2-ylamino]-ethyl}-3-methyl-benzenesulfonamide

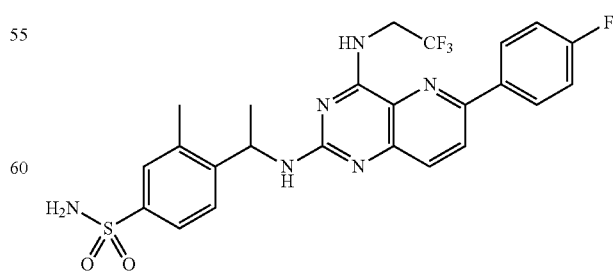

The title compound was synthesized in a manner analogous to Example 1, using 4-(1-Amino-ethyl)-N-tert-butyl-3- methyl-benzenesulfonamide in place of 3-[1,2,4]-Triazol-1-yl-benzylamine and removal of the t-butyl protecting group in a final step by stirring in trifluoroacetic acid at room temperature, and was characterized by its NMR and mass spectrum as follows: $^1$H NMR (d$_6$-DMSO): d 1.44-1.46 (m, 6H), 4.30-4.34 (m, 2H), 5.38-5.40 (m, 1H), 7.21-7.59 (m, 7H), 7.92-7.94 (m, 1H), 8.37-8.39 (m, 3H); MS (m/z): 535.1 ([M+H]$^+$, 100).

4-(1-Amino-ethyl)-N-tert-butyl-3-methyl-benzenesulfonamide was synthesized as follows:

butyl-benzenesulfonamide in place of 3-[1,2,4]Triazol-1-yl-benzylamine and removal of the t-butyl protecting group in a final step by stirring in trifluoroacetic acid at room temperature, and was characterized by its NMR and mass spectrum as follows: $^1$H NMR (d$_6$-DMSO): d 0.89 (t, 3H), 1.81-1.92 (m, 2H), 4.27-4.46 (m, 2H), 4.98-5.16 (m, 1H), 7.29-7.36 (m, 4H), 7.48-7.53 (m, 1H), 7.60-7.70 (m, 2H), 7.84-7.95 (m, 2H), 8.35-8.42 (m, 3H); 9.17 (bs, 1H), 9.86 (bs, 1H); MS (m/z): 535.1 ([M+H]$^+$, 100).

(R)-2-(1-Amino-propyl)-N-tert-butyl-benzenesulfonamide was synthesized as follows:

Scheme 4

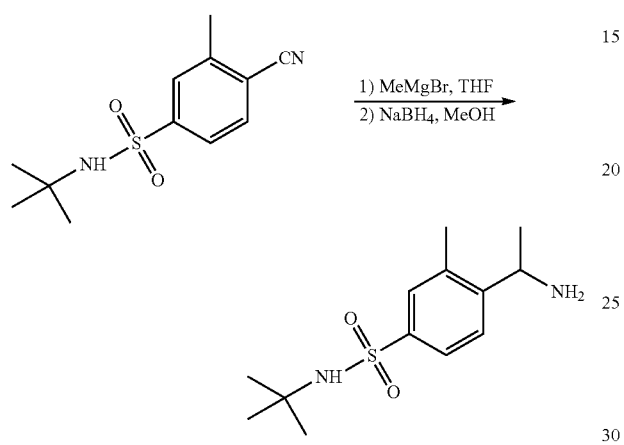

A solution of N-tert-butyl-4-cyano-3-methylbenzenesulfonamide (0.4861 g) in THF (19 ml) at 0° C. was treated with MeMgBr (1.4 M in THF, 4.13 ml). The reaction mixture was heated at reflux overnight. After cooling, the reaction was quenched with MeOH and sodium borohydride (3 eq) was added. The mixture was stirred at 0° C. for 1 h, warmed to room temperature and stirred for 4 hours. The reaction mixture was then quenched with H$_2$O, stirred overnight and concentrated to give a yellow solid. The solid was partitioned between EtOAc/H$_2$O and the organic layer was separated, dried (MgSO$_4$) and concentrated to give a yellow oil. The oil was purified by reverse phase HPLC (5-100% ACN/H$_2$O+ 0.1% TFA) to give 0.3403 g 4-(1-aminoethyl)-N-tert-butyl-3-methylbenzenesulfonamide as white powder after lyophilization.

EXAMPLE 11

Synthesis of (R)-2-{1-[6-(4-Fluoro-phenyl)-4-(2,2,2-trifluoro-ethylamino)-pyrido[3,2-d]pyrimidin-2-ylamino]-propyl}-benzenesulfonamide

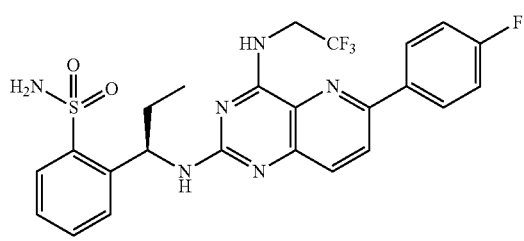 [SMILES: CC[C@@H](Nc1nc(NCC(F)(F)F)c2nc(-c3ccc(F)cc3)ccc2n1)c1ccccc1S(N)(=O)=O]

The title compound was synthesized in a manner analogous to Example 1, using (R)-2-(1-Amino-propyl)-N-tert- Scheme 5

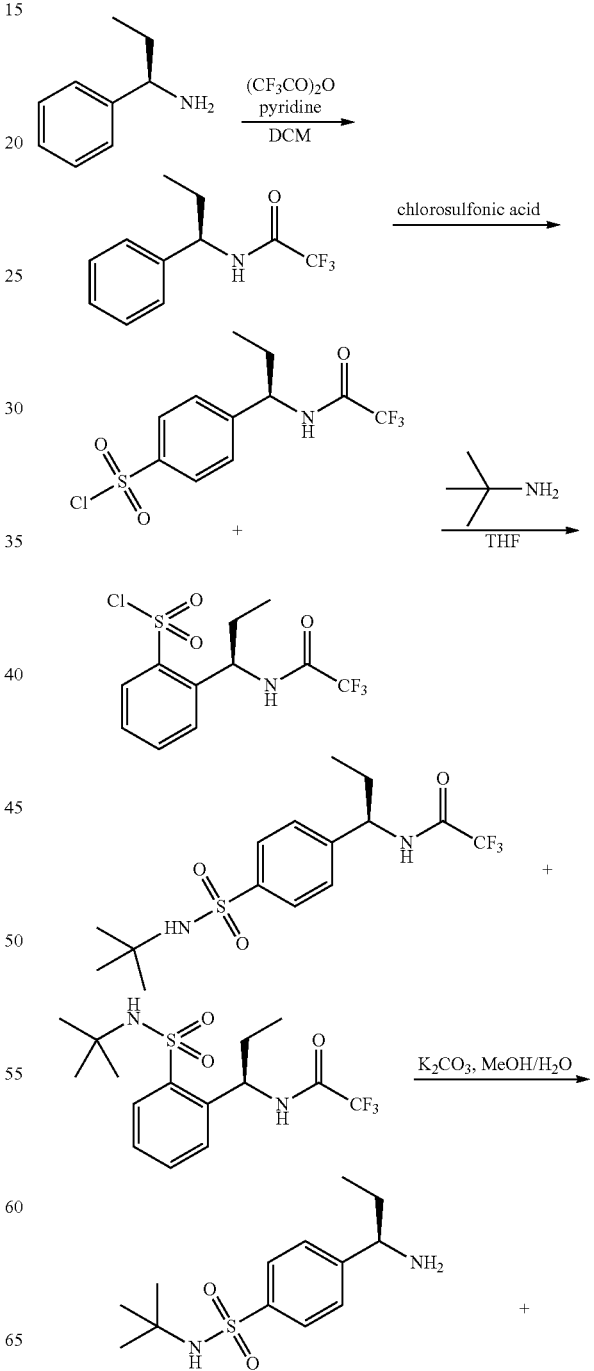

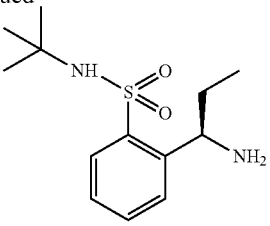

To a solution of (R)-1-phenylpropan-1-amine (2.5 g) in dichloromethane at 0° C. was added trifluoroacetic anhydride (3.13 ml), followed by pyridine (4.52 ml) to give a yellow solution. The reaction mixture was stirred at room temperature overnight. The mixture was diluted with EtOAc and washed with 1N HCl, sat. aq. NaHCO$_3$ solution and brine. The organic layer was dried (MgSO$_4$), concentrated and purified by silica gel column chromatography to give 2.55 g (R)-2,2,2-trifluoro-N-(1-phenylpropyl)acetamide as a white solid.

To a solution of chlorosulfonic acid (3.1 ml) in THF (5 ml) under Ar at 0° C. was added (R)-2,2,2-trifluoro-N-(1-phenylpropyl)acetamide (1.0822 g) and the reaction mixture was stirred at 0° C. for 3.5 hours. The reaction was quenched with ice and diluted with EtOAc. The organic layer was washed with brine, dried (MgSO$_4$) and concentrated to give an orange oil. The oil was diluted with THF and cooled to 0° C. To the mixture, tert-butylamine (3.0 ml) was added. The reaction mixture was stirred for 20 min, then concentrated and purified by silica gel column chromatography to give 0.501 g mixture of (R)-4-(1-(2,2,2-trifluoroacetamido)propyl)-N-tert-butyl-benzenesulfonamide and (R)-2-(1-(2,2,2-trifluoroacetamido)propyl)-N-tert-butyl-benzenesulfonamide as a yellow foam.

A mixture of (R)-4-(1-(2,2,2-trifluoroacetamido)propyl)-N-tert-butyl-benzenesulfonamide and (R)-2-(1-(2,2,2-trifluoroacetamido)propyl)-N-tert-butyl-benzenesulfonamide (0.501 g), K$_2$CO$_3$ (0.947 g) in MeOH/H$_2$O (1:1, 20 ml) was stirred at room temperature overnight and then heated at 60° C. for 3 hours. The reaction mixture was cooled to room temperature and concentrated to about 3 ml. The residue was acidified with TFA to ca. pH 1. The solution was co-evaporated with acetonitrile (2×) and then purified by reverse phase HPLC (5-100% ACN/H$_2$O+0.1% TFA) to give 0.2033 g (R)-4-(1-aminopropyl)-N-tert-butylbenzenesulfonamide as white powder after lyophilization and 63.4 mg (R)-2-(1-aminopropyl)-N-tert-butylbenzenesulfonamide as a white powder after lyophilization.

EXAMPLE 12

Synthesis of (R)-4-{1-[6-(4-Fluoro-phenyl)-4-(2,2,2-trifluoro-ethylamino)-pyrido[3,2-d]pyrimidin-2-ylamino]-propyl}-benzenesulfonamide

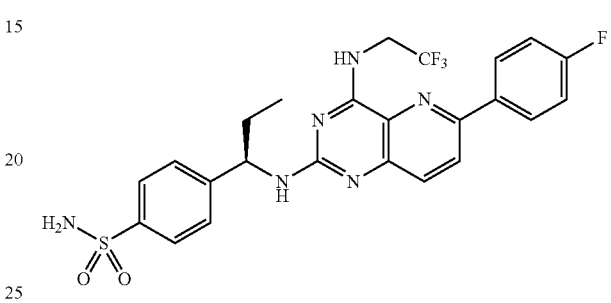

The title compound was synthesized in a manner analogous to Example 1, using (R)-4-(1-Amino-propyl)-N-tert-butyl-benzenesulfonamide in place of 3-[1,2,4]Triazol-1-yl-benzylamine and removal of the t-butyl protecting group in a final step by stirring in trifluoroacetic acid at room temperature, and was characterized by its NMR and mass spectrum as follows: $^1$H NMR (d$_6$-DMSO): d 0.89 (t, 3H), 1.79-1.93 (m, 2H), 4.22-4.58 (m, 2H), 5.02-5.16 (m, 1H), 7.27-7.36 (m, 4H), 7.54-7.57 (m, 2H), 7.74-7.76 (m, 2H), 7.90 (d, 1H), 8.35-8.43 (m, 3H), 9.46 (s, 1H), 9.92 (s, 1H); MS (m/z): 535.1 ([M+H]$^+$, 100).

EXAMPLE 13

Synthesis of (R)-4-{1-[6-(4-Fluoro-phenyl)-4-cyclopropoxy-pyrido[3,2-d]pyrimidin-2-ylamino]-ethyl}-benzenesulfonamide

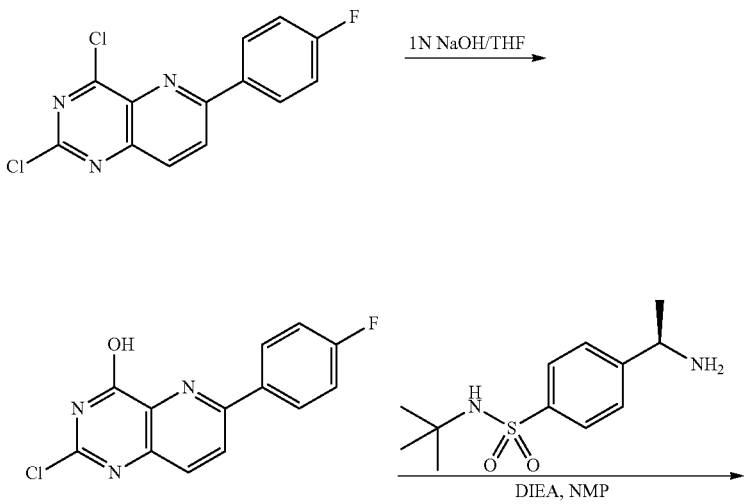

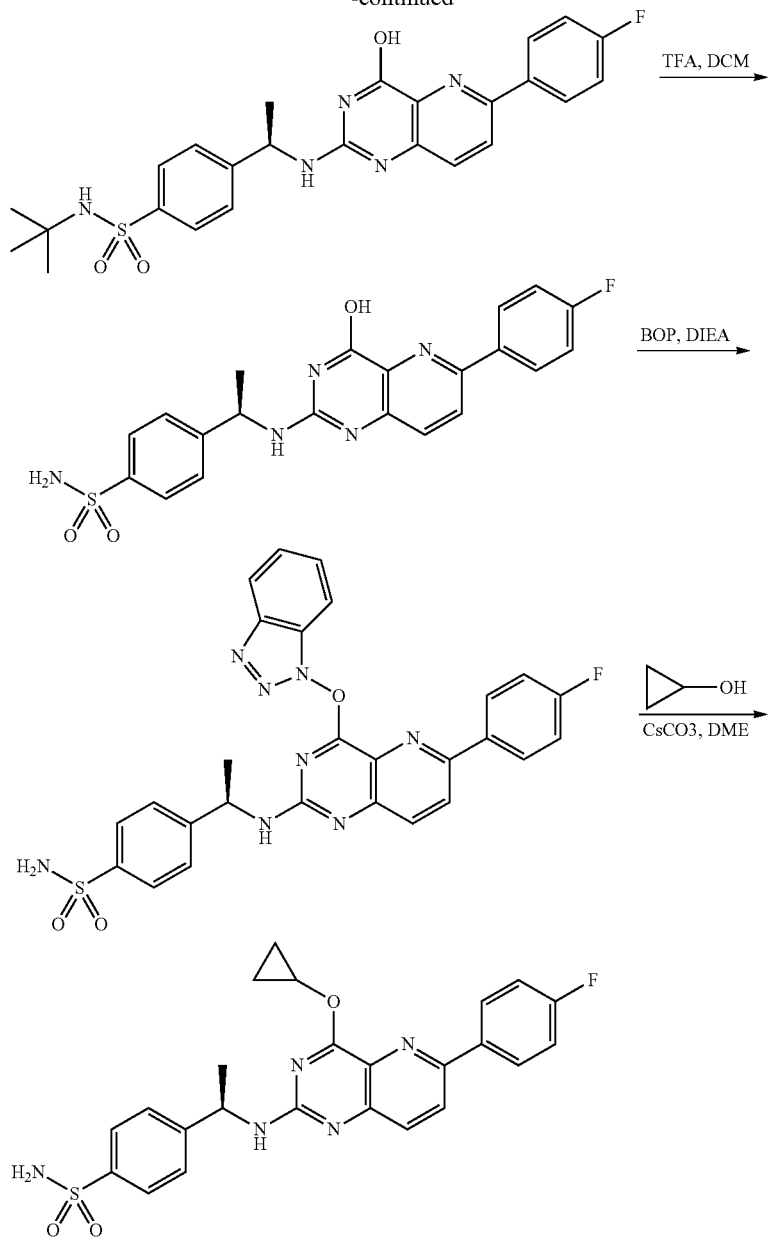

To a suspension of 2,4-dichloro-6-(4-fluorophenyl)pyrido[3,2-d]pyrimidine (1.3 g) in THF was added 1N NaOH (6.6 ml). The reaction mixture was stirred at room temperature for 30 min. Then another 2.2 ml 1N NaOH was added. After 2 hours, the reaction mixture was neutralized by adding 2N HCl and extracted with EtOAc. The organic layer was dried and concentrated until solid was formed. The solid was collected by filtration, washed with acetonitrile to give 0.97 g 2-chloro-6-(4-fluorophenyl)pyrido[3,2-d]pyrimidin-4-ol.

A mixture of 2-chloro-6-(4-fluorophenyl)pyrido[3,2-d]pyrimidin-4-ol (377 mg), (R)-4-(1-aminoethyl)-N-tert-butyl-benzenesulfonamide (456 mg) and DIEA (243 ml) in NMP (4 ml) was heated at 120° C. overnight. The reaction mixture was then added to H$_2$O/ACN (9:1) with vigorous stirring and extracted with EtOAc. The organic layer was dried and concentrated to give 1.1 g crude (R)—N-tert-butyl-4-(1-(6-(4-fluorophenyl)-4-hydroxypyrido[3,2-d]pyrimidin-2-ylamino)ethyl)benzenesulfonamide as golden brown oil, which was used in the next step without purification.

A mixture of crude (R)—N-tert-butyl-4-(1-(6-(4-fluorophenyl)-4-hydroxypyrido[3,2-d]pyrimidin-2-ylamino)ethyl)benzenesulfonamide (670 mg), TFA (5 ml) and dichloromethane (1 ml) was stirred at room temperature overnight. Solvents were removed under vacuum. To the residue was added a mixture of acetonitrile (5 ml) and water (50 ml) with vigorous stirring whereupon some oily material was formed. The mixture was diluted by EtOAc, neutralized by adding sat. aq. NaHCO$_3$ and extracted with EtOAc. The organic layer was dried and concentrated. The residue was dissolved in EtOAc (40 ml) and dichloromethane (20 ml) was added slowly, followed by hexanes (5 ml). The resulting solid was collected to give 328 mg (R)-4-(1-(6-(4-fluorophenyl)-4-hydroxypyrido[3,2-d]pyrimidin-2-ylamino)ethyl)benzenesulfonamide. The filtrate was concentrated and purified by reverse phase HPLC (eluting by ACN/H₂O+0.1% TFA) to give 200 mg (R)-4-(1-(6-(4-fluorophenyl)-4-hydroxypyrido[3,2-d]pyrimidin-2-ylamino)ethyl)benzenesulfonamide.

A mixture of (R)-4-(1-(6-(4-fluorophenyl)-4-hydroxypyrido[3,2-d]pyrimidin-2-ylamino)ethyl)benzenesulfonamide (200 mg), BOP (479 mg) and DIEA (314 μl) in THF (10 ml) was stirred at room temperature overnight. The reaction mixture was concentrated and purified by silicon gel column chromatography (eluting with EtOAc/CH₂Cl₂) to provide (R)-4-(1-(4-(1H-benzo[d][1,2,3]triazol-1-yloxy)-6-(4-fluorophenyl)pyrido[3,2-d]pyrimidin-2-ylamino)ethyl)benzenesulfonamide as a yellow solid.

A mixture of (R)-4-(1-(4-(1H-benzo[d][1, 2, 3]triazol-1-yloxy)-6-(4-fluorophenyl)pyrido[3,2-d]pyrimidin-2-ylamino)ethyl)benzenesulfonamide (80 mg), cyclopropanol (0.1 ml) and CsCO₃ (94 mg) in DME (3 ml) was stirred at room temperature over the weekend. The reaction mixture was concentrated and purified by reverse phase HPLC (eluting with ACN/H₂O+0.1% TFA) to give the title compound, which was characterized by its NMR and mass spectrum as follows: ¹H NMR (CD₃OD): d 0.83-1.04 (m, 4H), 1.66-1.70 (m, 3H). 4.50-4.58 (m, 1H), 5.40-5.49 (m, 1H), 7.19 (t, 2H), 7.61-7.88 (m, 4H), 7.99-8.02 (m, 1H), 8.08-8.13 (m, 2H), 8.30 (s, 1H); MS (m/z): 480.3 ([M+H]⁺, 100).

EXAMPLE 14

Synthesis of 3-{[6-(3-Methanesulfonyl-phenyl)-4-(2,2,2-trifluoro-ethylamino)-pyrido[3,2-d]pyrimidin-2-ylamino]-methyl}-benzenesulfonamide Scheme 7

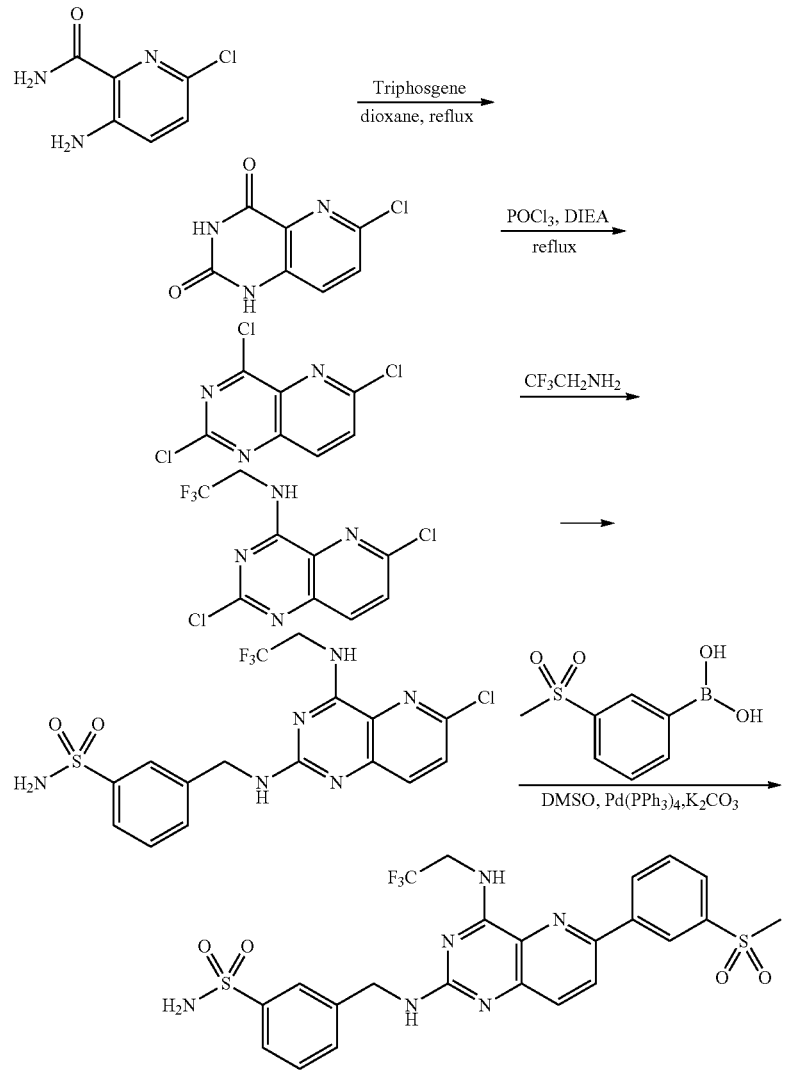

To 3-amino-6-chloro-pyridine-2-carboxylic acid amide (10 g, 58.3 mmol) in 1,4-dioxane (300 mL), was added triphosgene (6.9 g, 23.3 mmol). The reaction was heated to 100° C. for 1.5 hours. It was then cooled to RT and 3 ml of water was added to quench excess triphosgene. The solid was filtered and washed with EtOAc twice to provide 11 g of crude product which used without further purification.

A mixture of 6-chloro-1H-pyrido[3,2-d]pyrimidine-2,4-dione (11 g, 55.7 mmol), POCl₃ (100 ml) and DIEA (20 ml) was heated to reflux overnight. The POCl₃ was removed in vacuo and the residue was dissolved in dichloromethane and passed through a short silica gel plug. The combined organic fractions were concentrated to provide 8 g of the product as a beige solid.

To a solution of 2,4,6-Trichloro-pyrido[3,2-d]pyrimidine (9 g, 38.4 mmol) in THF (100 ml) was added trifluoroethylamine (3.62 ml, 46 mmol) and triethylamine (5.34 ml, 38.4 mmol). The reaction mixture was stirred at room temperature for 1.5 hours. Water (200 mL) was then added with vigorous stirring. The solid so formed was filtered and washed twice with water to provide 11.4 g of product as a white solid.

(2,6-Dichloro-pyrido[3,2-d]pyrimidin-4-yl)-(2,2,2-trifluoro-ethyl)-amine (2.3 g) and 3-Aminomethyl-benzenesulfonamide (0.336 g) were dissolved in NMP (10 mL) and dioxane (10 mL), treated with diisopropylethylamine (0.160 mL) and heated to reflux. After 8 h, additional portions of 3-Aminomethyl-benzenesulfonamide (440 mg) and diisopropylethylamine (0.200 mL). After an additional 12 h of heating, additional diisopropylethylamine was added (1.2 mL). The reaction mixture was stirred for another 24 h at reflux. Methanol (30 mL) was added followed by water (80 mL) and the mixture was allowed to cool to ambient temperature. A precipitate was collected and washed with 10% MeOH:water, and dried to give 1.2 g of the desired product which was used without further purification.

3-{[6-Chloro-4-(2,2,2-trifluoro-ethylamino)-pyrido[3,2-d]pyrimidin-2-ylamino]-methyl}-benzenesulfonamide (0.077 g) was combined with 3-methylsulfonyl-phenylboronic acid (0.067 g), palladium tetrakistriphenylphosphine (0.006 g) and potassium carbonate (0.121 g). The mixture was suspended in DME (1.6 mL) and water (0.8 mL), sealed and heated by microwave to 120° C. for 3 min. Crude product was precipitated by the addition of water. The precipitate was filtered and purified by reverse phase HPLC (5-100% ACN/H$_2$O+0.1% TFA) to give 0.048 g (41% yield) of the title compound, which was characterized by its NMR and mass spectrum as follows: $^1$H NMR (d$_6$-DMSO): d 3.34 (s, 3H), 4.40-4.46 (m, 2H), 4.73-4.82 (m, 2H), 7.35 (s, 2H), 7.52-7.7.64 (m, 2H), 7.73-7.75 (m, 1H), 7.83-7.87 (m, 2H), 8.03-8.06 (m, 2H), 8.58-8.62 (m, 1H), 8.68 (s, 1H), 8.80 (d, 1H), 9.10 (bs, 1H), 9.98 (bs, 1H); MS (m/z): 567.1 ([M+H]$^+$, 100).

3-Aminomethyl-benzenesulfonamide was prepared by the following method:

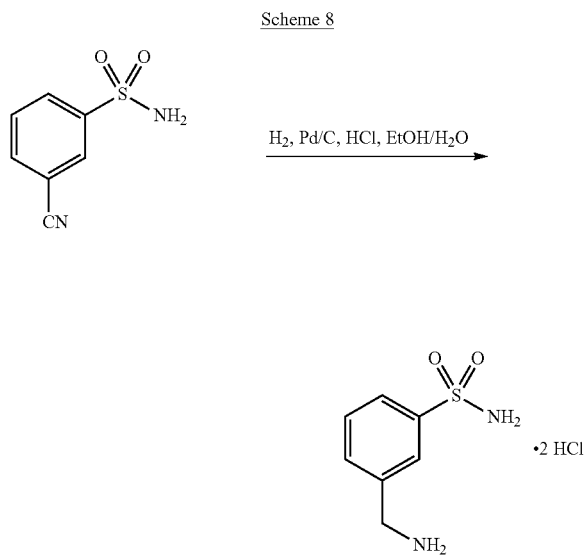

Scheme 8

2-Cyanophenylsulfonamide (200 mg, 1.1 mmol), ethanol (3.5 mL), water (3 mL), concentrated hydrochloric acid (0.2 mL, mmol), and 10% palladium on carbon (50 mg, 0.05 mmol) were hydrogenated at atmospheric temperature and pressure over the course of 18 hours. The solution was filtered and evaporated to dryness. The residue was washed with ethanol (10 mL) to obtain 49 mg (16%) of crude product. This material was used without further purification in the next step.

EXAMPLE 15

Synthesis of 4-{[6-(3-Methanesulfonyl-phenyl)-4-(2,2,2-trifluoro-ethylamino)-pyrido[3,2-d]pyrimidin-2-ylamino]-methyl}-benzenesulfonamide

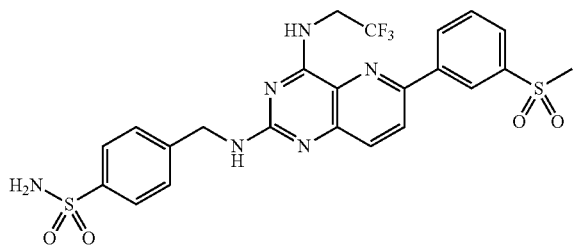 [SMILES: CS(=O)(=O)c1cccc(-c2ccc3nc(NCc4ccc(S(N)(=O)=O)cc4)nc(NCC(F)(F)F)c3n2)c1]

The title compound was synthesized in a manner analogous to Example 14, using 4-Aminomethyl-benzenesulfonamide in place of 3-Aminomethyl-benzenesulfonamide, and was characterized by its NMR and mass spectrum as follows: $^1$H NMR (d$_6$-DMSO): d 3.34 (s, 3H), 4.41-4.47 (m, 2H), 4.71-4.81 (m, 2H), 7.33 (s, 2H), 7.55-7.58 (m, 2H), 7.77-7.88 (m, 3H), 8.03-8.05 (m, 2H), 8.58-8.67 (m, 2H), 8.79 (d, 1H), 9.11 (bs, 1H), 9.95 (bs, 1H); MS (m/z): 567.2 ([M+H]$^+$, 100).

EXAMPLE 16

Synthesis of 6-(3-Methanesulfonyl-phenyl)-N2-(3-[1,2,4]-triazol-1-yl-benzyl)-N4-(2,2,2-trifluoro-ethyl)-pyrido[3,2-d]pyrimidine-2,4-diamine The title compound was synthesized in a manner analogous to Example 14, using 3-[1,2,4]-Triazol-1-yl-benzylamine in place of 3-Aminomethyl-benzenesulfonamide, and was characterized by its NMR and mass spectrum as follows: $^1$H NMR (d$_6$-DMSO): d 3.32 (s, 3H), 4.32-4.43 (m, 2H), 4.64-4.65 (m, 2H), 7.41-7.52 (m, 2H), 7.70-7.88 (m, 5H), 7.96 (d, 1H), 8.21 (s, 1H), 8.33 (d, 1H), 8.63-8.68 (m, 2H), 8.74 (d, 1H), 9.26 (s, 1H); MS (m/z): 555.1 ([M+H]+, 100).

EXAMPLE 17

Synthesis of (R)-4-{1-[6-(3-Methanesulfonyl-phenyl)-4-(2,2,2-trifluoro-ethylamino)-pyrido[3,2-d]pyrimidin-2-ylamino]-ethyl}-benzenesulfonamide

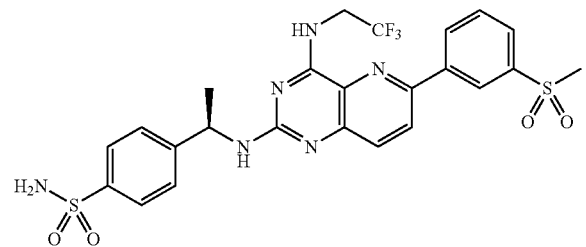 [SMILES: C[C@@H](Nc1nc(NCC(F)(F)F)c2nc(-c3cccc(S(C)(=O)=O)c3)ccc2n1)c1ccc(S(N)(=O)=O)cc1]

The title compound was synthesized in a manner analogous to Example 14, using (R)-4-(1-Amino-ethyl)-N-tert-butyl-benzenesulfonamide in place of 3-Aminomethyl-benzenesulfonamide and removal of the t-butyl protecting group in a final step by stirring in trifluoroacetic acid at room temperature, and was characterized by its NMR and mass spectrum as follows: ¹H NMR (CD₃OD): d 1.64 (d, 3H), 3.18 (s, 3H), 4.19-4.41 (m, 2H), 5.38-5.42 (m, 1H), 7.58-8.03 (m, 7H), 8.43 (d, 1H), 8.56 (d, 1H), 8.71 (s, 1H); MS (m/z): 581.3 ([M+H]+, 100).

(R)-4-(1-Amino-ethyl)-N-tert-butyl-benzenesulfonamide was synthesized in a manner analogous to (R)-4-(1-Amino-propyl)-N-tert-butyl-benzenesulfonamide in Example 12, using (R)-1-phenylethanamine in place of (R)-1-phenylpropan-1-amine.

EXAMPLE 18

Synthesis of 4-{[6-(3-Methanesulfonyl-4-methoxy-phenyl)-4-(2,2,2-trifluoro-ethylamino)-pyrido[3,2-a]pyrimidin-2-ylamino]-methyl}-benzenesulfonamide

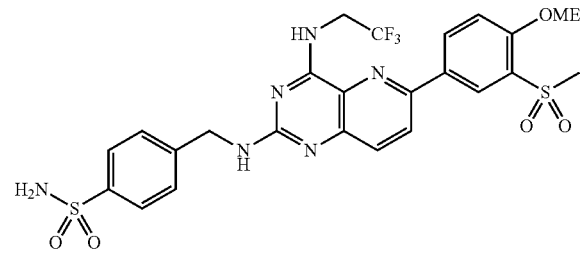

The title compound was synthesized in a manner analogous to Example 14, using 2-(3-Methanesulfonyl-4-methoxy-phenyl)-4,4,5,5-tetramethyl-[1,3,2]dioxaborolane in place of 3-(methylsulfonyl)phenyl boronic acid, and was characterized by its NMR and mass spectrum as follows: ¹H NMR (d₆-DMSO): d 3.28 (s, 3H), 4.03 (s, 3H), 4.37-4.45 (m, 2H), 4.72-4.79 (m, 2H), 7.31 (s, 2H), 7.45 (d, 1H), 7.53-7.55 (m, 2H), 7.75-7.77 (m, 2H), 7.97 (d, 1H), 8.40-8.42 (m, 1H), 8.46 (d, 1H), 8.72-8.75 (m, 1H), 9.30 (bs, 1H), 9.96 (bs, 1H); MS (m/z): 597.2 ([M+H]+, 100).

2-(3-Methanesulfonyl-4-methoxy-phenyl)-4,4,5,5-tetramethyl-[1,3,2]dioxaborolane was synthesized as follows:

Scheme 9

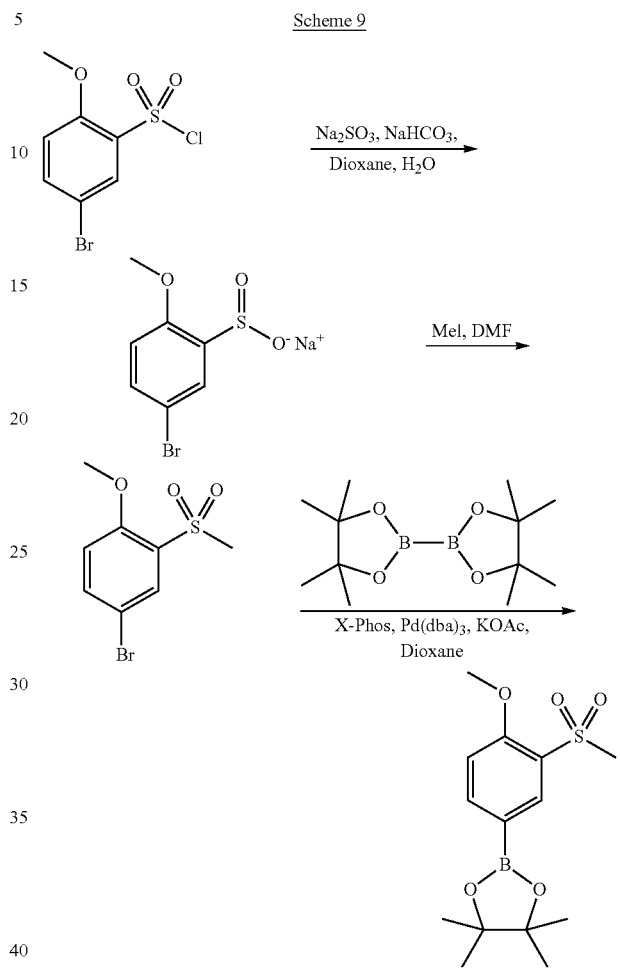

To a solution of Na₂SO₃ (1.42 g) and NaHCO₃ (0.948 g) in H₂O (17 ml) at 70° C. was added a solution of 5-bromo-2-methoxybenzene-1-sulfonyl chloride (2 g) in dioxane (17 ml) dropwise. The reaction mixture was stirred at 70° C. for 80 minutes and cooled to room temperature. The solvent was removed under vacuum to yield sodium 5-bromo-2-methoxybenzenesulfinate as white solid. The solid was placed under high vacuum overnight and used without further purification.

To a suspension of sodium 5-bromo-2-methoxybenzenesulfinate (1.99 g) in DMF (873 ml) was added iodomethane (32 ml). The reaction mixture turned yellow and was stirred at room temperature for 2 hours. The reaction was quenched by the addition of water (ca. 5 ml). The mixture was diluted with EtOAc and extracted with 5% LiCl (3×) and brine (1×). The organic layer was dried (Na₂SO₄/MgSO₄) and filtered. The filtrate was concentrated and purified by silica gel column chromatography to give 1.62 g 4-bromo-1-methoxy-2-(methylsulfonyl)benzene as a white crystalline solid.

To a mixture of Bis(pinacolato)diboron (1.78 g), X-phos (44 mg), Pd(dba)₃ (43 mg) and KOAc (0.604 g) in Dioxane (8 ml) at 110° C. was added a solution of 4-bromo-1-methoxy-2-(methylsulfonyl)benzene (0.62 g) in dioxane (4 ml) over 7 min. The reaction mixture was stirred at 110° C. for 1 hour, then cooled to room temperature and filtered through paper filtration and a layer of diatomaceous earth. The filtrate was washed with water (2×) and brine (2×). The organic layer was dried (MgSO₄/Na₂SO₄), filtered, concentrated and purified by silica gel column chromatography to give 640 mg 2-(4-methoxy-3-(methylsulfonyl)phenyl)-4,4,5,5-tetramethyl-1,3,2-dioxaborolane.

EXAMPLE 19

Synthesis of 6-(3-Methanesulfonyl-phenyl)-N2-[1-(4-[1,2,4]triazol-1-yl-phenyl)-ethyl]-N4-(2,2,2-trifluoro-ethyl)-pyrido[3,2-d]pyrimidine-2,4-diamine

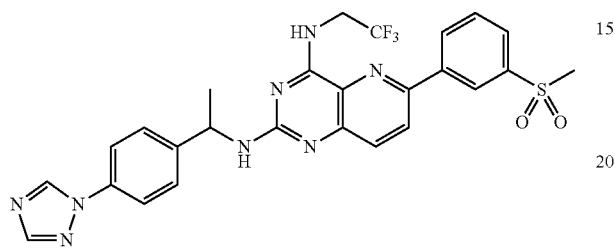

The title compound was synthesized in a manner analogous to Example 14, using 1-(4-[1,2,4]-Triazol-1-yl-phenyl)-ethylamine in place of 3-Aminomethyl-benzenesulfonamide, and was characterized by its NMR and mass spectrum as follows: ¹H NMR (d₆-DMSO): d 1.49 (d, 3H), 3.32 (s, 3H), 4.03 (s, 3H), 4.32-4.42 (m, 2H), 5.19-5.31 (m, 1H), 7.41 (d, 1H), 7.61-7.78 (m, 6H), 8.10-8.19 (m, 2H), 8.43-8.47 (m, 2H), 8.67 (d, 1H), 9.20 (s, 1H); MS (m/z): 599.1 ([M+H]⁺, 100).

EXAMPLE 20

Synthesis of 6-(3-Methanesulfonyl-phenyl)-N2-(3-[1,2,4]triazol-1-yl-benzyl)-N4-(2,2,2-trifluoro-ethyl)-pyrido[3,2-d]pyrimidine-2,4-diamine

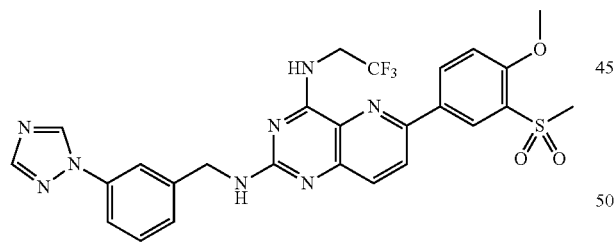

The title compound was synthesized in a manner analogous to Example 14, using 3-[1,2,4]Triazol-1-yl-benzylamine in place of 3-Aminomethyl-benzenesulfonamide, and was characterized by its NMR and mass spectrum as follows: ¹H NMR (d₆-DMSO): d 3.32 (s, 3H), 4.04 (s, 3H), 4.30-4.42 (m, 2H), 4.64 (d, 2H), 7.41-7.51 (m, 3H), 7.69-7.76 (m, 3H), 7.87 (s, 1H), 8.14 (d, 1H), 8.21 (s, 1H), 8.44 (d, 1H), 8.49-8.51 (m, 1H), 8.68 (d, 1H), 9.25 (s, 1H); MS (m/z): 585.3 ([M+H]⁺, 100).

EXAMPLE 21

Synthesis of 4-{[6-(4-Fluoro-3-methanesulfonyl-phenyl)-4-(2,2,2-trifluoro-ethylamino)-pyrido[3,2-d]pyrimidin-2-ylamino]-methyl}-benzenesulfonamide

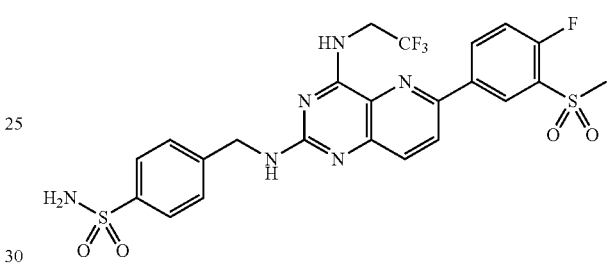

The title compound was synthesized in a manner analogous to Example 14, using 2-(3-Methanesulfonyl-4-fluoro-phenyl)-4,4,5,5-tetramethyl-[1,3,2]dioxaborolane in place of 3-(methylsulfonyl)phenyl boronic acid, and was characterized by its NMR and mass spectrum as follows: ¹H NMR (d₆-DMSO): d 3.42 (s, 3H), 4.41-4.49 (m, 2H), 4.73-4.83 (m, 2H), 7.34 (s, 2H), 7.56-7.58 (m, 2H), 7.74-7.80 (m, 3H), 8.02 (d, 1H), 8.52-8.54 (m, 2H), 8.87-8.89 (m, 1H), 9.43 (bs, 1H), 10.05 (bs, 1H); MS (m/z): 585.1 ([M+H]⁺, 100).

2-(3-Methanesulfonyl-4-fluoro-phenyl)-4,4,5,5-tetramethyl-[1,3,2]dioxaborolane was synthesized as follows:

The title compound was synthesized in a manner analogous to 2-(3-Methanesulfonyl-4-methoxy-phenyl)-4,4,5,5-tetramethyl-[1,3,2]dioxaborolane in Example 18, using 5-bromo-2-fluorobenzene-1-sulfonyl chloride in place of 5-bromo-2-methoxybenzene-1-sulfonyl chloride.

EXAMPLE 22

Synthesis of 4-{[4-Cyclopropoxy-6-(3-methanesulfonyl-phenyl)-pyrido[3,2-d]pyrimidin-2-ylamino]-methyl}-benzenesulfonamide Scheme 10

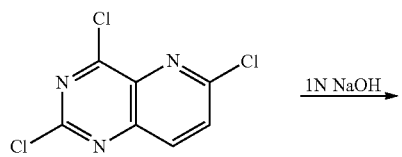

1N NaOH

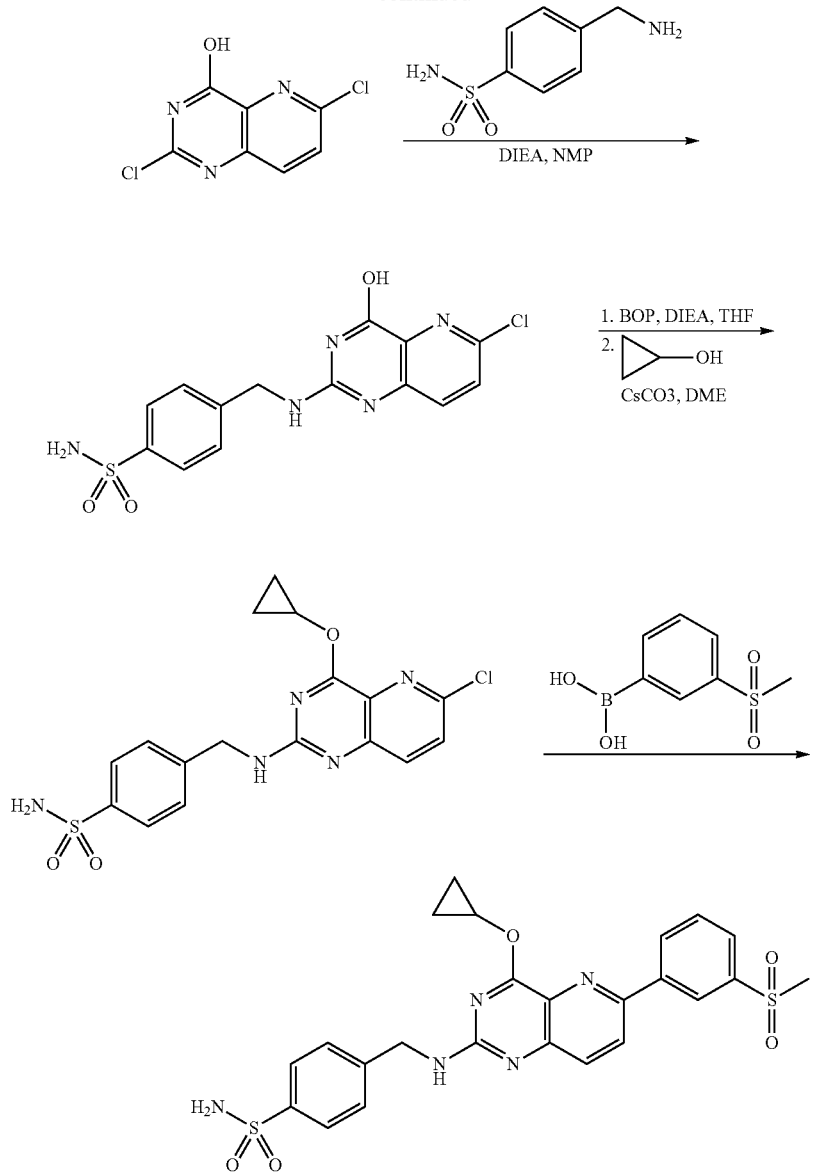

2,4,6-Trichloro-pyrido[3,2-d]pyrimidine (13.46 g) was suspended in THF (100 mL) and treated with sodium hydroxide (57.4 mL, 2.0 M aq) with vigorous stirring. After 90 min, the mixture was stored at 0° C. for 16 h. After warming to ambient temperature, the aqueous layer was separated and acidified to pH=5 with acetic acid. Desired hydroxy intermediate was collected as a white solid. The organic layer was treated with an additional 5 mL of 2M NaOH for 30 min. After acidification to pH=5 with acetic acid an additional crop of desired hydroxyl intermediate was collected as a tan solid. The combined solids were dried to 12.4 g (98% yield) of the desired product and were carried on to the next step without purification.

2,6-Dichloro-pyrido[3,2-d]pyrimidin-4-ol (9.9 g) and 4-Aminomethyl-benzenesulfonamide hydrochloride (12 g) in NMP (80 mL) was treated with diisopropylethylamine (17.5 mL) and heated to 110° C. for 2 h, followed by 120° C. for an additional 1 h. The reaction mixture was cooled to ambient temperature and slowly treated with water (120 mL) and acetic acid (3 mL). The resulting sticky solid was filtered, stirred with water (200 mL) and filtered again. After drying in vacuo, the resulting solid was stirred with acetonitrile (25 mL)/ether (150 mL) to afford a fine powder which was filtered and dried to 16.2 g (97% yield) of the desired intermediate which was used without further purification in the next step.

4-[(6-Chloro-4-cyclopropoxy-pyrido[3,2-d]pyrimidin-2-ylamino)-methyl]-benzenesulfonamide was prepared from 4-[(6-Chloro-4-hydroxy-pyrido[3,2-d]pyrimidin-2-ylamino)-methyl]-benzenesulfonamide in a manner analogous to steps 4 and 5 of Example 13.

The title compound was synthesized from 4-[(6-Chloro-4-hydroxy-pyrido[3,2-d]pyrimidin-2-ylamino)-methyl]-benzenesulfonamide in a manner analogous to the final step of Example 14 and was characterized by its NMR and mass spectrum as follows: $^1$H NMR ($d_6$-DMSO): d 0.91 (d, 4H), 3.30 (s, 3H), 4.52-4.56 (m, 1H), 4.68-4.73 (m, 2H), 7.30 (s, 2H), 7.57-7.59 (m, 2H), 7.76-7.82 (m, 3H), 7.93-8.01 (m, 2H), 8.35-8.46 (m, 2H), 8.60 (s, 1H); MS (m/z): 526.0 ([M+H]$^+$, 100).

EXAMPLE 23

Synthesis of 4-{[6-(4-fluoro-phenyl)-4-(1-trifluoromethyl-cyclopropylamino)-pyrido[3,2-d]pyrimidin-2-ylamino]-methyl}-benzenesulfonamide

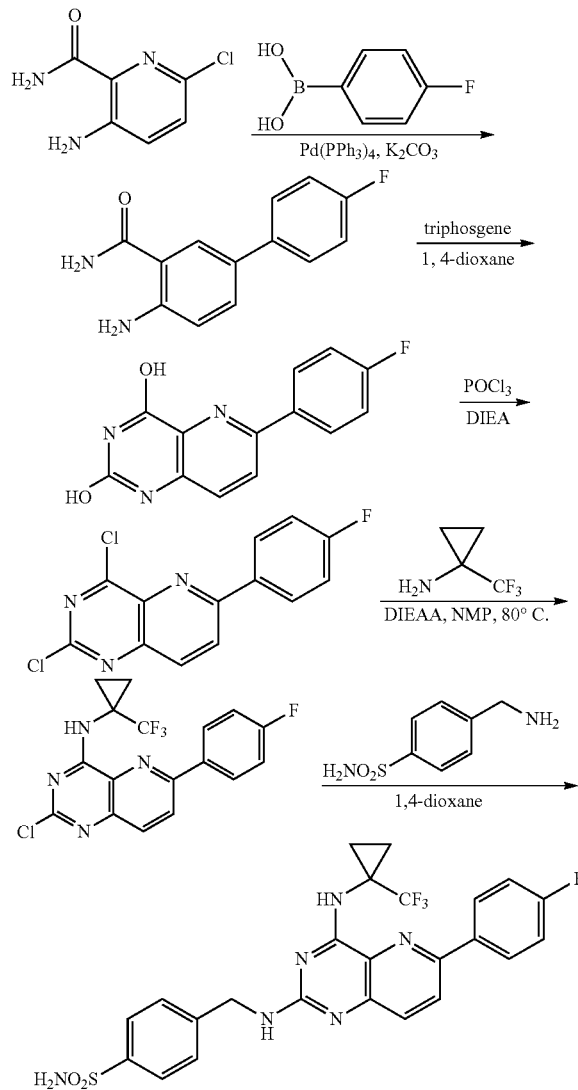

A mixture of 3-amino-6-chloropicolinamide (2 g), potassium carbonate (3.2 g), tetrakis(triphenylphosphine) palladium (0.674 g) and 4-fluorophenylboronic acid (1.79 g) in DMF (50 mL) and water (10 mL) was heated to 120° C. for 16 hours. Solvents were removed and 1N HCl (30 ml) was added to the mixture. The resulting solid was filtered to provide 2.48 g of 3-amino-6-(4-fluorophenyl)picolinamide which was characterized by its mass spectrum as follows: MS (m/z) 232 [M+H]+.

A solution of 3-amino-6-(4-fluorophenyl)picolinamide (2.48 g) and triphosgene in 1,4-dioxane (50 mL) was heated to 100° C. for 1 hour. Cooling and filtration provided 2.2 g of 6-(4-fluorophenyl)pyrido[3,2-d]pyrimidine-2,4-diol which was characterized by its mass spectrum as follows: MS (m/z) 258 [M+H]+.

A solution of 6-(4-fluorophenyl)pyrido[3,2-d]pyrimidine-2,4-diol (1 g), POCl₃ (20 ml) and DIEA (2.0 ml) was heated to reflux for 16 hours. POCl₃ was removed and the residue was dissolved in ethyl acetate. The organic layer was extracted with brine three times. It was dried and concentrated to provide 0.97 g of 2,4-dichloro-6-(4-fluorophenyl)pyrido[3,2-c]pyrimidine which was characterized by its mass spectrum as follows: MS (m/z) 294 [M+H]+.

2,4-Dichloro-6-(4-fluorophenyl)-pyrido[3,2-d]pyrimidine (3.3 g, 11.2 mmol), 1-trifluoromethyl-cyclopropylamine hydrochloride (2.25 g, 14.1 mmol, see Scheme 2 below) and diisopropylethylamine (4.8 ml, 25.5 mmol) were suspended in N-methylpyrrolidinone (10 mL) and stirred at 80° C. After 3 hours, the reaction mixture was cooled to 40° C. and stirred an additional 16 hours. Methanol (20 mL) was added and the solution was heated to 70° C. Water was slowly added until the mixture became cloudy. After cooling, a precipitate was collected, and washed with acetonitrile:water (1:1) followed by ether. Two additional batches of precipitate were formed in the filtrate which were collected and washed. The combined solids were dried to 3.46 g (81%). This material was used without further purification in the next step.

A mixture of [2-Chloro-6-(4-fluoro-phenyl)-pyrido[3,2-d]pyrimidin-4-yl]-(1-trifluoromethyl-cyclopropyl)-amine (51.6 mg) and 4-aminomethyl-benzenesulfonamide hydrochloride (51.4 mg) was dissolved in NMP (1 mL) and treated with diisopropylethylamine (0.065 mL). The reaction mixture was sealed and heated by microwave to 140° C. for 1.5 h. The reaction mixture was cooled and purified by preparative HPLC (5-95% acetonitrile:water with 0.1% TFA) to afford 36 mg (41% yield) of the title compound as its TFA which was characterized by its NMR and mass spectrum as follows: ¹H NMR (d₆-DMSO): d 1.26 (br s, 2H), 1.37 (br s, 2H), 4.80 (d, 2H), 7.34-7.40 (m, 4H), 7.55 (d, 2H), 7.78 (d, 2H), 7.99 (d, 1H), 8.48 (m, 3H), 8.9 (br s, 1H), 10.1 (br s, 1H); MS (m/z): 533.2 ([M+H]+, 100).

Scheme 2

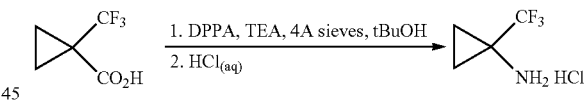

1-Trifluoromethyl-cyclopropylamine was synthesized using a variation of the procedure found in *J. Med. Chem.* 2006, 49, 4127 described below.

A solution of 1-(trifluoromethyl)cyclopropanecarboxylic acid (5.1 g, 33.1 mmol) and dry triethylamine (4.6 mL, 33 mmol) in dry tent-butanol (24 mL) was stirred at room temperature in the presence of 0.4 nm molecular sieves (3.4 g). Diphenyl phosphorazidate (7.5 mL, 34.7 mmol) was added dropwise and the mixture was heated to reflux for 22 h under nitrogen and then concentrated in vacuo. The residue was taken up in diethyl ether and sieves were removed by gravity filtration. The filtrate was washed sequentially with 5% citric acid solution, saturated aqueous NaHCO₃, and brine and dried. Concentration afforded 4.08 g (55%) of tert-butyl 1-(trifluoromethyl)cyclopropylcarbamate, which was used without further purification in the next step.

Tert-butyl 1-(trifluoromethyl)cyclopropylcarbamate (4.08 g, 18.3 mmol) was suspended in 1 N HCl(aq) (150 mL) and stirred at reflux for 3.5 h. The solution was concentrated in vacuo and the residue was triturated with acetone. The filtrate was collected, concentrated, and the residue triturated with diethyl ether to afford 2.67 g (91%) of 1-(trifluoromethyl) cyclopropylamine hydrochloride as a white solid.

EXAMPLE 24

Synthesis of (R)-4-{1-[6-(4-fluorophenyl)-4-(1-trifluoromethyl-cyclopropylamino)-pyrido[3,2-d]pyrimidin-2-ylamino]-ethyl}-benzenesulfonamide

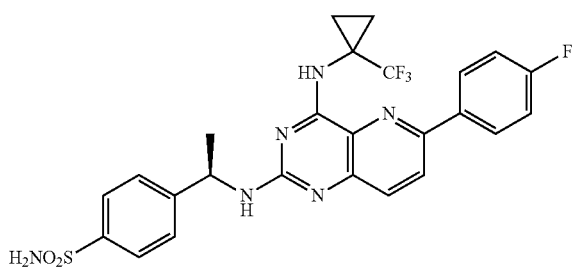 [SMILES: C[C@@H](Nc1nc(NC2(C(F)(F)F)CC2)c2nc(-c3ccc(F)cc3)ccc2n1)c1ccc(S(N)(=O)=O)cc1]

The title compound was synthesized in a manner analogous to Example 23, using (R)-4-(1-aminoethyl)-benzenesulfonamide (see Scheme 3) in place of 4-aminomethyl-benzenesulfonamide, and was characterized by its NMR and mass spectrum as follows: $^1$H NMR (d$_6$-DMSO): d 1.03 (m, 1H), 1.34 (m, 2H), 1.52, (m, 1H), 1.58 (d, 3H), 5.36 (m, 1H), 7.32-7.39 (M, 4H), 7.60 (d, 2H), 7.80 (d, 2H), 7.98 (d, 1H), 8.47 (m, 3H), 9.0 (br s, 1H), 10.0 (br s, 1H); MS (m/z): 547.1 ([M+H]$^+$, 100).

Scheme 3

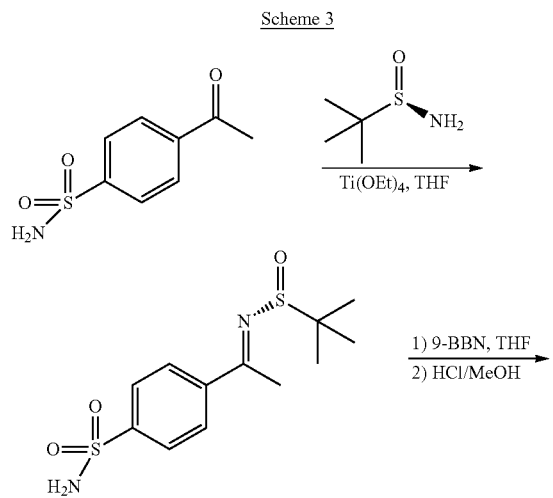

(R)-4-(1-Amino-ethyl)-benzenesulfonamide was synthesized using the following procedure.

A mixture of 4-acetylbenzenesulfonamide (15.6 g), Ti(OEt)$_4$ (35.8 g), (R)-2-methylpropane-2-sulfinamide (11.4 g) in THF (200 ml) was heated at 70° C. overnight. The reaction mixture allowed to cool to room temperature, poured into 100 ml of H$_2$O and filtered. The filtrate was washed and extracted with EtOAc (200 ml). The organic layer was dried and concentrated to give (R),(E)-4-(1-(2-methylpropan-2-yl-sulfinamido)ethyl)benzenesulfonamide as yellow solid, which was triturated with 20% DCM/ether, dried and used without further purification.

A solution of (R),(E)-4-(1-(2-methylpropan-2-ylsulfinamido)ethyl)benzenesulfonamide in THF (250 ml) was cooled at –5° C. To the solution was added 9-BBN/THF (0.5 M, 230 ml) in portions, maintaining internal temperature below 0° C. The reaction mixture was then allowed to stir for 1 h at 0-5° C. The reaction was quenched by adding 100 ml MeOH and then stirred with HCl/MeOH (1.25N, 100 ml) for 30 min. After the reaction was done, the solvent was removed. The residue was poured into ether and sonicated, and the precipitated solid was collected to yield 13.7 g (R)-4-(1-aminoethyl)benzenesulfonamide as HCl salt which was characterized by its NMR as follows: $^1$H NMR (d$_6$-DMSO): δ 1.52 (d, 3H), 4.45-4.55 (m, 1H), 7.42 (s, 2H), 7.68-7.71 (m, 2H), 7.83-7.86 (m, 2H), 8.67 (s, 3H).

EXAMPLE 25

Synthesis of 2-fluoro-5-{[6-(4-fluorophenyl)-4-(1-trifluoromethyl-cyclopropylamino)-pyrido[3,2-d]pyrimidin-2-ylamino]-methyl}-benzenesulfonamide

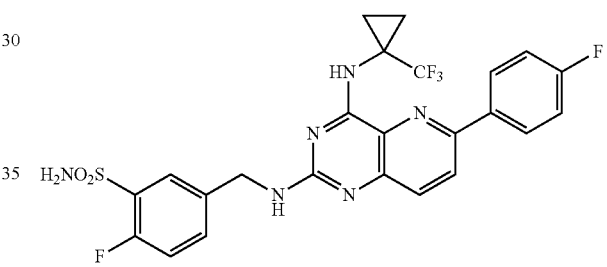

The title compound was synthesized in a manner analogous to Example 23, using 5-aminomethyl-N-tert-butyl-2-fluoro-benzenesulfonamide (see Scheme 4) in place of 4-aminomethyl-benzenesulfonamide and removal of the t-butyl protecting group in a final step by stirring in trifluoroacetic acid at room temperature, and was characterized by its NMR and mass spectrum as follows: $^1$H NMR (d$_6$-DMSO): d 1.26 (br s, 2H), 1.40 (br s, 2H), 4.75 (m, 2H), 7.34-7.43 (m, 3H), 7.64 (s, 3H), 7.80 (d, 1H), 7.98 (d, 1H), 8.50 (m, 3H), 9.1 (br s, 1H), 10.1 (br s, 1H); MS (m/z): 551.1 ([M+H]$^+$, 100).

Scheme 4

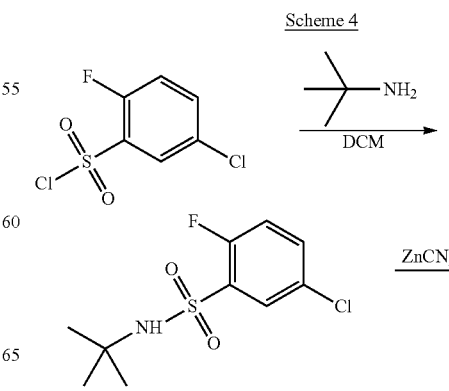

-continued

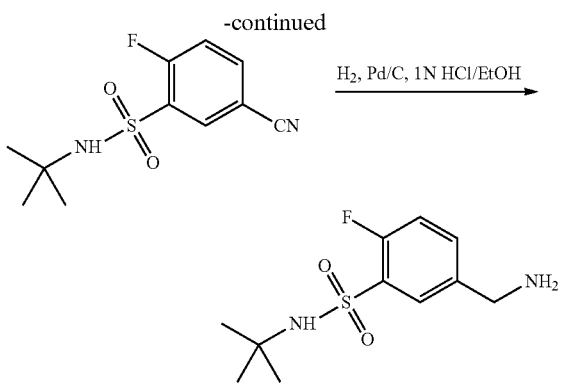

5-Aminomethyl-N-tert-butyl-2-fluoro-benzenesulfonamide was synthesized as follows.

A solution of 5-chloro-2-fluorobenzene-1-sulfonyl chloride (2.0 g) in tetrahydrofuran (30 ml) was added to a solution of tert-butylamine (9.15 ml) in tetrahydrofuran (70 ml) at 0° C. The reaction mixture was allowed to warm to room temperature and stirred for 2 h. The precipitate was removed by filtration and the filtrate was concentrated in vacuo to give N-tert-butyl-5-chloro-2-fluoro-benzenesulfonamide (2.2 g, 95% yield) as a white solid.

A mixture of N-tent-butyl-5-chloro-2-fluoro-benzenesulfonamide (1.06 g) and zinc cyanide (0.94 g) in NMP (5 ml) was purged with argon for 20 min. Then Pd(dppf)Cl$_2$ (292 mg) was added and the resulting mixture was heated at 120° C. for 15 h. The reaction mixture was diluted with EtOAc (300 ml) and washed with 5% LiCl (4×50 ml). The organic layer was dried over Na$_2$SO$_4$, concentrated and purified by silica gel column chromatography to give N-tert-butyl-5-cyano-2-fluoro-benzenesulfonamide (0.6 g, 59% yield) as a white solid.

A mixture of N-tert-butyl-5-cyano-2-fluoro-benzenesulfonamide (0.3 g) and Pd/C (50 mg) in 1N HCl/EtOH (1 ml 1N HCl in 10 ml EtOH) was stirred under H$_2$ for 2 hours. The reaction mixture was filtered through a pad of diatomaceous earth, washed with MeOH and concentrated to about 3 ml. The residue was diluted with H$_2$O and lyophilized to give 5-aminomethyl-N-tert-butyl-2-fluoro-benzenesulfonamide (0.27 g, 90% yield) as a white powder.

EXAMPLE 26

Synthesis of 3-{[6-(4-fluorophenyl)-4-(1-trifluoromethyl-cyclopropylamino)-pyrido[3,2-d]pyrimidin-2-ylamino]-methyl}-5-trifluoromethyl-benzenesulfonamide

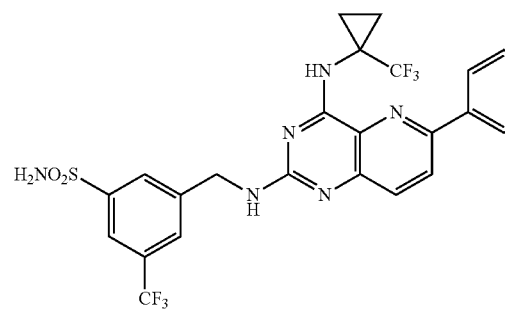

The title compound was synthesized in a manner analogous to Example 23, using 3-aminomethyl-N-tert-butyl-5-trifluoromethyl-benzenesulfonamide in place of 4-aminomethyl-benzenesulfonamide and removal of the t-butyl protecting group in a final step by stirring in trifluoroacetic acid at room temperature, and was characterized by its NMR and mass spectrum as follows: $^1$H NMR (d$_6$-DMSO): d 1.17 (m, 2H), 1.4 (m, 2H), 4.69 (d, 2H), 7.30 (t, 2H), 7.56 (s, 2H), 7.72 (d, 1H), 7.85 (m, 1H), 7.99 (s, 1H), 8.1 (m, 1H), 8.21 (d, 1H), 8.43 (m, 2H), 8.79 (br s, 1H); MS (m/z): 601.1 ([M+H]$^+$, 100).

3-Aminomethyl-N-tert-butyl-5-trifluoromethyl-benzenesulfonamide was synthesized in a manner analogous to 5-aminomethyl-N-tert-butyl-2-fluoro-benzenesulfonamide in Example 3, using 3-bromo-5-(trifluoromethyl)benzene-1-sulfonyl chloride in place of 5-chloro-2-fluorobenzene-1-sulfonyl chloride.

EXAMPLE 27

Synthesis of 3-chloro-5-{[6-(4-fluorophenyl)-4-(1-trifluoromethyl-cyclopropylamino)-pyrido[3,2-d]pyrimidin-2-ylamino]-methyl}-benzenesulfonamide

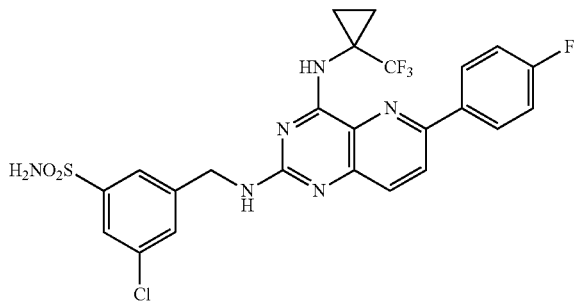 [SMILES: NS(=O)(=O)c1cc(Cl)cc(CNc2nc(NC3(C(F)(F)F)CC3)c3nc(-c4ccc(F)cc4)ccc3n2)c1]

The title compound was synthesized in a manner analogous to Example 23, using 5-aminomethyl-N-tert-butyl-3-chloro-benzenesulfonamide (see Scheme 5) in place of 4-aminomethyl-benzenesulfonamide and removal of the t-butyl protecting group in a final step by stirring in trifluoroacetic acid at room temperature, and was characterized by its NMR and mass spectrum as follows: $^1$H NMR (d$_6$-DMSO): d 1.1-1.5 (m, 4H), 4.60 (d, 2H), 7.30 (t, 2H), 7.47 (s, 2H), 7.6-7.8 (m, 5H), 8.21 (d, 1H), 8.43 (m, 2H), 8.77 (br s, 1H); MS (m/z): 567.1 ([M+H]$^+$, 100).

Scheme 5

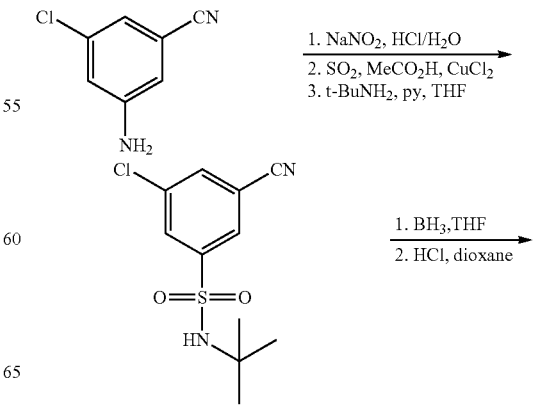

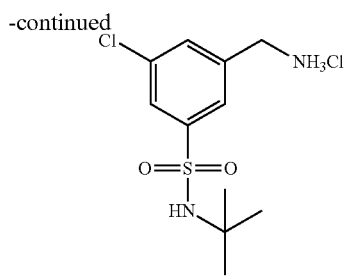

5-Aminomethyl-N-tert-butyl-3-chloro-benzenesulfonamide was synthesized as follows.

To a suspension of 5-cyano-3-chloroaniline (3.44 g) in concentrated HCl (84 ml) was added dropwise a solution of $NaNO_2$ (1.72 g) in $H_2O$ (6 ml) at −5° C. The reaction mixture was vigorously stirred at −5° C. for 1.5 h. To a solution of $CuCl_2$ (0.18 g) in $H_2O$ (2 ml) and acetic acid (150 m), $SO_2$ was bubbled at −5° C. for 20 min. The suspension of the prepared diazonium salt was added dropwise at −10° C. and stirred at room temperature for 3 h. The reaction mixture was poured into $H_2O$/ice (500 ml) and extracted with ether (2×300 ml). The organic layer was washed with $H_2O$ (3×200 ml), dried over $Na_2SO_4$ and concentrated. The crude sulfonylchloride was dissolved in THF (100 ml) and cooled to 0° C. Pyridine (6.2 ml) was added followed by t-$BuNH_2$ (2.86 g). The resulting mixture was warmed to room temperature and stirred for 2 h. The reaction mixture was diluted with EtOAc (300 ml) and washed with brine (2×100 ml), 1 N HCl (2×100 ml) and brine (100 ml). The organic layer was dried over $Na_2SO_4$, concentrated and purified by silica gel column chromatography to give N-t-butyl-3-chloro-5-cyano-benzenesulfonamide (3.18 g, 52% yield) as a white solid.

To a solution of N-t-butyl-3-chloro-5-cyano-benzenesulfonamide (1.3 g) in THF (10 ml) at 0° C. was added dropwise $BH_3$ (1 M in THF, 17.7 ml). The resulting mixture was warmed to room temperature and heated to reflux for 1 h. Ethanol (2 ml) was added dropwise at 0° C. The reaction mixture was diluted with EtOAc (100 ml) and washed with $H_2O$ (2×50 ml). The organic layer was dried over $Na_2SO_4$ and concentrated. The residue was dissolved in 2 N HCl in dioxane (100 ml) and stirred for 1 h. Removal of the solvent afforded the HCl salt of 5-aminomethyl-N-t-butyl-3-chloro-benzenesulfonamide (0.6 g, 46%) as an off-white powder.

EXAMPLE 28

Synthesis of 4-{[6-(3-Methanesulfonyl-4-methoxy-phenyl)-4-(1-trifluoromethyl-cyclopropylamino)-pyrido[3,2-d]pyrimidin-2-ylamino]-methyl}-benzenesulfonamide Scheme 6

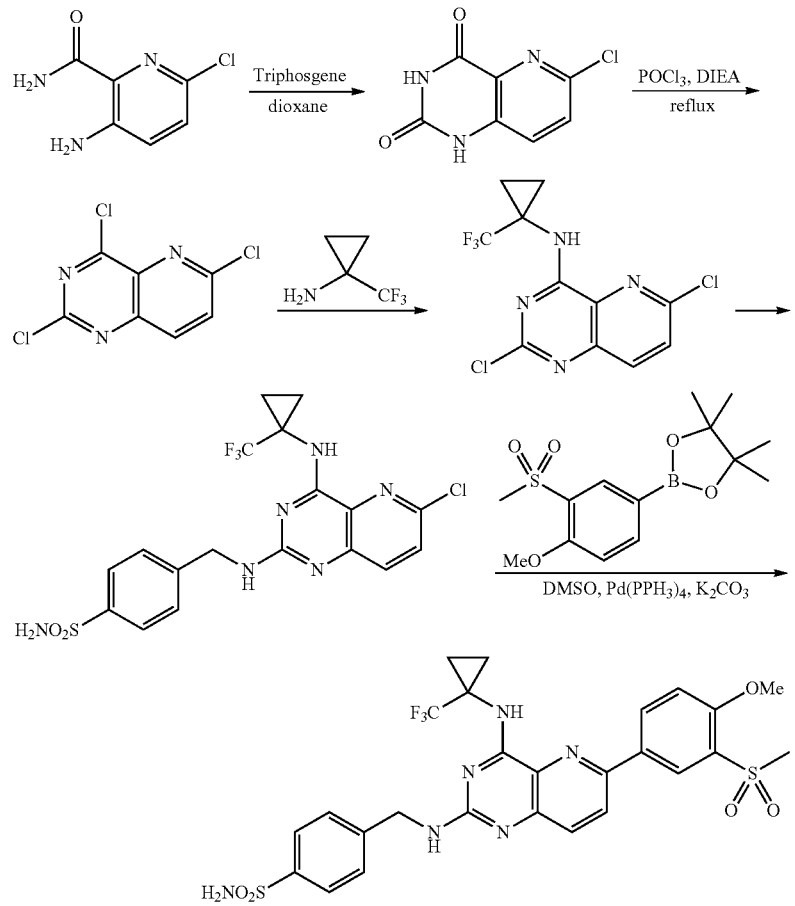

To 3-amino-6-chloro-pyridine-2-carboxylic acid amide (10 g, 58.3 mmol) in 1,4-dioxane (300 mL), was added triphosgene (6.9 g, 23.3 mmol). The reaction was heated to 100° C. for 1.5 hours. It was then cooled to RT and 3 ml of water was added to quench excess triphosgene. The solid was filtered and washed with EtOAc twice to provide 11 g of crude product which used without further purification.

A mixture of 6-chloro-1H-pyrido[3,2-d]pyrimidine-2,4-dione (11 g, 55.7 mmol), POCl$_3$ (100 ml) and DIEA (20 ml) was heated to reflux overnight. The POCl$_3$ was removed in vacuo and the residue was dissolved in dichloromethane and passed through a short silica gel plug. The combined organic fractions were concentrated to provide 8 g of the product as a beige solid.

To a solution of 2,4,6-trichloro-pyrido[3,2-d]pyrimidine (2 g, 8.52 mmol) in NMP (8.5 ml) was added 1-trifluoromethyl-cyclopropyl-ammonium chloride (1.63 g, 10.2 mmol) and diisopropylethylamine (3.57 ml, 20.4 mmol). The reaction mixture was stirred at room temperature for 6 h. Ice cold water (15 mL) was then added with vigorous stirring. The solid so formed was filtered, washed once with water and once with a water/acetonitrile solution (3:1) to provide 2.55 g of product as a red/orange solid.

(2,6-Dichloro-pyrido[3,2-d]pyrimidin-4-yl)-(1-trifluoromethyl-cyclopropyl)-amine (0.50 g) and 4-aminomethyl-benzenesulfonamide (0.37 g) were dissolved in NMP (6 mL), treated with diisopropylethylamine (0.35 mL) and heated to 120° C. After 5 h, water (20 mL) was added and the mixture was allowed to slowly cool to ambient temperature. A precipitate was collected and washed with 10% MeOH:water, and dried to give 0.59 g of the desired product which was used without further purification.

4-{[6-Chloro-4-(1-trifluoromethyl-cyclopropylamino)-pyrido[3,2-d]pyrimidin-2-ylamino]-methyl}benzenesulfonamide (0.100 g, 0.23 mmol) was combined with 2-(3-methanesulfonyl-4-methoxy-phenyl)-4,4,5,5-tetramethyl-[1,3,2]dioxaborolane (0.091 g, 0.34 mmol, see Scheme 7), palladium tetrakistriphenylphosphine (0.013 g, 0.011 mmol) and sodium bicarbonate (1.5 mL of a saturated aqueous solution). The mixture was suspended in DME (3 mL) and heated to 65° C. for 1 h. Crude product was precipitated by the addition of water (5 mL). The precipitate was filtered and purified by reverse phase HPLC (5-100% ACN/H$_2$O+0.1% TFA) to give 0.056 g (40% yield) of the title compound, and was characterized by its NMR and mass spectrum as follows: $^1$H NMR (d$_6$-DMSO): d 1.38-1.26 (m, 4H), 3.31 (s, 3H), 4.06 (s, 3H), 4.79 (m, 2H), 7.34 (s, 2H), 7.46 (d, J=8.7 Hz, 1H), 7.55 (d, J=8.4 Hz, 2H), 7.78 (d, J=8.4 Hz, 2H), 8.01 (d, J=9.0 Hz, 1H), 8.45-8.41 (m, 2H), 8.90 (d, J=11.4 Hz, 1H), 9.08 (bs, 1H), 10.15 (bs, 1H): MS (m/z): 623.2 ([M+H]$^+$, 100).

EXAMPLE 29

Synthesis of 4-{[6-(3-methanesulfonyl-4-methylphenyl)-4-(1-trifluoromethyl-cyclopropylamino)-pyrido[3,2-d]pyrimidin-2-ylamino]-methyl}-benzenesulfonamide

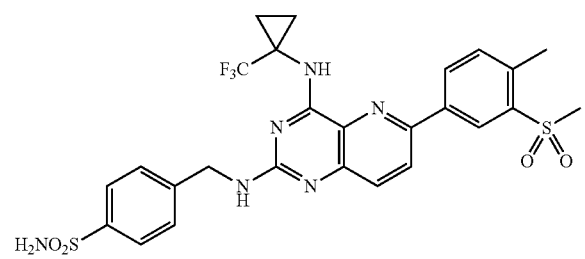 [SMILES: Cc1ccc(-c2ccc3nc(NCc4ccc(S(N)(=O)=O)cc4)nc(NC4(C(F)(F)F)CC4)c3n2)cc1S(C)(=O)=O]

The title compound was synthesized in a manner analogous to Example 28, using 2-(3-methanesulfonyl-4-methyl-phenyl)-4,4,5,5-tetramethyl-[1,3,2]dioxaborolane in place of 2-(3-methanesulfonyl-4-methoxy-phenyl)-4,4,5,5-tetramethyl-[1,3,2]dioxaborolane, and was characterized by its NMR and mass spectrum as follows: $^1$H NMR (d$_6$-DMSO): d 1.38-1.26 (m, 4H), 2.73 (s, 3H), 3.32 (s, 3H), 4.79 (m, 2H), 7.34 (s, 2H), 7.55 (d, J=7.8 Hz, 2H), 7.66 (d, J=8.1 Hz, 1H), 7.78 (d, J=8.1 Hz, 2H), 8.03 (d, J=9.0 Hz, 1H), 8.51 (d, J=8.8 Hz, 1H), 8.52 (s, 1H), 8.84 (d, J=6.3 Hz, 1H), 9.08 (bs, 1H), 10.13 (bs, 1H): MS (m/z): 607.2 ([M+H]$^+$, 100).

2-(3-Methanesulfonyl-4-methyl-phenyl)-4,4,5,5-tetramethyl-[1,3,2]dioxaborolane was synthesized as follows.

To a mixture of Bis(pinacolato)diboron (3.05 g, 12 mmol), X-phos (0.076 g, 0.16 mmol), Pd(dba)$_3$ (0.073 g, 0.08 mmol) and KOAc (1.17 g, 12 mmol) in dioxane (16 mL) at 110° C. was added a solution of 4-bromo-1-methyl-2-(methylsulfonyl)benzene (1.0 g, 4 mmol) in dioxane (10 mL) over 7 min. The reaction mixture was stirred at 110° C. for 2 hour, then cooled to room temperature and filtered through paper filtration and a layer of diatomaceous earth. The filtrate was washed twice with water and twice with brine. The organic layer was dried (Na$_2$SO$_4$), filtered, concentrated and purified by silica gel column chromatography to give 770 mg of 2-(4-methyl-3-(methylsulfonyl)phenyl)-4,4,5,5-tetramethyl-1,3,2-dioxaborolane.

EXAMPLE 30

Synthesis of 4-{[6-(3-methanesulfonyl-4-methoxymethylphenyl)-4-(1-trifluoromethyl-cyclopropylamino)-pyrido[3,2-d]pyrimidin-2-ylamino]-methyl}-benzenesulfonamide

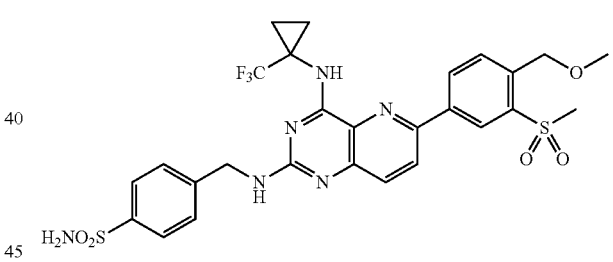

The title compound was synthesized in a manner analogous to Example 28, using 2-(3-methanesulfonyl-4-methoxymethyl-phenyl)-4,4,5,5-tetramethyl-[1,3,2]dioxaborolane in place of 2-(3-methanesulfonyl-4-methoxy-phenyl)-4,4,5,5-tetramethyl-[1,3,2]dioxaborolane, and was characterized by its NMR and mass spectrum as follows: $^1$H NMR (d$_6$-DMSO): d 1.39-1.26 (m, 4H), 3.35 (s, 3H), 3.42 (s, 3H), 4.79 (m, 2H), 4.9 (s, 2H), 7.33 (s, 2H), 7.56 (d, J=8.1 Hz, 2H), 7.78 (d, J=8.4 Hz, 2H), 7.85 (d, J=8.1 Hz, 1H), 8.04 (d, J=8.7 Hz, 1H), 8.51 (d, J=7.8 Hz, 1H), 8.55 (s, 1H), 8.93 (d, J=8.4 Hz, 1H), 9.08 (bs, 1H), 10.08 (bs, 1H): MS (m/z): 637.1 ([M+H]$^+$, 100).

2-(3-Methanesulfonyl-4-methoxymethyl-phenyl)-4,4,5,5-tetramethyl-[1,3,2]dioxaborolane was synthesized as follows.

To a solution of 4-bromo-2-methansulfonyl-benzaldehyde (1.0 g, 3.88 mmol) in EtOH (11 mL)/THF (2.5 mL) was added NaBH$_4$ (1.29 g, 34.2 mmol) in three portions. The reaction was carefully quenched with water and the product was extracted with EtOAc, dried (Na$_2$SO$_4$), and purified by silica gel chromatography to give 735 mg of (4-bromo-2-methansulfonyl-phenyl)-methanol.

To a mixture of (4-bromo-2-methansulfonyl-phenyl)-methanol (0.73 g, 2.78 mmol), sodium hydride (0.030 g, 8.4 mmol), and THF (10 mL) was added iodomethane (0.21 mL, 3.36 mmol). After 1 h, the reaction was poured into water (40 mL), diluted in $CH_2Cl_2$, and washed with brine (40 mL). The organic layer was dried over ($Na_2SO_4$), filtered, concentrated and purified by silica gel column chromatography to give 600 mg of 4-bromo-2-methansulfonyl-1-methoxymethyl-benzene.

To a mixture of Bis(pinacolato)diboron (2.13 g, 8.4 mmol), X-phos (0.053 g, 0.112 mmol), $Pd(dba)_3$ (0.052 g, 0.06 mmol) and KOAc (0.824 g, 8.4 mmol) in dioxane (15 mL) at 110° C. was added a solution of 4-bromo-2-methansulfonyl-1-methoxymethyl-benzene (0.60 g, 2.8 mmol) in dioxane (5 mL) over 7 min. The reaction mixture was stirred at 110° C. for 5 hour, then cooled to room temperature and filtered through paper and a layer of diatomaceous earth. The filtrate was washed with twice with water and twice with brine. The organic layer was dried ($Na_2SO_4$), filtered, concentrated and purified by silica gel column chromatography to give 0.851 g of 2-(3-Methanesulfonyl-4-methoxymethyl-phenyl)-4,4,5,5-tetramethyl-[1,3,2]dioxaborolane.

EXAMPLE 31

Synthesis of 6-(6-amino-pyridin-3-yl)-N2-(1-methyl-2-[1,2,4]triazol-1-yl-ethyl)-N4-(1-trifluoromethyl-cyclopropyl)-pyrido[3,2-d]pyrimidine-2,4-diamine

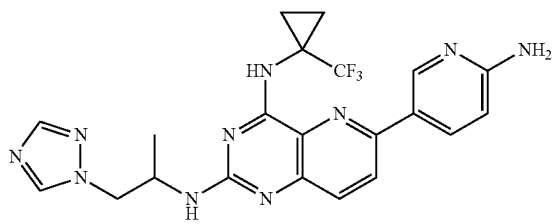 [SMILES: CC(Cn1cncn1)Nc1nc(NC2(C(F)(F)F)CC2)c2nc(-c3ccc(N)nc3)ccc2n1]

The title compound was synthesized in a manner analogous to Example 28, using 1-methyl-2-[1,2,4]triazol-1-yl-ethylamine in place of 4-aminomethyl-benzenesulfonamide, and 5-(4,4,5,5-Tetramethyl-[1,3,2]dioxaborolan-2-yl)-pyridin-2-ylamine in place of 2-(3-methanesulfonyl-4-methoxy-phenyl)-4,4,5,5-tetramethyl-[1,3,2]dioxaborolane. The title compound was characterized by its NMR and mass spectrum as follows: $^1H$ NMR ($d_6$-DMSO): d 1.22 (d, 3H), 1.39 (m, 2H), 1.60 (br s, 2H), 4.45 (m, 2H), 4.62 (m, 1H), 6.98 (m, 1H), 7.92-7.99 (m, 3H), 8.36 (m, 1H), 8.51 (s, 2H), 8.94 (s, 2H), 10.07 (br s, 1H), 12.0 (br s, 1H): MS (m/z): 471.2 ([M+H]$^+$, 100).

EXAMPLE 32

Synthesis of (R)-4-(1-(4-cyclopropoxy-6-(2-cyclopropylethynyl)pyrido[3,2-d]pyrimidin-2-ylamino)ethyl)benzenesulfonamide

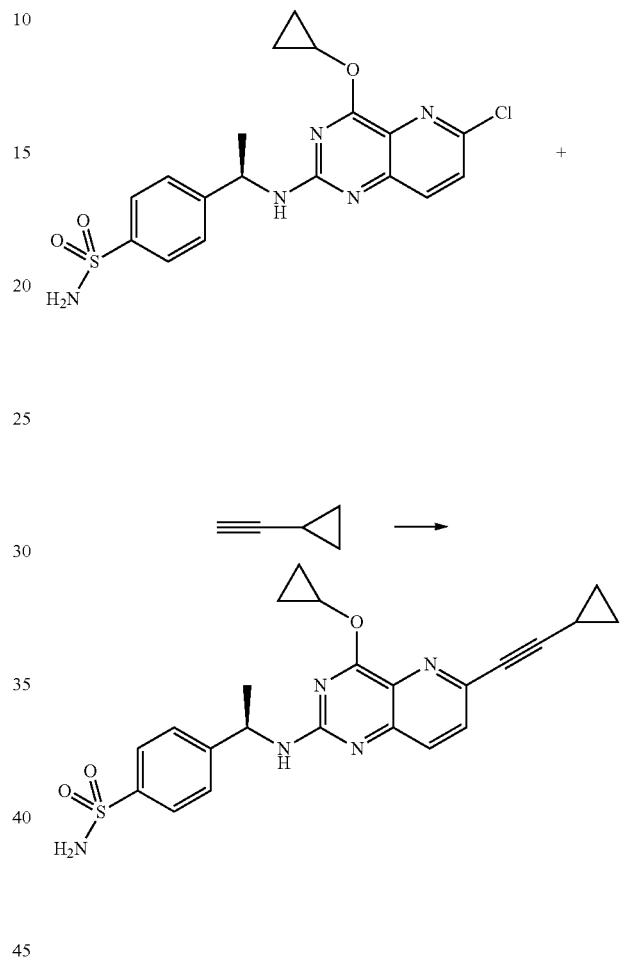

A mixture of 4-[1-(6-Chloro-4-cyclopropoxy-pyrido[3,2-d]pyrimidin-2-ylamino)-ethyl]-benzenesulfonamide (300 mg, 0.71 mmol), $PdCl_2(PPh_3)_2$ (25 mg, 0.035 mmol), CuI (13.5 mg, 0.07 mmol) in TEA (1 mL) and DMF (5 mL) was degassed for 10 min then purged with argon. Ethynyl-cyclopropane (0.3 mL, 3.5 mmol) was added and the reaction tube was sealed and heated at 80° C. for 3 hours. After cooling to room temperature, the reaction mixture was poured into water and extracted twice with EtOAc. The combined organic layers were washed with 5% LiCl solution and brine. Solvent was removed by concentration in vacuo and the residue was purified by RP HPLC using a C18 column with a gradient of $H_2O$, 0.1% TFA-acetonitrile, to provide 248 mg (62%) of desired product. MS (m/z) 450.0 [M+H]$^+$; HPLC $R_t$=2.16 min.

By modifying the methods and reagents used in the methods disclosed herein, the additional examples in Table III were prepared. MS is the mass ion plus H$^+$ and Ex=Example number.

TABLE III

| Ex | Structure | Name | MS |
|---|---|---|---|
| 34 | 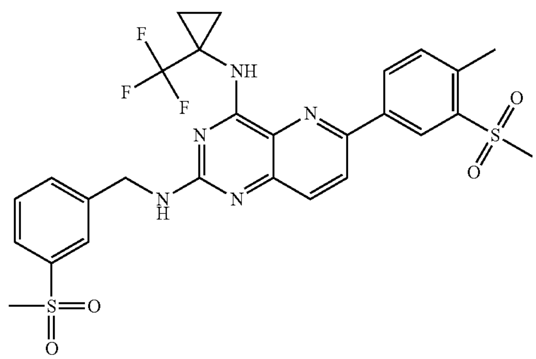 | $N^2$-(3-(methylsulfonyl)benzyl)-6-(4-methyl-3-(methylsulfonyl)phenyl)-$N^4$-(1-(trifluoromethyl)cyclopropyl)pyrido[3,2-d]pyrimidine-2,4-diamine | 606.4 |
| 35 | 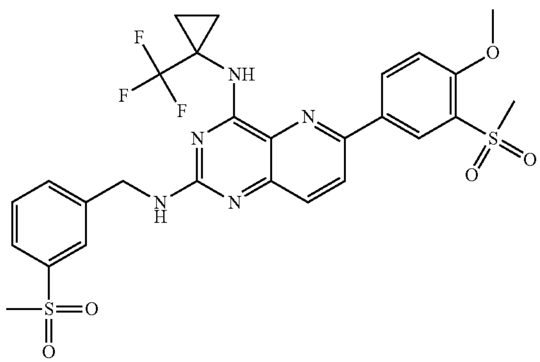 [SMILES: COc1ccc(-c2ccc3nc(NCc4cccc(S(C)(=O)=O)c4)nc(NC4(C(F)(F)F)CC4)c3n2)cc1S(C)(=O)=O] | $N^2$-(3-(methylsulfonyl)benzyl)-6-(4-methoxy-3-(methylsulfonyl)phenyl)-$N^4$-(1-(trifluoromethyl)cyclopropyl)pyrido[3,2-d]pyrimidine-2,4-diamine | 622.2 |
| 36 | 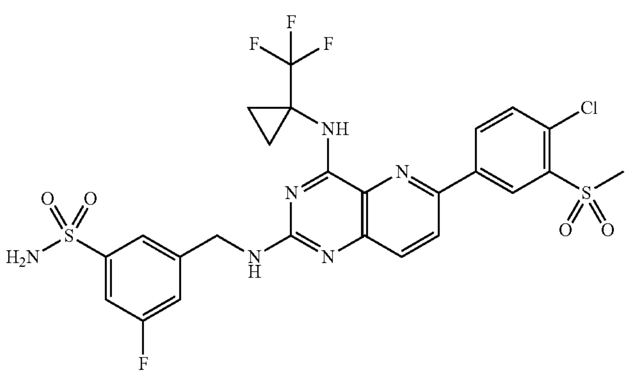 [SMILES: CS(=O)(=O)c1cc(-c2ccc3nc(NCc4cc(F)cc(S(N)(=O)=O)c4)nc(NC4(C(F)(F)F)CC4)c3n2)ccc1Cl] | 3-((6-(4-chloro-3-(methylsulfonyl)phenyl)-4-(1-(trifluoromethyl)cyclopropylamino)pyrido[3,2-d]pyrimidin-2-ylamino)methyl)-5-fluorobenzenesulfonamide | 645.2 |
| 37 | 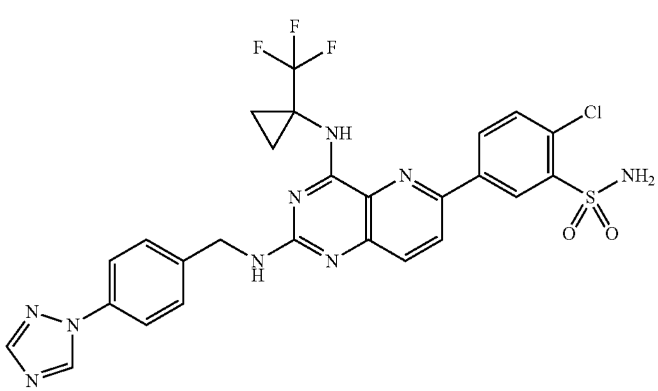 [SMILES: NS(=O)(=O)c1cc(-c2ccc3nc(NCc4ccc(-n5cncn5)cc4)nc(NC4(C(F)(F)F)CC4)c3n2)ccc1Cl] | 5-(2-(4-(1H-1,2,4-triazol-1-yl)benzylamino)-4-(1-(trifluoromethyl)cyclopropylamino)pyrido[3,2-d]pyrimidin-6-yl)-2-chlorobenzenesulfonamide | 616.3 |

TABLE III-continued

| Ex | Structure | Name | MS |
|---|---|---|---|
| 38 | 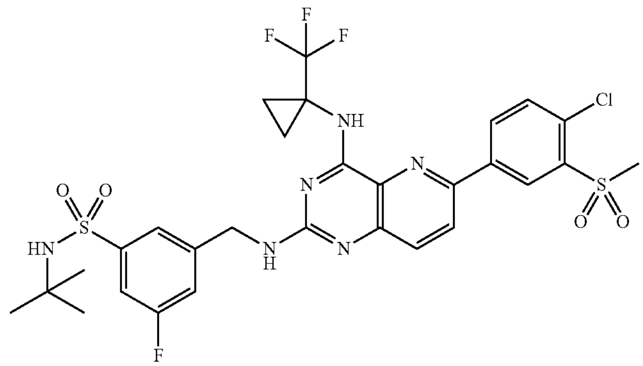 [SMILES: CC(C)(C)NS(=O)(=O)c1cc(F)cc(CNc2nc(NC3(C(F)(F)F)CC3)c3nc(-c4ccc(Cl)c(S(C)(=O)=O)c4)ccc3n2)c1] | N-tert-butyl-3-((6-(4-chloro-3-(methylsulfonyl)phenyl)-4-(1-(trifluoromethyl)cyclopropyl-amino)pyrido[3,2-d]pyrimidin-2-ylamino)methyl)-5-fluorobenzenesulfonamide | 701.3 |
| 39 | 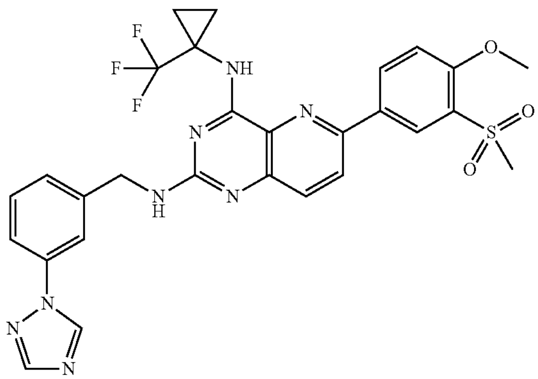 [SMILES: COc1ccc(-c2ccc3nc(NCc4cccc(-n5cncn5)c4)nc(NC4(C(F)(F)F)CC4)c3n2)cc1S(C)(=O)=O] | N²-(3-(1H-1,2,4-triazol-1-yl)benzyl)-6-(4-methoxy-3-(methylsulfonyl)phenyl)-N⁴-(1-(trifluoromethyl)cyclopropyl)pyrido[3,2-d]pyrimidine-2,4-diamine | 611.2 |
| 40 | 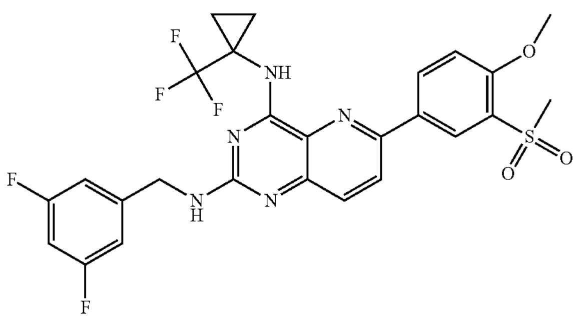 [SMILES: COc1ccc(-c2ccc3nc(NCc4cc(F)cc(F)c4)nc(NC4(C(F)(F)F)CC4)c3n2)cc1S(C)(=O)=O] | N²-(3,5-difluorobenzyl)-6-(4-methoxy-3-(methylsulfonyl)phenyl)-N⁴-(1-(trifluoromethyl)cyclopropyl)pyrido[3,2-d]pyrimidine-2,4-diamine | 508.1 |
| 41 | 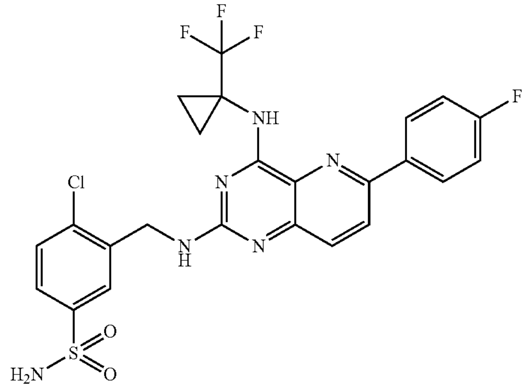 [SMILES: NS(=O)(=O)c1ccc(Cl)c(CNc2nc(NC3(C(F)(F)F)CC3)c3nc(-c4ccc(F)cc4)ccc3n2)c1] | 4-chloro-3-((6-(4-fluorophenyl)-4-(1-(trifluoromethyl)cyclopropyl-amino)pyrido[3,2-d]pyrimidin-2-ylamino)methyl)benzene-sulfonamide | 567.1 |

TABLE III-continued

| Ex | Structure | Name | MS |
|---|---|---|---|
| 42 | 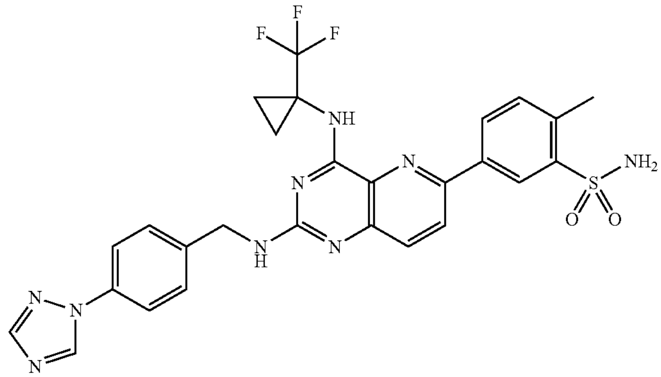 [SMILES: Cc1ccc(-c2ccc3nc(NCc4ccc(-n5cncn5)cc4)nc(NC4(C(F)(F)F)CC4)c3n2)cc1S(N)(=O)=O] | 5-(2-(4-(1H-1,2,4-triazol-1-yl)benzylamino)-4-(1-(trifluoromethyl)cyclopropyl-amino)pyrido[3,2-d]pyrimidin-6-yl)-2-methylbenzene-sulfonamide | 596.3 |
| 43 | 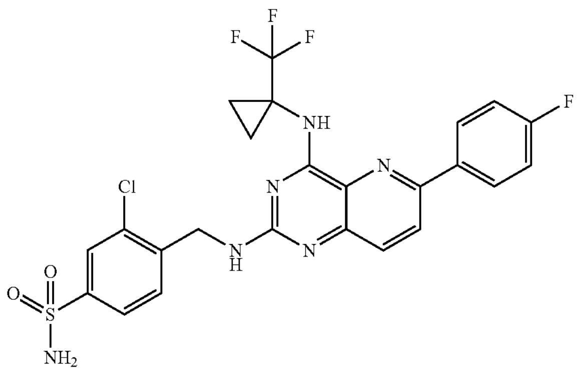 [SMILES: NS(=O)(=O)c1ccc(CNc2nc(NC3(C(F)(F)F)CC3)c3nc(-c4ccc(F)cc4)ccc3n2)c(Cl)c1] | 3-chloro-4-((6-(4-fluorophenyl)-4-(1-(trifluoromethyl)cyclopropyl-amino)pyrido[3,2-d]pyrimidin-2-ylamino)methyl)benzene-sulfonamide | 567.3 |
| 44 | 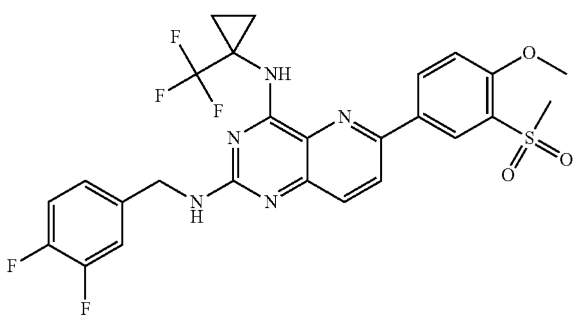 [SMILES: COc1ccc(-c2ccc3nc(NCc4ccc(F)c(F)c4)nc(NC4(C(F)(F)F)CC4)c3n2)cc1S(C)(=O)=O] | $N^2$-(3,4-difluorobenzyl)-6-(4-methoxy-3-(methylsulfonyl)phenyl)-$N^4$-(1-(trifluoromethyl)cyclopropyl)pyrido[3,2-d]pyrimidine-2,4-diamine | 580.1 |
| 45 | 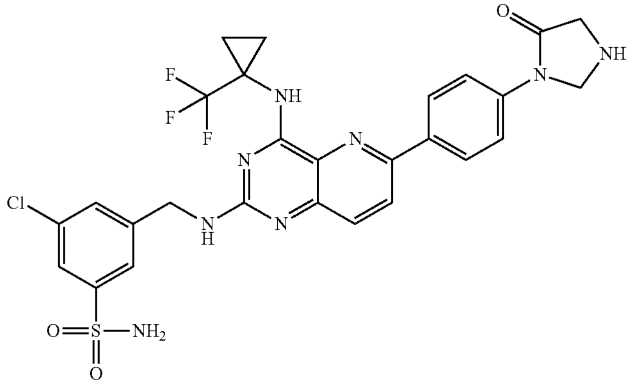 [SMILES: NS(=O)(=O)c1cc(Cl)cc(CNc2nc(NC3(C(F)(F)F)CC3)c3nc(-c4ccc(N5CNCC5=O)cc4)ccc3n2)c1] | 3-chloro-5-((6-(4-(5-oxoimidazolidin-1-yl)phenyl)-4-(1-(trifluoromethyl)cyclopropylamino)pyrido[3,2-d]pyrimidin-2-ylamino)methyl)benzenesulfonamide | 633.3 |

TABLE III-continued

| Ex | Structure | Name | MS |
|---|---|---|---|
| 46 | 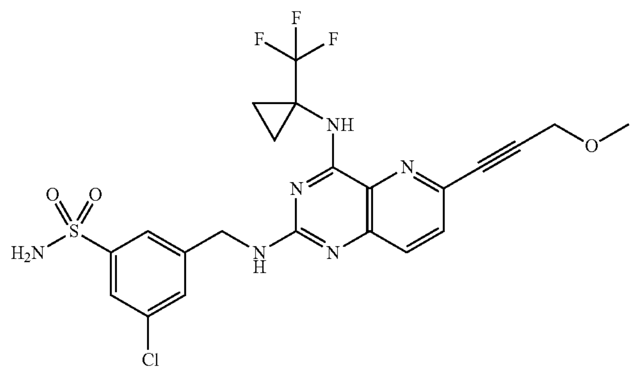 [SMILES: COCC#Cc1ccc2nc(NCc3cc(Cl)cc(S(N)(=O)=O)c3)nc(NC3(C(F)(F)F)CC3)c2n1] | 3-chloro-5-((6-(3-methoxyprop-1-ynyl)-4-(1-(trifluoromethyl)cyclopropyl-amino)pyrido[3,2-d]pyrimidin-2-ylamino)methyl)benzene-sulfonamide | 540.7 |
| 47 | 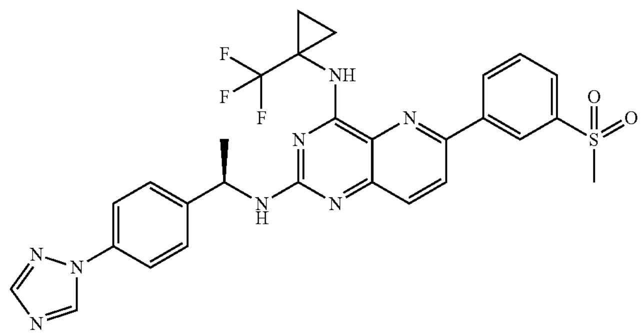 [SMILES: C[C@@H](Nc1nc(NC2(C(F)(F)F)CC2)c2nc(-c3cccc(S(C)(=O)=O)c3)ccc2n1)c1ccc(-n2cncn2)cc1] | $N^2$-((R)-1-(4-(1H-1,2,4-triazol-1-yl)phenyl)ethyl)-6-(3-(methylsulfonyl)phenyl)-$N^4$-(1-(trifluoromethyl)cyclopropyl)pyrido[3,2-d]pyrimidine-2,4-diamine | 595.1 |
| 48 | 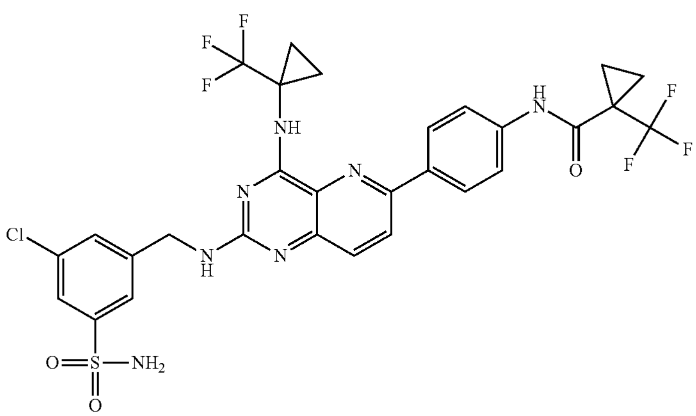 [SMILES: NS(=O)(=O)c1cc(Cl)cc(CNc2nc(NC3(C(F)(F)F)CC3)c3nc(-c4ccc(NC(=O)C5(C(F)(F)F)CC5)cc4)ccc3n2)c1] | 3-chloro-5-((6-(4-(1-(trifluoromethyl)cyclopropyl-carboxamido)phenyl)-4-(1-(trifluoromethyl)cyclopropyl-amino)pyrido[3,2-d]pyrimidin-2-ylamino)methyl)benzene-sulfonamide | 700.3 |
| 49 | 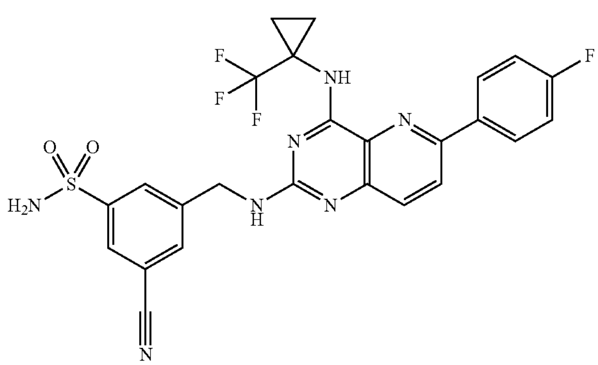 [SMILES: N#Cc1cc(CNc2nc(NC3(C(F)(F)F)CC3)c3nc(-c4ccc(F)cc4)ccc3n2)cc(S(N)(=O)=O)c1] | 3-cyano-5-((6-(4-fluorophenyl)-4-(1-(trifluoromethyl)cyclopropyl-amino)pyrido[3,2-d]pyrimidin-2-ylamino)methyl)benzene-sulfonamide | 558.2 |

TABLE III-continued

| Ex | Structure | Name | MS |
|---|---|---|---|
| 50 | 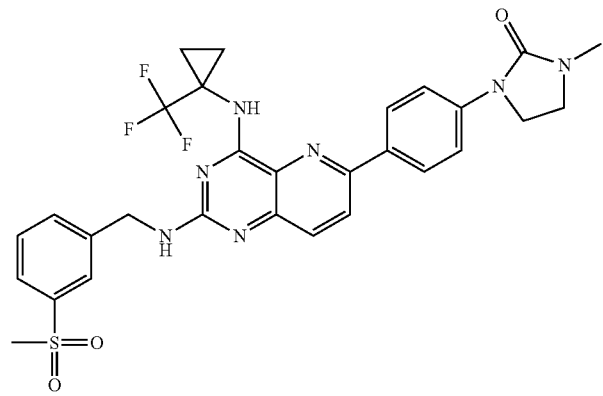 | 1-(4-(2-(3-(methylsulfonyl)benzylamino)-4-(1-(trifluoromethyl)cyclopropylamino)pyrido[3,2-d]pyrimidin-6-yl)phenyl)-3-methylimidazolidin-2-one | 612.3 |
| 51 | 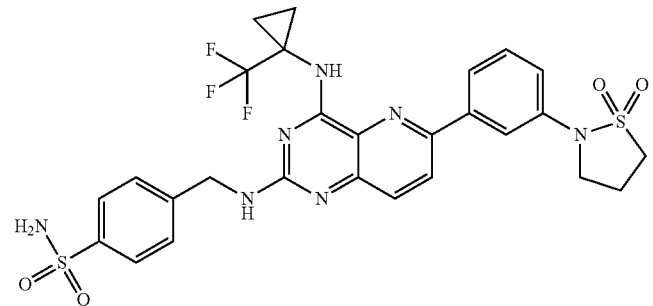 [SMILES: NS(=O)(=O)c1ccc(CNc2nc(NC3(C(F)(F)F)CC3)c3nc(-c4cccc(N5CCCS5(=O)=O)c4)ccc3n2)cc1] | 4-((6-(3-(1,1-dioxo-isothiazolidin-2-yl)phenyl)-4-(1-(trifluoromethyl)cyclopropyl-amino)pyrido[3,2-d]pyrimidin-2-ylamino)methyl)benzene-sulfonamide | 634.3 |
| 52 | 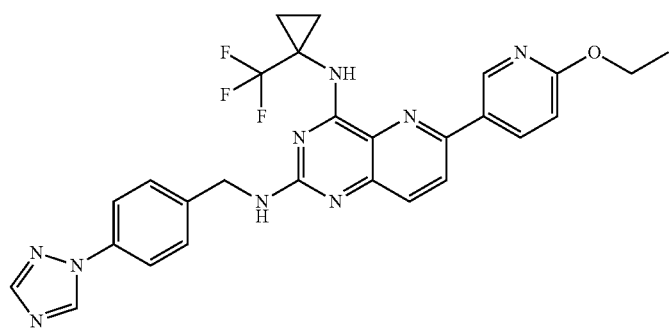 [SMILES: CCOc1ccc(-c2ccc3nc(NCc4ccc(-n5cncn5)cc4)nc(NC4(C(F)(F)F)CC4)c3n2)cn1] | $N^2$-(4-(1H-1,2,4-triazol-1-yl)benzyl)-6-(6-ethoxypyridin-3-yl)-$N^4$-(1-(trifluoromethyl)cyclopropyl)pyrido[3,2-d]pyrimidine-2,4-diamine | 548.3 |
| 53 | 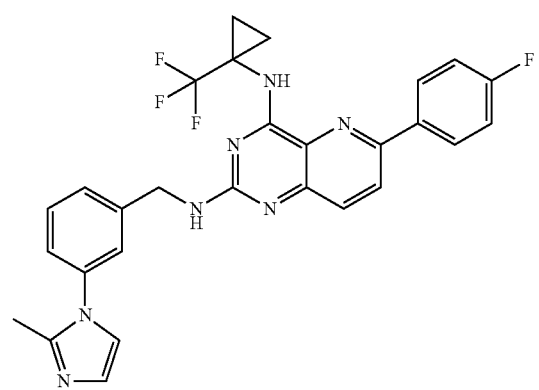 [SMILES: Cc1nccn1-c1cccc(CNc2nc(NC3(C(F)(F)F)CC3)c3nc(-c4ccc(F)cc4)ccc3n2)c1] | $N^2$-(3-(2-methyl-1H-imidazol-1-yl)benzyl)-6-(4-fluorophenyl)-$N^4$-(1-(trifluoromethyl)cyclopropyl)pyrido[3,2-d]pyrimidine-2,4-diamine | 534.2 |

TABLE III-continued

| Ex | Structure | Name | MS |
|---|---|---|---|
| 54 | 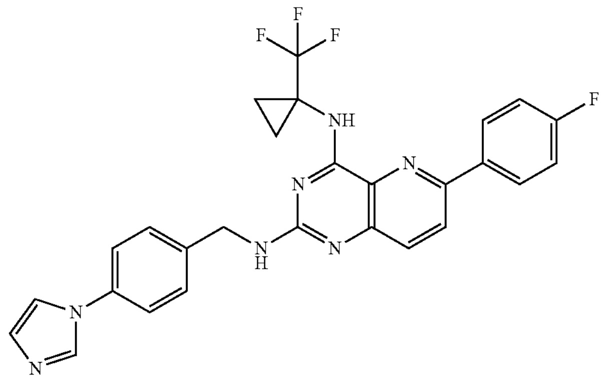 [SMILES: Fc1ccc(-c2ccc3nc(NCc4ccc(-n5ccnc5)cc4)nc(NC4(C(F)(F)F)CC4)c3n2)cc1] | N²-(4-(1H-imidazol-1-yl)benzyl)-6-(4-fluorophenyl)-N⁴-(1-(trifluoromethyl)cyclopropyl)pyrido[3,2-d]pyrimidine-2,4-diamine | 520.2 |
| 55 | 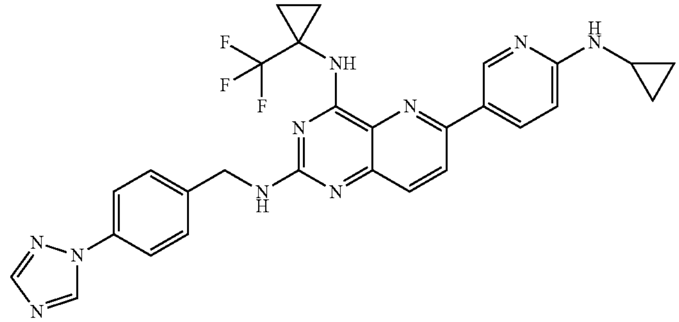 [SMILES: FC(F)(F)C1(Nc2nc(NCc3ccc(-n4cncn4)cc3)nc3ccc(-c4ccc(NC5CC5)nc4)nc23)CC1] | N²-(4-(1H-1,2,4-triazol-1-yl)benzyl)-6-(6-(cyclopropylamino)pyridin-3-yl)-N⁴-(1-(trifluoromethyl)cyclopropyl)pyrido[3,2-d]pyrimidine-2,4-diamine | 559.2 |
| 56 | 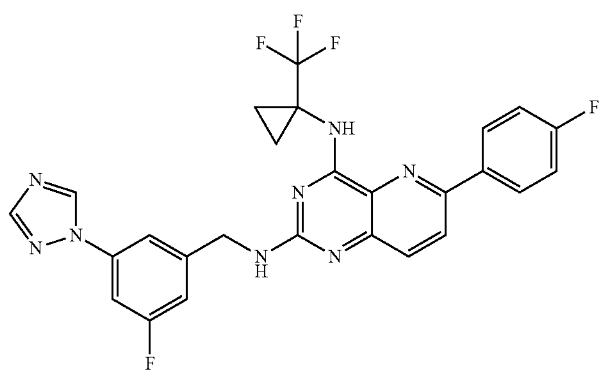 [SMILES: Fc1ccc(-c2ccc3nc(NCc4cc(F)cc(-n5cncn5)c4)nc(NC4(C(F)(F)F)CC4)c3n2)cc1] | N²-(3-fluoro-5-(1H-1,2,4-triazol-1-yl)benzyl)-6-(4-fluorophenyl)-N⁴-(1-(trifluoromethyl)cyclopropyl)pyrido[3,2-d]pyrimidine-2,4-diamine | 539.23 |
| 57 | 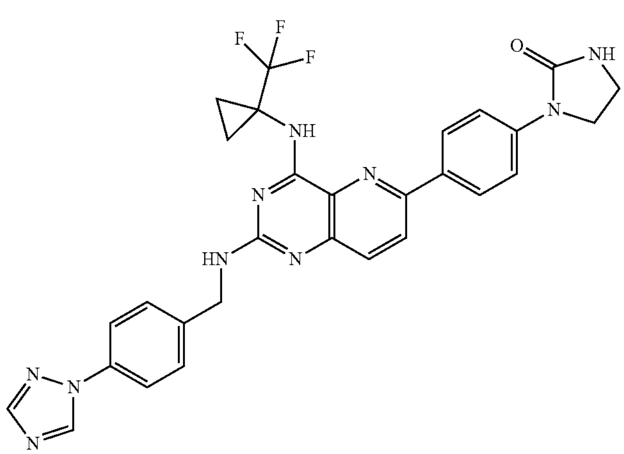 [SMILES: O=C1NCCN1c1ccc(-c2ccc3nc(NCc4ccc(-n5cncn5)cc4)nc(NC4(C(F)(F)F)CC4)c3n2)cc1] | 1-(4-(2-(4-(1H-1,2,4-triazol-1-yl)benzylamino)-4-(1-(trifluoromethyl)cyclopropylamino)pyrido[3,2-d]pyrimidin-6-yl)phenyl)imidazolidin-2-one | 587.3 |

TABLE III-continued

| Ex | Structure | Name | MS |
|---|---|---|---|
| 58 | 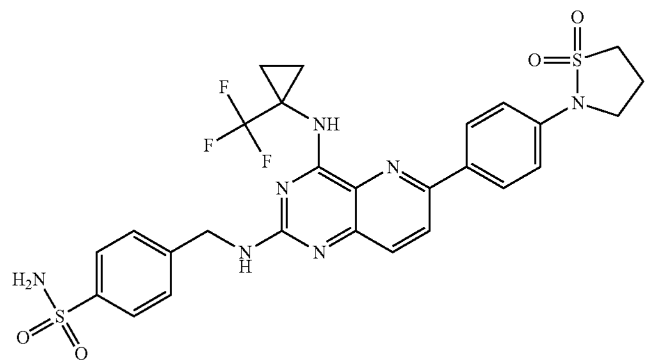 [SMILES: NS(=O)(=O)c1ccc(CNc2nc(NC3(C(F)(F)F)CC3)c3nc(-c4ccc(N5CCCS5(=O)=O)cc4)ccc3n2)cc1] | 4-((6-(4-(1,1-dioxo-isothiazolidin-2-yl)phenyl)-4-(1-(trifluoromethyl)cyclopropyl-amino)pyrido[3,2-d]pyrimidin-2-ylamino)methyl)benzene-sulfonamide | 634.1 |
| 59 | 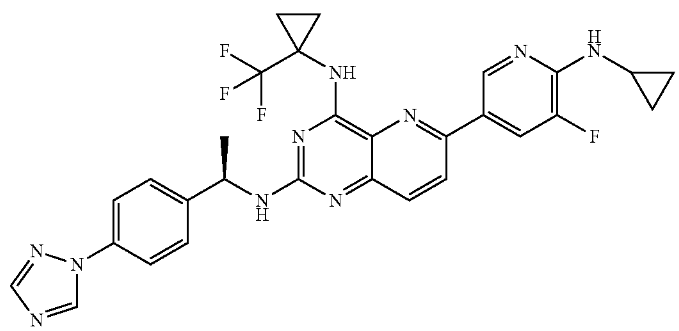 [SMILES: C[C@@H](Nc1nc(NC2(C(F)(F)F)CC2)c2nc(-c3cnc(NC4CC4)c(F)c3)ccc2n1)c1ccc(-n2cncn2)cc1] | $N^2$-((R)-1-(4-(1H-1,2,4-triazol-1-yl)phenyl)ethyl)-6-(6-(cyclopropylamino)-5-fluoropyridin-3-yl)-$N^4$-(1-(trifluoromethyl)cyclopropyl)pyrido[3,2-d]pyrimidine-2,4-diamine | 591.2 |
| 60 | 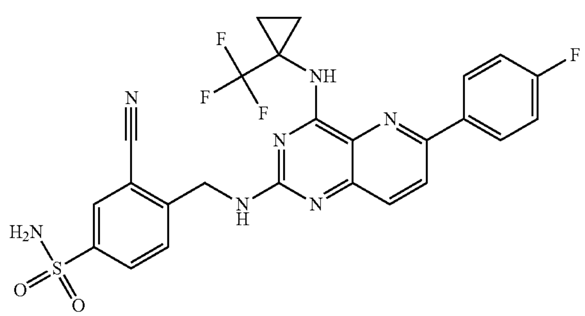 [SMILES: N#Cc1cc(S(N)(=O)=O)ccc1CNc1nc(NC2(C(F)(F)F)CC2)c2nc(-c3ccc(F)cc3)ccc2n1] | 3-cyano-4-((6-(4-fluorophenyl)-4-(1-(trifluoromethyl)cyclopropyl-amino)pyrido[3,2-d]pyrimidin-2-ylamino)methyl)benzene-sulfonamide | 559.2 |
| 61 | 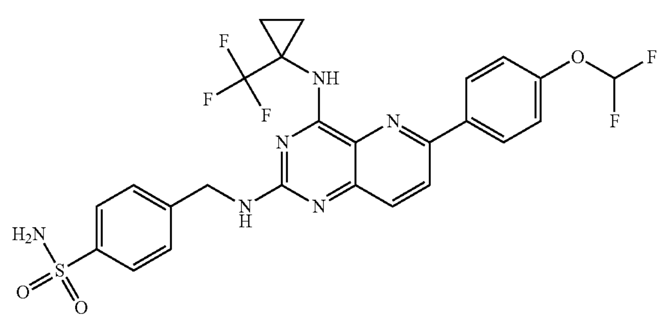 [SMILES: NS(=O)(=O)c1ccc(CNc2nc(NC3(C(F)(F)F)CC3)c3nc(-c4ccc(OC(F)F)cc4)ccc3n2)cc1] | 4-((6-(4-(difluoromethoxy)phenyl)-4-(1-(trifluoromethyl)cyclopropylamino)pyrido[3,2-d]pyrimidin-2-ylamino)methyl)benzenesulfonamide | 581.2 |

TABLE III-continued

| Ex | Structure | Name | MS |
|---|---|---|---|
| 62 | 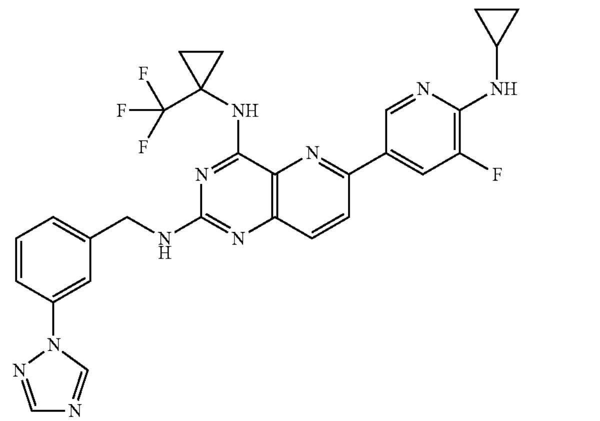 [SMILES: Fc1cc(-c2ccc3nc(NCc4cccc(-n5cncn5)c4)nc(NC4(C(F)(F)F)CC4)c3n2)cnc1NC1CC1] | N²-(3-(1H-1,2,4-triazol-1-yl)benzyl)-6-(6-(cyclopropylamino)-5-fluoropyridin-3-yl)-N⁴-(1-(trifluoromethyl)cyclopropyl)pyrido[3,2-d]pyrimidine-2,4-diamine | 577.2 |
| 63 | 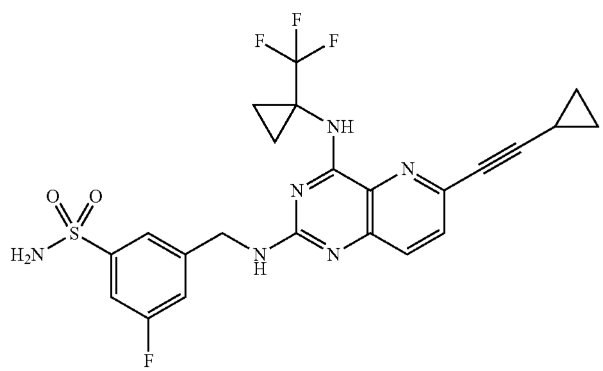 | 3-((6-(2-cyclopropylethynyl)-4-(1-(trifluoromethyl)cyclopropylamino)pyrido[3,2-d]pyrimidin-2-ylamino)methyl)-5-fluorobenzenesulfonamide | 521.2 |
| 65 | 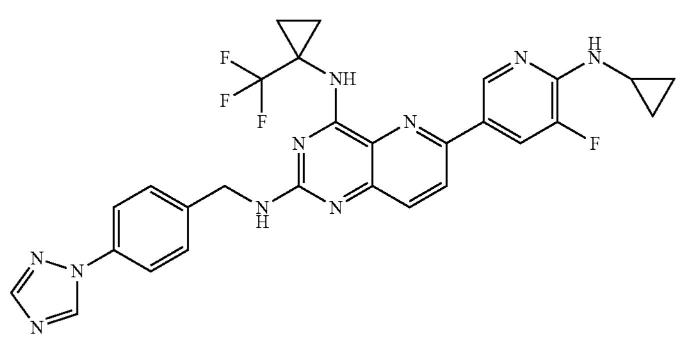 [SMILES: Fc1cc(-c2ccc3nc(NCc4ccc(-n5cncn5)cc4)nc(NC4(C(F)(F)F)CC4)c3n2)cnc1NC1CC1] | N²-(4-(1H-1,2,4-triazol-1-yl)benzyl)-6-(6-(cyclopropylamino)-5-fluoropyridin-3-yl)-N⁴-(1-(trifluoromethyl)cyclopropyl)pyrido[3,2-d]pyrimidine-2,4-diamine | 577.2 |
| 66 | 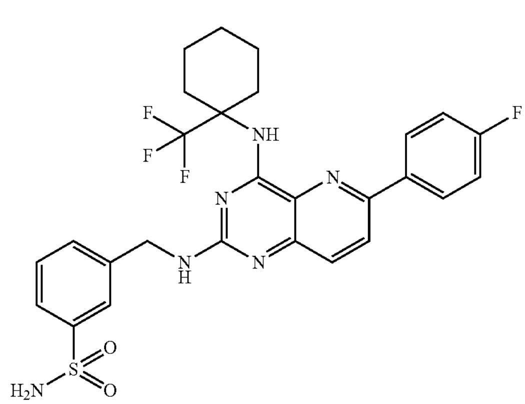 [SMILES: NS(=O)(=O)c1cccc(CNc2nc(NC3(C(F)(F)F)CCCCC3)c3nc(-c4ccc(F)cc4)ccc3n2)c1] | 3-((6-(4-fluorophenyl)-4-(1-(trifluoromethyl)cyclohexylamino)pyrido[3,2-d]pyrimidin-2-ylamino)methyl)benzenesulfonamide | 575.3 |

TABLE III-continued

| Ex | Structure | Name | MS |
|---|---|---|---|
| 67 | 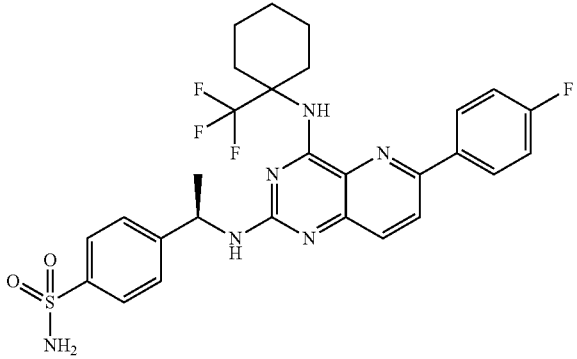 [SMILES: C[C@@H](Nc1nc(NC2(C(F)(F)F)CCCCC2)c2nc(-c3ccc(F)cc3)ccc2n1)c1ccc(S(N)(=O)=O)cc1] | (R)-4-(1-(6-(4-fluorophenyl)-4-(1-(trifluoromethyl)cyclohexylamino)pyrido[3,2-d]pyrimidin-2-ylamino)ethyl)benzenesulfonamide | 589.3 |
| 68 | 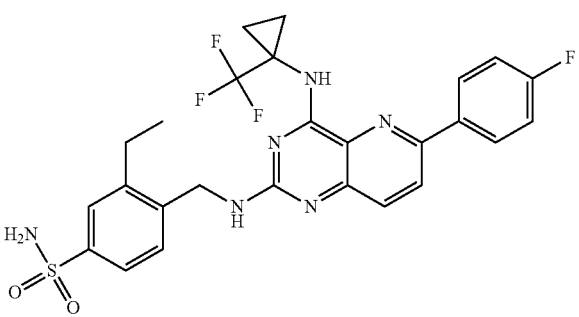 [SMILES: CCc1cc(S(N)(=O)=O)ccc1CNc1nc(NC2(C(F)(F)F)CC2)c2nc(-c3ccc(F)cc3)ccc2n1] | 3-ethyl-4-((6-(4-fluorophenyl)-4-(1-(trifluoromethyl)cyclopropylamino)pyrido[3,2-d]pyrimidin-2-ylamino)methyl)benzenesulfonamide | 561.1 |
| 69 | 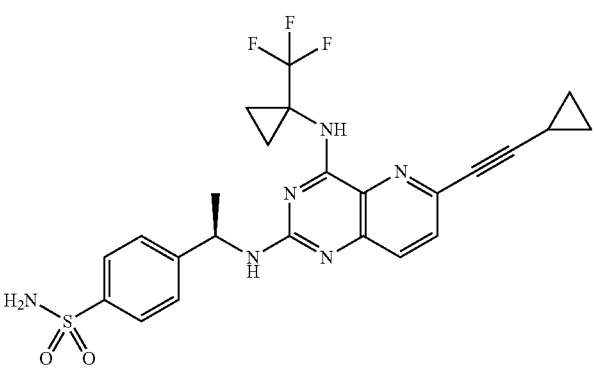 [SMILES: C[C@@H](Nc1nc(NC2(C(F)(F)F)CC2)c2nc(C#CC3CC3)ccc2n1)c1ccc(S(N)(=O)=O)cc1] | (R)-4-(1-(6-(2-cyclopropylethynyl)-4-(1-(trifluoromethyl)cyclopropylamino)pyrido[3,2-d]pyrimidin-2-ylamino)ethyl)benzenesulfonamide | 517.2 |
| 70 | 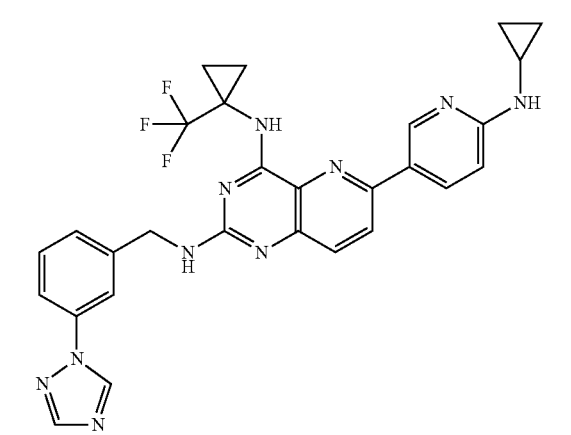 [SMILES: FC(F)(F)C1(Nc2nc(NCc3cccc(-n4cncn4)c3)nc3ccc(-c4ccc(NC5CC5)nc4)nc23)CC1] | $N^2$-(3-(1H-1,2,4-triazol-1-yl)benzyl)-6-(6-(cyclopropylamino)pyridin-3-yl)-$N^4$-(1-(trifluoromethyl)cyclopropyl)pyrido[3,2-d]pyrimidine-2,4-diamine | 559.2 |

TABLE III-continued

| Ex | Structure | Name | MS |
|---|---|---|---|
| 71 | 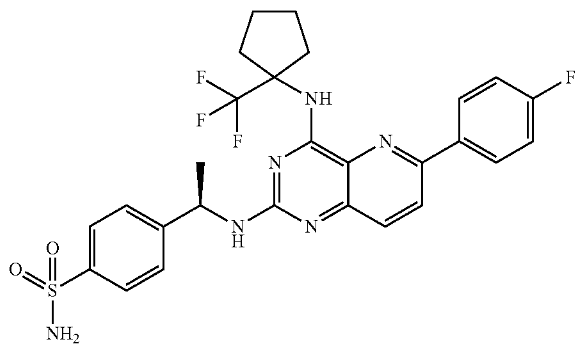 [SMILES: C[C@@H](Nc1nc(NC2(C(F)(F)F)CCCC2)c2nc(-c3ccc(F)cc3)ccc2n1)c1ccc(S(N)(=O)=O)cc1] | (R)-4-(1-(6-(4-fluorophenyl)-4-(1-(trifluoromethyl)cyclo-pentylamino)pyrido[3,2-d]pyrimidin-2-ylamino)ethyl)benzenesulfonamide | 575.3 |
| 72 | 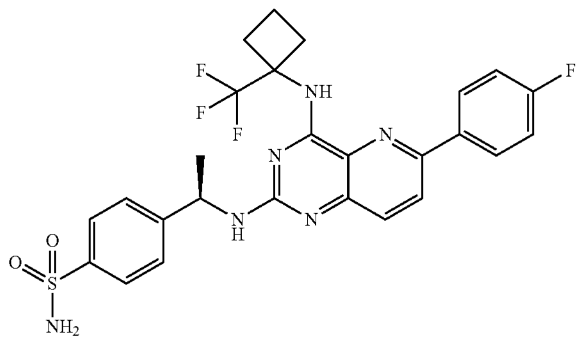 [SMILES: C[C@@H](Nc1nc(NC2(C(F)(F)F)CCC2)c2nc(-c3ccc(F)cc3)ccc2n1)c1ccc(S(N)(=O)=O)cc1] | (R)-4-(1-(6-(4-fluorophenyl)-4-(1-(trifluoromethyl)cyclo-butylamino)pyrido[3,2-d]pyrimidin-2-ylamino)ethyl)benzenesulfonamide | 561.2 |
| 73 | 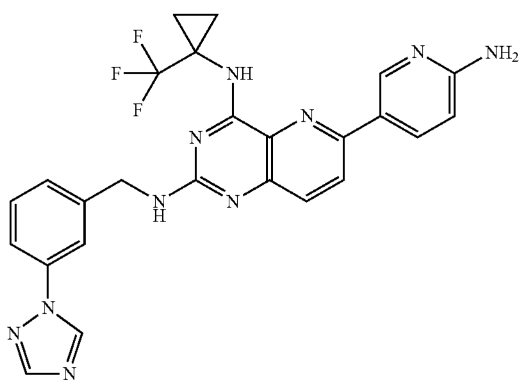 [SMILES: Nc1ccc(-c2ccc3nc(NCc4cccc(-n5cncn5)c4)nc(NC4(C(F)(F)F)CC4)c3n2)cn1] | $N^2$-(3-(1H-1,2,4-triazol-1-yl)benzyl)-6-(6-aminopyridin-3-yl)-$N^4$-(1-(trifluoromethyl)cyclopropyl)pyrido[3,2-d]pyrimidine-2,4-diamine | 519.2 |
| 74 | 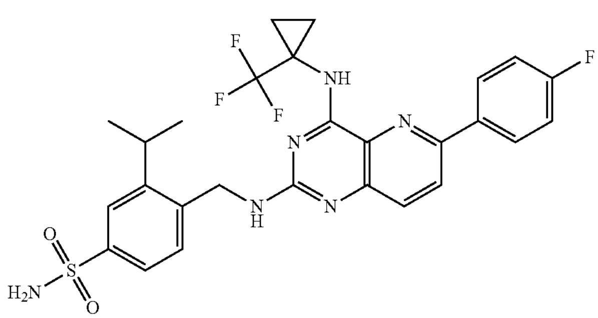 [SMILES: CC(C)c1cc(S(N)(=O)=O)ccc1CNc1nc(NC2(C(F)(F)F)CC2)c2nc(-c3ccc(F)cc3)ccc2n1] | 4-((6-(4-fluorophenyl)-4-(1-(trifluoromethyl)cyclopropyl-amino)pyrido[3,2-d]pyrimidin-2-ylamino)methyl)-3-isopropyl-benzenesulfonamide | 575.2 |

TABLE III-continued

| Ex | Structure | Name | MS |
|---|---|---|---|
| 75 | 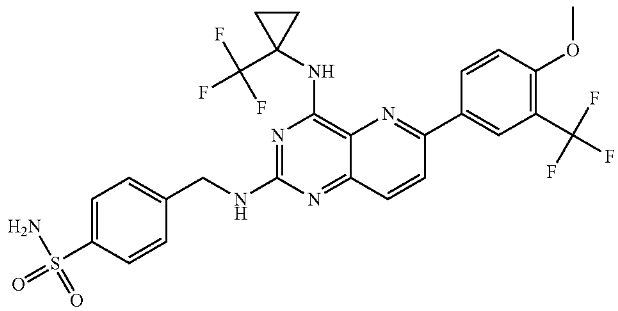 [SMILES: COc1ccc(-c2ccc3nc(NCc4ccc(S(N)(=O)=O)cc4)nc(NC4(C(F)(F)F)CC4)c3n2)cc1C(F)(F)F] | 4-((6-(4-methoxy-3-(trifluoromethyl)phenyl)-4-(1-(trifluoromethyl)cyclopropyl-amino)pyrido[3,2-d]pyrimidin-2-ylamino)methyl)benzene-sulfonamide | 613.1 |
| 76 | 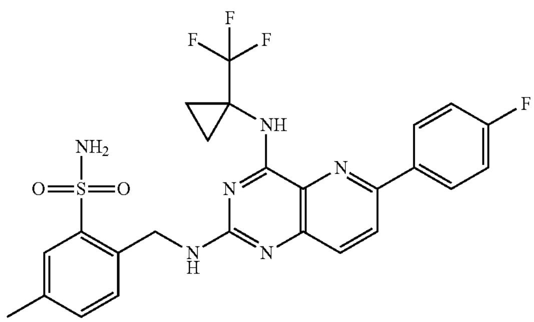 [SMILES: Cc1ccc(CNc2nc(NC3(C(F)(F)F)CC3)c3nc(-c4ccc(F)cc4)ccc3n2)c(S(N)(=O)=O)c1] | 2-((6-(4-fluorophenyl)-4-(1-(trifluoromethyl)cyclopropyl-amino)pyrido[3,2-d]pyrimidin-2-ylamino)methyl)-5-methylbenzenesulfonamide | 547.2 |
| 77 | 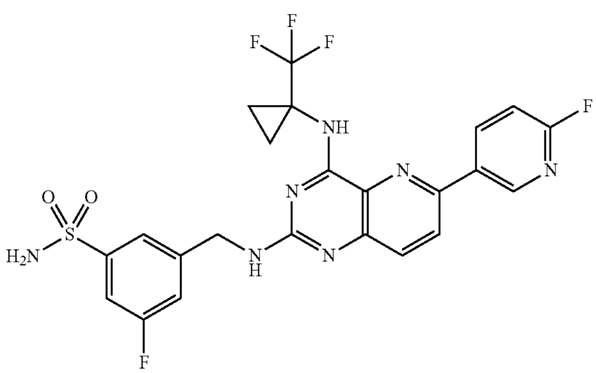 [SMILES: NS(=O)(=O)c1cc(F)cc(CNc2nc(NC3(C(F)(F)F)CC3)c3nc(-c4ccc(F)nc4)ccc3n2)c1] | 3-fluoro-5-((6-(6-fluoropyridin-3-yl)-4-(1-(trifluoromethyl)cyclopropylamino)pyrido[3,2-d]pyrimidin-2-ylamino)methyl)benzenesulfonamide | 552.2 |
| 78 | 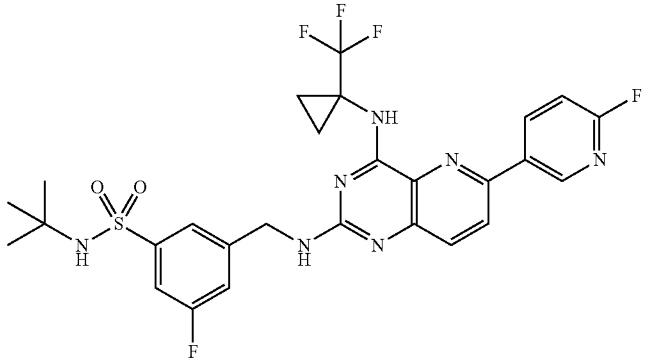 [SMILES: CC(C)(C)NS(=O)(=O)c1cc(F)cc(CNc2nc(NC3(C(F)(F)F)CC3)c3nc(-c4ccc(F)nc4)ccc3n2)c1] | N-tert-butyl-3-fluoro-5-((6-(6-fluoropyridin-3-yl)-4-(1-(trifluoromethyl)cyclopropyl-amino)pyrido[3,2-d]pyrimidin-2-ylamino)methyl)benzene-sulfonamide | 608.3 |

TABLE III-continued

| Ex | Structure | Name | MS |
|---|---|---|---|
| 79 | 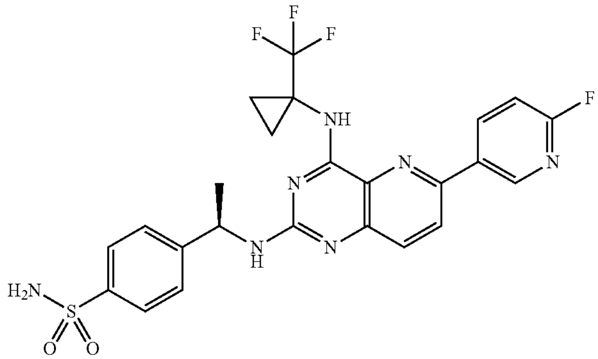 [SMILES: C[C@@H](Nc1nc(NC2(C(F)(F)F)CC2)c2nc(-c3ccc(F)nc3)ccc2n1)c1ccc(S(N)(=O)=O)cc1] | 4-((R)-1-(6-(6-fluoropyridin-3-yl)-4-(1-(trifluoromethyl)cyclopropylamino)pyrido[3,2-d]pyrimidin-2-ylamino)ethyl)benzenesulfonamide | 548.3 |
| 80 | 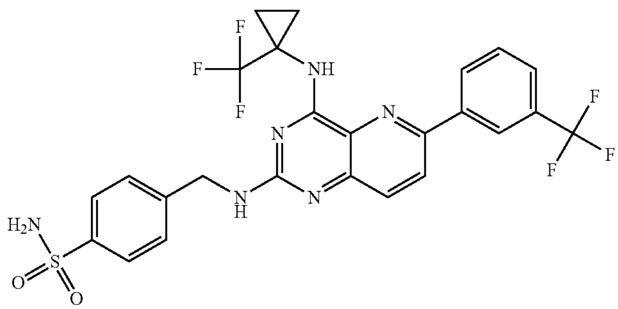 [SMILES: NS(=O)(=O)c1ccc(CNc2nc(NC3(C(F)(F)F)CC3)c3nc(-c4cccc(C(F)(F)F)c4)ccc3n2)cc1] | 4-((4-(1-(trifluoromethyl)cyclopropylamino)-6-(3-(trifluoromethyl)phenyl)pyrido[3,2-d]pyrimidin-2-ylamino)methyl)benzenesulfonamide | 583.2 |
| 81 | 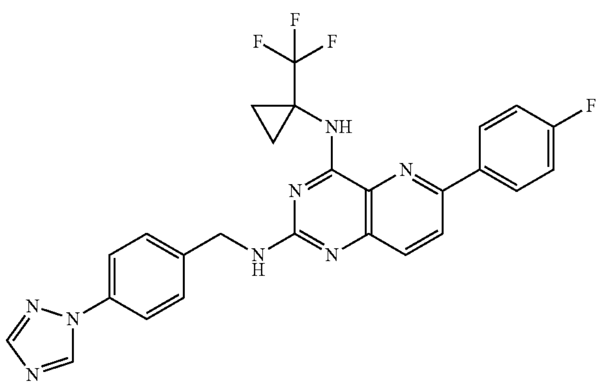 [SMILES: Fc1ccc(-c2ccc3nc(NCc4ccc(-n5cncn5)cc4)nc(NC4(C(F)(F)F)CC4)c3n2)cc1] | $N^2$-(4-(1H-1,2,4-triazol-1-yl)benzyl)-6-(4-fluorophenyl)-$N^4$-(1-(trifluoromethyl)cyclopropyl)pyrido[3,2-d]pyrimidine-2,4-diamine | 521.2 |
| 82 | 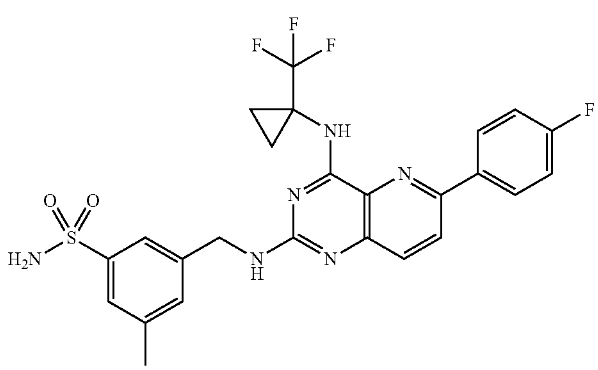 [SMILES: Cc1cc(CNc2nc(NC3(C(F)(F)F)CC3)c3nc(-c4ccc(F)cc4)ccc3n2)cc(S(N)(=O)=O)c1] | 3-((6-(4-fluorophenyl)-4-(1-(trifluoromethyl)cyclopropyl-amino)pyrido[3,2-d]pyrimidin-2-ylamino)methyl)-5-methylbenzenesulfonamide | 547.3 |

TABLE III-continued

| Ex | Structure | Name | MS |
|---|---|---|---|
| 83 | 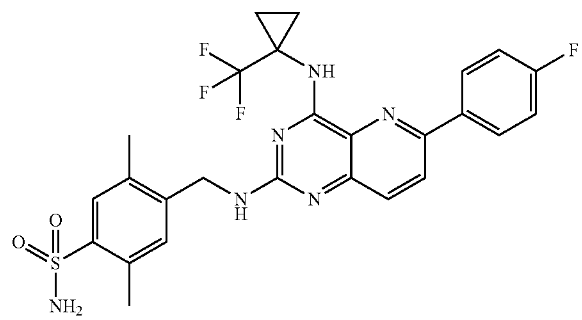 [SMILES: Cc1cc(S(N)(=O)=O)c(C)cc1CNc1nc(NC2(C(F)(F)F)CC2)c2nc(-c3ccc(F)cc3)ccc2n1] | 4-((6-(4-fluorophenyl)-4-(1-(trifluoromethyl)cyclopropylamino)pyrido[3,2-d]pyrimidin-2-ylamino)methyl)-2,5-dimethylbenzenesulfonamide | 561.1 |
| 84 | 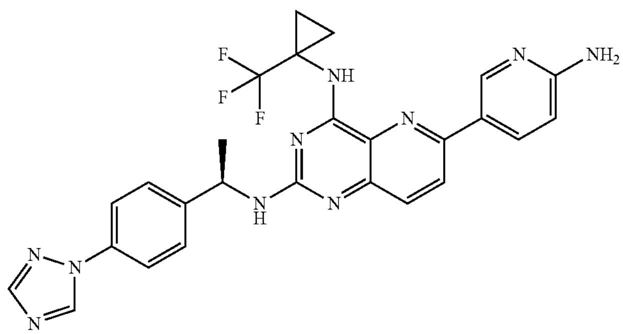 [SMILES: C[C@@H](Nc1nc(NC2(C(F)(F)F)CC2)c2nc(-c3ccc(N)nc3)ccc2n1)c1ccc(-n2cncn2)cc1] | $N^2$-((R)-1-(4-(1H-1,2,4-triazol-1-yl)phenyl)ethyl)-6-(6-aminopyridin-3-yl)-$N^4$-(1-(trifluoromethyl)cyclopropyl)pyrido[3,2-d]pyrimidine-2,4-diamine | 533.1 |
| 86 | 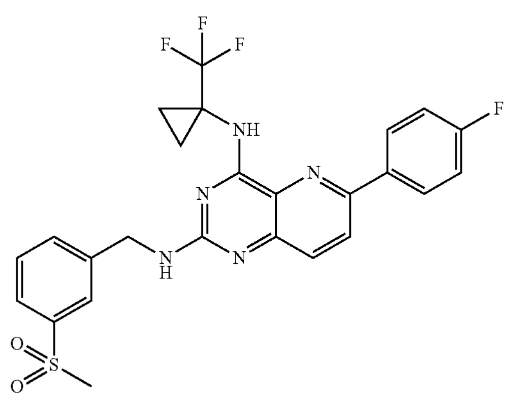 [SMILES: CS(=O)(=O)c1cccc(CNc2nc(NC3(C(F)(F)F)CC3)c3nc(-c4ccc(F)cc4)ccc3n2)c1] | $N^2$-(3-(methylsulfonyl)benzyl)-6-(4-fluorophenyl)-$N^4$-(1-(trifluoromethyl)cyclopropyl)pyrido[3,2-d]pyrimidine-2,4-diamine | 532.2 |
| 87 | 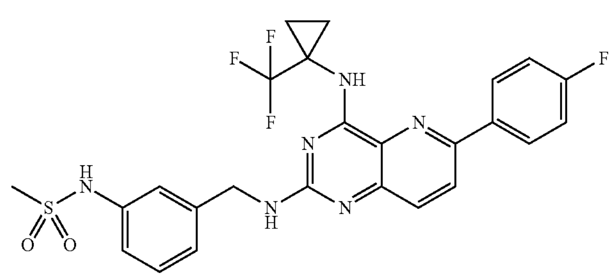 [SMILES: CS(=O)(=O)Nc1cccc(CNc2nc(NC3(C(F)(F)F)CC3)c3nc(-c4ccc(F)cc4)ccc3n2)c1] | N-(3-((6-(4-fluorophenyl)-4-(1-(trifluoromethyl)cyclopropyl-amino)pyrido[3,2-d]pyrimidin-2-ylamino)methyl)phenyl)methanesulfonamide | 547.1 |

TABLE III-continued

| Ex | Structure | Name | MS |
|---|---|---|---|
| 88 | 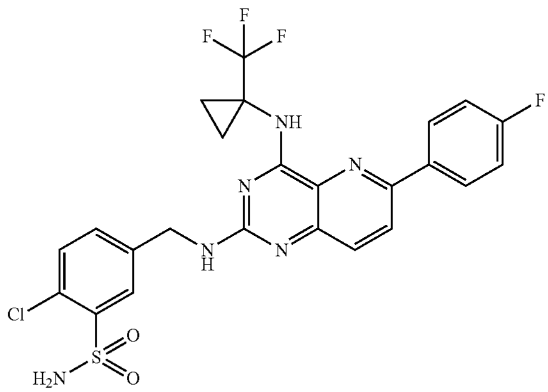 [SMILES: NS(=O)(=O)c1cc(CNc2nc(NC3(C(F)(F)F)CC3)c3nc(-c4ccc(F)cc4)ccc3n2)ccc1Cl] | 2-chloro-5-((6-(4-fluorophenyl)-4-(1-(trifluoromethyl)cyclopropyl-amino)pyrido[3,2-d]pyrimidin-2-ylamino)methyl)benzene-sulfonamide | 567.2 |
| 89 | 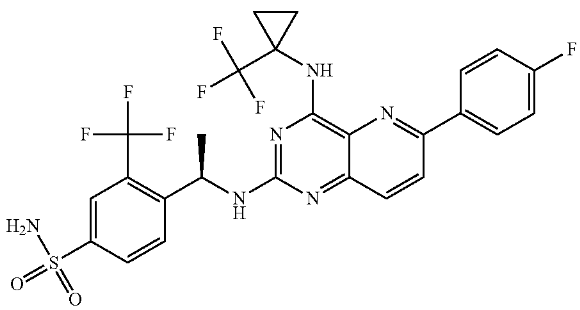 [SMILES: C[C@@H](Nc1nc(NC2(C(F)(F)F)CC2)c2nc(-c3ccc(F)cc3)ccc2n1)c1ccc(S(N)(=O)=O)cc1C(F)(F)F] | (R)-4-(1-(6-(4-fluorophenyl)-4-(1-(trifluoromethyl)cyclopropylamino)pyrido[3,2-d]pyrimidin-2-ylamino)ethyl)-3-(trifluoromethyl)benzene-sulfonamide | 615.1 |
| 90 | 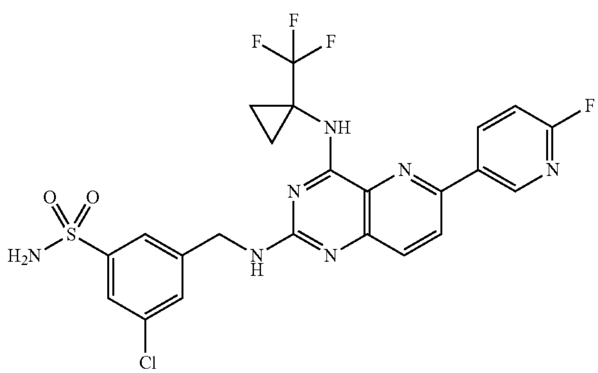 [SMILES: NS(=O)(=O)c1cc(Cl)cc(CNc2nc(NC3(C(F)(F)F)CC3)c3nc(-c4ccc(F)nc4)ccc3n2)c1] | 3-chloro-5-((6-(6-fluoropyridin-3-yl)-4-(1-(trifluoromethyl)cyclopropyl-amino)pyrido[3,2-d]pyrimidin-2-ylamino)methyl)benzene-sulfonamide | 568.0 |
| 91 | 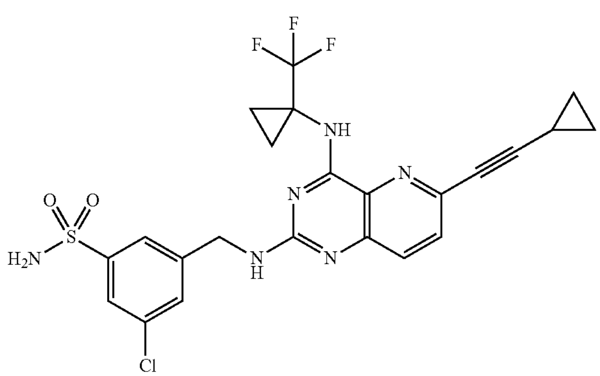 [SMILES: NS(=O)(=O)c1cc(Cl)cc(CNc2nc(NC3(C(F)(F)F)CC3)c3nc(C#CC4CC4)ccc3n2)c1] | 3-chloro-5-((6-(2-cyclopropylethynyl)-4-(1-(trifluoromethyl)cyclopropyl-amino)pyrido[3,2-d]pyrimidin-2-ylamino)methyl)benzene-sulfonamide | 536.7 |

TABLE III-continued

| Ex | Structure | Name | MS |
|---|---|---|---|
| 92 | 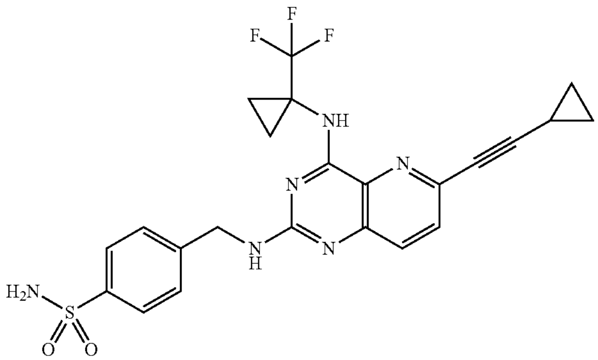 [SMILES: NS(=O)(=O)c1ccc(CNc2nc(NC3(C(F)(F)F)CC3)c3nc(C#CC4CC4)ccc3n2)cc1] | 4-((6-(2-cyclopropylethynyl)-4-(1-(trifluoromethyl)cyclopropyl-amino)pyrido[3,2-d]pyrimidin-2-ylamino)methyl)benzene-sulfonamide | 503.2 |
| 93 | 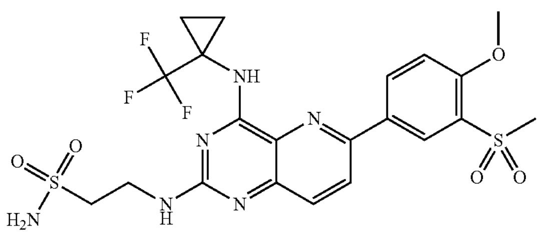 [SMILES: COc1ccc(-c2ccc3nc(NCCS(N)(=O)=O)nc(NC4(C(F)(F)F)CC4)c3n2)cc1S(C)(=O)=O] | 2-(6-(4-methoxy-3-(methylsulfonyl)phenyl)-4-(1-(trifluoromethyl)cyclopropyl-amino)pyrido[3,2-d]pyrimidin-2-ylamino)ethanesulfonamide | 561.1 |
| 94 | 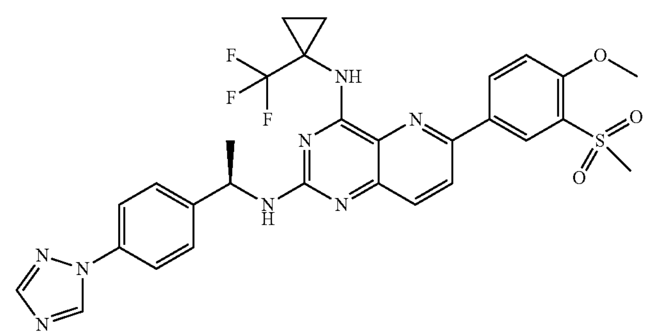 [SMILES: COc1ccc(-c2ccc3nc(N[C@H](C)c4ccc(-n5cncn5)cc4)nc(NC4(C(F)(F)F)CC4)c3n2)cc1S(C)(=O)=O] | $N^2$-((R)-1-(4-(1H-1,2,4-triazol-1-yl)phenyl)ethyl)-6-(4-methoxy-3-(methylsulfonyl)phenyl)-$N^4$-(1-(trifluoromethyl)cyclopropyl)pyrido[3,2-d]pyrimidine-2,4-diamine | 625.1 |
| 95 | 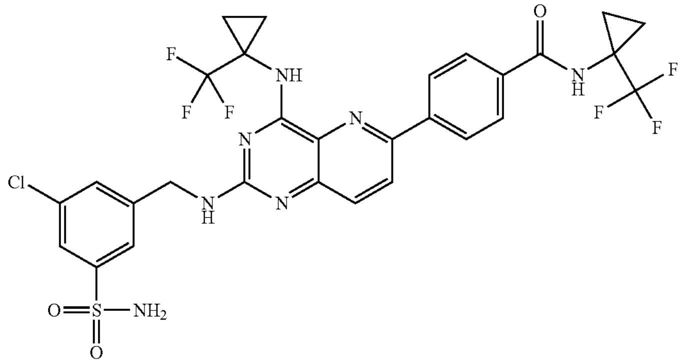 [SMILES: NS(=O)(=O)c1cc(Cl)cc(CNc2nc(NC3(C(F)(F)F)CC3)c3nc(-c4ccc(C(=O)NC5(C(F)(F)F)CC5)cc4)ccc3n2)c1] | 3-chloro-5-((6-(4-(1-(trifluoromethyl)cyclopropyl-aminocarbonyl)phenyl)-4-(1-(trifluoromethyl)cyclopropyl-amino)pyrido[3,2-d]pyrimidin-2-ylamino)methyl)benzene-sulfonamide | 700.3 |

TABLE III-continued

| Ex | Name | MS |
|---|---|---|
| 96 | 4-((6-(6-fluoropyridin-3-yl)-4-(1-(trifluoromethyl)cyclopropyl-amino)pyrido[3,2-d]pyrimidin-2-ylamino)methyl)benzene-sulfonamide | 534.0 |
| 97 | $N^2$-(1-(4-(1H-1,2,4-triazol-1-yl)phenyl)ethyl)-6-(4-methoxy-3-(methylsulfonyl)phenyl)-$N^4$-(1-(trifluoromethyl)cyclopropyl)pyrido[3,2-d]pyrimidine-2,4-diamine | 625.2 |
| 98 | 3-((6-(2-cyano-4-fluorophenyl)-4-(1-(trifluoromethyl)cyclopropyl-amino)pyrido[3,2-d]pyrimidin-2-ylamino)methyl)benzene-sulfonamide | 558.3 |
| 99 | 3-((6-(2-cyano-4-fluorophenyl)-4-(1-(trifluoromethyl)cyclopropyl-amino)pyrido[3,2-d]pyrimidin-2-ylamino)methyl)-5-(trifluoro-methyl)benzenesulfonamide | 626.2 |

TABLE III-continued

| Ex | Structure | Name | MS |
|---|---|---|---|
| 100 | 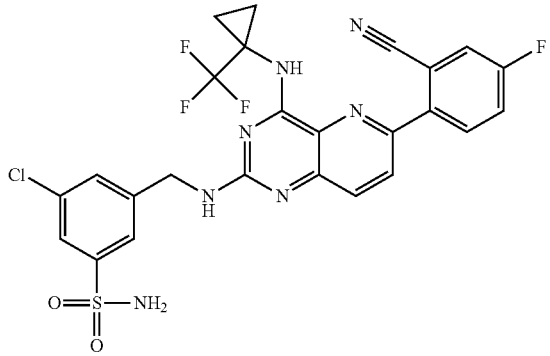 [SMILES: N#Cc1cc(F)ccc1-c1ccc2nc(NCc3cc(Cl)cc(S(N)(=O)=O)c3)nc(NC3(C(F)(F)F)CC3)c2n1] | 3-chloro-5-((6-(2-cyano-4-fluorophenyl)-4-(1-(trifluoromethyl)cyclopropyl-amino)pyrido[3,2-d]pyrimidin-2-ylamino)methyl)benzene-sulfonamide | 593.0 |
| 101 | 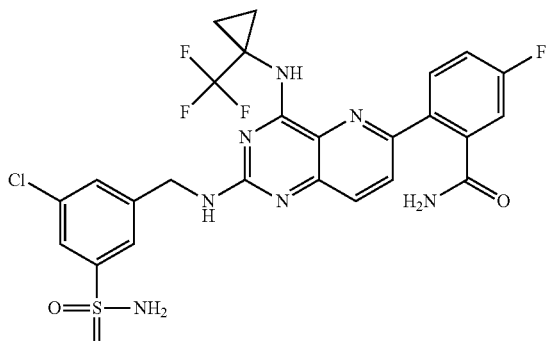 | 3-chloro-5-((6-(4-fluoro-2-aminocarbonylphenyl)-4-(1-(trifluoromethyl)cyclopropyl-amino)pyrido[3,2-d]pyrimidin-2-ylamino)methyl)benzene-sulfonamide | 611.0 |
| 102 | 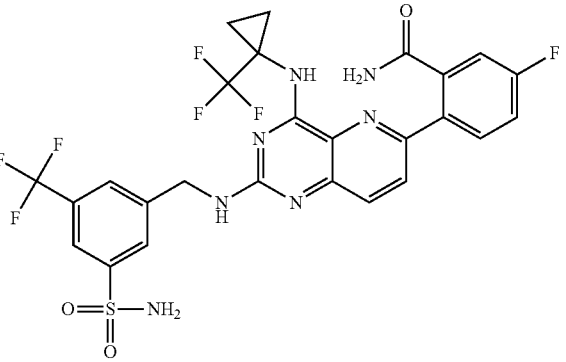 | 3-((6-(4-fluoro-2-aminocarbonylphenyl)-4-(1-(trifluoromethyl)cyclopropyl-amino)pyrido[3,2-d]pyrimidin-2-ylamino)methyl)-5-(trifluoromethyl)benzene-sulfonamide | 644.2 |
| 103 | 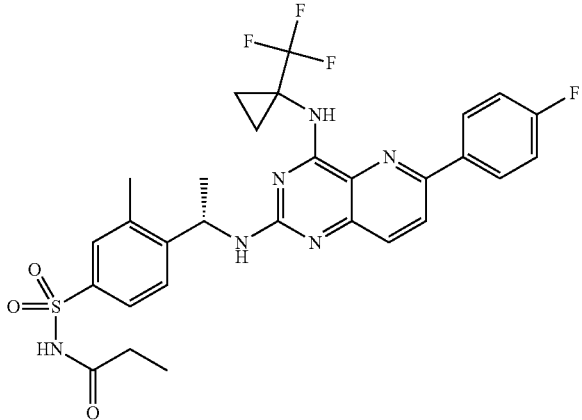 [SMILES: CCC(=O)NS(=O)(=O)c1ccc([C@H](C)Nc2nc(NC3(C(F)(F)F)CC3)c3nc(-c4ccc(F)cc4)ccc3n2)c(C)c1] | (S)-N-(4-(1-(6-(4-fluorophenyl)-4-(1-(trifluoromethyl)cyclopropyl-amino)pyrido[3,2-d]pyrimidin-2-ylamino)ethyl)-3-methylphenylsulfonyl)propionamide | 617.2 |

TABLE III-continued

| Ex | Structure | Name | MS |
|---|---|---|---|
| 104 | 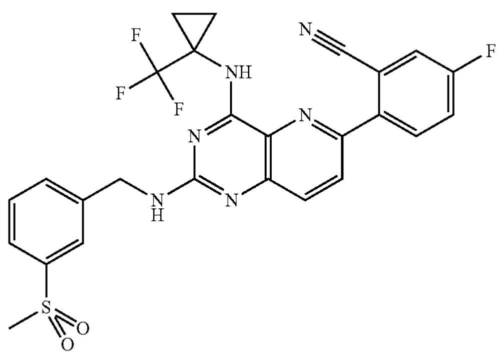 [SMILES: CS(=O)(=O)c1cccc(CNc2nc(NC3(C(F)(F)F)CC3)c3nc(-c4ccc(F)cc4C#N)ccc3n2)c1] | 2-(2-(3-(methylsulfonyl)benzylamino)-4-(1-(trifluoromethyl)cyclopropyl-amino)pyrido[3,2-d]pyrimidin-6-yl)-5-fluorobenzonitrile | 557.2 |
| 105 | 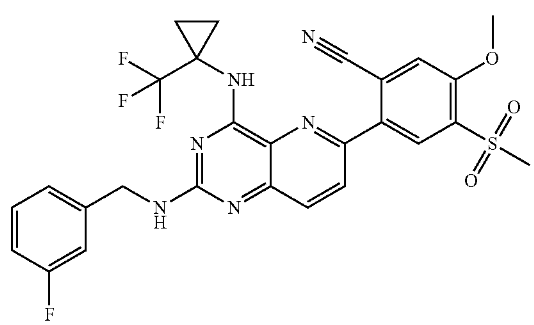 [SMILES: COc1cc(C#N)c(-c2ccc3nc(NCc4cccc(F)c4)nc(NC4(C(F)(F)F)CC4)c3n2)cc1S(C)(=O)=O] | $N^2$-(3-fluorobenzyl)-6-(4-methoxy-3-(methylsulfonyl)phenyl)-$N^4$-(1-(trifluoromethyl)cyclopropyl)pyrido[3,2-d]pyrimidine-2,4-diamine | 562.2 |
| 106 | 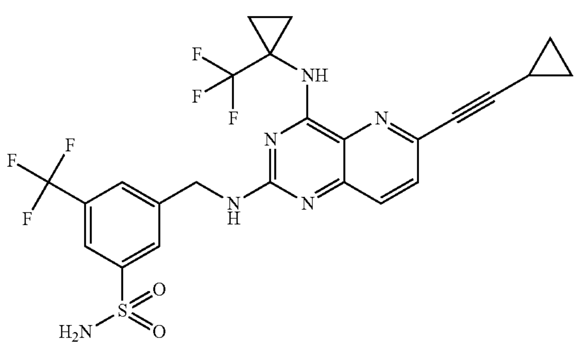 [SMILES: NS(=O)(=O)c1cc(CNc2nc(NC3(C(F)(F)F)CC3)c3nc(C#CC4CC4)ccc3n2)cc(C(F)(F)F)c1] | 3-((6-(2-cyclopropylethynyl)-4-(1-(trifluoromethyl)cyclo-propylamino)pyrido[3,2-d]pyrimidin-2-ylamino)methyl)-5-(trifluoromethyl)benzene-sulfonamide | 571.2 |
| 107 | 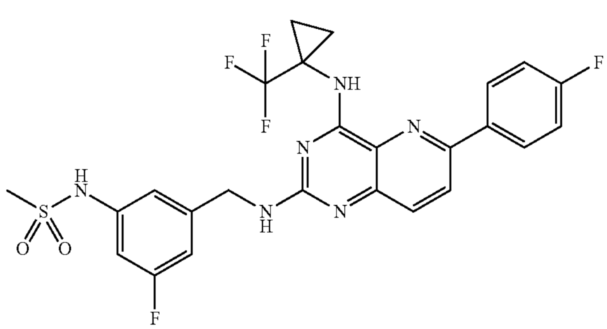 [SMILES: CS(=O)(=O)Nc1cc(F)cc(CNc2nc(NC3(C(F)(F)F)CC3)c3nc(-c4ccc(F)cc4)ccc3n2)c1] | N-(3-fluoro-5-((6-(4-fluorophenyl)-4-(1-(trifluoromethyl)cyclopropyl-amino)pyrido[3,2-d]pyrimidin-2-ylamino)methyl)phenyl)methane-sulfonamide | 565.3 |

TABLE III-continued

| Ex | Structure | Name | MS |
|---|---|---|---|
| 108 | 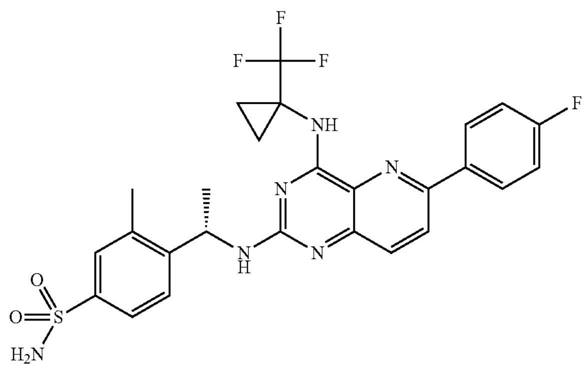 [SMILES: Cc1cc(S(N)(=O)=O)ccc1[C@H](C)Nc1nc(NC2(C(F)(F)F)CC2)c2nc(-c3ccc(F)cc3)ccc2n1] | (S)-4-(1-(6-(4-fluorophenyl)-4-(1-(trifluoromethyl)cyclopropyl-amino)pyrido[3,2-d]pyrimidin-2-ylamino)ethyl)-3-methylbenzene-sulfonamide | 561.2 |
| 109 | 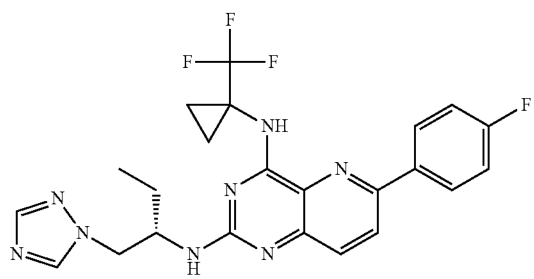 [SMILES: CC[C@@H](Cn1cncn1)Nc1nc(NC2(C(F)(F)F)CC2)c2nc(-c3ccc(F)cc3)ccc2n1] | (S)-$N^2$-(1-(1H-1,2,4-triazol-1-yl)butan-2-yl)-6-(4-fluorophenyl)-$N^4$-(1-(trifluoromethyl)cyclopropyl)pyrido[3,2-d]pyrimidine-2,4-diamine | 487.2 |
| 110 | 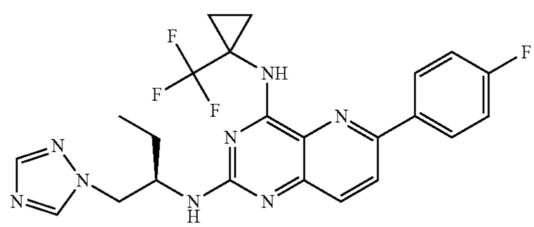 [SMILES: CC[C@H](Cn1cncn1)Nc1nc(NC2(C(F)(F)F)CC2)c2nc(-c3ccc(F)cc3)ccc2n1] | (R)-$N^2$-(1-(1H-1,2,4-triazol-1-yl)butan-2-yl)-6-(4-fluorophenyl)-$N^4$-(1-(trifluoromethyl)cyclopropyl)pyrido[3,2-d]pyrimidine-2,4-diamine | 487.3 |
| 111 | 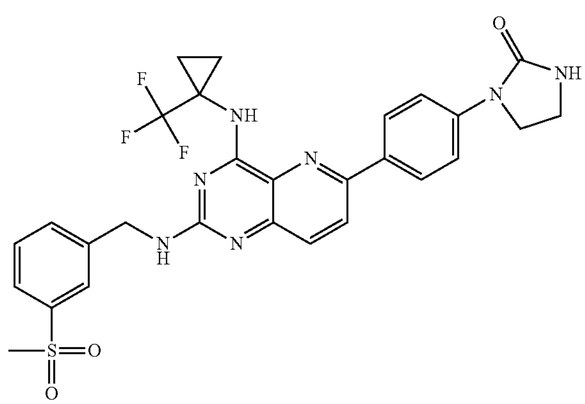 [SMILES: CS(=O)(=O)c1cccc(CNc2nc(NC3(C(F)(F)F)CC3)c3nc(-c4ccc(N5CCNC5=O)cc4)ccc3n2)c1] | 1-(4-(2-(3-(methylsulfonyl)benzylamino)-4-(1-(trifluoromethyl)cyclopropyl-amino)pyrido[3,2-d]pyrimidin-6-yl)phenyl)imidazolidin-2-one | 598.4 |
| 112 | 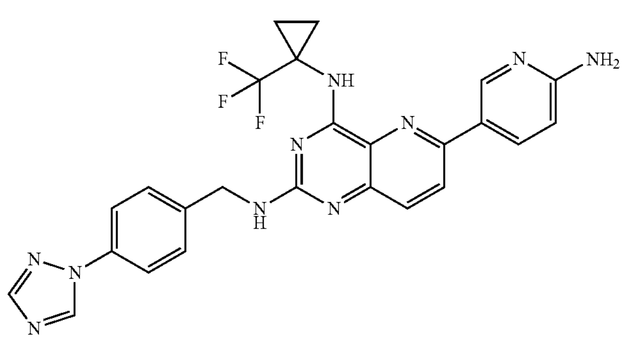 [SMILES: Nc1ccc(-c2ccc3nc(NCc4ccc(-n5cncn5)cc4)nc(NC4(C(F)(F)F)CC4)c3n2)cn1] | $N^2$-(4-(1H-1,2,4-triazol-1-yl)benzyl)-6-(6-aminopyridin-3-yl)-$N^4$-(1-(trifluoromethyl)cyclopropyl)pyrido[3,2-d]pyrimidine-2,4-diamine | 519.3 |

TABLE III-continued

| Ex | Structure | Name | MS |
|---|---|---|---|
| 113 | 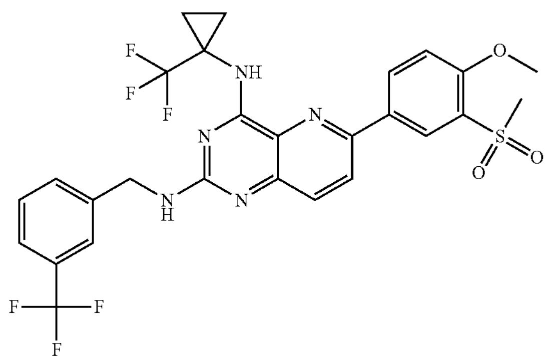 [SMILES: COc1ccc(-c2ccc3nc(NCc4cccc(C(F)(F)F)c4)nc(NC4(C(F)(F)F)CC4)c3n2)cc1S(C)(=O)=O] | N²-(3-(trifluoromethyl)benzyl)-6-(4-methoxy-3-(methylsulfonyl)phenyl)-N⁴-(1-(trifluoromethyl)cyclopropyl)pyrido[3,2-d]pyrimidine-2,4-diamine | 612.1 |
| 114 | 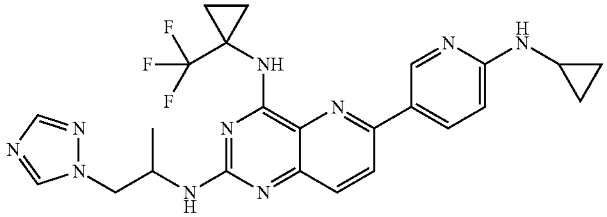 [SMILES: CC(Cn1cncn1)Nc1nc(NC2(C(F)(F)F)CC2)c2nc(-c3ccc(NC4CC4)nc3)ccc2n1] | N²-(1-(1H-1,2,4-triazol-1-yl)propan-2-yl)-6-(6-(cyclopropylamino)pyridin-3-yl)-N⁴-(1-(trifluoromethyl)cyclopropyl)pyrido[3,2-d]pyrimidine-2,4-diamine | 511.2 |
| 115 | 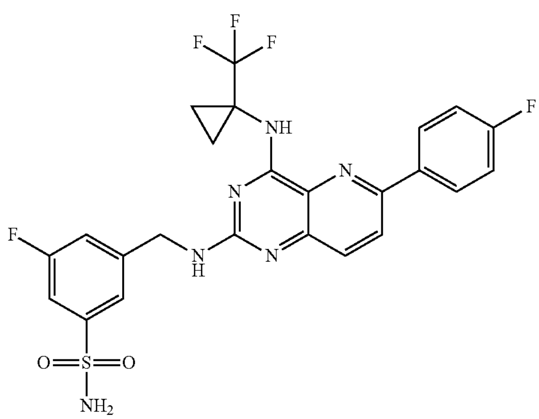 [SMILES: NS(=O)(=O)c1cc(F)cc(CNc2nc(NC3(C(F)(F)F)CC3)c3nc(-c4ccc(F)cc4)ccc3n2)c1] | 3-fluoro-5-((6-(4-fluorophenyl)-4-(1-(trifluoromethyl)cyclopropyl-amino)pyrido[3,2-d]pyrimidin-2-ylamino)methyl)benzene-sulfonamide | 551.2 |
| 116 | 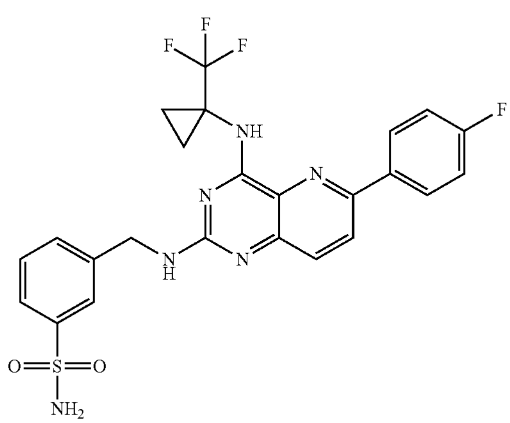 [SMILES: NS(=O)(=O)c1cccc(CNc2nc(NC3(C(F)(F)F)CC3)c3nc(-c4ccc(F)cc4)ccc3n2)c1] | 3-((6-(4-fluorophenyl)-4-(1-(trifluoromethyl)cyclopropyl-amino)pyrido[3,2-d]pyrimidin-2-ylamino)methyl)benzene-sulfonamide | 533.2 |

TABLE III-continued

| Ex | Structure | Name | MS |
|---|---|---|---|
| 117 | 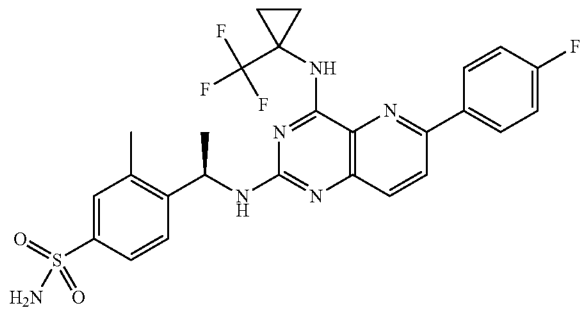 [SMILES: Cc1cc(S(N)(=O)=O)ccc1[C@@H](C)Nc1nc(NC2(C(F)(F)F)CC2)c2nc(-c3ccc(F)cc3)ccc2n1] | (R)-4-(1-(6-(4-fluorophenyl)-4-(1-(trifluoromethyl)cyclopropyl-amino)pyrido[3,2-d]pyrimidin-2-ylamino)ethyl)-3-methylbenzene-sulfonamide | 561.1 |
| 118 | 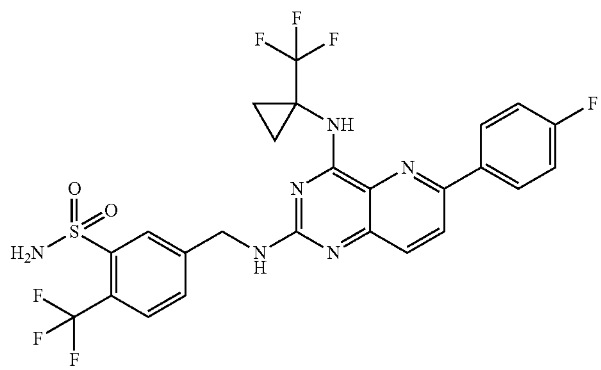 [SMILES: NS(=O)(=O)c1cc(CNc2nc(NC3(C(F)(F)F)CC3)c3nc(-c4ccc(F)cc4)ccc3n2)ccc1C(F)(F)F] | 5-((6-(4-fluorophenyl)-4-(1-(trifluoromethyl)cyclopropyl-amino)pyrido[3,2-d]pyrimidin-2-ylamino)methyl)-2-(trifluoro-methyl)benzenesulfonamide | 601.2 |
| 119 | 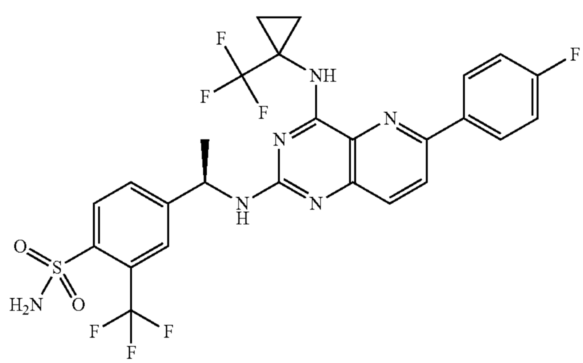 [SMILES: C[C@@H](Nc1nc(NC2(C(F)(F)F)CC2)c2nc(-c3ccc(F)cc3)ccc2n1)c1ccc(S(N)(=O)=O)c(C(F)(F)F)c1] | (R)-4-(1-(6-(4-fluorophenyl)-4-(1-(trifluoromethyl)cyclo-propylamino)pyrido[3,2-d]pyrimidin-2-ylamino)ethyl)-2-(trifluoromethyl)benzene-sulfonamide | 615.2 |
| 120 | 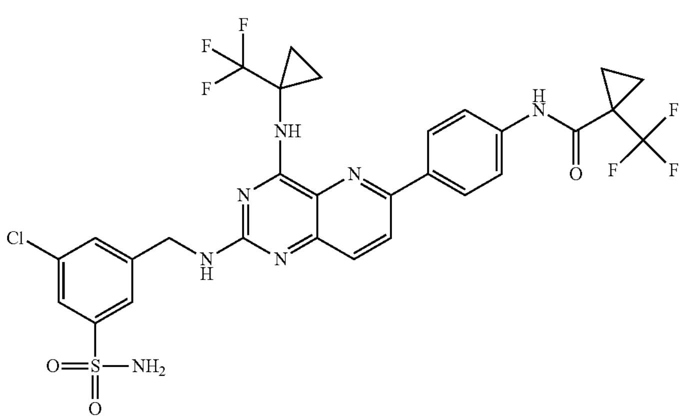 [SMILES: NS(=O)(=O)c1cc(Cl)cc(CNc2nc(NC3(C(F)(F)F)CC3)c3nc(-c4ccc(NC(=O)C5(C(F)(F)F)CC5)cc4)ccc3n2)c1] | 3-chloro-5-((6-(4-(1-(trifluoromethyl)cyclopropyl-carboxamido)phenyl)-4-(1-(trifluoromethyl)cyclopropyl-amino)pyrido[3,2-d]pyrimidin-2-ylamino)methyl)benzene-sulfonamide | 700.3 |

TABLE III-continued

| Ex | Structure | Name | MS |
|---|---|---|---|
| 121 | 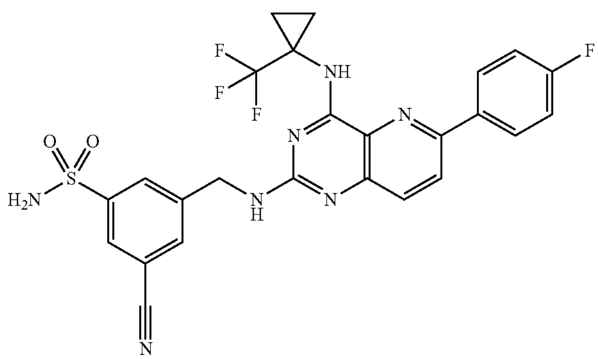 [SMILES: N#Cc1cc(CNc2nc(NC3(C(F)(F)F)CC3)c3nc(-c4ccc(F)cc4)ccc3n2)cc(S(N)(=O)=O)c1] | 3-cyano-5-((6-(4-fluorophenyl)-4-(1-(trifluoromethyl)cyclopropyl-amino)pyrido[3,2-d]pyrimidin-2-ylamino)methyl)benzene-sulfonamide | 558.2 |
| 122 | 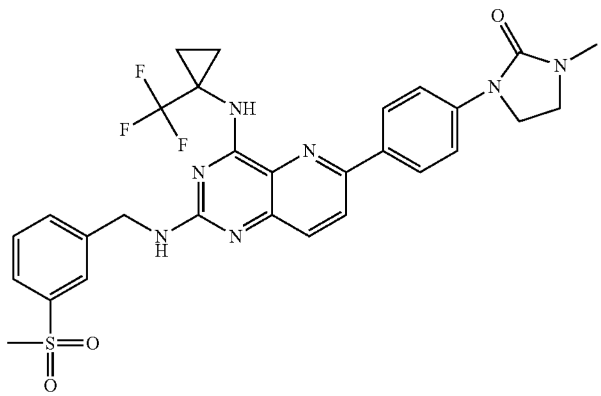 | 1-(4-(2-(3-(methylsulfonyl)benzylamino)-4-(1-(trifluoromethyl)cyclopropyl-amino)pyrido[3,2-d]pyrimidin-6-yl)phenyl)-3-methylimidazolidin-2-one | 612.3 |
| 123 | 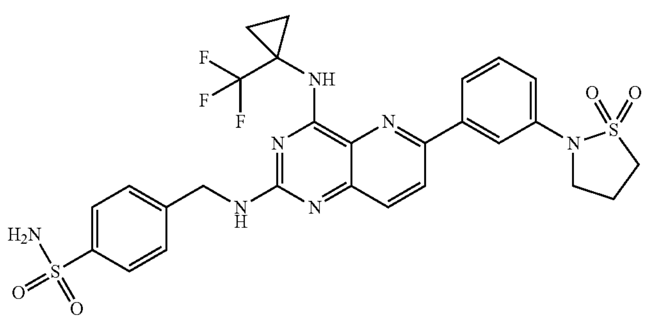 [SMILES: NS(=O)(=O)c1ccc(CNc2nc(NC3(C(F)(F)F)CC3)c3nc(-c4cccc(N5CCCS5(=O)=O)c4)ccc3n2)cc1] | 4-((6-(3-(1,1-dioxo-isothiazolidin-2-yl)phenyl)-4-(1-(trifluoromethyl)cyclopropyl-amino)pyrido[3,2-d]pyrimidin-2-ylamino)methyl)benzene-sulfonamide | 634.4 |
| 124 | 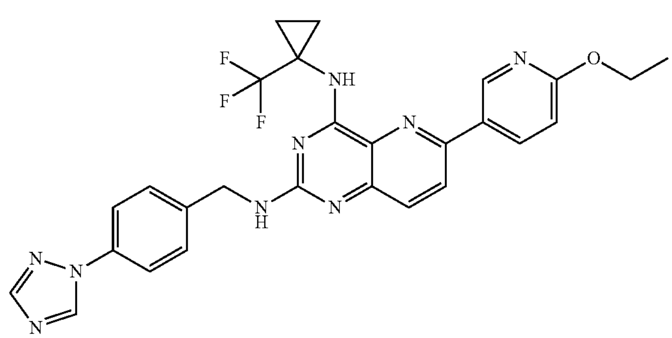 [SMILES: CCOc1ccc(-c2ccc3nc(NCc4ccc(-n5cncn5)cc4)nc(NC4(C(F)(F)F)CC4)c3n2)cn1] | $N^2$-(4-(1H-1,2,4-triazol-1-yl)benzyl)-6-(6-ethoxypyridin-3-yl)-$N^4$-(1-(trifluoromethyl)cyclopropyl)pyrido[3,2-d]pyrimidine-2,4-diamine | 548.3 |

TABLE III-continued

| Ex | Structure | Name | MS |
|---|---|---|---|
| 125 | 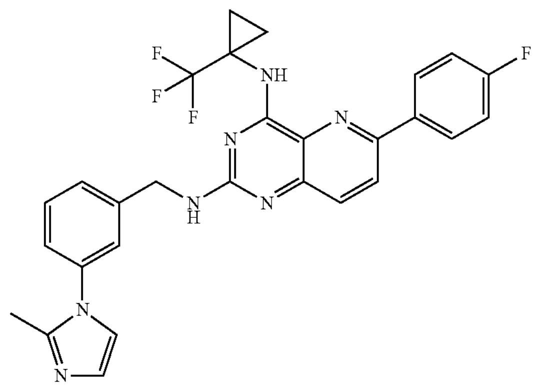 [SMILES: Cc1nccn1-c1cccc(CNc2nc(NC3(C(F)(F)F)CC3)c3nc(-c4ccc(F)cc4)ccc3n2)c1] | N²-(3-(2-methyl-1H-imidazol-1-yl)benzyl)-6-(4-fluorophenyl)-N⁴-(1-(trifluoromethyl)cyclopropyl)pyrido[3,2-d]pyrimidine-2,4-diamine | 534.2 |
| 126 | 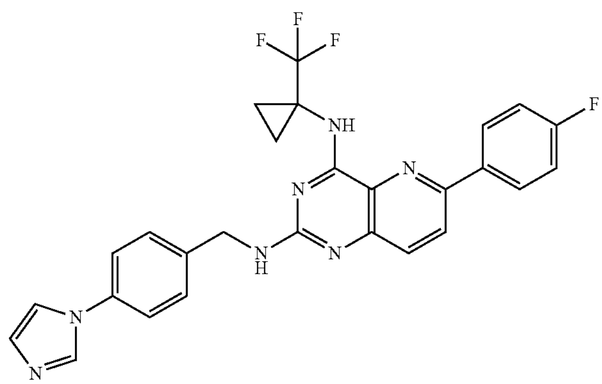 [SMILES: Fc1ccc(-c2ccc3nc(NCc4ccc(-n5ccnc5)cc4)nc(NC4(C(F)(F)F)CC4)c3n2)cc1] | N²-(4-(1H-imidazol-1-yl)benzyl)-6-(4-fluorophenyl)-N⁴-(1-(trifluoromethyl)cyclopropyl)pyrido[3,2-d]pyrimidine-2,4-diamine | 520.2 |
| 127 | 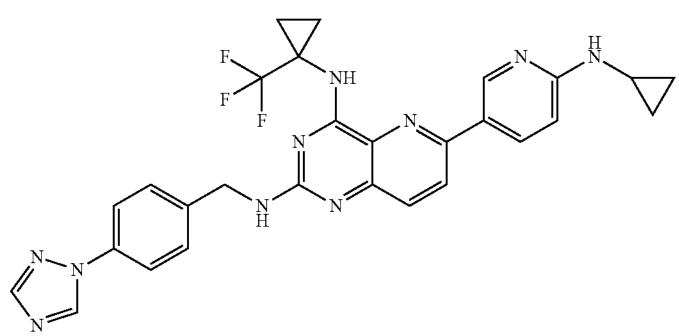 [SMILES: FC(F)(F)C1(Nc2nc(NCc3ccc(-n4cncn4)cc3)nc3ccc(-c4ccc(NC5CC5)nc4)nc23)CC1] | N²-(4-(1H-1,2,4-triazol-1-yl)benzyl)-6-(6-(cyclopropylamino)pyridin-3-yl)-N⁴-(1-(trifluoromethyl)cyclopropyl)pyrido[3,2-d]pyrimidine-2,4-diamine | 559.2 |
| 128 | 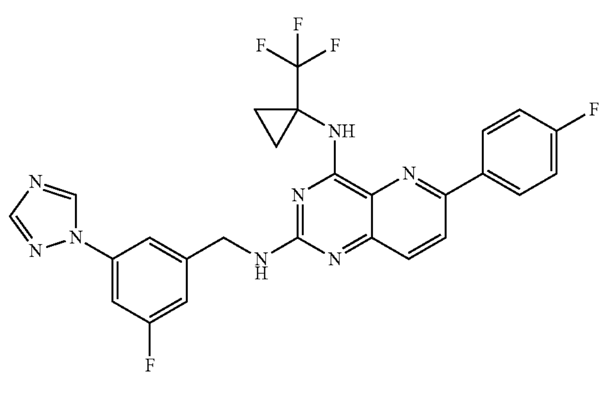 [SMILES: Fc1ccc(-c2ccc3nc(NCc4cc(F)cc(-n5cncn5)c4)nc(NC4(C(F)(F)F)CC4)c3n2)cc1] | N²-(3-fluoro-5-(1H-1,2,4-triazol-1-yl)benzyl)-6-(4-fluorophenyl)-N⁴-(1-(trifluoromethyl)cyclopropyl)pyrido[3,2-d]pyrimidine-2,4-diamine | 539.23 |

TABLE III-continued

| Ex | Name | MS |
|---|---|---|
| 129 | 1-(4-(2-(4-(1H-1,2,4-triazol-1-yl)benzylamino)-4-(1-(trifluoromethyl)cyclopropyl-amino)pyrido[3,2-d]pyrimidin-6-yl)phenyl)imidazolidin-2-one | 587.3 |
| 130 | 4-((6-(4-(1,1-dioxo-isothiazolidin-2-yl)phenyl)-4-(1-(trifluoromethyl)cyclopropyl-amino)pyrido[3,2-d]pyrimidin-2-ylamino)methyl)benzene-sulfonamide | 634.1 |
| 131 | $N^2$-((R)-1-(4-(1H-1,2,4-triazol-1-yl)phenyl)ethyl)-6-(6-(cyclopropylamino)-5-fluoropyridin-3-yl)-$N^4$-(1-(trifluoromethyl)cyclopropyl)pyrido[3,2-d]pyrimidine-2,4-diamine | 591.2 |
| 132 | 4-((4-(1-cyanocyclopropylamino)-6-(6-methoxypyridin-3-yl)pyrido[3,2-d]pyrimidin-2-ylamino)methyl)benzene-sulfonamide | 503.2 |

TABLE III-continued

| Ex | Structure | Name | MS |
|---|---|---|---|
| 133 | 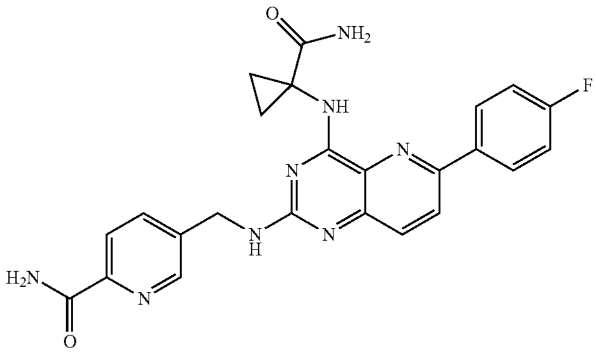 [SMILES: NC(=O)c1ccc(CNc2nc(NC3(C(N)=O)CC3)c3nc(-c4ccc(F)cc4)ccc3n2)cn1] | 5-((4-(1-carbamoylcyclo-propylamino)-6-(4-fluorophenyl)pyrido[3,2-d]pyrimidin-2-ylamino)methyl)picolinamide | 473.2 |
| 134 | 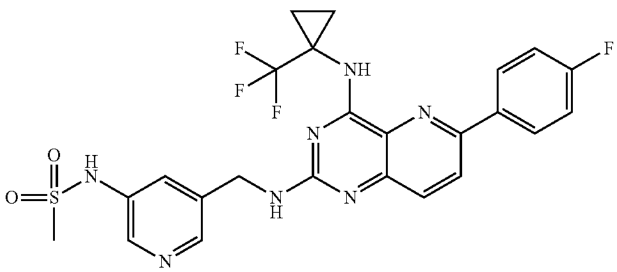 [SMILES: CS(=O)(=O)Nc1cncc(CNc2nc(NC3(C(F)(F)F)CC3)c3nc(-c4ccc(F)cc4)ccc3n2)c1] | N-(5-((6-(4-fluorophenyl)-4-(1-(trifluoromethyl)cyclopropyl-amino)pyrido[3,2-d]pyrimidin-2-ylamino)methyl)pyridin-3-yl)methanesulfonamide | 548.2 |
| 135 | 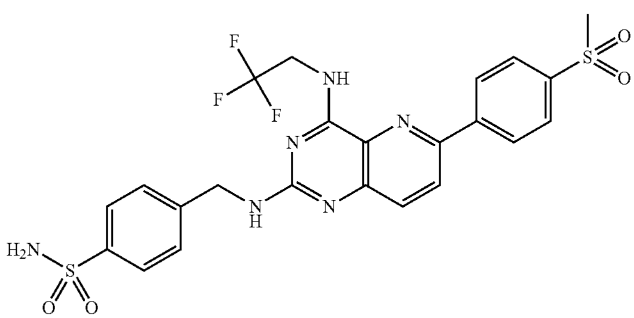 [SMILES: CS(=O)(=O)c1ccc(-c2ccc3nc(NCc4ccc(S(N)(=O)=O)cc4)nc(NCC(F)(F)F)c3n2)cc1] | 4-((6-(4-(methylsulfonyl)phenyl)-4-(2,2,2-trifluoroethylamino)pyrido[3,2-d]pyrimidin-2-ylamino)methyl)benzene-sulfonamide | 567.1 |
| 136 | 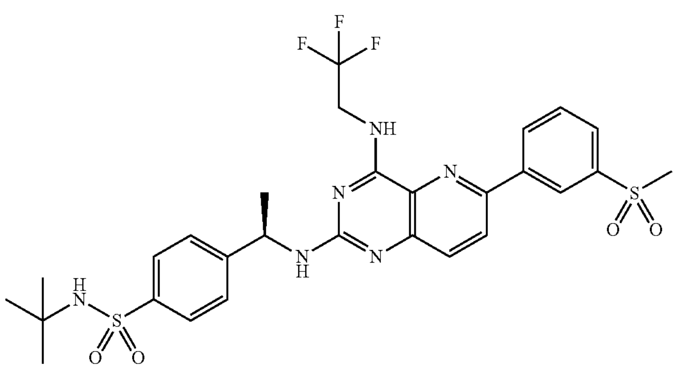 [SMILES: C[C@@H](Nc1nc(NCC(F)(F)F)c2nc(-c3cccc(S(C)(=O)=O)c3)ccc2n1)c1ccc(S(=O)(=O)NC(C)(C)C)cc1] | N-tert-butyl-4-((R)-1-(6-(3-(methylsulfonyl)phenyl)-4-(2,2,2-trifluoroethylamino)pyrido[3,2-d]pyrimidin-2-ylamino)ethyl)benzene-sulfonamide | 637.4 |
| 137 | 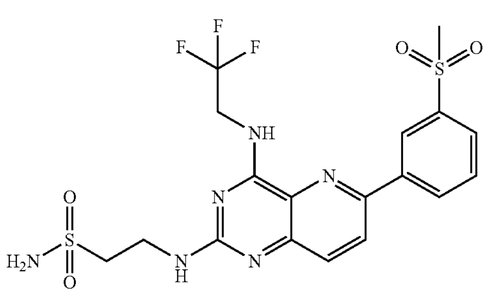 [SMILES: CS(=O)(=O)c1cccc(-c2ccc3nc(NCCS(N)(=O)=O)nc(NCC(F)(F)F)c3n2)c1] | 2-(6-(3-(methylsulfonyl)phenyl)-4-(2,2,2-trifluoroethylamino)pyrido[3,2-d]pyrimidin-2-ylamino)ethanesulfonamide | 505.16 |

TABLE III-continued

| Ex | Structure | Name | MS |
|---|---|---|---|
| 138 | 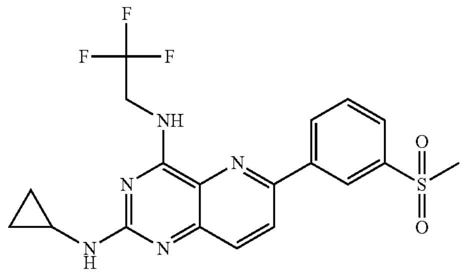 [SMILES: CS(=O)(=O)c1cccc(-c2ccc3nc(NC4CC4)nc(NCC(F)(F)F)c3n2)c1] | $N^2$-cyclopropyl-6-(3-(methylsulfonyl)phenyl)-$N^4$-(2,2,2-trifluoroethyl)pyrido[3,2-d]pyrimidine-2,4-diamine | 438.1 |
| 139 | 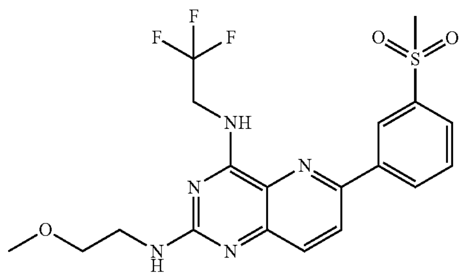 [SMILES: COCCNc1nc(NCC(F)(F)F)c2nc(-c3cccc(S(C)(=O)=O)c3)ccc2n1] | $N^2$-(2-methoxyethyl)-6-(3-(methylsulfonyl)phenyl)-$N^4$-(2,2,2-trifluoroethyl)pyrido[3,2-d]pyrimidine-2,4-diamine | 456.19 |
| 140 | 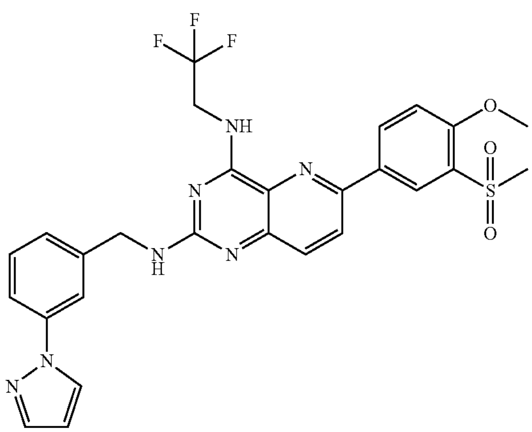 [SMILES: COc1ccc(-c2ccc3nc(NCc4cccc(-n5cccn5)c4)nc(NCC(F)(F)F)c3n2)cc1S(C)(=O)=O] | $N^2$-(3-(1H-pyrazol-1-yl)benzyl)-6-(4-methoxy-3-(methylsulfonyl)phenyl)-$N^4$-(2,2,2-trifluoroethyl)pyrido[3,2-d]pyrimidine-2,4-diamine | 584.1 |
| 141 | 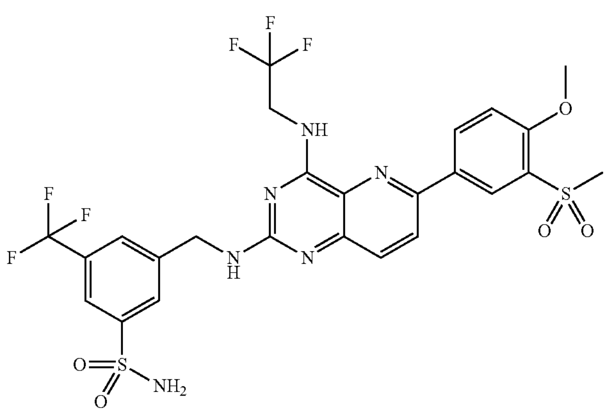 [SMILES: COc1ccc(-c2ccc3nc(NCc4cc(C(F)(F)F)cc(S(N)(=O)=O)c4)nc(NCC(F)(F)F)c3n2)cc1S(C)(=O)=O] | 3-((6-(4-methoxy-3-(methylsulfonyl)phenyl)-4-(2,2,2-trifluoroethylamino)pyrido[3,2-d]pyrimidin-2-ylamino)methyl)-5-(trifluoromethyl)benzenesulfonamide | 665.20 |

TABLE III-continued

| Ex | Structure | Name | MS |
|---|---|---|---|
| 142 | 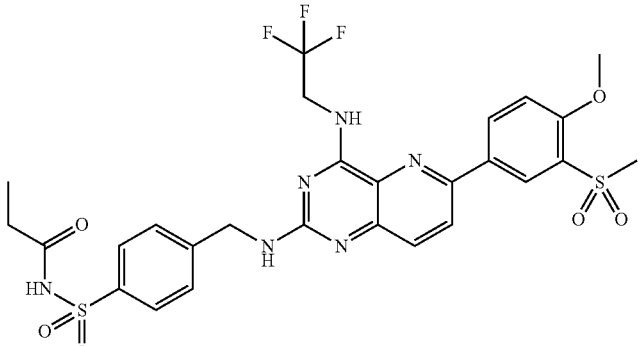 | N-(4-((6-(4-methoxy-3-(methylsulfonyl)phenyl)-4-(2,2,2-trifluoroethylamino)pyrido[3,2-d]pyrimidin-2-ylamino)methyl)phenylsulfonyl)propionamide | 653.19 |
| 143 | 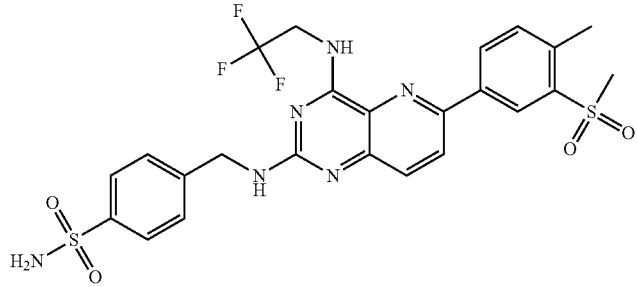 [SMILES: Cc1ccc(-c2ccc3nc(NCc4ccc(S(N)(=O)=O)cc4)nc(NCC(F)(F)F)c3n2)cc1S(C)(=O)=O] | 4-((6-(4-methyl-3-(methylsulfonyl)phenyl)-4-(2,2,2-trifluoroethylamino)pyrido[3,2-d]pyrimidin-2-ylamino)methyl)benzenesulfonamide | 581.1 |
| 144 | 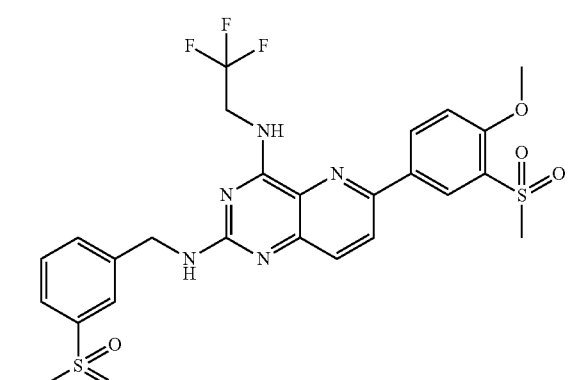 | 3-((6-(4-methoxy-3-(methylsulfonyl)phenyl)-4-(2,2,2-trifluoroethylamino)pyrido[3,2-d]pyrimidin-2-ylamino)methyl)benzenesulfonamide | 597.2 |
| 145 | 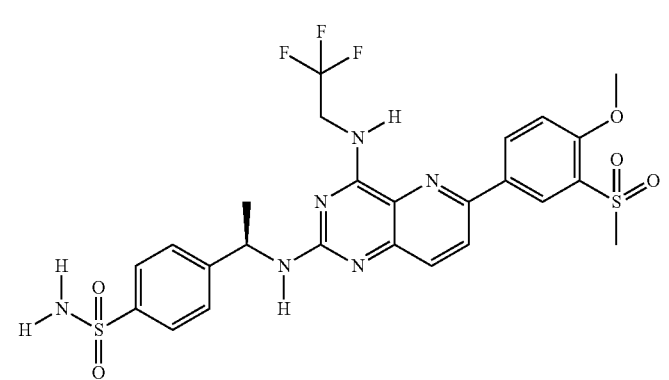 [SMILES: COc1ccc(-c2ccc3nc(N[C@H](C)c4ccc(S(N)(=O)=O)cc4)nc(NCC(F)(F)F)c3n2)cc1S(C)(=O)=O] | 4-((R)-1-(6-(4-methoxy-3-(methylsulfonyl)phenyl)-4-(2,2,2-trifluoroethylamino)pyrido[3,2-d]pyrimidin-2-ylamino)ethyl)benzenesulfonamide | 611.17 |

TABLE III-continued

| Ex | Structure | Name | MS |
|---|---|---|---|
| 146 | 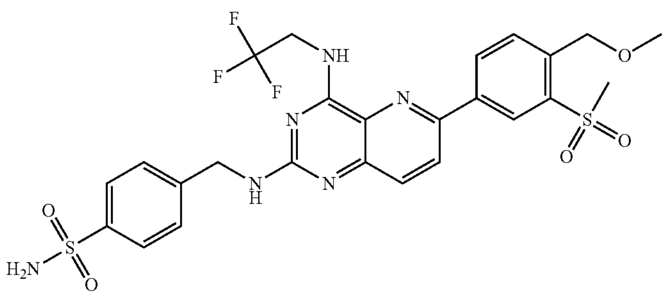 [SMILES: COCc1ccc(-c2ccc3nc(NCc4ccc(S(N)(=O)=O)cc4)nc(NCC(F)(F)F)c3n2)cc1S(C)(=O)=O] | 4-((6-(4-(methoxymethyl)-3-(methylsulfonyl)phenyl)-4-(2,2,2-trifluoroethylamino)pyrido[3,2-d]pyrimidin-2-ylamino)methyl)benzenesulfonamide | 611.1 |
| 147 | 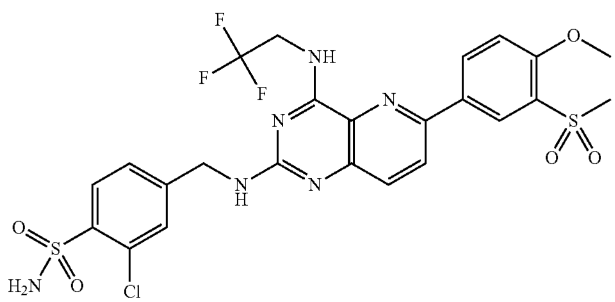 [SMILES: COc1ccc(-c2ccc3nc(NCc4ccc(S(N)(=O)=O)c(Cl)c4)nc(NCC(F)(F)F)c3n2)cc1S(C)(=O)=O] | 2-chloro-4-((6-(4-methoxy-3-(methylsulfonyl)phenyl)-4-(2,2,2-trifluoroethylamino)pyrido[3,2-d]pyrimidin-2-ylamino)methyl)benzenesulfonamide | 631.1, 633.0 |
| 148 | 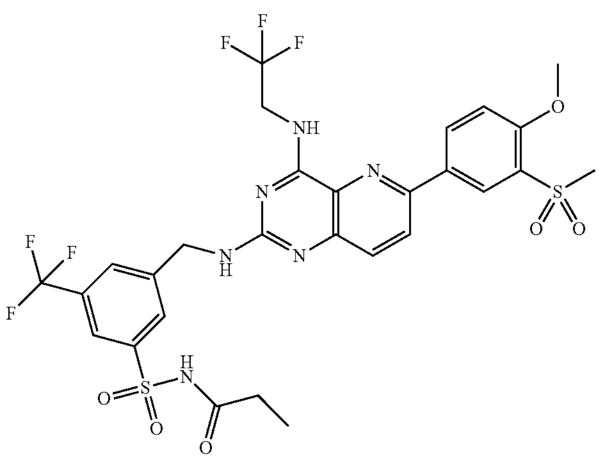 [SMILES: CCC(=O)NS(=O)(=O)c1cc(CNc2nc(NCC(F)(F)F)c3nc(-c4ccc(OC)c(S(C)(=O)=O)c4)ccc3n2)cc(C(F)(F)F)c1] | N-(3-((6-(4-methoxy-3-(methylsulfonyl)phenyl)-4-(2,2,2-trifluoroethylamino)pyrido[3,2-d]pyrimidin-2-ylamino)methyl)-5-(trifluoromethyl)phenylsulfonyl)propionamide | 721.19 |
| 149 | 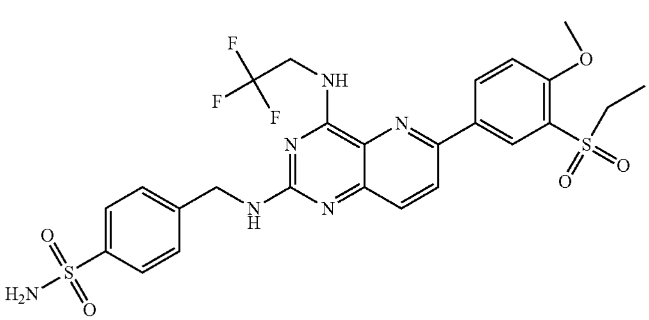 [SMILES: CCS(=O)(=O)c1cc(-c2ccc3nc(NCc4ccc(S(N)(=O)=O)cc4)nc(NCC(F)(F)F)c3n2)ccc1OC] | 4-((6-(3-(ethylsulfonyl)-4-methoxyphenyl)-4-(2,2,2-trifluoroethylamino)pyrido[3,2-d]pyrimidin-2-ylamino)methyl)benzenesulfonamide | 611.1 |

TABLE III-continued

| Ex | Structure | Name | MS |
|---|---|---|---|
| 150 | 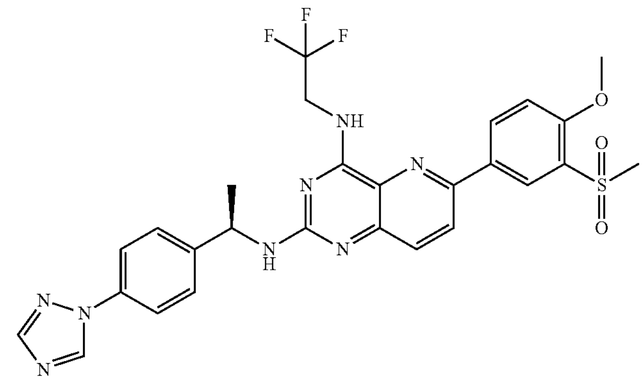 [SMILES: COc1ccc(-c2ccc3nc(N[C@H](C)c4ccc(-n5cncn5)cc4)nc(NCC(F)(F)F)c3n2)cc1S(C)(=O)=O] | $N^2$-((R)-1-(4-(1H-1,2,4-triazol-1-yl)phenyl)ethyl)-6-(4-methoxy-3-(methylsulfonyl)phenyl)-$N^4$-(2,2,2-trifluoroethyl)pyrido[3,2-d]pyrimidine-2,4-diamine | 599.1 |
| 151 | 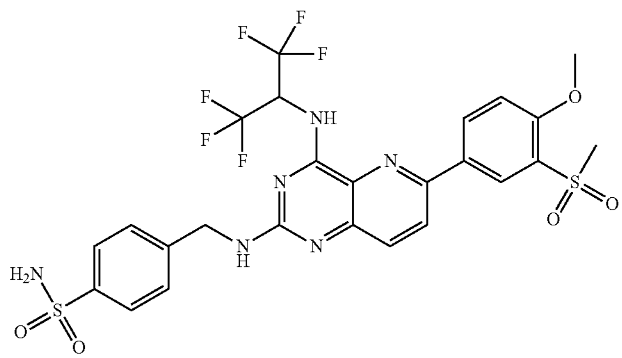 [SMILES: COc1ccc(-c2ccc3nc(NCc4ccc(S(N)(=O)=O)cc4)nc(NC(C(F)(F)F)C(F)(F)F)c3n2)cc1S(C)(=O)=O] | 4-((4-(1,1,1,3,3,3-hexafluoropropan-2-ylamino)-6-(4-methoxy-3-(methylsulfonyl)phenyl)pyrido[3,2-d]pyrimidin-2-ylamino)methyl)benzene-sulfonamide | 665.2 |
| 152 | 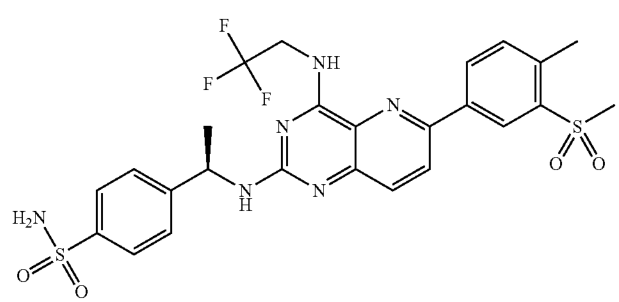 [SMILES: Cc1ccc(-c2ccc3nc(N[C@H](C)c4ccc(S(N)(=O)=O)cc4)nc(NCC(F)(F)F)c3n2)cc1S(C)(=O)=O] | 4-((R)-1-(6-(4-methyl-3-(methylsulfonyl)phenyl)-4-(2,2,2-trifluoroethylamino)pyrido[3,2-d]pyrimidin-2-ylamino)ethyl)benzene-sulfonamide | 595.1 |
| 153 | 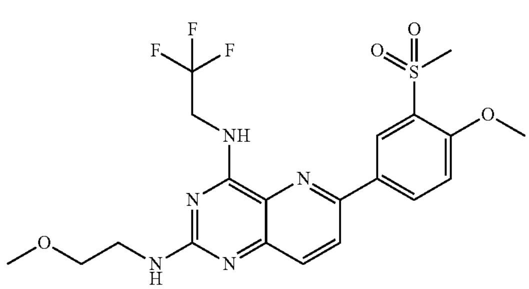 | 6-(4-methoxy-3-(methylsulfonyl)phenyl)-$N^2$-(2-methoxyethyl)-$N^4$-(2,2,2-trifluoroethyl)pyrido[3,2-d]pyrimidine-2,4-diamine | 486.23 |

TABLE III-continued

| Ex | Structure | Name | MS |
|---|---|---|---|
| 154 | 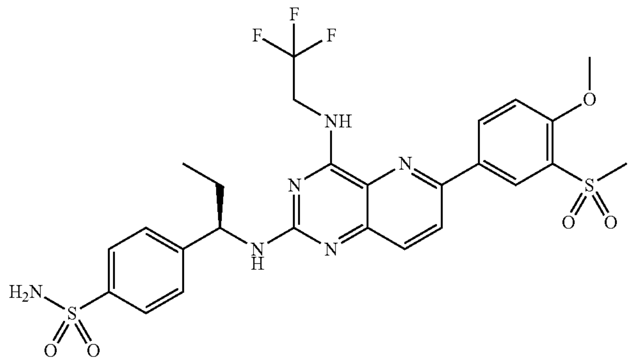 [SMILES: CC[C@@H](Nc1nc(NCC(F)(F)F)c2nc(-c3ccc(OC)c(S(C)(=O)=O)c3)ccc2n1)c1ccc(S(N)(=O)=O)cc1] | 4-((R)-1-(6-(4-methoxy-3-(methylsulfonyl)phenyl)-4-(2,2,2-trifluoroethylamino)pyrido[3,2-d]pyrimidin-2-ylamino)propyl)benzenesulfonamide | 625.2 |
| 155 | 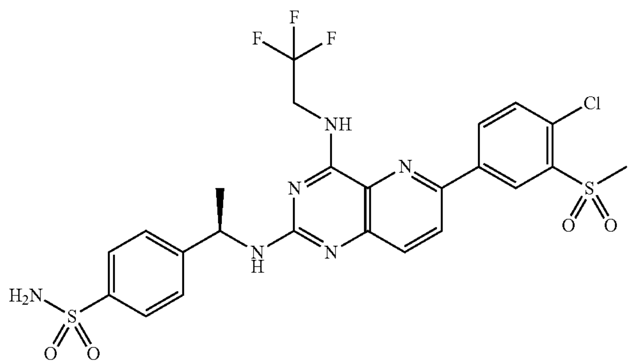 [SMILES: C[C@@H](Nc1nc(NCC(F)(F)F)c2nc(-c3ccc(Cl)c(S(C)(=O)=O)c3)ccc2n1)c1ccc(S(N)(=O)=O)cc1] | 4-((R)-1-(6-(4-chloro-3-(methylsulfonyl)phenyl)-4-(2,2,2-trifluoroethylamino)pyrido[3,2-d]pyrimidin-2-ylamino)ethyl)benzenesulfonamide | 615.3 |
| 156 | 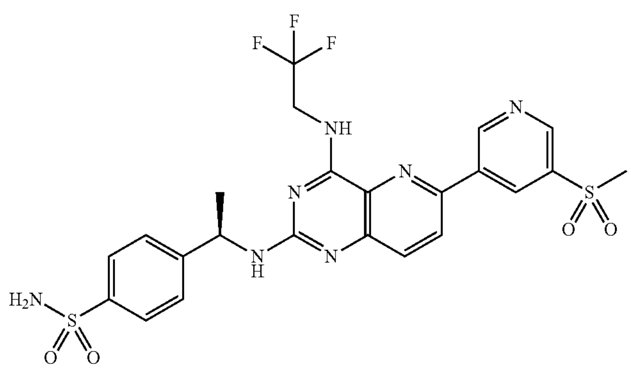 [SMILES: C[C@@H](Nc1nc(NCC(F)(F)F)c2nc(-c3cncc(S(C)(=O)=O)c3)ccc2n1)c1ccc(S(N)(=O)=O)cc1] | 4-((R)-1-(6-(5-(methylsulfonyl)pyridin-3-yl)-4-(2,2,2-trifluoroethylamino)pyrido[3,2-d]pyrimidin-2-ylamino)ethyl)benzenesulfonamide | 582.3 |
| 157 | 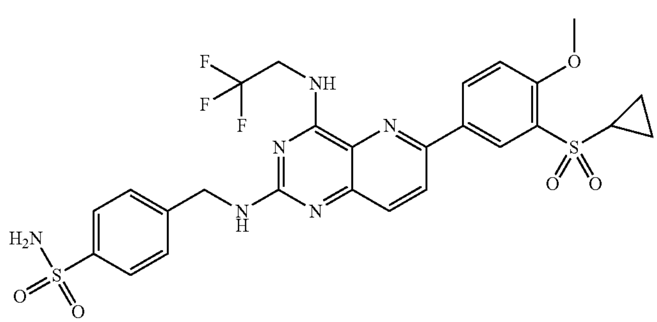 [SMILES: COc1ccc(-c2ccc3nc(NCc4ccc(S(N)(=O)=O)cc4)nc(NCC(F)(F)F)c3n2)cc1S(=O)(=O)C1CC1] | 4-((6-(3-(cyclopropylsulfonyl)-4-methoxyphenyl)-4-(2,2,2-trifluoroethylamino)pyrido[3,2-d]pyrimidin-2-ylamino)methyl)benzenesulfonamide | 623.2 |

TABLE III-continued

| Ex | Structure | Name | MS |
|---|---|---|---|
| 158 | 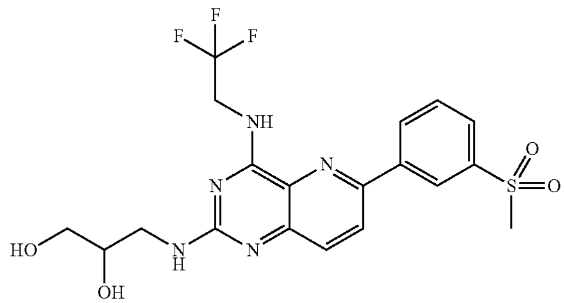 [SMILES: CS(=O)(=O)c1cccc(-c2ccc3nc(NCC(O)CO)nc(NCC(F)(F)F)c3n2)c1] | 3-(6-(3-(methylsulfonyl)phenyl)-4-(2,2,2-trifluoroethylamino)pyrido[3,2-d]pyrimidin-2-ylamino)propane-1,2-diol | 472.21 |
| 159 | 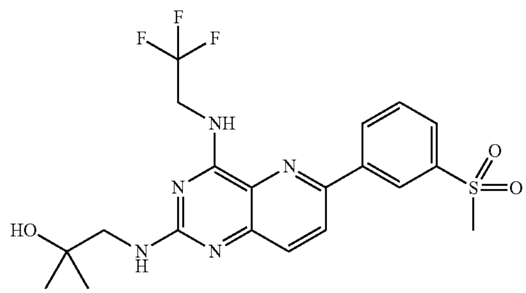 [SMILES: CC(C)(O)CNc1nc(NCC(F)(F)F)c2nc(-c3cccc(S(C)(=O)=O)c3)ccc2n1] | 2-methyl-1-(6-(3-(methylsulfonyl)phenyl)-4-(2,2,2-trifluoroethylamino)pyrido[3,2-d]pyrimidin-2-ylamino)propan-2-ol | 470.13 |
| 160 | 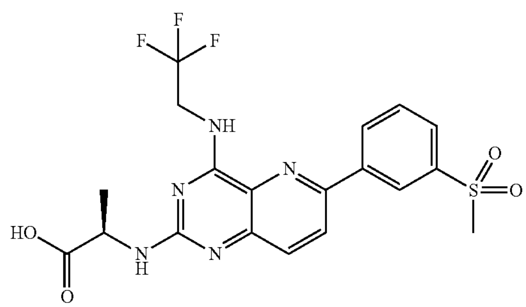 [SMILES: C[C@@H](Nc1nc(NCC(F)(F)F)c2nc(-c3cccc(S(C)(=O)=O)c3)ccc2n1)C(=O)O] | (2R)-2-(6-(3-(methylsulfonyl)phenyl)-4-(2,2,2-trifluoroethyl-amino)pyrido[3,2-d]pyrimidin-2-ylamino)propanoic acid | 470.12 |
| 161 | 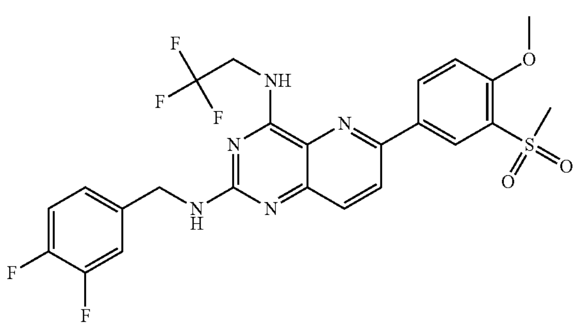 [SMILES: COc1ccc(-c2ccc3nc(NCc4ccc(F)c(F)c4)nc(NCC(F)(F)F)c3n2)cc1S(C)(=O)=O] | $N^2$-(3,4-difluorobenzyl)-6-(4-methoxy-3-(methylsulfonyl)phenyl)-$N^4$-(2,2,2-trifluoroethyl)pyrido[3,2-d]pyrimidine-2,4-diamine | 554.1 |
| 162 | 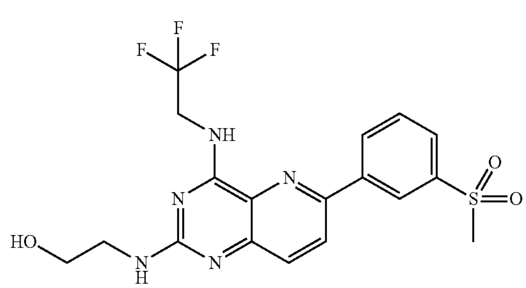 [SMILES: CS(=O)(=O)c1cccc(-c2ccc3nc(NCCO)nc(NCC(F)(F)F)c3n2)c1] | 2-(6-(3-(methylsulfonyl)phenyl)-4-(2,2,2-trifluoroethyl-amino)pyrido[3,2-d]pyrimidin-2-ylamino)ethanol | 442.22 |

TABLE III-continued

| Ex | Structure | Name | MS |
|---|---|---|---|
| 163 | 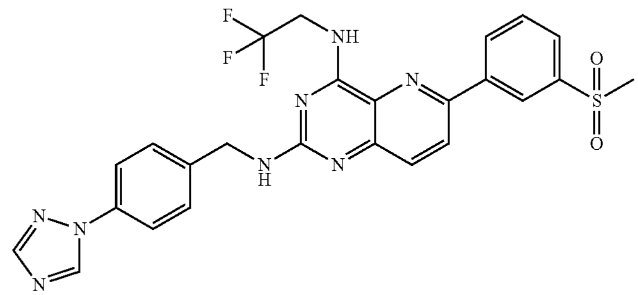 [SMILES: CS(=O)(=O)c1cccc(-c2ccc3nc(NCc4ccc(-n5cncn5)cc4)nc(NCC(F)(F)F)c3n2)c1] | $N^2$-(4-(1H-1,2,4-triazol-1-yl)benzyl)-6-(3-(methylsulfonyl)phenyl)-$N^4$-(2,2,2-trifluoroethyl)pyrido[3,2-d]pyrimidine-2,4-diamine | 555.3 |
| 164 | 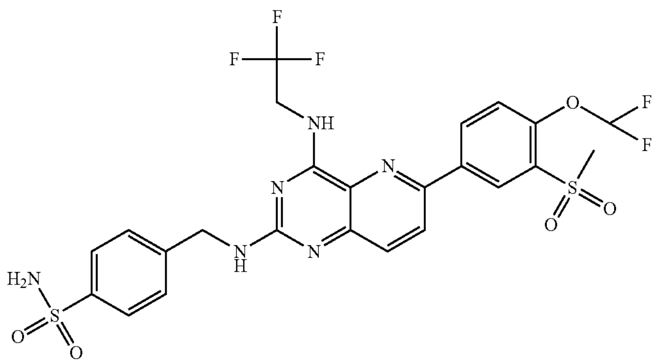 [SMILES: CS(=O)(=O)c1cc(-c2ccc3nc(NCc4ccc(S(N)(=O)=O)cc4)nc(NCC(F)(F)F)c3n2)ccc1OC(F)F] | 4-((6-(4-(difluoromethoxy)-3-(methylsulfonyl)phenyl)-4-(2,2,2-trifluoroethylamino)pyrido[3,2-d]pyrimidin-2-ylamino)methyl)benzene-sulfonamide | 633.4 |
| 165 | 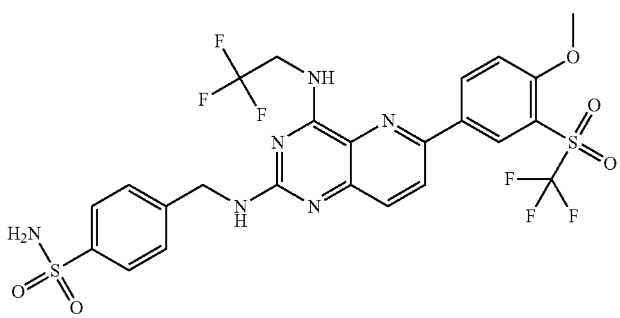 [SMILES: COc1ccc(-c2ccc3nc(NCc4ccc(S(N)(=O)=O)cc4)nc(NCC(F)(F)F)c3n2)cc1S(=O)(=O)C(F)(F)F] | 4-((6-(4-methoxy-3-(trifluoromethylsulfonyl)phenyl)-4-(2,2,2-trifluoroethylamino)pyrido[3,2-d]pyrimidin-2-ylamino)methyl)benzene-sulfonamide | 601.2 |
| 166 | 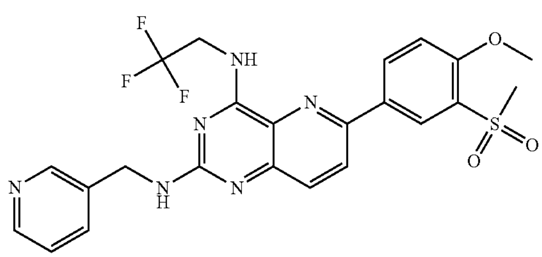 [SMILES: COc1ccc(-c2ccc3nc(NCc4cccnc4)nc(NCC(F)(F)F)c3n2)cc1S(C)(=O)=O] | 6-(4-methoxy-3-(methylsulfonyl)phenyl)-$N^2$-(pyridin-3-ylmethyl)-$N^4$-(2,2,2-trifluoroethyl)pyrido[3,2-d]pyrimidine-2,4-diamine | 519.3 |
| 167 | 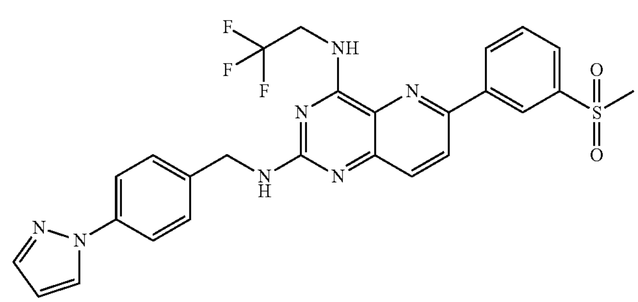 [SMILES: CS(=O)(=O)c1cccc(-c2ccc3nc(NCc4ccc(-n5cccn5)cc4)nc(NCC(F)(F)F)c3n2)c1] | $N^2$-(4-(1H-pyrazol-1-yl)benzyl)-6-(3-(methylsulfonyl)phenyl)-$N^4$-(2,2,2-trifluoroethyl)pyrido[3,2-d]pyrimidine-2,4-diamine | 554.2 |

TABLE III-continued

| Ex | Structure | Name | MS |
|---|---|---|---|
| 168 | 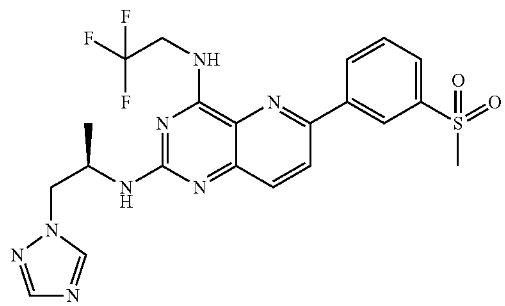 [SMILES: C[C@H](Cn1cncn1)Nc1nc(NCC(F)(F)F)c2nc(-c3cccc(S(C)(=O)=O)c3)ccc2n1] | N²-((R)-1-(1H-1,2,4-triazol-1-yl)propan-2-yl)-6-(3-(methylsulfonyl)phenyl)-N⁴-(2,2,2-trifluoroethyl)pyrido[3,2-d]pyrimidine-2,4-diamine | 507.2 |
| 169 | 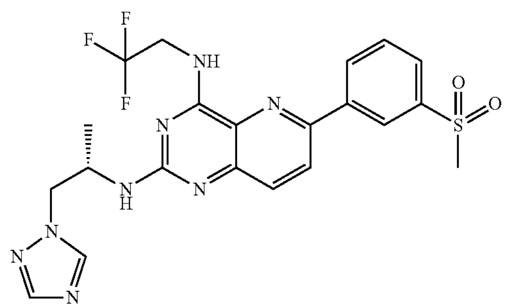 [SMILES: C[C@@H](Cn1cncn1)Nc1nc(NCC(F)(F)F)c2nc(-c3cccc(S(C)(=O)=O)c3)ccc2n1] | N²-((S)-1-(1H-1,2,4-triazol-1-yl)propan-2-yl)-6-(3-(methylsulfonyl)phenyl)-N⁴-(2,2,2-trifluoroethyl)pyrido[3,2-d]pyrimidine-2,4-diamine | 507.2 |
| 170 | 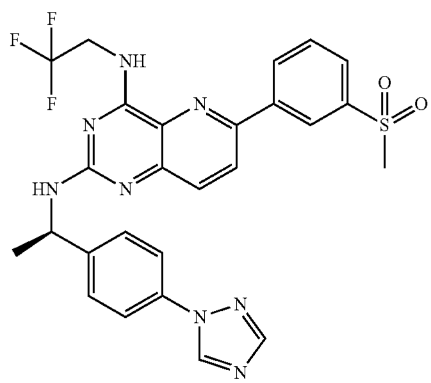 [SMILES: C[C@@H](Nc1nc(NCC(F)(F)F)c2nc(-c3cccc(S(C)(=O)=O)c3)ccc2n1)c1ccc(-n2cncn2)cc1] | N²-((R)-1-(4-(1H-1,2,4-triazol-1-yl)phenyl)ethyl)-6-(3-(methylsulfonyl)phenyl)-N⁴-(2,2,2-trifluoroethyl)pyrido[3,2-d]pyrimidine-2,4-diamine | 569.2 |
| 171 | 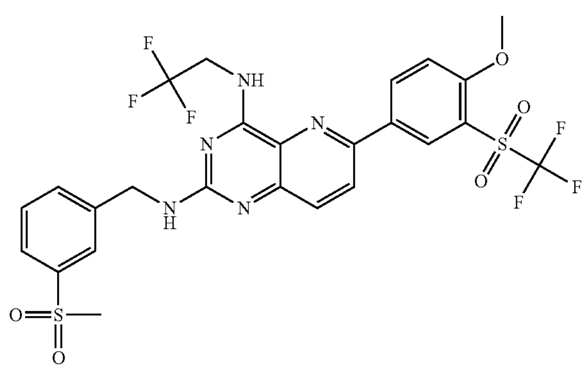 [SMILES: COc1ccc(-c2ccc3nc(NCc4cccc(S(C)(=O)=O)c4)nc(NCC(F)(F)F)c3n2)cc1S(=O)(=O)C(F)(F)F] | N²-(3-(methylsulfonyl)benzyl)-6-(4-methoxy-3-(trifluoromethylsulfonyl)phenyl)-N⁴-(2,2,2-trifluoroethyl)pyrido[3,2-d]pyrimidine-2,4-diamine | 598.2 |
| 172 | 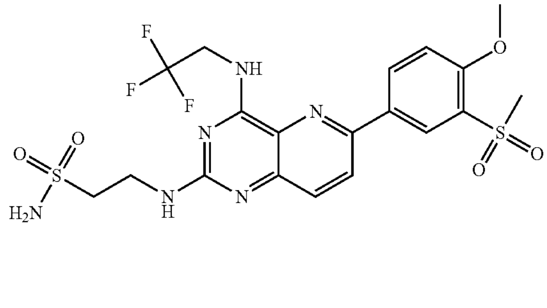 [SMILES: COc1ccc(-c2ccc3nc(NCCS(N)(=O)=O)nc(NCC(F)(F)F)c3n2)cc1S(C)(=O)=O] | 2-(6-(4-methoxy-3-(methylsulfonyl)phenyl)-4-(2,2,2-trifluoroethylamino)pyrido[3,2-d]pyrimidin-2-ylamino)ethanesulfonamide | 535.2 |

TABLE III-continued

| Ex | Structure | Name | MS |
|---|---|---|---|
| 173 | 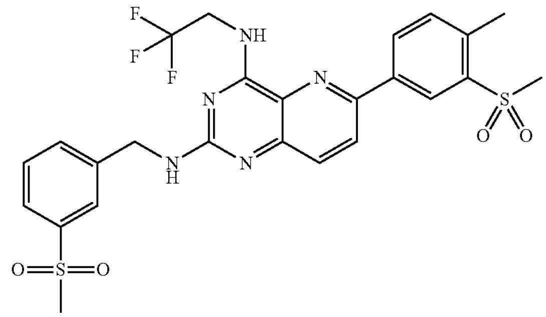 [SMILES: Cc1ccc(-c2ccc3nc(NCc4cccc(S(C)(=O)=O)c4)nc(NCC(F)(F)F)c3n2)cc1S(C)(=O)=O] | $N^2$-(3-(methylsulfonyl)benzyl)-6-(4-methyl-3-(methylsulfonyl)phenyl)-$N^4$-(2,2,2-trifluoroethyl)pyrido[3,2-d]pyrimidine-2,4-diamine | 581.2 |
| 174 | 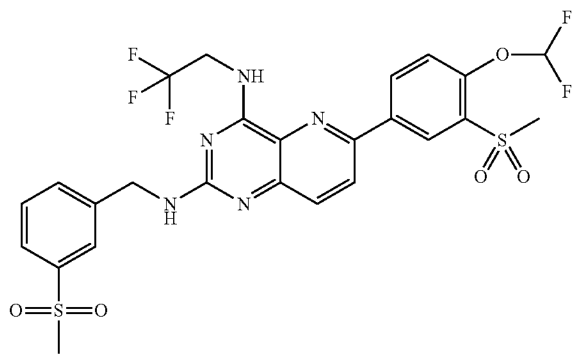 [SMILES: CS(=O)(=O)c1cccc(CNc2nc(NCC(F)(F)F)c3nc(-c4ccc(OC(F)F)c(S(C)(=O)=O)c4)ccc3n2)c1] | $N^2$-(3-(methylsulfonyl)benzyl)-6-(4-(difluoromethoxy)-3-(methylsulfonyl)phenyl)-$N^4$-(2,2,2-trifluoroethyl)pyrido[3,2-d]pyrimidine-2,4-diamine | 632.3 |
| 175 | 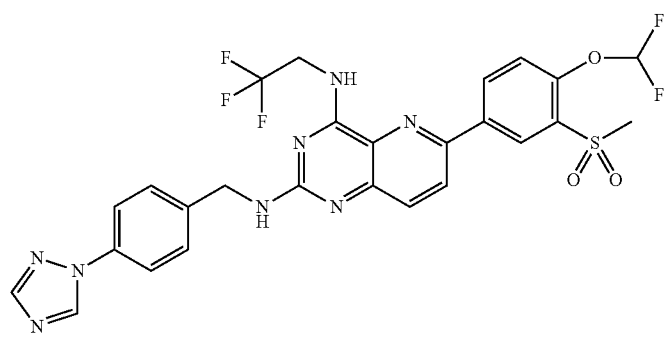 [SMILES: CS(=O)(=O)c1cc(-c2ccc3nc(NCc4ccc(-n5cncn5)cc4)nc(NCC(F)(F)F)c3n2)ccc1OC(F)F] | $N^2$-(4-(1H-1,2,4-triazol-1-yl)benzyl)-6-(4-(difluoromethoxy)-3-(methylsulfonyl)phenyl)-$N^4$-(2,2,2-trifluoroethyl)pyrido[3,2-d]pyrimidine-2,4-diamine | 621.3 |
| 176 | 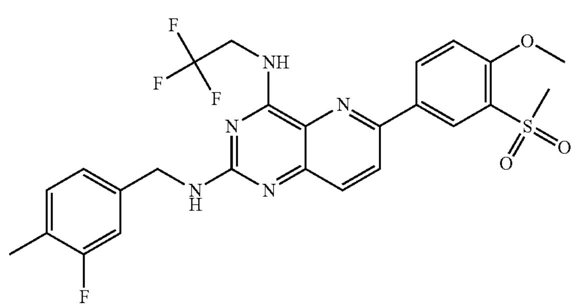 [SMILES: COc1ccc(-c2ccc3nc(NCc4ccc(C)c(F)c4)nc(NCC(F)(F)F)c3n2)cc1S(C)(=O)=O] | $N^2$-(3-fluoro-4-methylbenzyl)-6-(4-methoxy-3-(methylsulfonyl)phenyl)-$N^4$-(2,2,2-trifluoroethyl)pyrido[3,2-d]pyrimidine-2,4-diamine | 550.3 |

TABLE III-continued

| Ex | Structure | Name | MS |
|---|---|---|---|
| 177 | 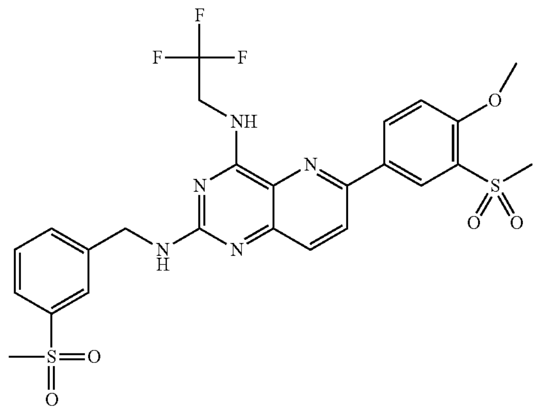 | $N^2$-(3-(methylsulfonyl)benzyl)-6-(4-methoxy-3-(methylsulfonyl)phenyl)-$N^4$-(2,2,2-trifluoroethyl)pyrido[3,2-d]pyrimidine-2,4-diamine | 596.3 |
| 178 | 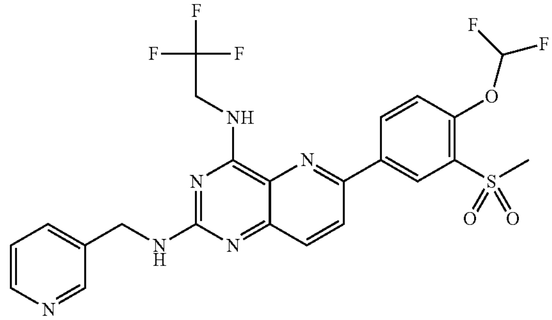 [SMILES: CS(=O)(=O)c1cc(-c2ccc3nc(NCc4cccnc4)nc(NCC(F)(F)F)c3n2)ccc1OC(F)F] | 6-(4-(difluoromethoxy)-3-(methylsulfonyl)phenyl)-$N^2$-(pyridin-3-ylmethyl)-$N^4$-(2,2,2-trifluoroethyl)pyrido[3,2-d]pyrimidine-2,4-diamine | 555.2 |
| 179 | 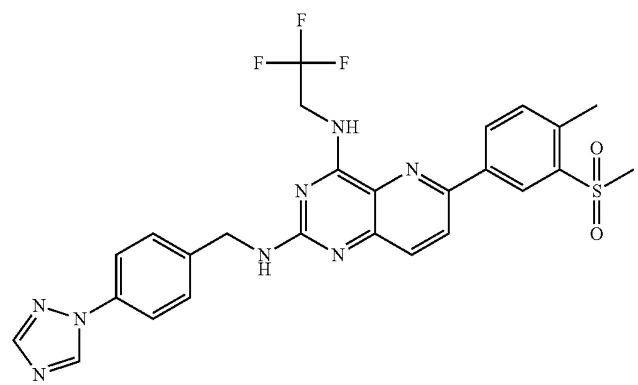 [SMILES: Cc1ccc(-c2ccc3nc(NCc4ccc(-n5cncn5)cc4)nc(NCC(F)(F)F)c3n2)cc1S(C)(=O)=O] | $N^2$-(4-(1H-1,2,4-triazol-1-yl)benzyl)-6-(4-methyl-3-(methylsulfonyl)phenyl)-$N^4$-(2,2,2-trifluoroethyl)pyrido[3,2-d]pyrimidine-2,4-diamine | 569.2 |
| 180 | 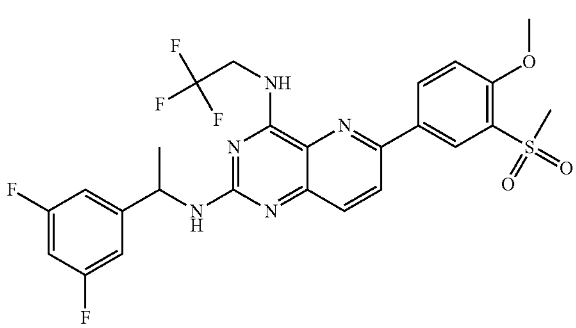 [SMILES: COc1ccc(-c2ccc3nc(NC(C)c4cc(F)cc(F)c4)nc(NCC(F)(F)F)c3n2)cc1S(C)(=O)=O] | $N^2$-(1-(3,5-difluorophenyl)ethyl)-6-(4-methoxy-3-(methylsulfonyl)phenyl)-$N^4$-(2,2,2-trifluoroethyl)pyrido[3,2-d]pyrimidine-2,4-diamine | 568.2 |

TABLE III-continued

| Ex | Structure | Name | MS |
|---|---|---|---|
| 181 | 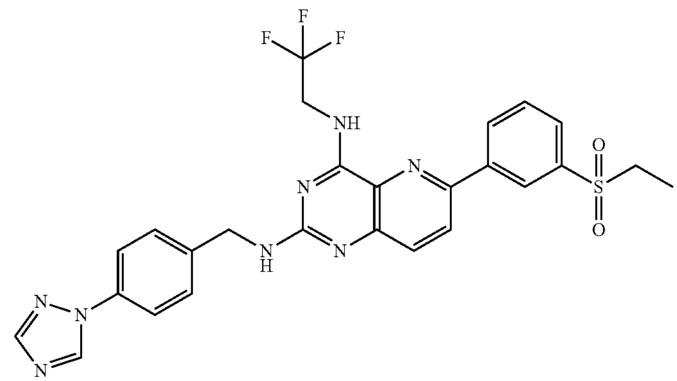 [SMILES: CCS(=O)(=O)c1cccc(-c2ccc3nc(NCc4ccc(-n5cncn5)cc4)nc(NCC(F)(F)F)c3n2)c1] | N²-(4-(1H-1,2,4-triazol-1-yl)benzyl)-6-(3-(ethylsulfonyl)phenyl)-N⁴-(2,2,2-trifluoroethyl)pyrido[3,2-d]pyrimidine-2,4-diamine | 569.3 |
| 182 | 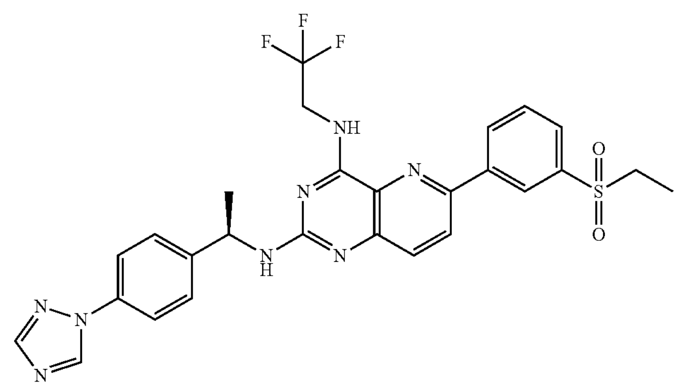 [SMILES: CCS(=O)(=O)c1cccc(-c2ccc3nc(N[C@H](C)c4ccc(-n5cncn5)cc4)nc(NCC(F)(F)F)c3n2)c1] | N²-((R)-1-(4-(1H-1,2,4-triazol-1-yl)phenyl)ethyl)-6-(3-(ethylsulfonyl)phenyl)-N⁴-(2,2,2-trifluoroethyl)pyrido[3,2-d]pyrimidine-2,4-diamine | 583.3 |
| 183 | 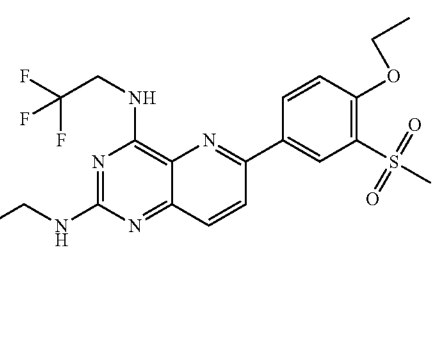 | N²-(4-(1H-1,2,4-triazol-1-yl)benzyl)-6-(4-ethoxy-3-(methylsulfonyl)phenyl)-N⁴-(2,2,2-trifluoroethyl)pyrido[3,2-d]pyrimidine-2,4-diamine | 599.2 |
| 184 | 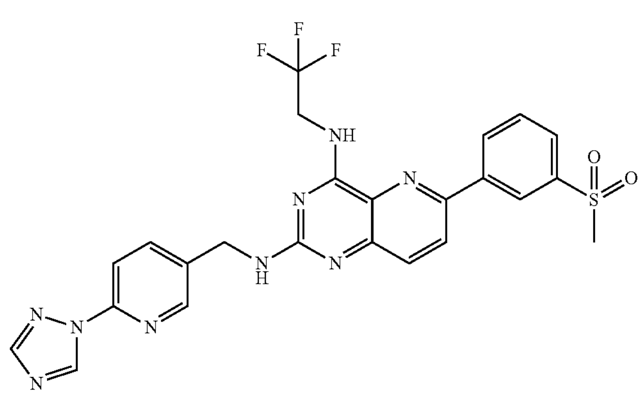 [SMILES: CS(=O)(=O)c1cccc(-c2ccc3nc(NCc4ccc(-n5cncn5)nc4)nc(NCC(F)(F)F)c3n2)c1] | N²-((6-(1H-1,2,4-triazol-1-yl)pyridin-3-yl)methyl)-6-(3-(methylsulfonyl)phenyl)-N⁴-(2,2,2-trifluoroethyl)pyrido[3,2-d]pyrimidine-2,4-diamine | 556.1 |

TABLE III-continued

| Ex | Structure | Name | MS |
|---|---|---|---|
| 185 | 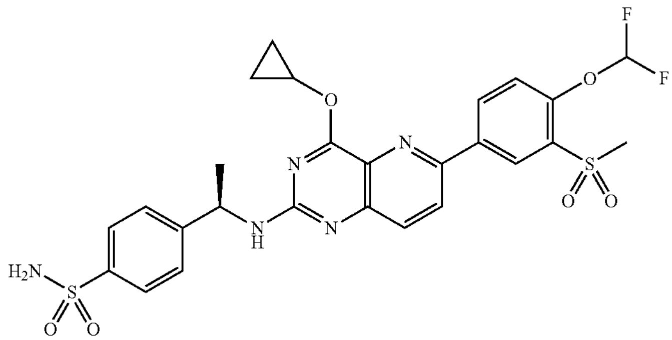 [SMILES: C[C@@H](Nc1nc(OC2CC2)c2nc(-c3ccc(OC(F)F)c(S(C)(=O)=O)c3)ccc2n1)c1ccc(S(N)(=O)=O)cc1] | 4-((R)-1-(4-cyclopropoxy-6-(4-(difluoromethoxy)-3-(methylsulfonyl)phenyl)pyrido[3,2-d]pyrimidin-2-ylamino)ethyl)benzenesulfonamide | 606.1 |
| 186 | 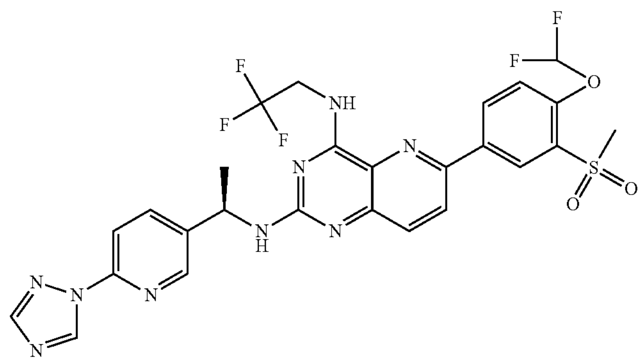 [SMILES: C[C@@H](Nc1nc(NCC(F)(F)F)c2nc(-c3ccc(OC(F)F)c(S(C)(=O)=O)c3)ccc2n1)c1ccc(-n2cncn2)nc1] | N²-((R)-1-(4-(1H-1,2,4-triazol-1-yl)phenyl)ethyl)-6-(4-(difluoromethoxy)-3-(methylsulfonyl)phenyl)-N⁴-(2,2,2-trifluoroethyl)pyrido[3,2-d]pyrimidine-2,4-diamine | 635.2 |
| 187 | 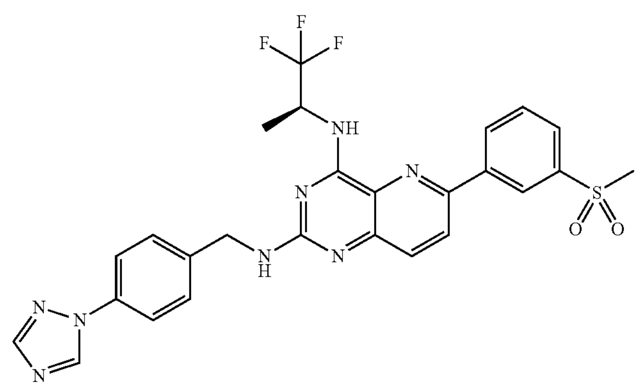 [SMILES: C[C@H](Nc1nc(NCc2ccc(-n3cncn3)cc2)nc2ccc(-c3cccc(S(C)(=O)=O)c3)nc12)C(F)(F)F] | N²-(4-(1H-1,2,4-triazol-1-yl)benzyl)-6-(3-(methylsulfonyl)phenyl)-N⁴-((S)-1,1,1-trifluoropropan-2-yl)pyrido[3,2-d]pyrimidine-2,4-diamine | 569.1 |
| 188 | 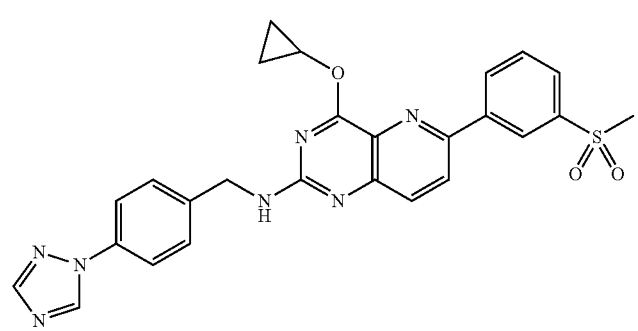 [SMILES: CS(=O)(=O)c1cccc(-c2ccc3nc(NCc4ccc(-n5cncn5)cc4)nc(OC4CC4)c3n2)c1] | N-(4-(1H-1,2,4-triazol-1-yl)benzyl)-4-cyclopropoxy-6-(3-(methylsulfonyl)phenyl)pyrido[3,2-d]pyrimidin-2-amine | 514.1 |

TABLE III-continued

| Ex | Structure | Name | MS |
|---|---|---|---|
| 189 | 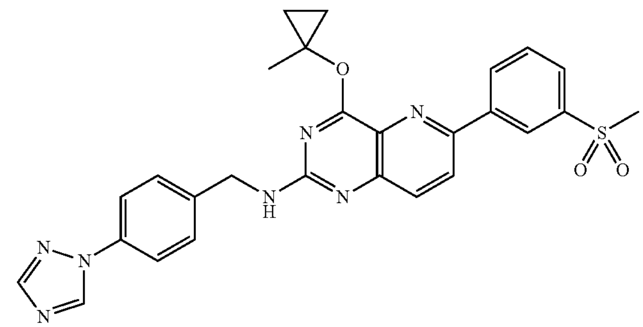 [SMILES: CC1(Oc2nc(NCc3ccc(-n4cncn4)cc3)nc3ccc(-c4cccc(S(C)(=O)=O)c4)nc23)CC1] | N-(4-(1H-1,2,4-triazol-1-yl)benzyl)-4-(1-methylcyclopropoxy)-6-(3-(methylsulfonyl)phenyl)pyrido[3,2-d]pyrimidin-2-amine | 528.1 |
| 190 | 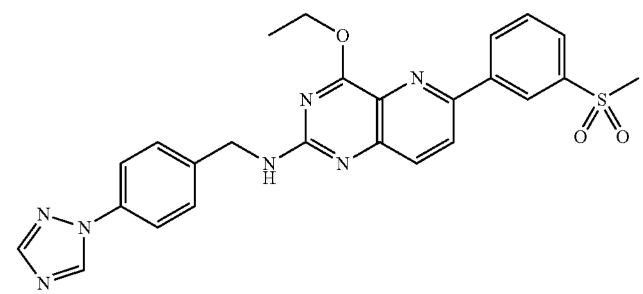 [SMILES: CCOc1nc(NCc2ccc(-n3cncn3)cc2)nc2ccc(-c3cccc(S(C)(=O)=O)c3)nc12] | N-(4-(1H-1,2,4-triazol-1-yl)benzyl)-4-ethoxy-6-(3-(methylsulfonyl)phenyl)pyrido[3,2-d]pyrimidin-2-amine | 502.1 |
| 191 | 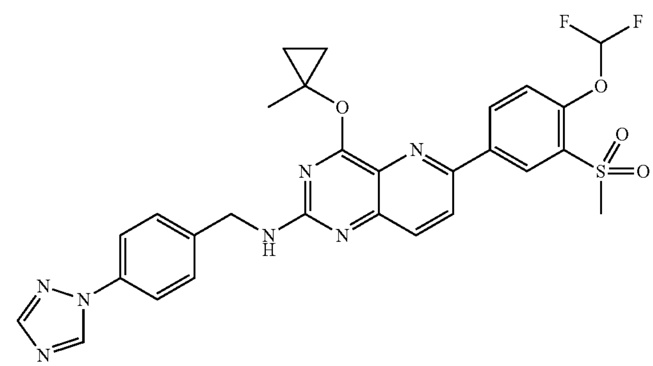 [SMILES: CC1(Oc2nc(NCc3ccc(-n4cncn4)cc3)nc3ccc(-c4ccc(OC(F)F)c(S(C)(=O)=O)c4)nc23)CC1] | N-(4-(1H-1,2,4-triazol-1-yl)benzyl)-6-(4-(difluoromethoxy)-3-(methylsulfonyl)phenyl)-4-(1-methylcyclopropoxy)pyrido[3,2-d]pyrimidin-2-amine | 594 |
| 192 | 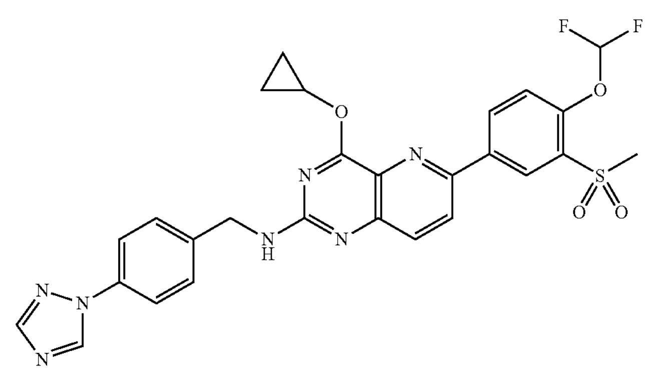 [SMILES: CS(=O)(=O)c1cc(-c2ccc3nc(NCc4ccc(-n5cncn5)cc4)nc(OC4CC4)c3n2)ccc1OC(F)F] | N-(4-(1H-1,2,4-triazol-1-yl)benzyl)-4-cyclopropoxy-6-(4-(difluoromethoxy)-3-(methylsulfonyl)phenyl)pyrido[3,2-d]pyrimidin-2-amine | 580.1 |

TABLE III-continued

| Ex | Structure | Name | MS |
|---|---|---|---|
| 193 | 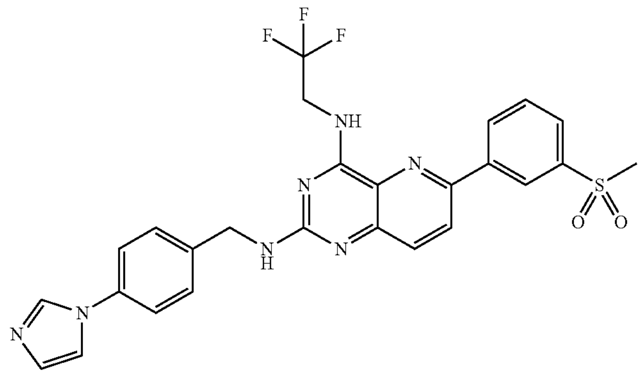 [SMILES: CS(=O)(=O)c1cccc(-c2ccc3nc(NCc4ccc(-n5ccnc5)cc4)nc(NCC(F)(F)F)c3n2)c1] | $N^2$-(4-(1H-imidazol-1-yl)benzyl)-6-(3-(methylsulfonyl)phenyl)-$N^4$-(2,2,2-trifluoroethyl)pyrido[3,2-d]pyrimidine-2,4-diamine | 554.2 |
| 194 | 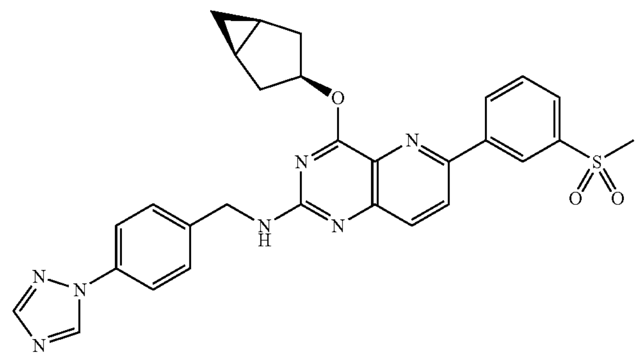 [SMILES: CS(=O)(=O)c1cccc(-c2ccc3nc(NCc4ccc(-n5cncn5)cc4)nc(O[C@@H]4C[C@@H]5C[C@@H]5C4)c3n2)c1] | N-(4-(1H-1,2,4-triazol-1-yl)benzyl)-4-((1S,3r,5R)-bicyclo[3.1.0]hexan-3-yloxy)-6-(3-(methylsulfonyl)phenyl)pyrido[3,2-d]pyrimidin-2-amine | 554.2 |
| 195 | 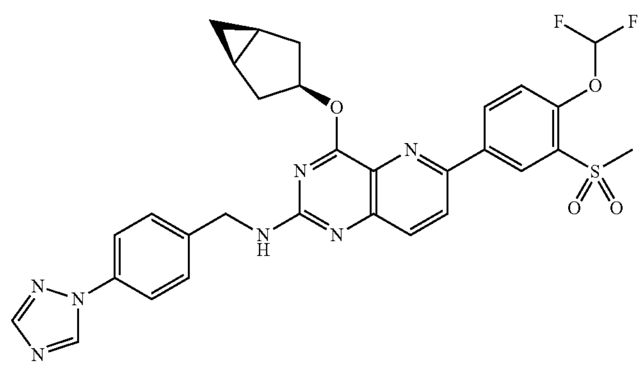 [SMILES: CS(=O)(=O)c1cc(-c2ccc3nc(NCc4ccc(-n5cncn5)cc4)nc(O[C@@H]4C[C@@H]5C[C@@H]5C4)c3n2)ccc1OC(F)F] | N-(4-(1H-1,2,4-triazol-1-yl)benzyl)-4-((1S,3r,5R)-bicyclo[3.1.0]hexan-3-yloxy)-6-(4-(difluoromethoxy)-3-(methylsulfonyl)phenyl)pyrido[3,2-d]pyrimidin-2-amine | 620.2 |
| 196 | 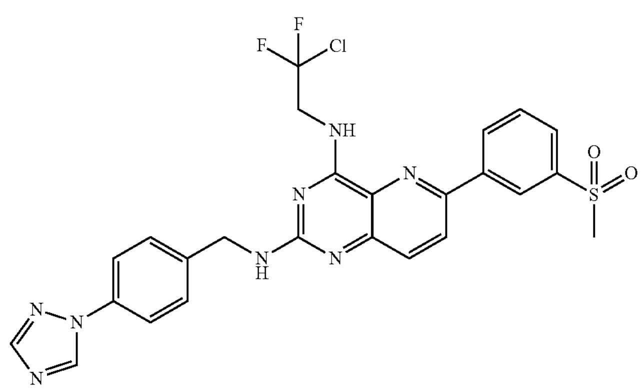 [SMILES: CS(=O)(=O)c1cccc(-c2ccc3nc(NCc4ccc(-n5cncn5)cc4)nc(NCC(F)(F)Cl)c3n2)c1] | $N^2$-(4-(1H-1,2,4-triazol-1-yl)benzyl)-$N^4$-(2-chloro-2,2-difluoroethyl)-6-(3-(methylsulfonyl)phenyl)pyrido[3,2-d]pyrimidine-2,4-diamine | 571.1 |

TABLE III-continued

| Ex | Name | MS |
|---|---|---|
| 197 | N-(4-(1H-1,2,4-triazol-1-yl)benzyl)-4-tert-butoxy-6-(3-(methylsulfonyl)phenyl)pyrido[3,2-d]pyrimidin-2-amine | 530.1 |
| 198 | N-(4-(1H-1,2,4-triazol-1-yl)benzyl)-4-isopropoxy-6-(3-(methylsulfonyl)phenyl)pyrido[3,2-d]pyrimidin-2-amine | 516.2 |
| 199 | N-(4-(1H-1,2,4-triazol-1-yl)benzyl)-6-(4-(difluoromethoxy)-3-(methylsulfonyl)phenyl)-4-isopropoxypyrido[3,2-d]pyrimidin-2-amine | 582.2 |
| 200 | 4-((R)-1-(4-cyclobutoxy-6-(3-(methylsulfonyl)phenyl)pyrido[3,2-d]pyrimidin-2-ylamino)ethyl)benzenesulfonamide | 554.2 |

TABLE III-continued

| Ex | Structure | Name | MS |
|---|---|---|---|
| 202 | 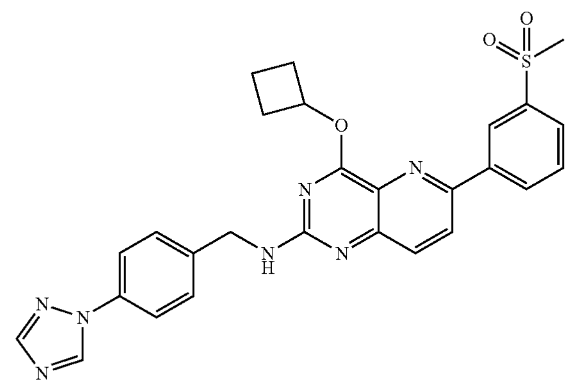 [SMILES: CS(=O)(=O)c1cccc(-c2ccc3nc(NCc4ccc(-n5cncn5)cc4)nc(OC4CCC4)c3n2)c1] | N-(4-(1H-1,2,4-triazol-1-yl)benzyl)-4-cyclobutoxy-6-(3-(methylsulfonyl)phenyl)pyrido[3,2-d]pyrimidin-2-amine | 528.2 |
| 203 | 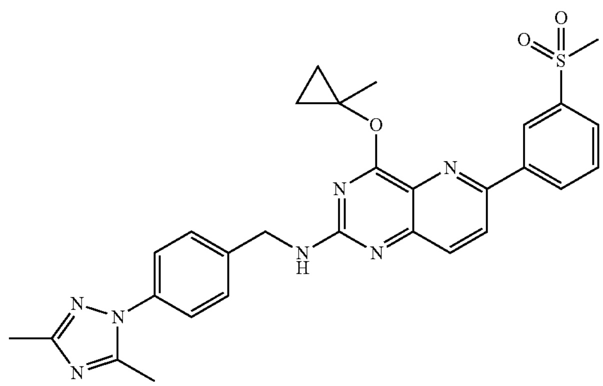 | N-(4-(3,5-dimethyl-1H-1,2,4-triazol-1-yl)benzyl)-4-(1-methylcyclopropoxy)-6-(3-(methylsulfonyl)phenyl)pyrido[3,2-d]pyrimidin-2-amine | 556.2 |
| 204 | 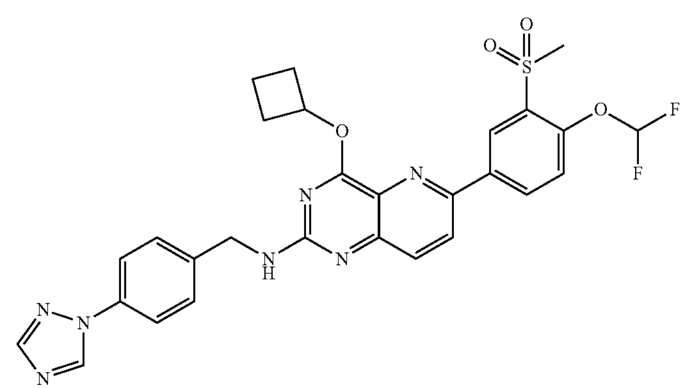 [SMILES: CS(=O)(=O)c1cc(-c2ccc3nc(NCc4ccc(-n5cncn5)cc4)nc(OC4CCC4)c3n2)ccc1OC(F)F] | N-(4-(1H-1,2,4-triazol-1-yl)benzyl)-4-cyclobutoxy-6-(4-(difluoromethoxy)-3-(methylsulfonyl)phenyl)pyrido[3,2-d]pyrimidin-2-amine | 594.1 |
| 205 | 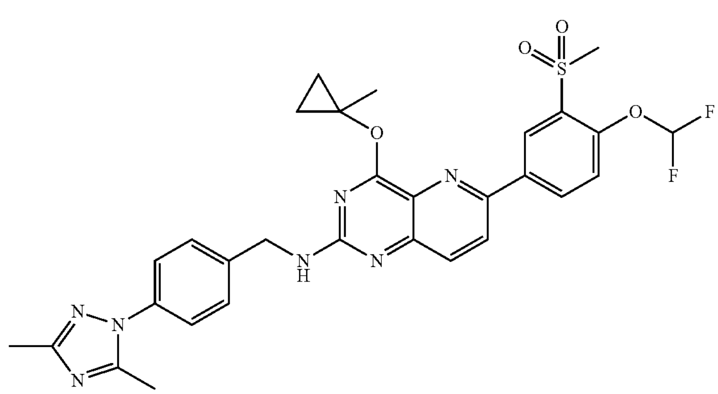 [SMILES: Cc1nc(C)n(-c2ccc(CNc3nc(OC4(C)CC4)c4nc(-c5ccc(OC(F)F)c(S(C)(=O)=O)c5)ccc4n3)cc2)n1] | N-(4-(3,5-dimethyl-1H-1,2,4-triazol-1-yl)benzyl)-6-(4-(difluoromethoxy)-3-(methylsulfonyl)phenyl)-4-(1-methylcyclopropoxy)pyrido[3,2-d]pyrimidin-2-amine | 622.2 |

TABLE III-continued

| Ex | Structure | Name | MS |
|---|---|---|---|
| 206 | 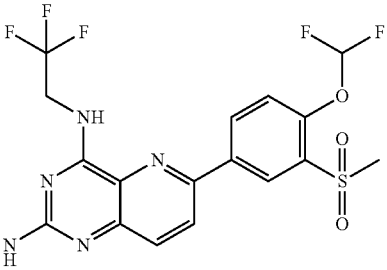 | N²-((R)-1-(1H-1,2,4-triazol-1-yl)propan-2-yl)-6-(4-(difluoromethoxy)-3-(methylsulfonyl)phenyl)-N⁴-(2,2,2-trifluoroethyl)pyrido[3,2-d]pyrimidine-2,4-diamine | 573.0 |
| 207 | 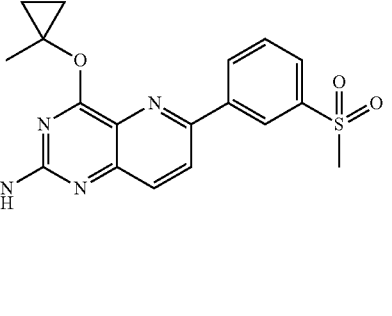 | N-(4-(pyrimidin-5-yl)benzyl)-4-(1-methylcyclopropoxy)-6-(3-(methylsulfonyl)phenyl)pyrido[3,2-d]pyrimidin-2-amine | 539.2 |
| 208 | 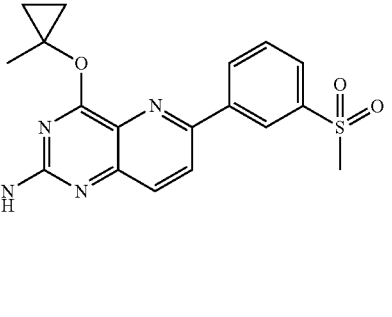 | N-(4-(thiazol-5-yl)benzyl)-4-(1-methylcyclopropoxy)-6-(3-(methylsulfonyl)phenyl)pyrido[3,2-d]pyrimidin-2-amine | 544.2 |
| 209 | 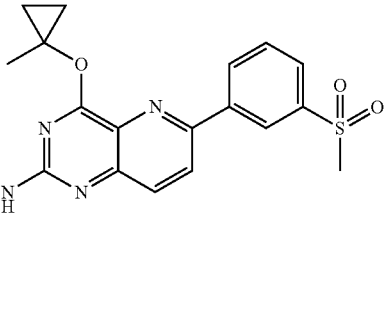 | N-(4-(1H-imidazol-5-yl)benzyl)-4-(1-methylcyclopropoxy)-6-(3-(methylsulfonyl)phenyl)pyrido[3,2-d]pyrimidin-2-amine | 527.2 |
| 210 | 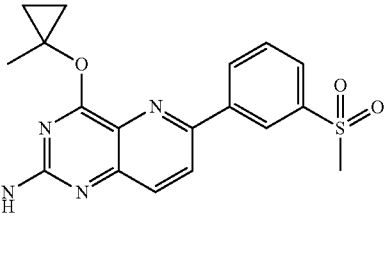 | 4-((4-(1-methylcyclopropoxy)-6-(3-(methylsulfonyl)pheny))pyrido[3,2-d]pyrimidin-2-ylamino)methyl)phenol | 477.2 |

TABLE III-continued

| Ex | Structure | Name | MS |
|---|---|---|---|
| 211 | 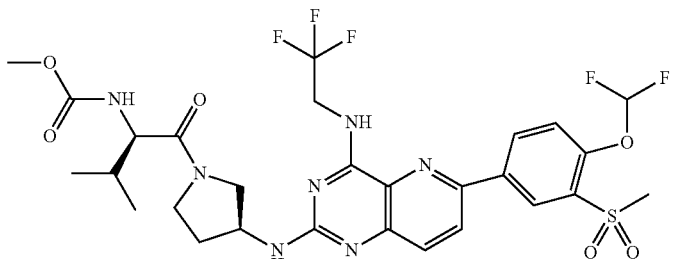 | methyl (R)-1-((S)-3-(6-(4-(difluoromethoxy)-3-(methylsulfonyl)phenyl)-4-(2,2,2-trifluoroethylamino)pyrido[3,2-d]pyrimidin-2-ylamino)pyrrolidin-1-yl)-3-methyl-1-oxobutan-2-ylcarbamate | 690.1 |
| 212 | 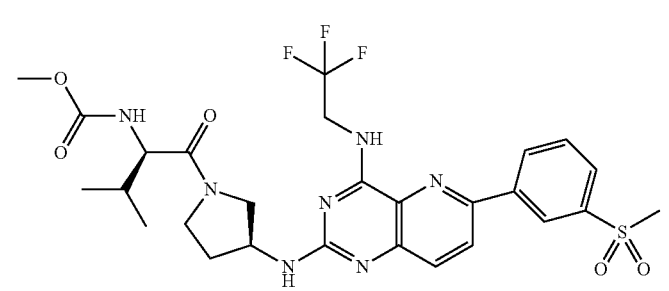 | methyl (R)-3-methyl-1-(S)-3-(6-(3-(methylsulfonyl)phenyl)-4-(2,2,2-trifluoroethylamino)pyrido[3,2-d]pyrimidin-2-ylamino)pyrrolidin-1-yl)-1-oxobutan-2-ylcarbamate | 624.2 |
| 213 | 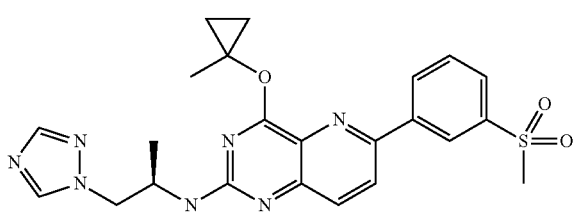 | N-((R)-1-(1H-1,2,4-triazol-1-yl)propan-2-yl)-4-(1-methylcyclopropoxy)-6-(3-(methylsulfonyl)phenyl)pyrido[3,2-d]pyrimidin-2-amine | 480.0 |
| 214 | 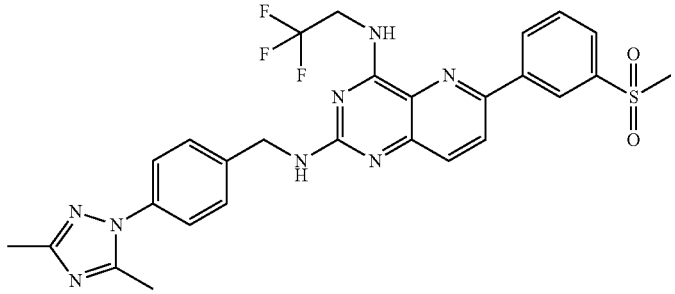 | $N^2$-(4-(3,5-dimethyl-1H-1,2,4-triazol-1-yl)benzyl)-6-(3-(methylsulfonyl)phenyl)-$N^4$-(2,2,2-trifluoroethyl)pyrido[3,2-d]pyrimidine-2,4-diamine | 583.1 |
| 215 | 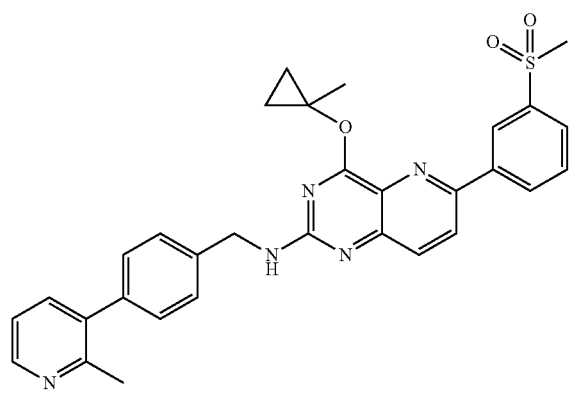 [SMILES: Cc1ncccc1-c1ccc(CNc2nc(OC3(C)CC3)c3nc(-c4cccc(S(C)(=O)=O)c4)ccc3n2)cc1] | N-(4-(2-methylpyridin-3-yl)benzyl)-4-(1-methylcyclopropoxy)-6-(3-(methylsulfonyl)phenyl)pyrido[3,2-d]pyrimidin-2-amine | 552.1 |

TABLE III-continued

| Ex | Structure | Name | MS |
|---|---|---|---|
| 216 | 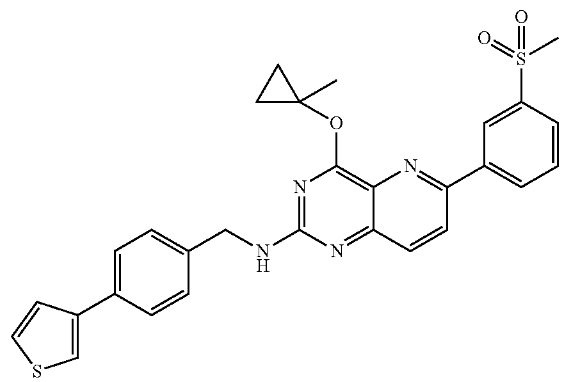 | N-(4-(thiophen-3-yl)benzyl)-4-(1-methylcyclopropoxy)-6-(3-(methylsulfonyl)phenyl)pyrido[3,2-d]pyrimidin-2-amine | 543 |
| 218 | 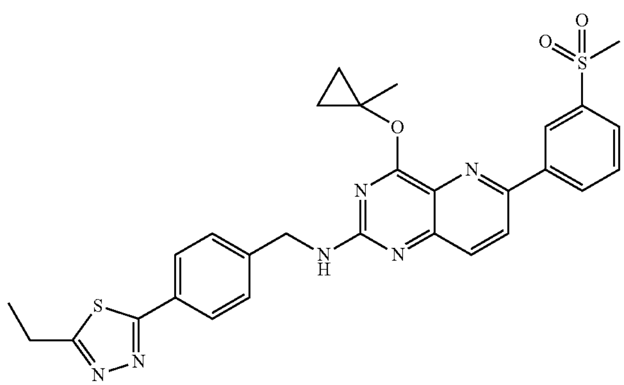 [SMILES: CCc1nnc(-c2ccc(CNc3nc(OC4(C)CC4)c4nc(-c5cccc(S(C)(=O)=O)c5)ccc4n3)cc2)s1] | N-(4-(5-ethyl-1,3,4-thiadiazol-2-yl)benzyl)-4-(1-methylcyclopropoxy)-6-(3-(methylsulfonyl)phenyl)pyrido[3,2-d]pyrimidin-2-amine | 573.1 |
| 219 | 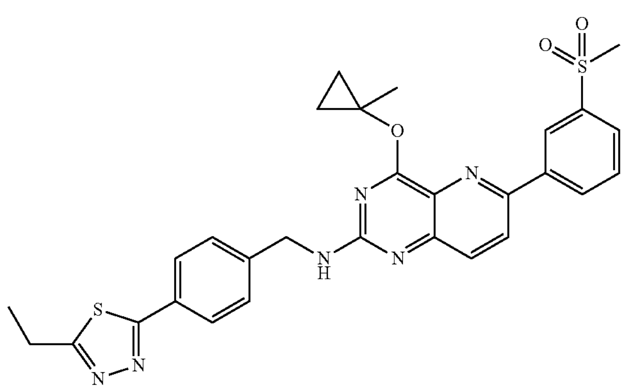 [SMILES: CCc1nnc(-c2ccc(CNc3nc(OC4(C)CC4)c4nc(-c5cccc(S(C)(=O)=O)c5)ccc4n3)cc2)s1] | N-(4-(1-methyl-1H-imidazol-5-yl)benzyl)-4-(1-methylcyclopropoxy)-6-(3-(methylsulfonyl)phenyl)pyrido[3,2-d]pyrimidin-2-amine | 541.1 |
| 220 | 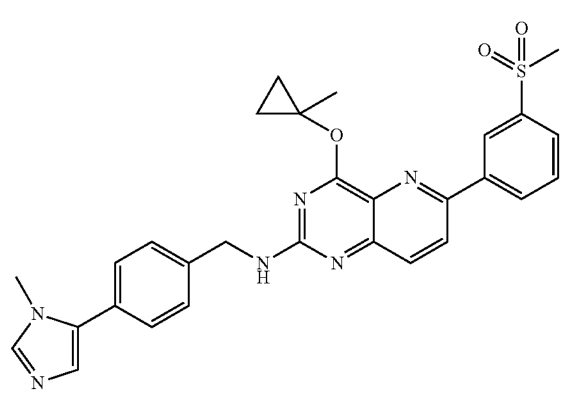 [SMILES: Cn1cncc1-c1ccc(CNc2nc(OC3(C)CC3)c3nc(-c4cccc(S(C)(=O)=O)c4)ccc3n2)cc1] | N-(4-(1-methyl-1H-imidazol-4-yl)benzyl)-4-(1-methylcyclopropoxy)-6-(3-(methylsulfonyl)phenyl)pyrido[3,2-d]pyrimidin-2-amine | 541.1 |

TABLE III-continued

| Ex | Structure | Name | MS |
|---|---|---|---|
| 221 | 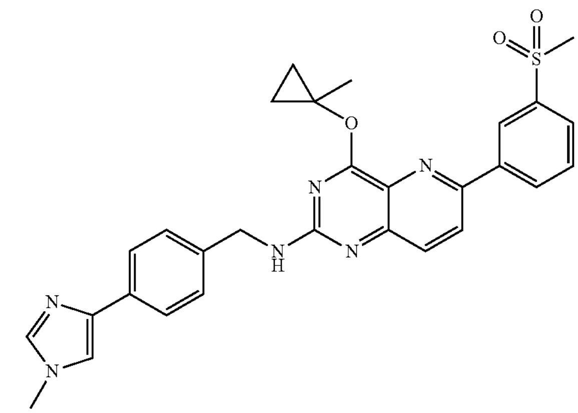 [SMILES: Cn1cnc(-c2ccc(CNc3nc(OC4(C)CC4)c4nc(-c5cccc(S(C)(=O)=O)c5)ccc4n3)cc2)c1] | N-(4-(furan-3-yl)benzyl)-4-(1-methylcyclopropoxy)-6-(3-(methylsulfonyl)phenyl)pyrido[3,2-d]pyrimidin-2-amine | 527.2 |
| 222 | 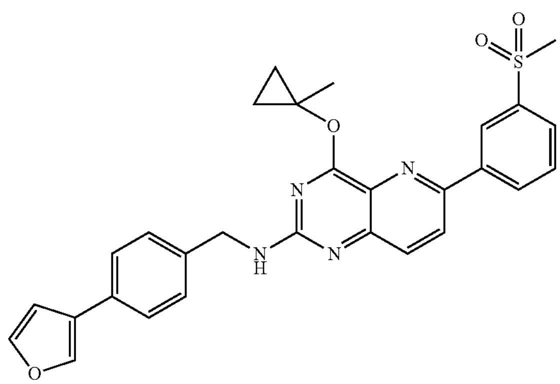 [SMILES: CC1(Oc2nc(NCc3ccc(-c4ccoc4)cc3)nc3ccc(-c4cccc(S(C)(=O)=O)c4)nc23)CC1] | N-(4-(6-methylpyridin-2-yl)benzyl)-4-(1-methylcyclopropoxy)-6-(3-(methylsulfonyl)phenyl)pyrido[3,2-d]pyrimidin-2-amine | 552.3 |
| 223 | 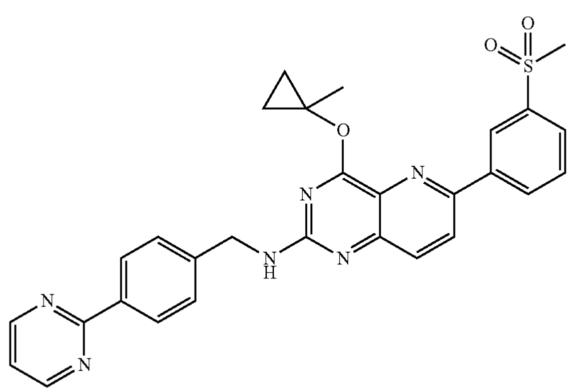 [SMILES: CC1(Oc2nc(NCc3ccc(-c4ncccn4)cc3)nc3ccc(-c4cccc(S(C)(=O)=O)c4)nc23)CC1] | N-(4-(pyrimidin-2-yl)benzyl)-4-(1-methylcyclopropoxy)-6-(3-(methylsulfonyl)phenyl)pyrido[3,2-d]pyrimidin-2-amine | 539.5 |
| 224 | 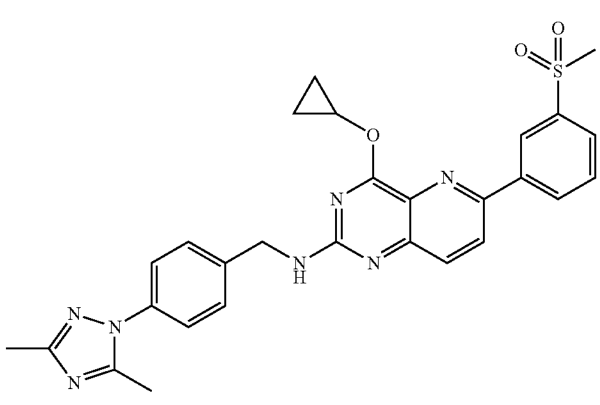 | N-(4-(3,5-dimethyl-1H-1,2,4-triazol-1-yl)benzyl)-4-cyclopropoxy-6-(3-(methylsulfonyl)phenyl)pyrido[3,2-d]pyrimidin-2-amine | 542.2 |

TABLE III-continued

| Ex | Structure | Name | MS |
|---|---|---|---|
| 225 | 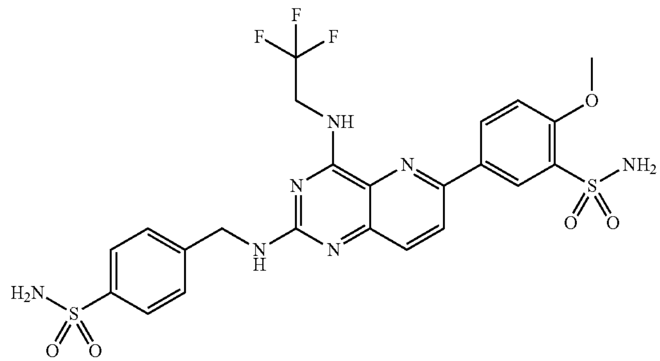 [SMILES: COc1ccc(-c2ccc3nc(NCc4ccc(S(N)(=O)=O)cc4)nc(NCC(F)(F)F)c3n2)cc1S(N)(=O)=O] | 4-((6-(4-methoxy-3-(aminosulfonyl)phenyl)-4-(2,2,2-trifluoroethylamino)pyrido[3,2-d]pyrimidin-2-ylamino)methyl)benzenesulfonamide | 598.16 |
| 226 | 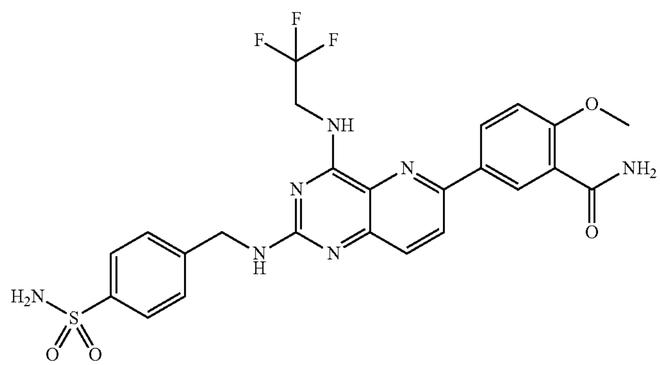 [SMILES: COc1ccc(-c2ccc3nc(NCc4ccc(S(N)(=O)=O)cc4)nc(NCC(F)(F)F)c3n2)cc1C(N)=O] | 4-((6-(3-(aminocarbonyl)-4-methoxyphenyl)-4-(2,2,2-trifluoroethylamino)pyrido[3,2-d]pyrimidin-2-ylamino)methyl)benzenesulfonamide | 562.21 |
| 227 | 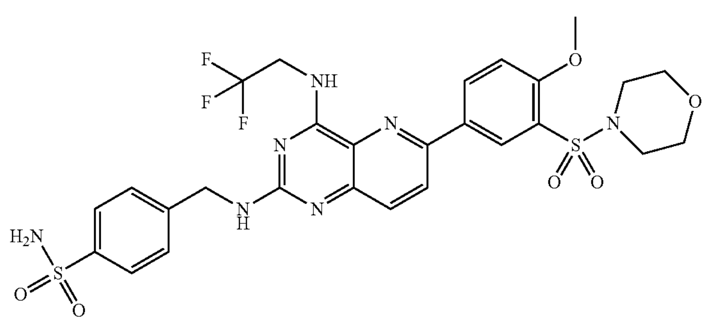 [SMILES: COc1ccc(-c2ccc3nc(NCc4ccc(S(N)(=O)=O)cc4)nc(NCC(F)(F)F)c3n2)cc1S(=O)(=O)N1CCOCC1] | 4-((6-(4-methoxy-3-(morpholinosulfonyl)phenyl)-4-(2,2,2-trifluoroethylamino)pyrido[3,2-d]pyrimidin-2-ylamino)methyl)benzenesulfonamide | 668.2 |
| 228 | 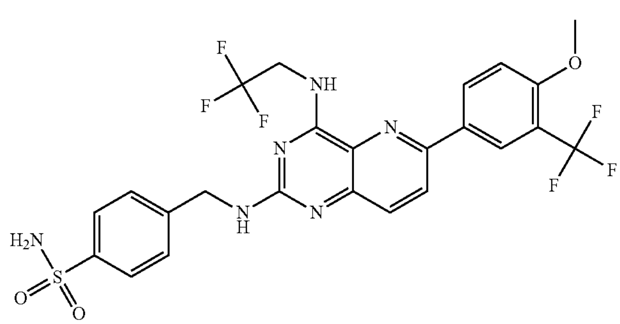 [SMILES: COc1ccc(-c2ccc3nc(NCc4ccc(S(N)(=O)=O)cc4)nc(NCC(F)(F)F)c3n2)cc1C(F)(F)F] | 4-((6-(4-methoxy-3-(trifluoromethyl)phenyl)-4-(2,2,2-trifluoroethylamino)pyrido[3,2-d]pyrimidin-2-ylamino)methyl)benzenesulfonamide | 587.2 |

TABLE III-continued

| Ex | Structure | Name | MS |
|---|---|---|---|
| 229 | 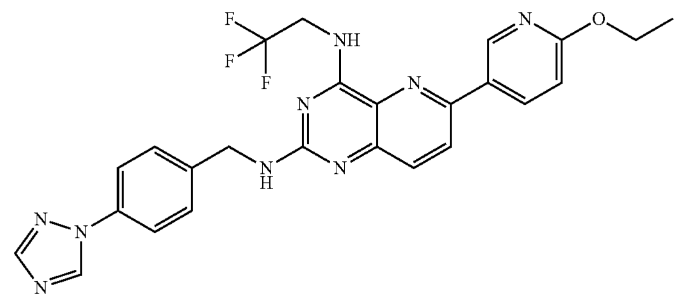 [SMILES: CCOc1ccc(-c2ccc3nc(NCc4ccc(-n5cncn5)cc4)nc(NCC(F)(F)F)c3n2)cn1] | N²-(4-(1H-1,2,4-triazol-1-yl)benzyl)-6-(6-ethoxypyridin-3-yl)-N⁴-(2,2,2-trifluoroethyl)pyrido[3,2-d]pyrimidine-2,4-diamine | 522.2 |
| 230 | 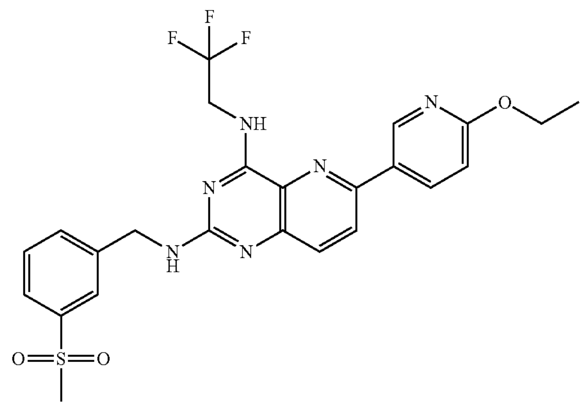 [SMILES: CCOc1ccc(-c2ccc3nc(NCc4cccc(S(C)(=O)=O)c4)nc(NCC(F)(F)F)c3n2)cn1] | N²-(3-(methylsulfonyl)benzyl)-6-(6-ethoxypyridin-3-yl)-N⁴-(2,2,2-trifluoroethyl)pyrido[3,2-d]pyrimidine-2,4-diamine | 533.3 |
| 231 | 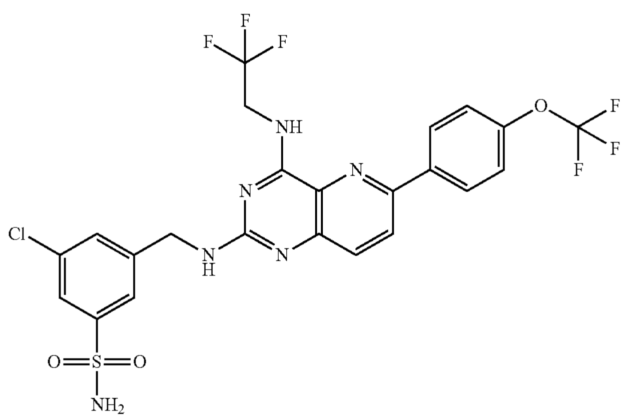 [SMILES: NS(=O)(=O)c1cc(Cl)cc(CNc2nc(NCC(F)(F)F)c3nc(-c4ccc(OC(F)(F)F)cc4)ccc3n2)c1] | 3-chloro-5-((4-(2,2,2-trifluoroethylamino)-6-(4-(trifluoromethoxy)phenyl)pyrido[3,2-d]pyrimidin-2-ylamino)methyl)benzenesulfonamide | 607.3 |
| 232 | 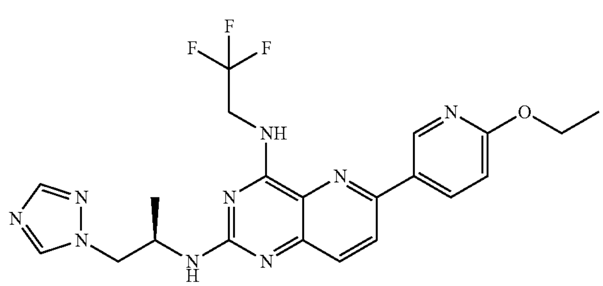 [SMILES: CCOc1ccc(-c2ccc3nc(N[C@H](C)Cn4cncn4)nc(NCC(F)(F)F)c3n2)cn1] | N²-((R)-1-(1H-1,2,4-triazol-1-yl)propan-2-yl)-6-(6-ethoxypyridin-3-yl)-N⁴-(2,2,2-trifluoroethyl)pyrido[3,2-d]pyrimidine-2,4-diamine | 474.2 |

| Ex | Structure | Name | MS |
|---|---|---|---|
| 233 | 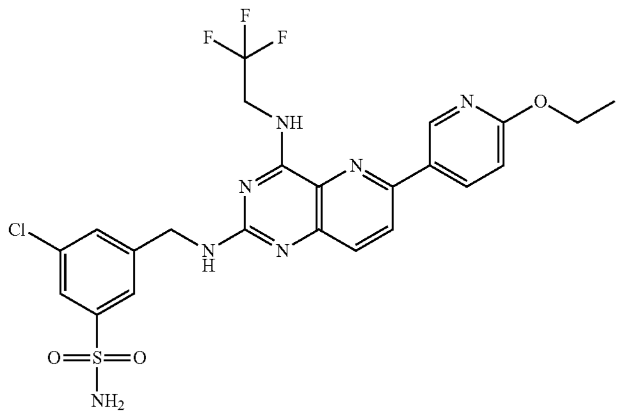 [SMILES: CCOc1ccc(-c2ccc3nc(NCc4cc(Cl)cc(S(N)(=O)=O)c4)nc(NCC(F)(F)F)c3n2)cn1] | 3-chloro-5-((6-(6-ethoxypyridin-3-yl)-4-(2,2,2-trifluoroethylamino)pyrido[3,2-d]pyrimidin-2-ylamino)methyl)benzenesulfonamide | 568.3 |
| 234 | 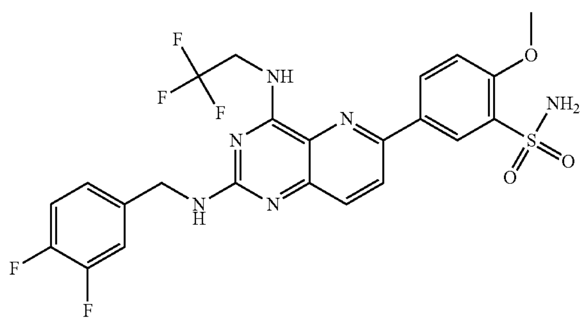 [SMILES: COc1ccc(-c2ccc3nc(NCc4ccc(F)c(F)c4)nc(NCC(F)(F)F)c3n2)cc1S(N)(=O)=O] | 5-(2-(3,4-difluorobenzylamino)-4-(2,2,2-trifluoroethylamino)pyrido[3,2-d]pyrimidin-6-yl)-2-methoxybenzenesulfonamide | 551.2 |
| 235 | 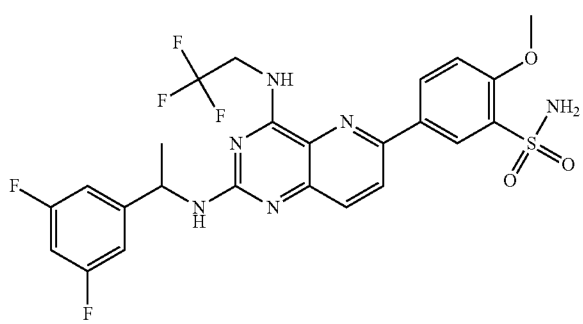 [SMILES: COc1ccc(-c2ccc3nc(NC(C)c4cc(F)cc(F)c4)nc(NCC(F)(F)F)c3n2)cc1S(N)(=O)=O] | 5-(2-(1-(3,5-difluorophenyl)ethylamino)-4-(2,2,2-trifluoroethylamino)pyrido[3,2-d]pyrimidin-6-yl)-2-methoxybenzenesulfonamide | 569.2 |
| 236 | 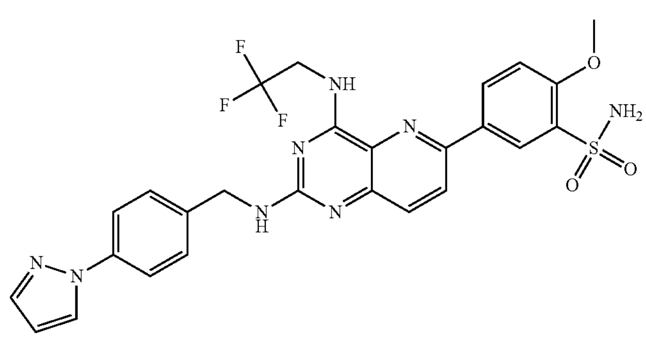 [SMILES: COc1ccc(-c2ccc3nc(NCc4ccc(-n5cccn5)cc4)nc(NCC(F)(F)F)c3n2)cc1S(N)(=O)=O] | 5-(2-(4-(1H-pyrazol-1-yl)benzylamino)-4-(2,2,2-trifluoroethylamino)pyrido[3,2-d]pyrimidin-6-yl)-2-methoxybenzenesulfonamide | 585.3 |

TABLE III-continued

| Ex | Structure | Name | MS |
|---|---|---|---|
| 237 | 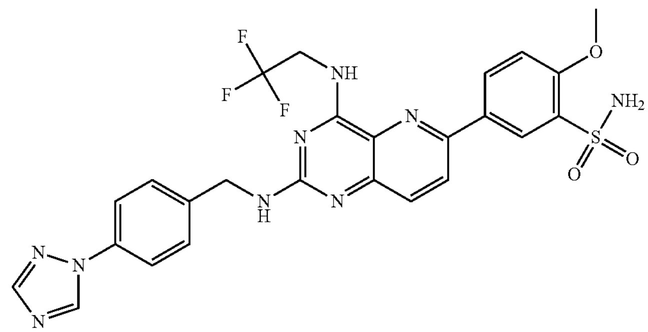 [SMILES: COc1ccc(-c2ccc3nc(NCc4ccc(-n5cncn5)cc4)nc(NCC(F)(F)F)c3n2)cc1S(N)(=O)=O] | 5-(2-(4-(1H-1,2,4-triazol-1-yl)benzylamino)-4-(2,2,2-trifluoroethylamino)pyrido[3,2-d]pyrimidin-6-yl)-2-methoxybenzenesulfonamide | 600.3 |
| 238 | 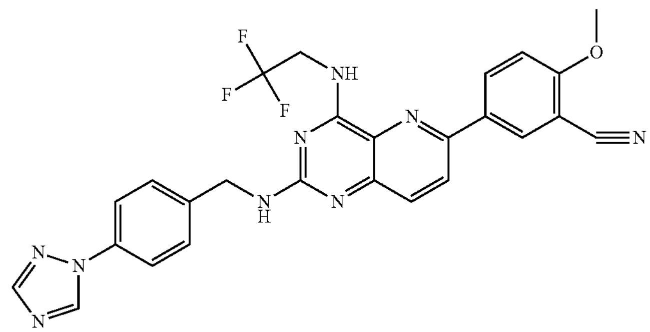 [SMILES: COc1ccc(-c2ccc3nc(NCc4ccc(-n5cncn5)cc4)nc(NCC(F)(F)F)c3n2)cc1C#N] | 5-(2-(4-(1H-1,2,4-triazol-1-yl)benzylamino)-4-(2,2,2-trifluoroethylamino)pyrido[3,2-d]pyrimidin-6-yl)-2-methoxybenzonitrile | 532.3 |
| 239 | 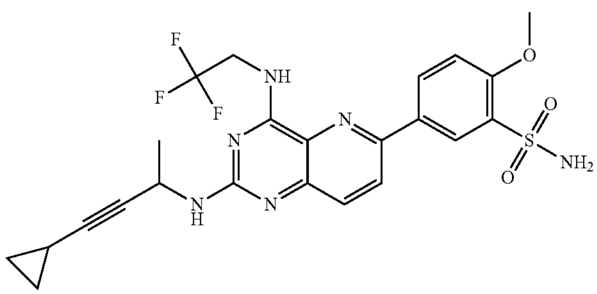 [SMILES: COc1ccc(-c2ccc3nc(NC(C)C#CC4CC4)nc(NCC(F)(F)F)c3n2)cc1S(N)(=O)=O] | 5-(2-(4-cyclopropylbut-3-yn-2-ylamino)-4-(2,2,2-trifluoroethylamino)pyrido[3,2-d]pyrimidin-6-yl)-2-methoxybenzenesulfonamide | 491.2 |
| 240 | 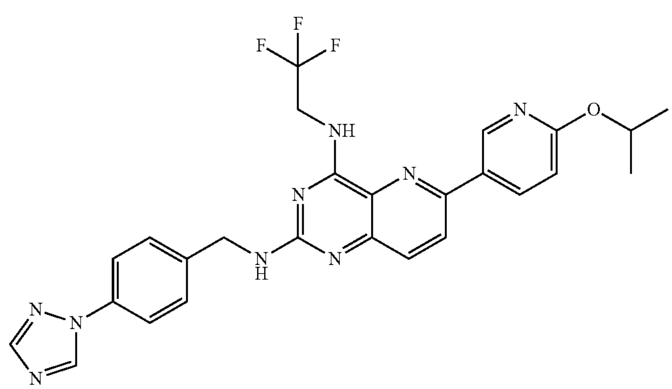 [SMILES: CC(C)Oc1ccc(-c2ccc3nc(NCc4ccc(-n5cncn5)cc4)nc(NCC(F)(F)F)c3n2)cn1] | $N^2$-(4-(1H-1,2,4-triazol-1-yl)benzyl)-6-(6-isopropoxy-pyridin-3-yl)-$N^4$-(2,2,2-trifluoroethyl)pyrido[3,2-d]pyrimidine-2,4-diamine | 536.4 |

TABLE III-continued

| Ex | Structure | Name | MS |
|---|---|---|---|
| 241 | 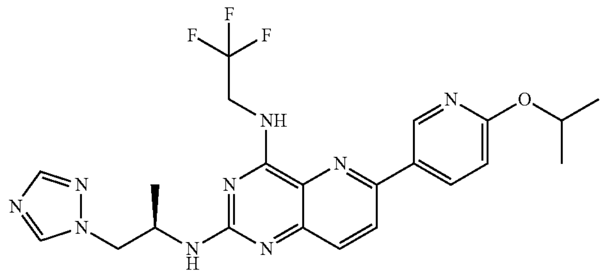 [SMILES: CC(C)Oc1ccc(-c2ccc3nc(N[C@H](C)Cn4cncn4)nc(NCC(F)(F)F)c3n2)cn1] | $N^2$-((R)-1-(1H-1,2,4-triazol-1-yl)propan-2-yl)-6-(6-isopropoxypyridin-3-yl)-$N^4$-(2,2,2-trifluoroethyl)pyrido[3,2-d]pyrimidine-2,4-diamine | 488.3 |
| 242 | 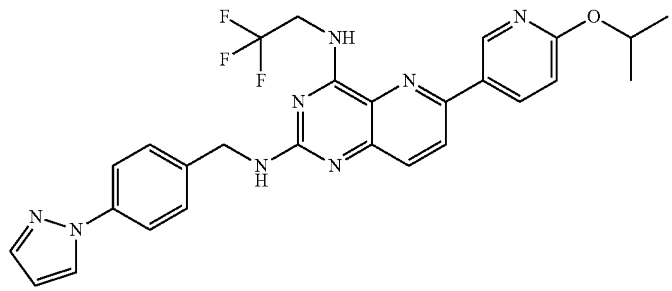 [SMILES: CC(C)Oc1ccc(-c2ccc3nc(NCc4ccc(-n5cccn5)cc4)nc(NCC(F)(F)F)c3n2)cn1] | $N^2$-(4-(1H-pyrazol-1-yl)benzyl)-6-(6-isopropoxypyridin-3-yl)-$N^4$-(2,2,2-trifluoroethyl)pyrido[3,2-d]pyrimidine-2,4-diamine | 535.2 |
| 243 | 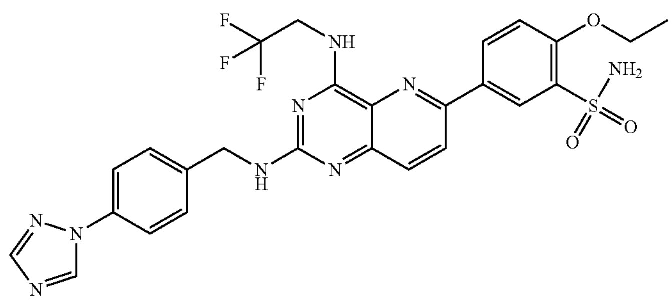 [SMILES: CCOc1ccc(-c2ccc3nc(NCc4ccc(-n5cncn5)cc4)nc(NCC(F)(F)F)c3n2)cc1S(N)(=O)=O] | 5-(2-(4-(1H-1,2,4-triazol-1-yl)benzylamino)-4-(2,2,2-trifluoroethylamino)pyrido[3,2-d]pyrimidin-6-yl)-2-ethoxybenzenesulfonamide | 598.3 |
| 244 | 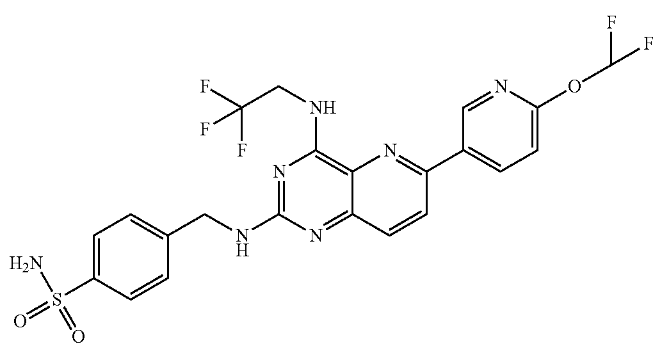 [SMILES: NS(=O)(=O)c1ccc(CNc2nc(NCC(F)(F)F)c3nc(-c4ccc(OC(F)F)nc4)ccc3n2)cc1] | 4-((6-(6-(difluoromethoxy)pyridin-3-yl)-4-(2,2,2-trifluoroethylamino)pyrido[3,2-d]pyrimidin-2-ylamino)methyl)benzenesulfonamide | 556.1 |
| 245 | 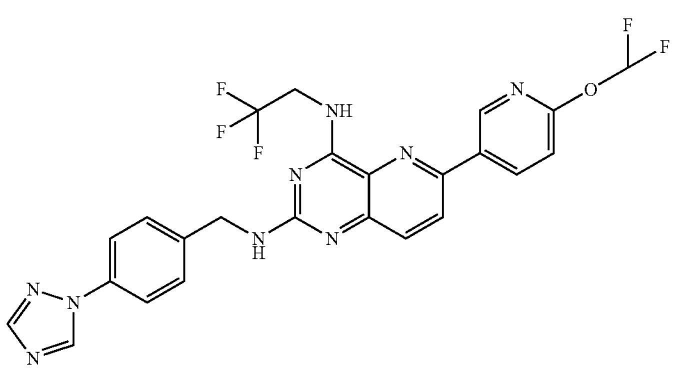 [SMILES: FC(F)Oc1ccc(-c2ccc3nc(NCc4ccc(-n5cncn5)cc4)nc(NCC(F)(F)F)c3n2)cn1] | $N^2$-(4-(1H-1,2,4-triazol-1-yl)benzyl)-6-(6-(difluoromethoxy)pyridin-3-yl)-$N^4$-(2,2,2-trifluoroethyl)pyrido[3,2-d]pyrimidine-2,4-diamine | 544.1 |

TABLE III-continued

| Ex | Structure | Name | MS |
|---|---|---|---|
| 246 | 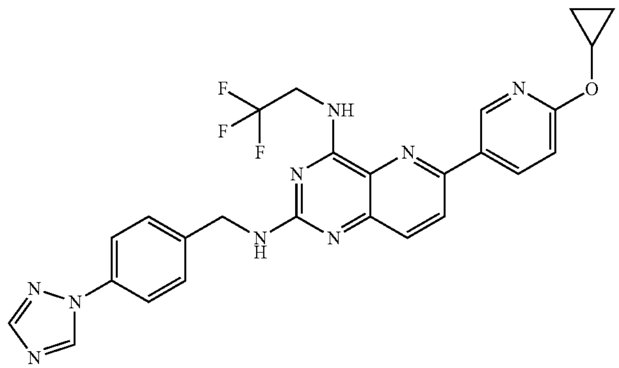 [SMILES: FC(F)(F)CNc1nc(NCc2ccc(-n3cncn3)cc2)nc2ccc(-c3ccc(OC4CC4)nc3)nc12] | N²-(4-(1H-1,2,4-triazol-1-yl)benzyl)-6-(6-cyclopropoxy-pyridin-3-yl)-N⁴-(2,2,2-trifluoroethyl)pyrido[3,2-d]pyrimidine-2,4-diamine | 534.3 |
| 247 | 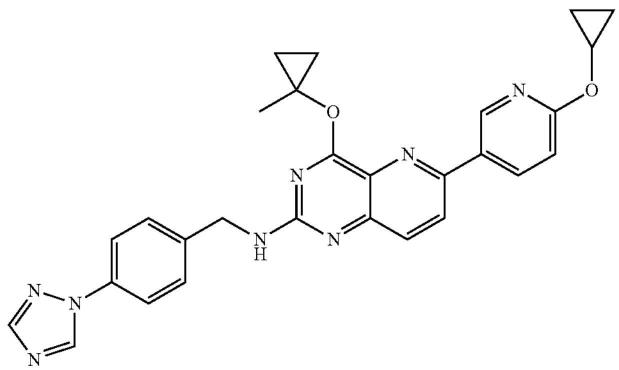 [SMILES: CC1(Oc2nc(NCc3ccc(-n4cncn4)cc3)nc3ccc(-c4ccc(OC5CC5)nc4)nc23)CC1] | N-(4-(1H-1,2,4-triazol-1-yl)benzyl)-6-(6-cyclopropoxy-pyridin-3-yl)-4-(1-methylcyclopropoxy)pyrido[3,2-d]pyrimidin-2-amine | 507.1 |
| 248 | 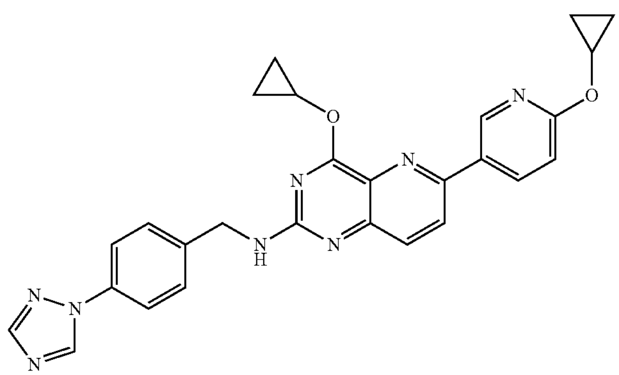 [SMILES: c1ncn(-c2ccc(CNc3nc(OC4CC4)c4nc(-c5ccc(OC6CC6)nc5)ccc4n3)cc2)n1] | N-(4-(1H-1,2,4-triazol-1-yl)benzyl)-4-cyclopropoxy-6-(6-cyclopropoxypyridin-3-yl)pyrido[3,2-d]pyrimidin-2-amine | 493.1 |
| 249 | 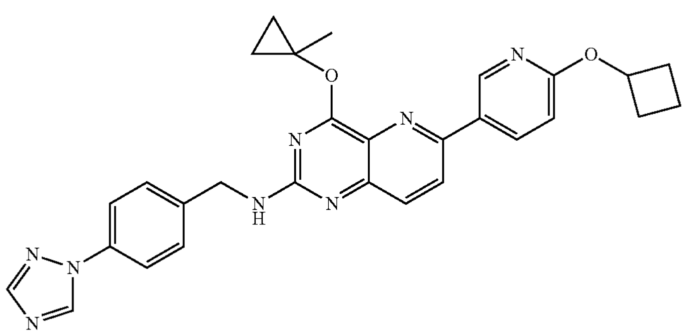 [SMILES: CC1(Oc2nc(NCc3ccc(-n4cncn4)cc3)nc3ccc(-c4ccc(OC5CCC5)nc4)nc23)CC1] | N-(4-(1H-1,2,4-triazol-1-yl)benzyl)-6-(6-cyclobutoxy-pyridin-3-yl)-4-(1-methylcyclopropoxy)pyrido[3,2-d]pyrimidin-2-amine | 521.1 |

TABLE III-continued

| Ex | Structure | Name | MS |
|---|---|---|---|
| 250 | 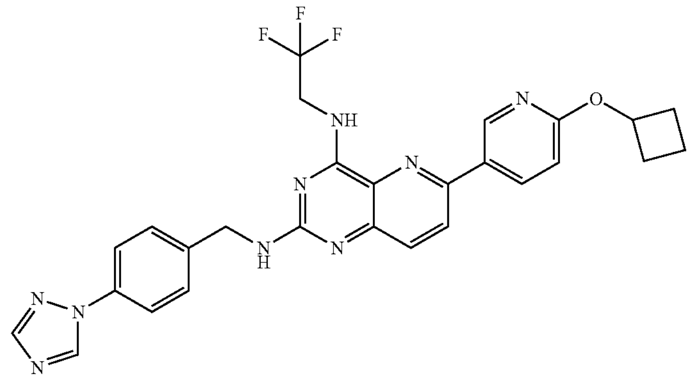 [SMILES: FC(F)(F)CNc1nc(NCc2ccc(-n3cncn3)cc2)nc2ccc(-c3ccc(OC4CCC4)nc3)nc12] | N²-(4-(1H-1,2,4-triazol-1-yl)benzyl)-6-(6-cyclobutoxy-pyridin-3-yl)-N⁴-(2,2,2-trifluoroethyl)pyrido[3,2-d]pyrimidine-2,4-diamine | 548.1 |
| 251 | 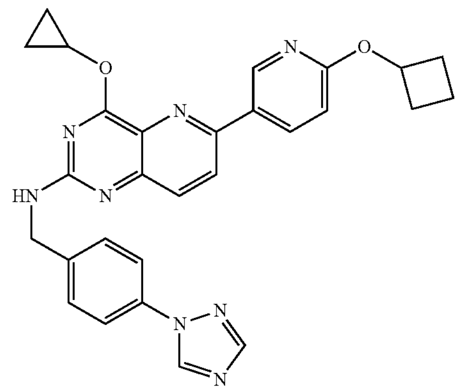 [SMILES: c1ncn(-c2ccc(CNc3nc(OC4CC4)c4nc(-c5ccc(OC6CCC6)nc5)ccc4n3)cc2)n1] | N-(4-(1H-1,2,4-triazol-1-yl)benzyl)-6-(6-cyclobutoxy-pyridin-3-yl)-4-cyclopropoxy-pyrido[3,2-d]pyrimidin-2-amine | 507.1 |
| 252 | 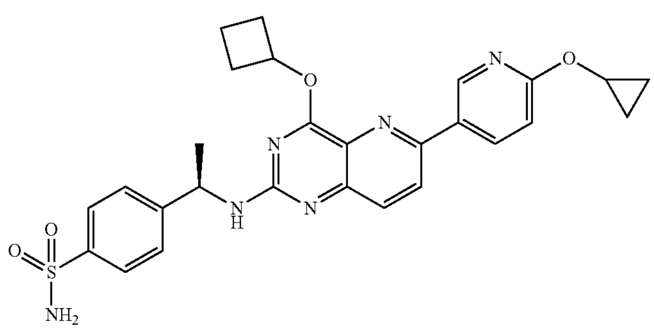 [SMILES: C[C@@H](Nc1nc(OC2CCC2)c2nc(-c3ccc(OC4CC4)nc3)ccc2n1)c1ccc(S(N)(=O)=O)cc1] | 4-((R)-1-(4-cyclobutoxy-6-(6-cyclopropoxypyridin-3-yl)pyrido[3,2-d]pyrimidin-2-ylamino)ethyl)benzene-sulfonamide | 533.2 |
| 253 | 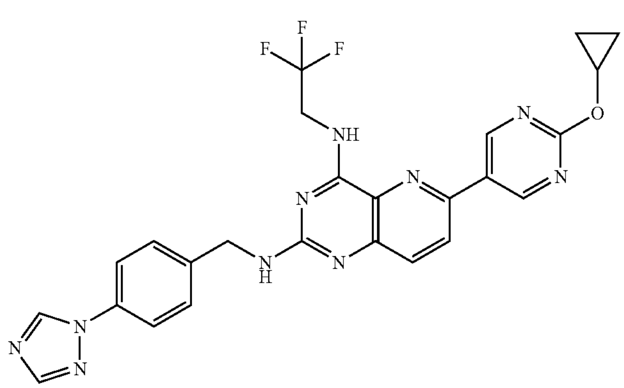 [SMILES: FC(F)(F)CNc1nc(NCc2ccc(-n3cncn3)cc2)nc2ccc(-c3cnc(OC4CC4)nc3)nc12] | N²-(4-(1H-1,2,4-triazol-1-yl)benzyl)-6-(2-cyclopropoxy-pyrimidin-5-yl)-N⁴-(2,2,2-trifluoroethyl)pyrido[3,2-d]pyrimidine-2,4-diamine | 535.1 |

TABLE III-continued

| Ex | Structure | Name | MS |
|---|---|---|---|
| 254 | 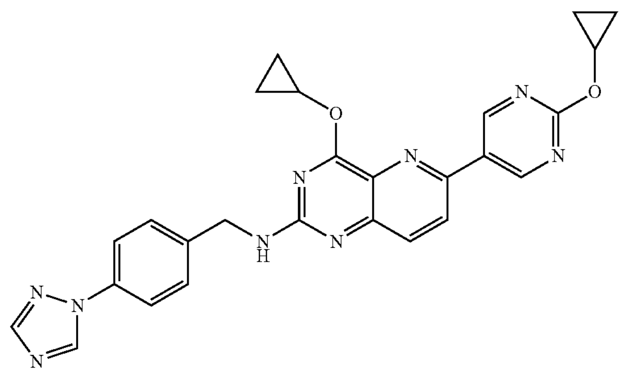 [SMILES: c1ncn(-c2ccc(CNc3nc(OC4CC4)c4nc(-c5cnc(OC6CC6)nc5)ccc4n3)cc2)n1] | N-(4-(1H-1,2,4-triazol-1-yl)benzyl)-4-cyclopropoxy-6-(2-cyclopropoxypyrimidin-5-yl)pyrido[3,2-d]pyrimidin-2-amine | 494.1 |
| 255 | 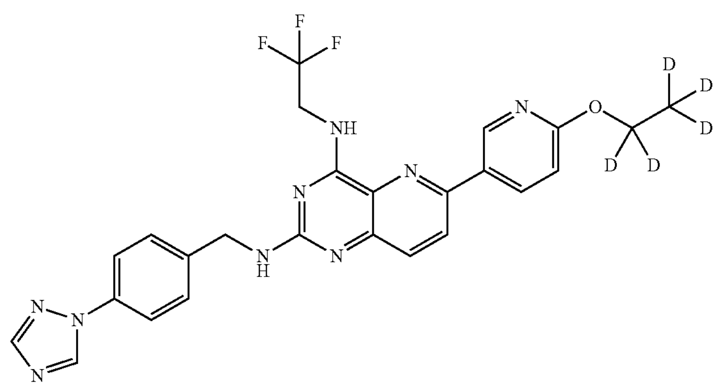 [SMILES: [2H]C([2H])([2H])C([2H])([2H])Oc1ccc(-c2ccc3nc(NCc4ccc(-n5cncn5)cc4)nc(NCC(F)(F)F)c3n2)cn1] | $N^2$-((R)-1-(4-(1H-1,2,4-triazol-1-yl)phenyl)ethyl)-6-(6-pentadeuteroethoxypyridin-3-yl)-$N^4$-(2,2,2-trifluoroethyl)pyrido[3,2-d]pyrimidine-2,4-diamine | 541.1 |
| 256 | 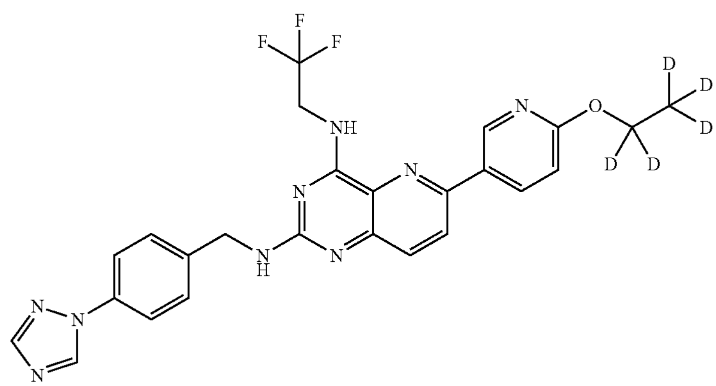 [SMILES: [2H]C([2H])([2H])C([2H])([2H])Oc1ccc(-c2ccc3nc(NCc4ccc(-n5cncn5)cc4)nc(NCC(F)(F)F)c3n2)cn1] | $N^2$-(4-(1H-1,2,4-triazol-1-yl)benzyl)-6-(6-pentadeuteroethoxypyridin-3-yl)-$N^4$-(2,2,2-trifluoroethyl)pyrido[3,2-d]pyrimidine-2,4-diamine | 527.1 |
| 257 | 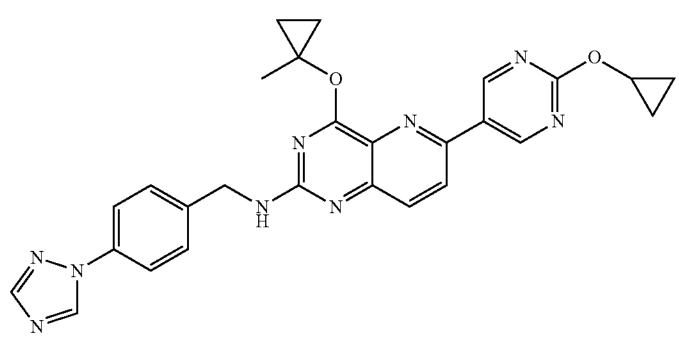 [SMILES: CC1(Oc2nc(NCc3ccc(-n4cncn4)cc3)nc3ccc(-c4cnc(OC5CC5)nc4)nc23)CC1] | N-(4-(1H-1,2,4-triazol-1-yl)benzyl)-6-(2-cyclopropoxypyrimidin-5-yl)-4-(1-methylcyclopropoxy)pyrido[3,2-d]pyrimidin-2-amine | 508.1 |

TABLE III-continued

| Ex | Structure | Name | MS |
|---|---|---|---|
| 258 | 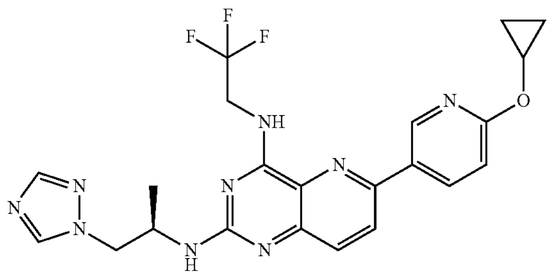 [SMILES: C[C@H](Cn1cncn1)Nc1nc(NCC(F)(F)F)c2nc(-c3ccc(OC4CC4)nc3)ccc2n1] | $N^2$-((R)-1-(1H-1,2,4-triazol-1-yl)propan-2-yl)-6-(6-cyclopropoxypyridin-3-yl)-$N^4$-(2,2,2-trifluoroethyl)pyrido[3,2-d]pyrimidine-2,4-diamine | 486.1 |
| 259 | 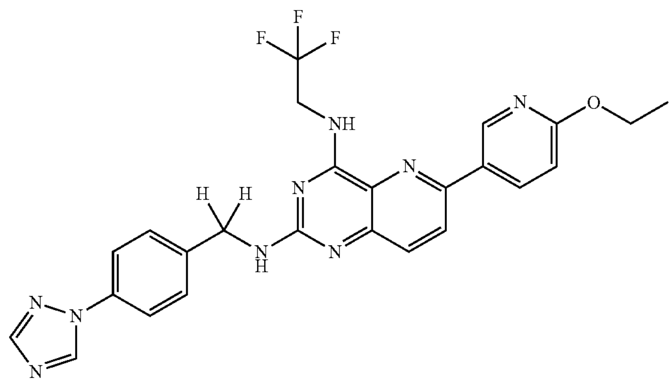 [SMILES: CCOc1ccc(-c2ccc3nc(NCc4ccc(-n5cncn5)cc4)nc(NCC(F)(F)F)c3n2)cn1] | $N^2$-(4-(1H-1,2,4-triazol-1-yl)benzyl)-6-(6-ethoxypyridin-3-yl)-$N^4$-(2,2,2-trifluoroethyl)pyrido[3,2-d]pyrimidine-2,4-diamine | 524.1 |
| 260 | 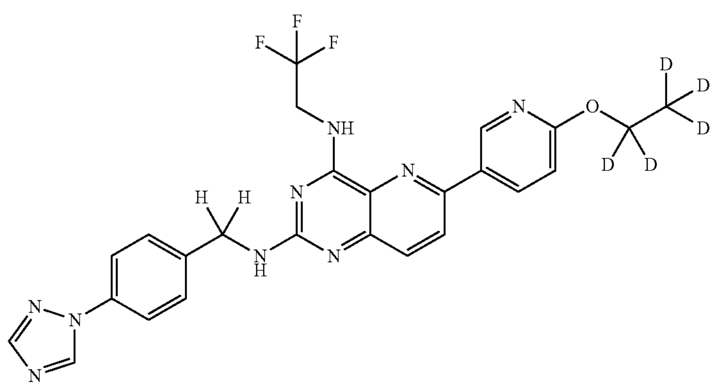 [SMILES: [2H]C([2H])([2H])C([2H])([2H])Oc1ccc(-c2ccc3nc(NCc4ccc(-n5cncn5)cc4)nc(NCC(F)(F)F)c3n2)cn1] | $N^2$-(4-(1H-1,2,3-triazol-1-yl)benzyl)-6-(6-pentadeutero-ethoxypyridin-3-yl)-$N^4$-(2,2,2-trifluoroethyl)pyrido[3,2-d]pyrimidine-2,4-diamine | 529.2 |
| 261 | 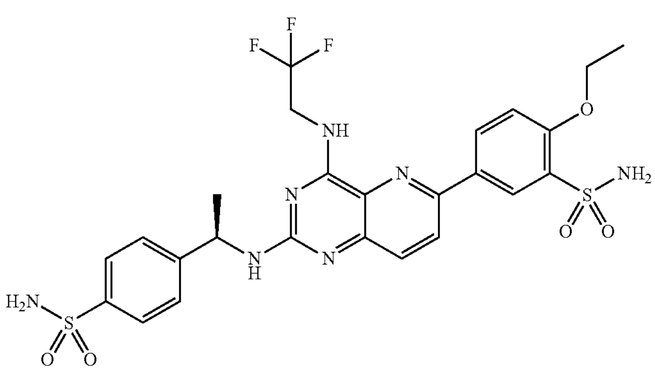 [SMILES: CCOc1ccc(-c2ccc3nc(N[C@H](C)c4ccc(S(N)(=O)=O)cc4)nc(NCC(F)(F)F)c3n2)cc1S(N)(=O)=O] | 4-((R)-1-(6-(4-ethoxy-3-(aminosulfonyl)phenyl)-4-(2,2,2-trifluoroethylamino)pyrido[3,2-d]pyrimidin-2-ylamino)ethyl)benzenesulfonamide | 626 |

TABLE III-continued

| Ex | Structure | Name | MS |
|---|---|---|---|
| 262 | 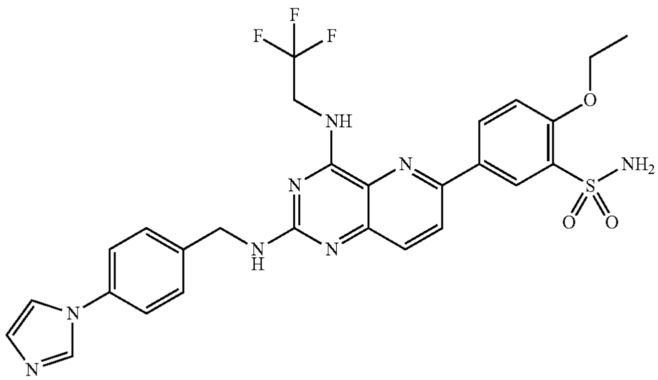 [SMILES: CCOc1ccc(-c2ccc3nc(NCc4ccc(-n5ccnc5)cc4)nc(NCC(F)(F)F)c3n2)cc1S(N)(=O)=O] | 5-(2-(4-(1H-imidazol-1-yl)benzylamino)-4-(2,2,2-trifluoroethylamino)pyrido[3,2-d]pyrimidin-6-yl)-2-ethoxybenzenesulfonamide | 599.2 |
| 263 | 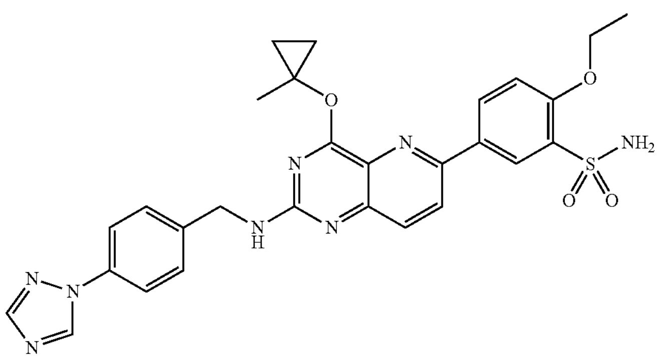 [SMILES: CCOc1ccc(-c2ccc3nc(NCc4ccc(-n5cncn5)cc4)nc(OC4(C)CC4)c3n2)cc1S(N)(=O)=O] | 5-(2-(4-(1H-1,2,4-triazol-1-yl)benzylamino)-4-(1-methylcyclopropoxy)pyrido[3,2-d]pyrimidin-6-yl)-2-ethoxybenzenesulfonamide | 573.2 |
| 264 | 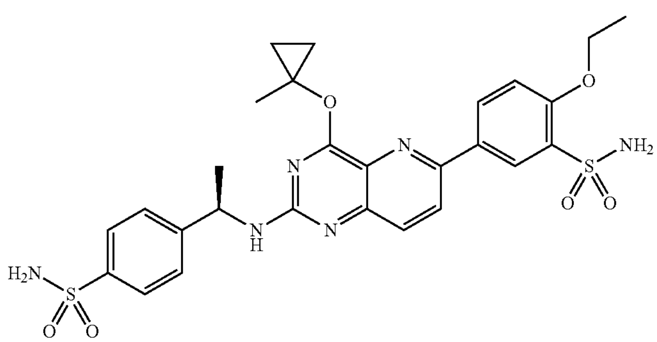 [SMILES: CCOc1ccc(-c2ccc3nc(N[C@H](C)c4ccc(S(N)(=O)=O)cc4)nc(OC4(C)CC4)c3n2)cc1S(N)(=O)=O] | 4-((R)-1-(6-(4-ethoxy-3-(aminosulfonyl)phenyl)-4-(1-methylcyclopropoxy)pyrido[3,2-d]pyrimidin-2-ylamino)ethyl)benzenesulfonamide | 599.2 |
| 265 | 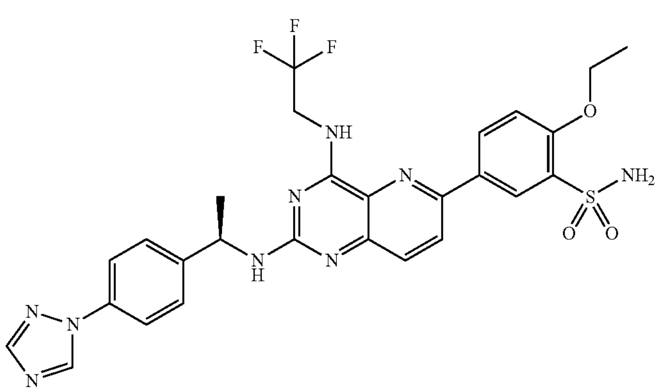 [SMILES: CCOc1ccc(-c2ccc3nc(N[C@H](C)c4ccc(-n5cncn5)cc4)nc(NCC(F)(F)F)c3n2)cc1S(N)(=O)=O] | 5-(2-((R)-1-(4-(1H-1,2,4-triazol-1-yl)phenyl)ethylamino)-4-(2,2,2-trifluoroethylamino)pyrido[3,2-d]pyrimidin-6-yl)-2-ethoxybenzenesulfonamide | 614.2 |

TABLE III-continued

| Ex | Structure | Name | MS |
|---|---|---|---|
| 266 | 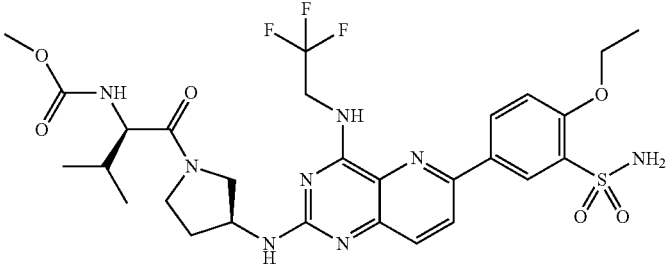 [SMILES: CCOc1ccc(-c2ccc3nc(N[C@H]4CCN(C(=O)[C@H](NC(=O)OC)C(C)C)C4)nc(NCC(F)(F)F)c3n2)cc1S(N)(=O)=O] | methyl (R)-1-((S)-3-(6-(4-ethoxy-3-(aminosulfonyl)phenyl)-4-(2,2,2-trifluoroethylamino)pyrido[3,2-d]pyrimidin-2-ylamino)pyrrolidin-1-yl)-3-methyl-1-oxobutan-2-ylcarbamate | 669.3 |
| 267 | 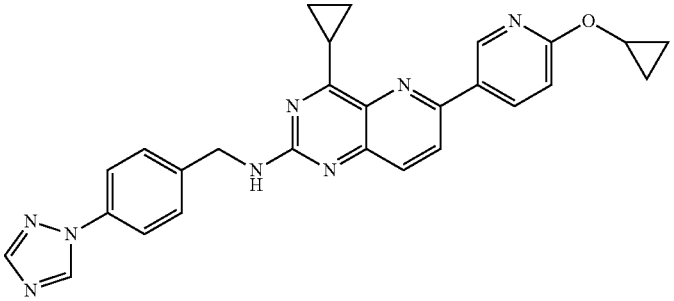 [SMILES: c1ncn(-c2ccc(CNc3nc(C4CC4)c4nc(-c5ccc(OC6CC6)nc5)ccc4n3)cc2)n1] | N-(4-(1H-1,2,4-triazol-1-yl)benzyl)-6-(6-cyclopropoxy-pyridin-3-yl)-4-cyclopropyl-pyrido[3,2-d]pyrimidin-2-amine | 477.2 |
| 268 | 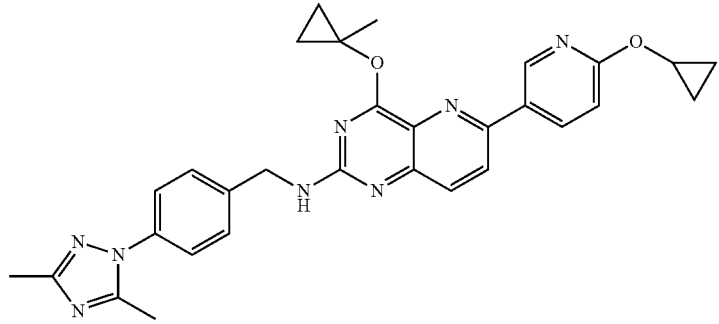 [SMILES: Cc1nc(C)n(-c2ccc(CNc3nc(OC4(C)CC4)c4nc(-c5ccc(OC6CC6)nc5)ccc4n3)cc2)n1] | N-(4-(3,5-dimethyl-1H-1,2,4-triazol-1-yl)benzyl)-6-(6-cyclopropoxypyridin-3-yl)-4-(1-methylcyclopropoxy)pyrido[3,2-d]pyrimidin-2-amine | 535.3 |
| 269 | 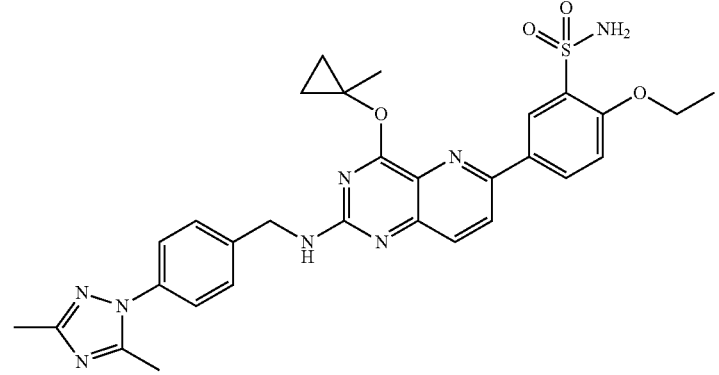 [SMILES: CCOc1ccc(-c2ccc3nc(NCc4ccc(-n5nc(C)nc5C)cc4)nc(OC4(C)CC4)c3n2)cc1S(N)(=O)=O] | 5-(2-(4-(3,5-dimethyl-1H-1,2,4-triazol-1-yl)benzylamino)-4-(1-methylcyclopropoxy)pyrido[3,2-d]pyrimidin-6-yl)-2-ethoxybenzenesulfonamide | 601.3 |
| 270 | 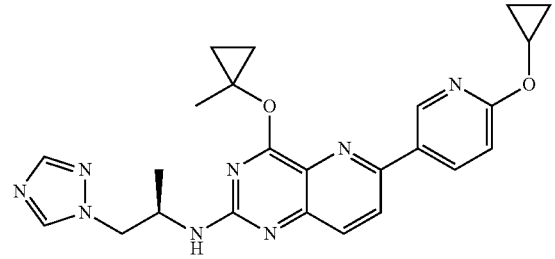 [SMILES: C[C@H](Cn1cncn1)Nc1nc(OC2(C)CC2)c2nc(-c3ccc(OC4CC4)nc3)ccc2n1] | N-((R)-1-(1H-1,2,4-triazol-1-yl)propan-2-yl)-6-(6-cyclopropoxy-pyridin-3-yl)-4-(1-methylcyclopropoxy)pyrido[3,2-d]pyrimidin-2-amine | 459.1 |

TABLE III-continued

| Ex | Structure | Name | MS |
|---|---|---|---|
| 271 | 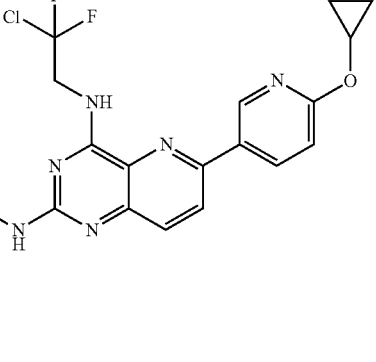 | N²-(4-(1H-1,2,4-triazol-1-yl)benzyl)-N⁴-(2-chloro-2,2-difluoroethyl)-6-(6-cyclo-propoxypyridin-3-yl)pyrido[3,2-d]pyrimidine-2,4-diamine | 550.1 |
| 272 | 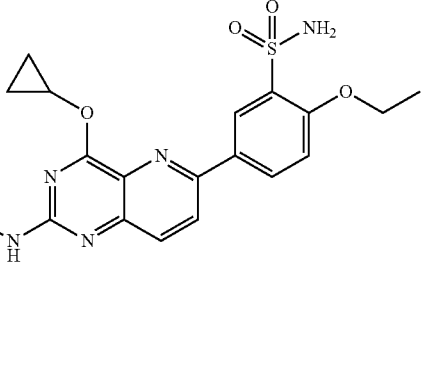 | 5-(2-(4-(3,5-dimethyl-1H-1,2,4-triazol-1-yl)benzylamino)-4-cyclopropoxypyrido[3,2-d]pyrimidin-6-yl)-2-ethoxy-benzenesulfonamide | 587.3 |
| 273 | 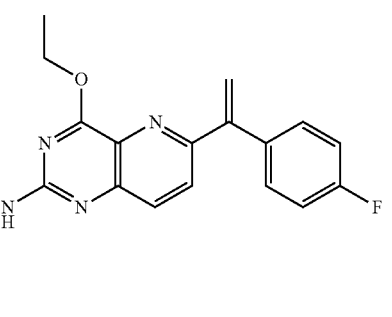 | 4-((4-ethoxy-6-(1-(4-fluoro-phenyl)vinyl)pyrido[3,2-d]pyrimidin-2-ylamino)methyl)benzenesulfonamide | 480.05 |
| 274 | 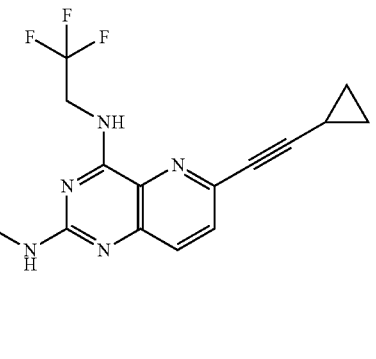 | (R)-N-tert-butyl-4-(1-(6-(2-cyclopropylethynyl)-4-(2,2,2-trifluoroethylamino)pyrido[3,2-d]pyrimidin-2-ylamino)ethyl)benzenesulfonamide | 547.3 |

TABLE III-continued

| Ex | Structure | Name | MS |
|---|---|---|---|
| 275 | 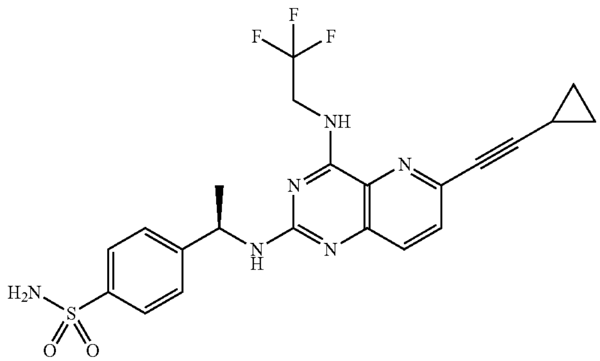 [SMILES: C[C@@H](Nc1nc(NCC(F)(F)F)c2nc(C#CC3CC3)ccc2n1)c1ccc(S(N)(=O)=O)cc1] | (R)-4-(1-(6-(2-cyclopropyl-ethynyl)-4-(2,2,2-trifluoro-ethylamino)pyrido[3,2-d]pyrimidin-2-ylamino)ethyl)benzenesulfonamide | 491.3 |
| 276 | 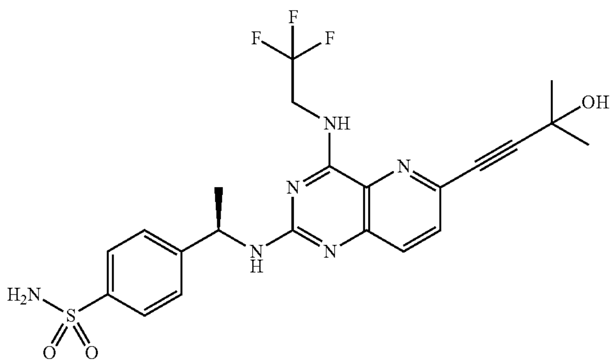 [SMILES: C[C@@H](Nc1nc(NCC(F)(F)F)c2nc(C#CC(C)(C)O)ccc2n1)c1ccc(S(N)(=O)=O)cc1] | (R)-4-(1-(6-(3-hydroxy-3-methylbut-1-ynyl)-4-(2,2,2-trifluoroethylamino)pyrido[3,2-d]pyrimidin-2-ylamino)ethyl)benzenesulfonamide | 509.2 |
| 277 | 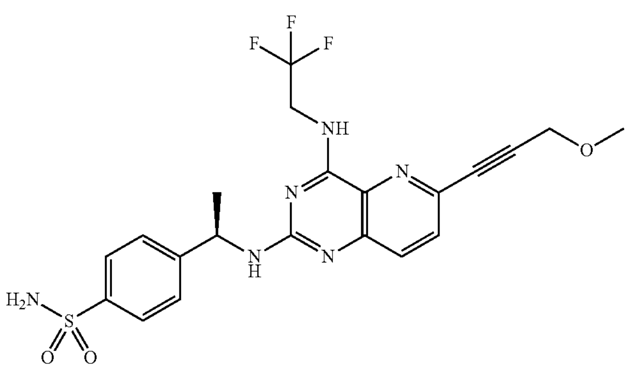 [SMILES: COCC#Cc1ccc2nc(N[C@H](C)c3ccc(S(N)(=O)=O)cc3)nc(NCC(F)(F)F)c2n1] | (R)-4-(1-(6-(3-methoxyprop-1-ynyl)-4-(2,2,2-trifluoroethyl-amino)pyrido[3,2-d]pyrimidin-2-ylamino)ethyl)benzene-sulfonamide | 495.2 |
| 278 | 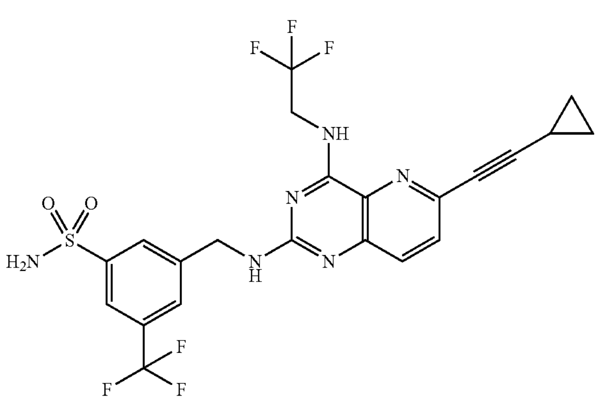 [SMILES: NS(=O)(=O)c1cc(CNc2nc(NCC(F)(F)F)c3nc(C#CC4CC4)ccc3n2)cc(C(F)(F)F)c1] | 3-((6-(2-cyclopropylethynyl)-4-(2,2,2-trifluoroethylamino)pyrido[3,2-d]pyrimidin-2-ylamino)methyl)-5-(trifluoro-methyl)benzenesulfonamide | 545.1 |

| Ex | Structure | Name | MS |
|---|---|---|---|
| 279 | 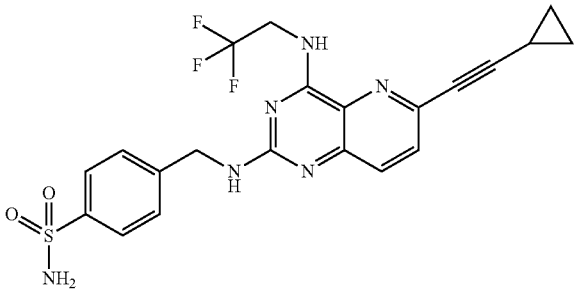 [SMILES: NS(=O)(=O)c1ccc(CNc2nc(NCC(F)(F)F)c3nc(C#CC4CC4)ccc3n2)cc1] | 4-((6-(2-cyclopropylethynyl)-4-(2,2,2-trifluoroethylamino)pyrido[3,2-d]pyrimidin-2-ylamino)methyl)benzenesulfonamide | 477.2 |
| 280 | 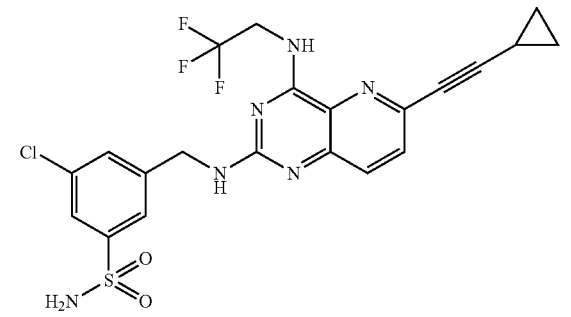 [SMILES: NS(=O)(=O)c1cc(Cl)cc(CNc2nc(NCC(F)(F)F)c3nc(C#CC4CC4)ccc3n2)c1] | 3-chloro-5-((6-(2-cyclopropylethynyl)-4-(2,2,2-trifluoroethylamino)pyrido[3,2-d]pyrimidin-2-ylamino)methyl)benzenesulfonamide | 511.2 |
| 281 | 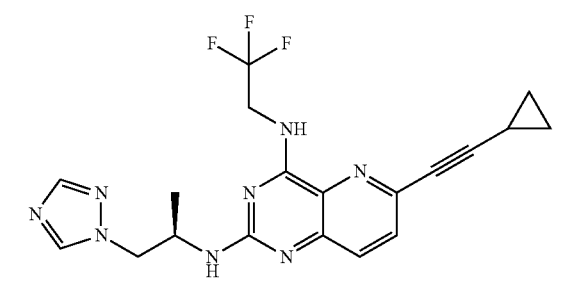 [SMILES: C[C@H](Cn1cncn1)Nc1nc(NCC(F)(F)F)c2nc(C#CC3CC3)ccc2n1] | (R)-$N^2$-(1-(1H-1,2,4-triazol-1-yl)propan-2-yl)-6-(2-cyclopropylethynyl)-$N^4$-(2,2,2-trifluoroethyl)pyrido[3,2-d]pyrimidine-2,4-diamine | 417.2 |
| 282 | 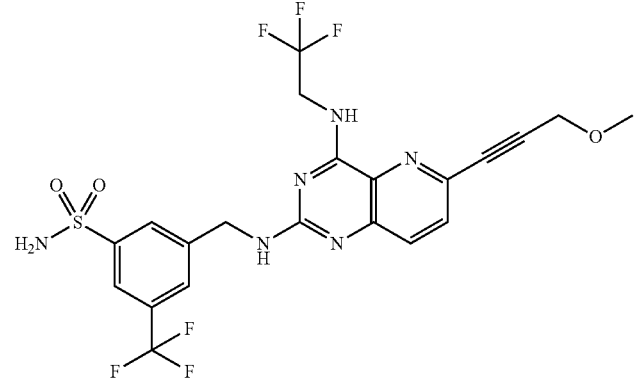 [SMILES: COCC#Cc1ccc2nc(NCc3cc(C(F)(F)F)cc(S(N)(=O)=O)c3)nc(NCC(F)(F)F)c2n1] | 3-((6-(3-methoxyprop-1-ynyl)-4-(2,2,2-trifluoroethylamino)pyrido[3,2-d]pyrimidin-2-ylamino)methyl)-5-(trifluoromethyl)benzenesulfonamide | 549.0 |

TABLE III-continued

| Ex | Structure | Name | MS |
|---|---|---|---|
| 283 | 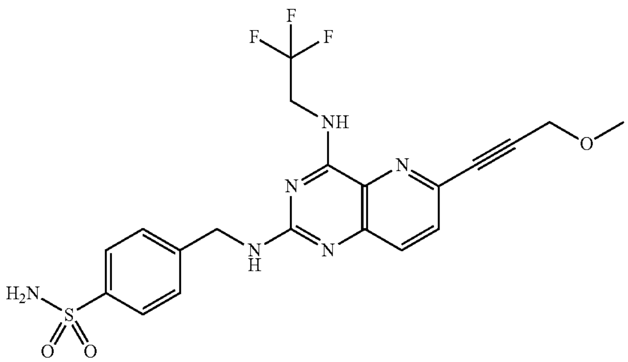 [SMILES: COCC#Cc1ccc2nc(NCc3ccc(S(N)(=O)=O)cc3)nc(NCC(F)(F)F)c2n1] | 4-((6-(3-methoxyprop-1-ynyl)-4-(2,2,2-trifluoroethylamino)pyrido[3,2-d]pyrimidin-2-ylamino)methyl)benzenesulfonamide | 480.9 |
| 284 | 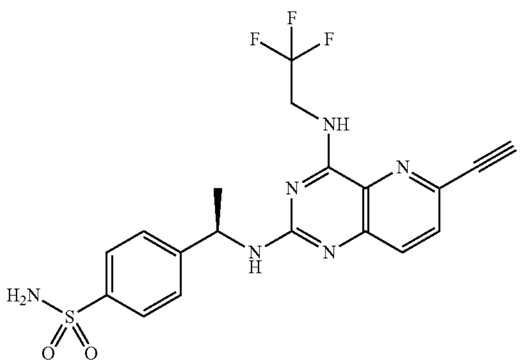 [SMILES: C#Cc1ccc2nc(N[C@H](C)c3ccc(S(N)(=O)=O)cc3)nc(NCC(F)(F)F)c2n1] | (R)-4-(1-(6-ethynyl-4-(2,2,2-trifluoroethylamino)pyrido[3,2-d]pyrimidin-2-ylamino)ethyl)benzenesulfonamide | 450.9 |
| 285 | 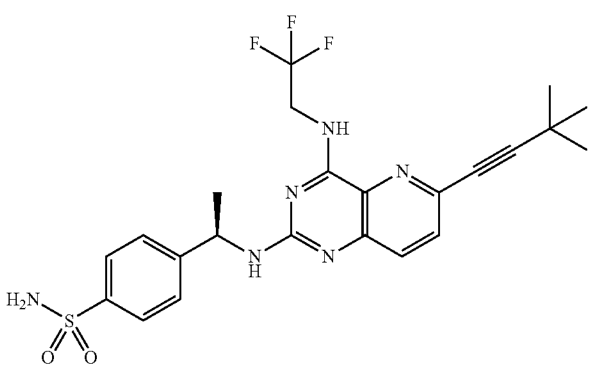 [SMILES: C[C@@H](Nc1nc(NCC(F)(F)F)c2nc(C#CC(C)(C)C)ccc2n1)c1ccc(S(N)(=O)=O)cc1] | (R)-4-(1-(6-(3,3-dimethylbut-1-ynyl)-4-(2,2,2-trifluoroethylamino)pyrido[3,2-d]pyrimidin-2-ylamino)ethyl)benzenesulfonamide | 507.1 |
| 286 | 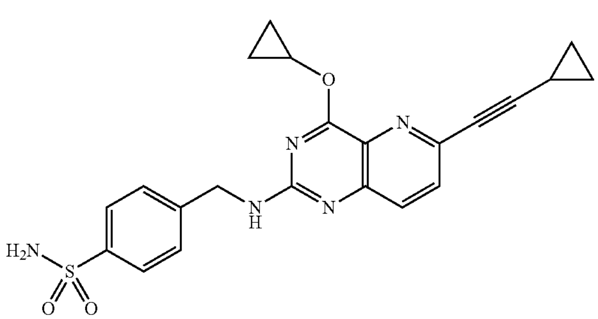 [SMILES: NS(=O)(=O)c1ccc(CNc2nc(OC3CC3)c3nc(C#CC4CC4)ccc3n2)cc1] | 4-((4-cyclopropoxy-6-(2-cyclopropylethynyl)pyrido[3,2-d]pyrimidin-2-ylamino)methyl)benzenesulfonamide | 436.0 |

TABLE III-continued

| Ex | Structure | Name | MS |
|----|-----------|------|-----|
| 287 | 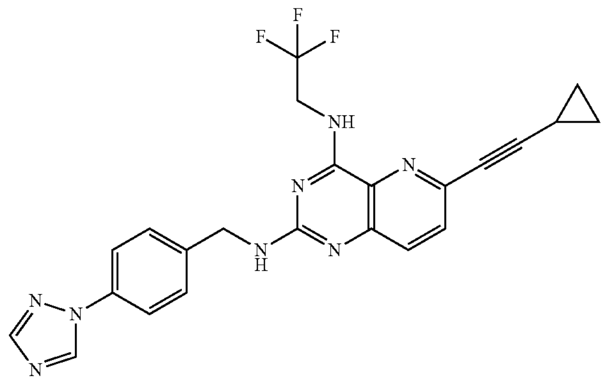 [SMILES: FC(F)(F)CNc1nc(NCc2ccc(-n3cncn3)cc2)nc2ccc(C#CC3CC3)nc12] | N²-(4-(1H-1,2,4-triazol-1-yl)benzyl)-6-(2-cyclopropyl-ethynyl)-N⁴-(2,2,2-trifluoroethyl)pyrido[3,2-d]pyrimidine-2,4-diamine | 464.9 |
| 288 | 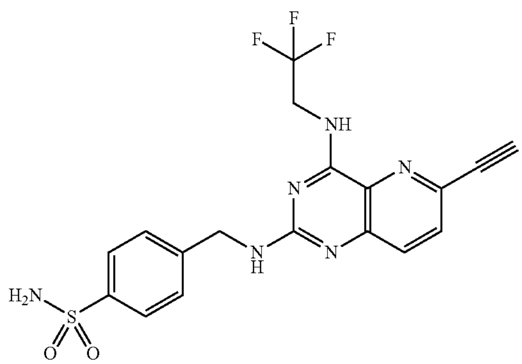 [SMILES: C#Cc1ccc2nc(NCc3ccc(S(N)(=O)=O)cc3)nc(NCC(F)(F)F)c2n1] | 4-((6-ethynyl-4-(2,2,2-trifluoroethylamino)pyrido[3,2-d]pyrimidin-2-ylamino)methyl)benzenesulfonamide | 436.9 |
| 289 | 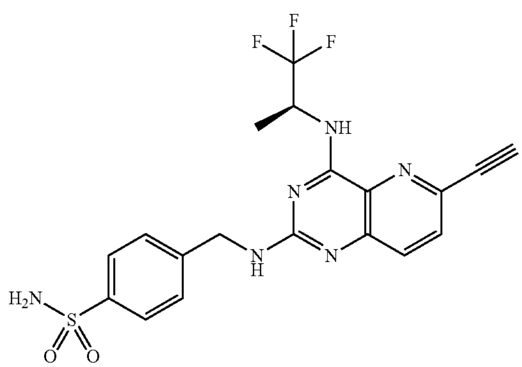 [SMILES: C#Cc1ccc2nc(NCc3ccc(S(N)(=O)=O)cc3)nc(N[C@@H](C)C(F)(F)F)c2n1] | (S)-4-((6-ethynyl-4-(1,1,1-trifluoropropan-2-ylamino)pyrido[3,2-d]pyrimidin-2-ylamino)methyl)benzenesulfonamide | 450.9 |
| 290 | 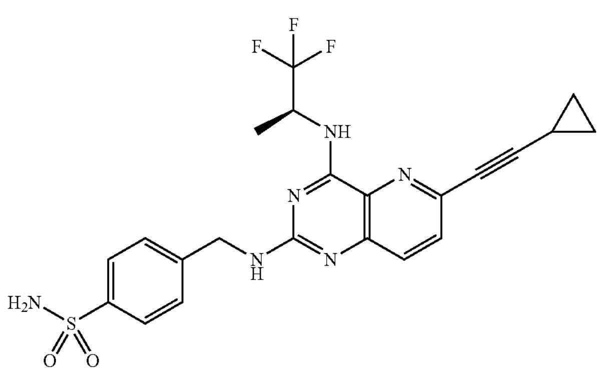 [SMILES: C[C@H](Nc1nc(NCc2ccc(S(N)(=O)=O)cc2)nc2ccc(C#CC3CC3)nc12)C(F)(F)F] | (S)-4-((6-(2-cyclopropyl-ethynyl)-4-(1,1,1-trifluoropropan-2-ylamino)pyrido[3,2-d]pyrimidin-2-ylamino)methyl)benzenesulfonamide | 491.0 |

TABLE III-continued

| Ex | Structure | Name | MS |
|---|---|---|---|
| 291 | 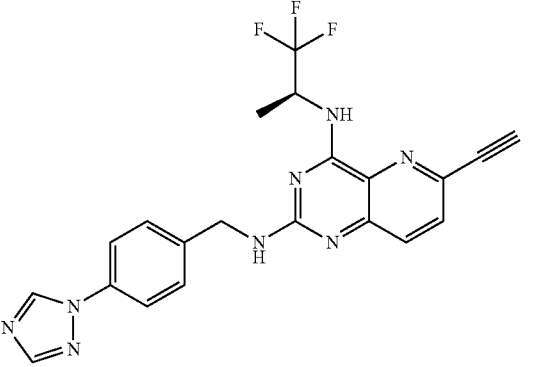 [SMILES: C#Cc1ccc2nc(NCc3ccc(-n4cncn4)cc3)nc(N[C@@H](C)C(F)(F)F)c2n1] | (S)-N²-(4-(1H-1,2,4-triazol-1-yl)benzyl)-6-ethynyl-N⁴-(1,1,1-trifluoropropan-2-yl)pyrido[3,2-d]pyrimidine-2,4-diamine | 439.0 |
| 292 | 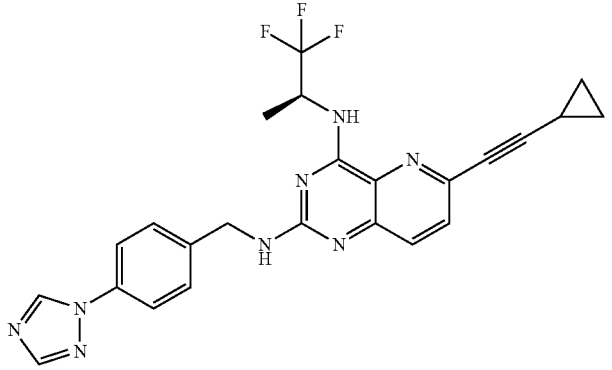 [SMILES: C[C@H](Nc1nc(NCc2ccc(-n3cncn3)cc2)nc2ccc(C#CC3CC3)nc12)C(F)(F)F] | (S)-N²-(4-(1H-1,2,4-triazol-1-yl)benzyl)-6-(2-cyclopropyl-ethynyl)-N⁴-(1,1,1-trifluoro-propan-2-yl)pyrido[3,2-d]pyrimidine-2,4-diamine | 479.1 |
| 293 | 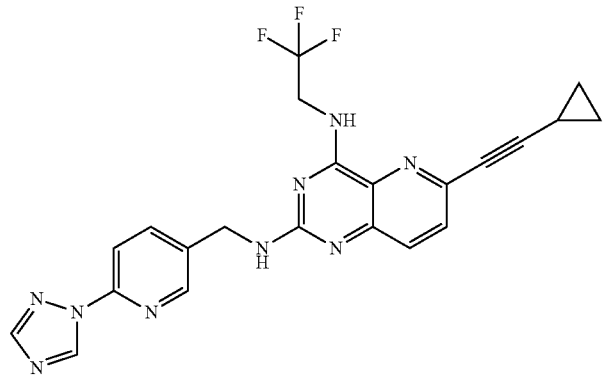 [SMILES: FC(F)(F)CNc1nc(NCc2ccc(-n3cncn3)nc2)nc2ccc(C#CC3CC3)nc12] | N²-((6-(1H-1,2,4-triazol-1-yl)pyridin-3-yl)methyl)-6-(2-cyclopropylethynyl)-N⁴-(2,2,2-trifluoroethyl)pyrido[3,2-d]pyrimidine-2,4-diamine | 466.1 |
| 294 | 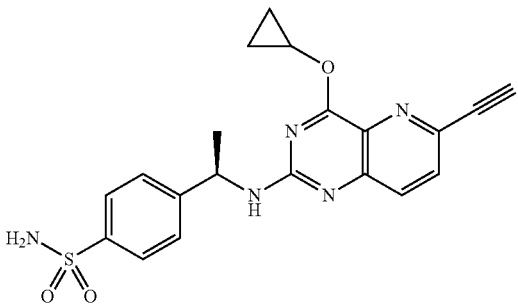 [SMILES: C#Cc1ccc2nc(N[C@H](C)c3ccc(S(N)(=O)=O)cc3)nc(OC3CC3)c2n1] | (R)-4-(1-(4-cyclopropoxy-6-ethynylpyrido[3,2-d]pyrimidin-2-ylamino)ethyl)benzene-sulfonamide | 410.1 |

TABLE III-continued

| Ex | Structure | Name | MS |
|---|---|---|---|
| 295 | 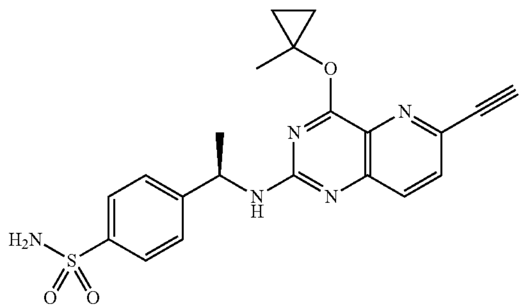 [SMILES: C#Cc1ccc2nc(N[C@H](C)c3ccc(S(N)(=O)=O)cc3)nc(OC3(C)CC3)c2n1] | (R)-4-(1-(6-ethynyl-4-(1-methylcyclopropoxy)pyrido[3,2-d]pyrimidin-2-ylamino)ethyl)benzenesulfonamide | 424.1 |
| 296 | 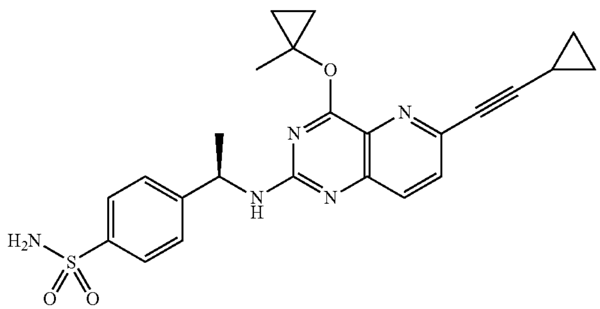 [SMILES: C[C@@H](Nc1nc(OC2(C)CC2)c2nc(C#CC3CC3)ccc2n1)c1ccc(S(N)(=O)=O)cc1] | (R)-4-(1-(6-(2-cyclopropylethynyl)-4-(1-methylcyclopropoxy)pyrido[3,2-d]pyrimidin-2-ylamino)ethyl)benzenesulfonamide | 464.2 |
| 297 | 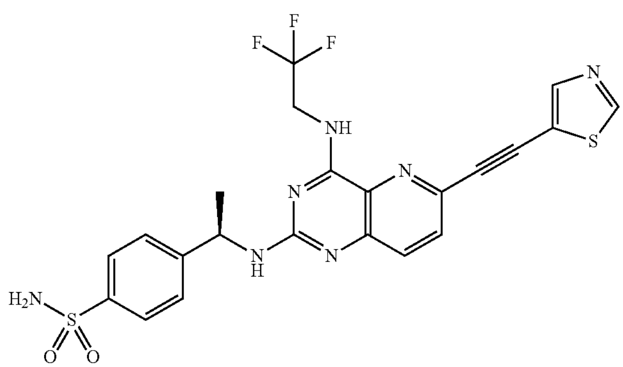 [SMILES: C[C@@H](Nc1nc(NCC(F)(F)F)c2nc(C#Cc3cncs3)ccc2n1)c1ccc(S(N)(=O)=O)cc1] | (R)-4-(1-(6-(2-(thiazol-5-yl)ethynyl)-4-(2,2,2-trifluoroethylamino)pyrido[3,2-d]pyrimidin-2-ylamino)ethyl)benzenesulfonamide | 534.1 |
| 298 | 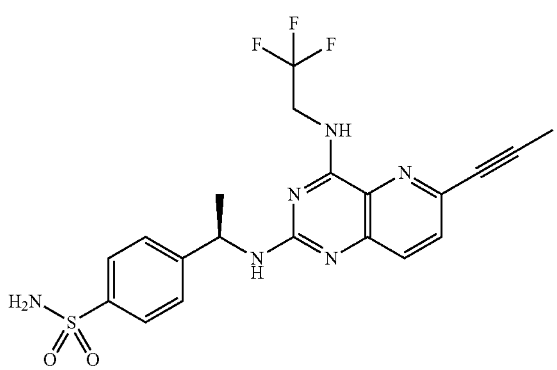 [SMILES: CC#Cc1ccc2nc(N[C@H](C)c3ccc(S(N)(=O)=O)cc3)nc(NCC(F)(F)F)c2n1] | (R)-4-(1-(6-(prop-1-ynyl)-4-(2,2,2-trifluoroethylamino)pyrido[3,2-d]pyrimidin-2-ylamino)ethyl)benzenesulfonamide | 465.0 |

TABLE III-continued

| Ex | Structure | Name | MS |
|----|-----------|------|-----|
| 299 | 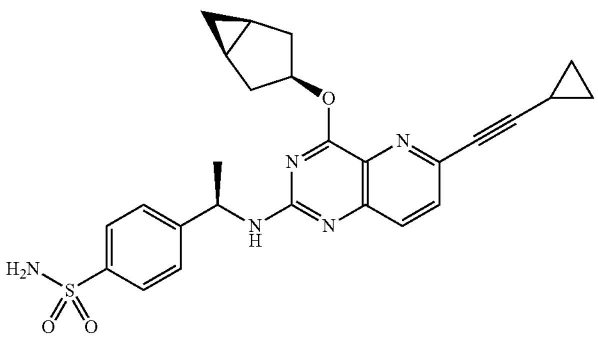 [SMILES: C[C@@H](Nc1nc(O[C@@H]2C[C@@H]3C[C@@H]3C2)c2nc(C#CC3CC3)ccc2n1)c1ccc(S(N)(=O)=O)cc1] | 4-((R)-1-(4-((1S,3r,5R)-bicyclo[3.1.0]hexan-3-yloxy)-6-(2-cyclopropylethynyl)pyrido[3,2-d]pyrimidin-2-ylamino)ethyl)benzenesulfonamide | 490.2 |
| 300 | 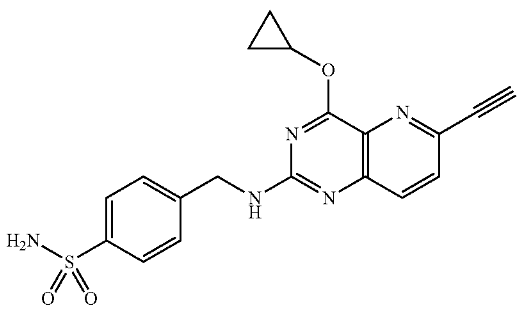 [SMILES: C#Cc1ccc2nc(NCc3ccc(S(N)(=O)=O)cc3)nc(OC3CC3)c2n1] | 4-((4-cyclopropoxy-6-ethynylpyrido[3,2-d]pyrimidin-2-ylamino)methyl)benzenesulfonamide | 396.0 |
| 301 | 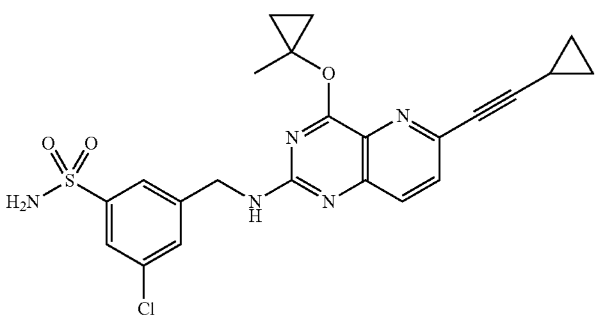 [SMILES: CC1(Oc2nc(NCc3cc(Cl)cc(S(N)(=O)=O)c3)nc3ccc(C#CC4CC4)nc23)CC1] | 3-chloro-5-((6-(2-cyclopropyl-ethynyl)-4-(1-methylcyclopropoxy)pyrido[3,2-d]pyrimidin-2-ylamino)methyl)benzenesulfonamide | 484.1 |
| 302 | 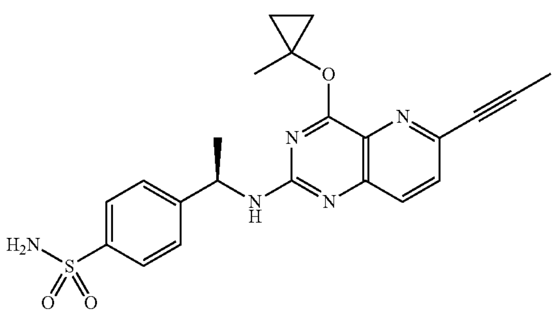 [SMILES: CC#Cc1ccc2nc(N[C@H](C)c3ccc(S(N)(=O)=O)cc3)nc(OC3(C)CC3)c2n1] | (R)-4-(1-(4-(1-methylcyclopropoxy)-6-(prop-1-ynyl)pyrido[3,2-d]pyrimidin-2-ylamino)ethyl)benzenesulfonamide | 438.2 |
| 303 | 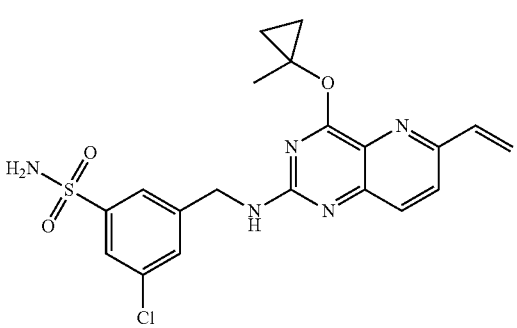 [SMILES: C=Cc1ccc2nc(NCc3cc(Cl)cc(S(N)(=O)=O)c3)nc(OC3(C)CC3)c2n1] | 3-chloro-5-((4-(1-methylcyclopropoxy)-6-vinylpyrido[3,2-d]pyrimidin-2-ylamino)methyl)benzenesulfonamide | 446.1 |

TABLE III-continued

| Ex | Structure | Name | MS |
|---|---|---|---|
| 304 | 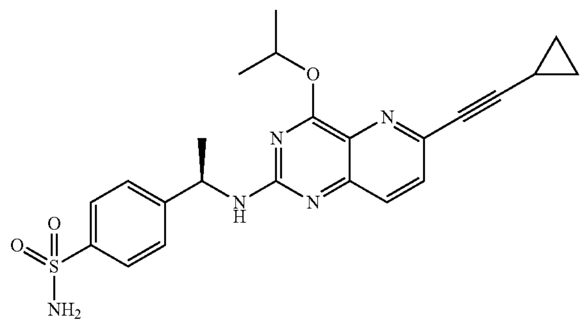 [SMILES: CC(C)Oc1nc(N[C@H](C)c2ccc(S(N)(=O)=O)cc2)nc2ccc(C#CC3CC3)nc12] | (R)-4-(1-(6-(2-cyclopropyl-ethynyl)-4-isopropoxypyrido[3,2-d]pyrimidin-2-ylamino)ethyl)benzenesulfonamide | 452.2 |
| 305 | 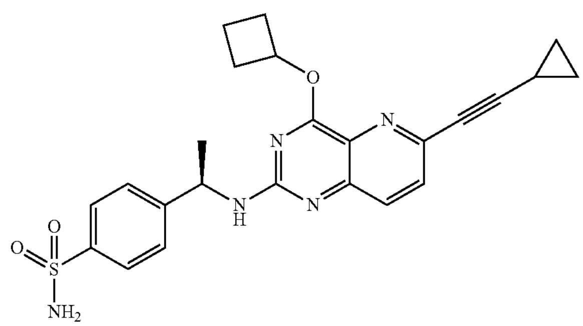 [SMILES: C[C@@H](Nc1nc(OC2CCC2)c2nc(C#CC3CC3)ccc2n1)c1ccc(S(N)(=O)=O)cc1] | (R)-4-(1-(4-cyclobutoxy-6-(2-cyclopropylethynyl)pyrido[3,2-d]pyrimidin-2-ylamino)ethyl)benzenesulfonamide | 464.2 |
| 306 | 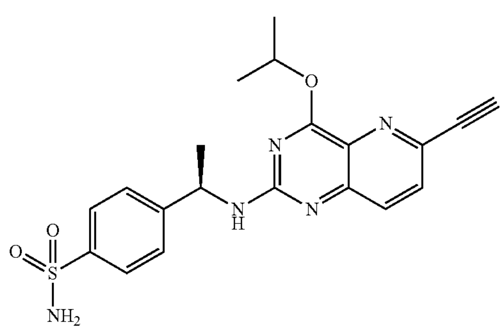 [SMILES: C#Cc1ccc2nc(N[C@H](C)c3ccc(S(N)(=O)=O)cc3)nc(OC(C)C)c2n1] | (R)-4-(1-(6-ethynyl-4-isopropoxypyrido[3,2-d]pyrimidin-2-ylamino)ethyl)benzenesulfonamide | 411.2 |
| 307 | 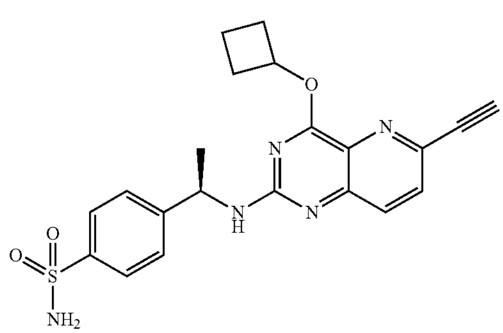 [SMILES: C#Cc1ccc2nc(N[C@H](C)c3ccc(S(N)(=O)=O)cc3)nc(OC3CCC3)c2n1] | (R)-4-(1-(4-cyclobutoxy-6-ethynylpyrido[3,2-d]pyrimidin-2-ylamino)ethyl)benzenesulfonamide | 423.2 |

TABLE III-continued

| Ex | Structure | Name | MS |
|---|---|---|---|
| 308 | 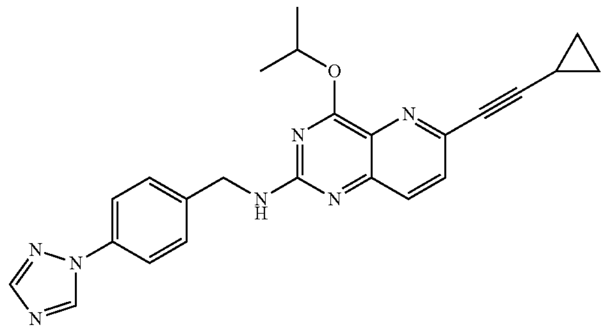 [SMILES: CC(C)Oc1nc(NCc2ccc(-n3cncn3)cc2)nc2ccc(C#CC3CC3)nc12] | N-(4-(1H-1,2,4-triazol-1-yl)benzyl)-6-(2-cyclopropyl-ethynyl)-4-isopropoxypyrido[3,2-d]pyrimidin-2-amine | 426.2 |
| 309 | 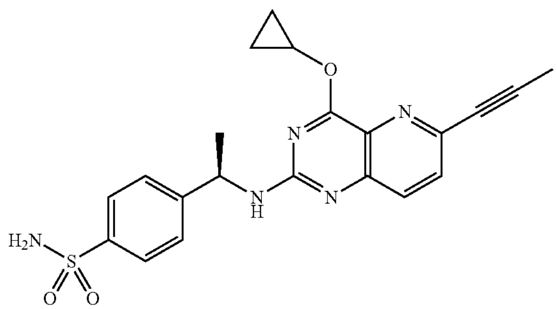 [SMILES: CC#Cc1ccc2nc(N[C@H](C)c3ccc(S(N)(=O)=O)cc3)nc(OC3CC3)c2n1] | (R)-4-(1-(4-cyclopropoxy-6-(prop-1-ynyl)pyrido[3,2-d]pyrimidin-2-ylamino)ethyl)benzenesulfonamide | 424.1 |
| 310 | 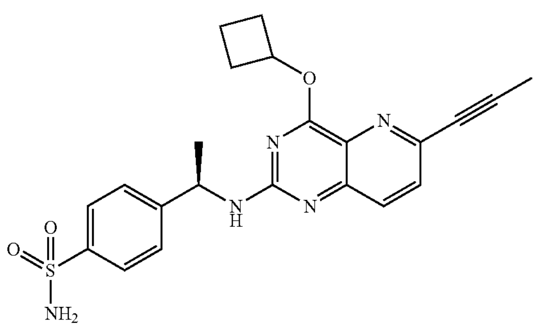 [SMILES: CC#Cc1ccc2nc(N[C@H](C)c3ccc(S(N)(=O)=O)cc3)nc(OC3CCC3)c2n1] | (R)-4-(1-(4-cyclobutoxy-6-(prop-1-ynyl)pyrido[3,2-d]pyrimidin-2-ylamino)ethyl)benzenesulfonamide | 438.2 |
| 311 | 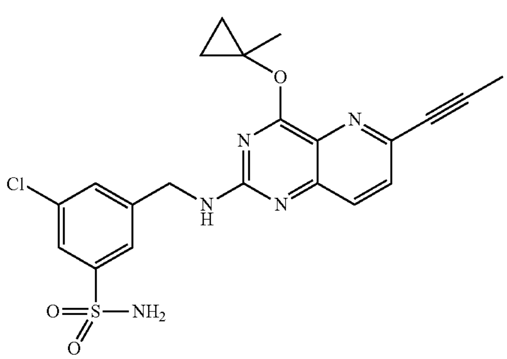 [SMILES: CC#Cc1ccc2nc(NCc3cc(Cl)cc(S(N)(=O)=O)c3)nc(OC3(C)CC3)c2n1] | 3-chloro-5-((4-(1-methylcyclo-propoxy)-6-(prop-1-ynyl)pyrido[3,2-d]pyrimidin-2-ylamino)methyl)benzenesulfonamide | 458.1 |

TABLE III-continued

| Ex | Structure | Name | MS |
|---|---|---|---|
| 312 | 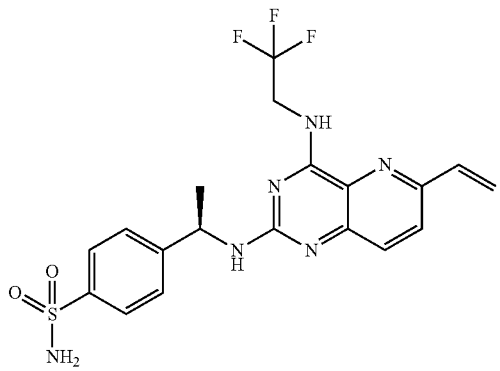 [SMILES: C=Cc1ccc2nc(N[C@H](C)c3ccc(S(N)(=O)=O)cc3)nc(NCC(F)(F)F)c2n1] | (R)-4-(1-(4-(2,2,2-trifluoro-ethylamino)-6-vinylpyrido[3,2-d]pyrimidin-2-ylamino)ethyl)benzenesulfonamide | 453.1 |
| 313 | 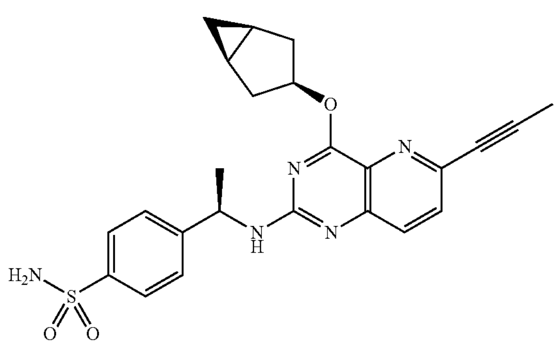 [SMILES: CC#Cc1ccc2nc(N[C@H](C)c3ccc(S(N)(=O)=O)cc3)nc(O[C@@H]3C[C@@H]4C[C@@H]4C3)c2n1] | 4-((R)-1-(4-((1S,3r,5R)-bicyclo[3.1.0]hexan-3-yloxy)-6-(prop-1-ynyl)pyrido[3,2-d]pyrimidin-2-ylamino)ethyl)benzenesulfonamide | 464.2 |
| 314 | 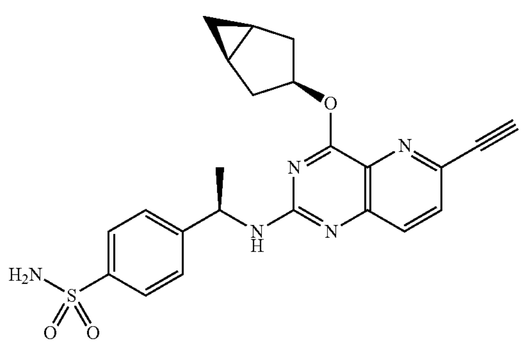 [SMILES: C#Cc1ccc2nc(N[C@H](C)c3ccc(S(N)(=O)=O)cc3)nc(O[C@@H]3C[C@@H]4C[C@@H]4C3)c2n1] | 4-((R)-1-(4-((1S,3r,5R)-bicyclo[3.1.0]hexan-3-yloxy)-6-ethynylpyrido[3,2-d]pyrimidin-2-ylamino)ethyl)benzenesulfonamide | 450.0 |
| 315 | 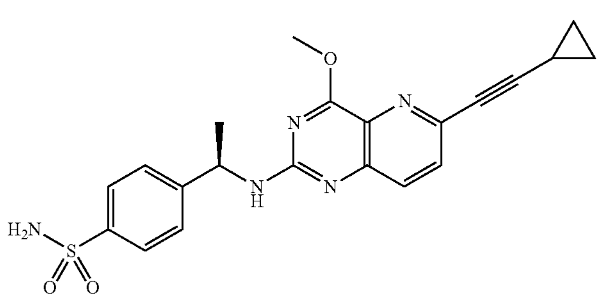 [SMILES: COc1nc(N[C@H](C)c2ccc(S(N)(=O)=O)cc2)nc2ccc(C#CC3CC3)nc12] | (R)-4-(1-(6-(2-cyclopropyl-ethynyl)-4-methoxypyrido[3,2-d]pyrimidin-2-ylamino)ethyl)benzenesulfonamide | 424.5 |

TABLE III-continued

| Ex | Structure | Name | MS |
|---|---|---|---|
| 316 | 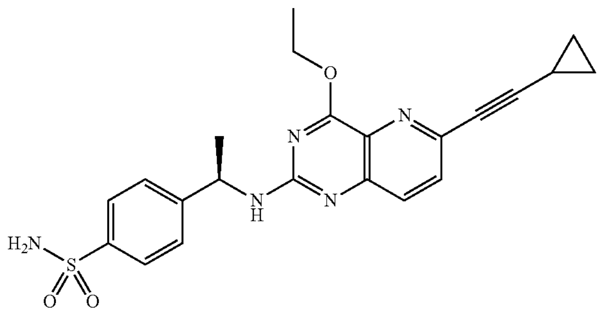 [SMILES: CCOc1nc(N[C@H](C)c2ccc(S(N)(=O)=O)cc2)nc2ccc(C#CC3CC3)nc12] | (R)-4-(1-(6-(2-cyclopropyl-ethynyl)-4-ethoxypyrido[3,2-d]pyrimidin-2-ylamino)ethyl)benzenesulfonamide | 438.2 |
| 317 | 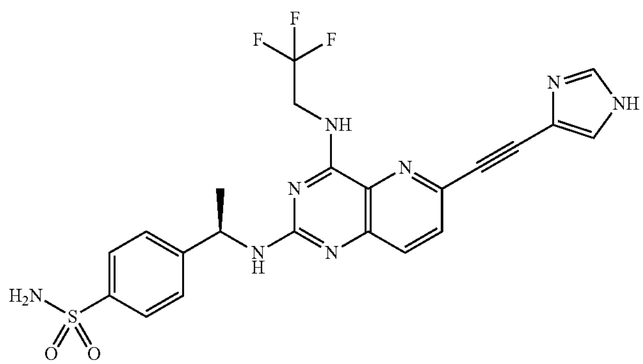 [SMILES: C[C@@H](Nc1nc(NCC(F)(F)F)c2nc(C#Cc3c[nH]cn3)ccc2n1)c1ccc(S(N)(=O)=O)cc1] | (R)-4-(1-(6-(2-(1H-imidazol-4-yl)ethynyl)-4-(2,2,2-trifluoro-ethylamino)pyrido[3,2-d]pyrimidin-2-ylamino)ethyl)benzenesulfonamide | 517.1 |
| 318 | 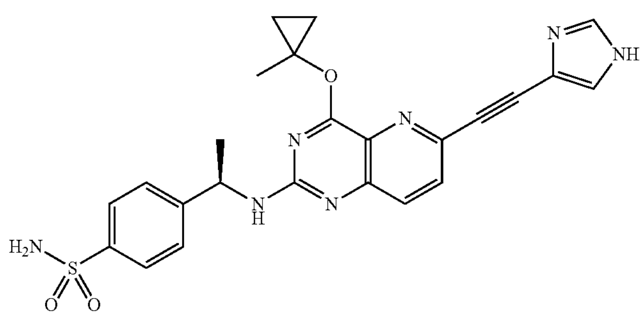 [SMILES: C[C@@H](Nc1nc(OC2(C)CC2)c2nc(C#Cc3c[nH]cn3)ccc2n1)c1ccc(S(N)(=O)=O)cc1] | (R)-4-(1-(6-(2-(1H-imidazol-4-yl)ethynyl)-4-(1-methylcyclopropoxy)pyrido[3,2-d]pyrimidin-2-ylamino)ethyl)benzenesulfonamide | 490.2 |
| 319 | 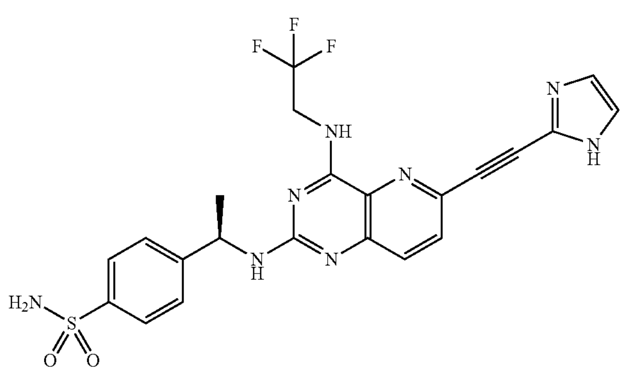 [SMILES: C[C@@H](Nc1nc(NCC(F)(F)F)c2nc(C#Cc3ncc[nH]3)ccc2n1)c1ccc(S(N)(=O)=O)cc1] | (R)-4-(1-(6-(2-(1H-imidazol-2-yl)ethynyl)-4-(2,2,2-trifluoroethyl-amino)pyrido[3,2-d]pyrimidin-2-ylamino)ethyl)benzene-sulfonamide | 517.2 |

TABLE III-continued

| Ex | Structure | Name | MS |
|---|---|---|---|
| 320 | 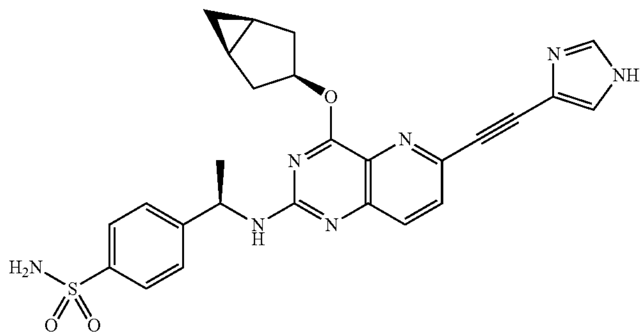 [SMILES: C[C@@H](Nc1nc(O[C@@H]2C[C@@H]3C[C@@H]3C2)c2nc(C#Cc3c[nH]cn3)ccc2n1)c1ccc(S(N)(=O)=O)cc1] | 4-((R)-1-(6-(2-(1H-imidazol-4-yl)ethynyl)-4-((1S,3r,5R)-bicyclo[3.1.0]hexan-3-yloxy)pyrido[3,2-d]pyrimidin-2-ylamino)ethyl)benzenesulfonamide | 516.2 |

EXAMPLE 33

Anti-HCV assay/Replicon assay

The anti-HCV activity of the pyrido[3,2-d]pyrimidine derivatives of this invention was tested in a human hepatoma Huh-7 cell line harboring a HCV replicon. The assay comprised the following steps:

Step 1: compound preparation and serial dilution: serial dilution is performed in 50% DMSO in a 384-well plate. A solution containing a compound at 100-fold concentration of the starting final serial dilution concentration was prepared in 50% DMSO and added to the pre-specified wells in column 1 of a polypropylene 384-well plate. The plate was then placed on a Precision 2000 Workstation to start the serial dilution. After the serial dilution, a volume of 2 μL of the solution was transferred from the 384-well plate to a 96-well cell culture plate containing 100 μL of cell media on a Biomek FX Workstation. The DMSO concentration in the final assay condition was 0.5% after cells are added to the plate and the total volume in each well is brought to 200 μL.

Step 2: to each well of the serial dilution plate prepared above, 100 μL of cell media containing 6000 suspended Huh-7 HCV replicon cells was added with a Multidrop workstation. The plates were incubated for 3 days at 37° C. with 5% $CO_2$.

Step 3: detection:
a) for the $EC_{50}$ assay, the media in a 96-well cell culture plate was aspirated with a Biotek EL405 plate-washer. A volume of 200 μL of a solution containing a 1:1 mixture of cell-lysis buffer (Promega, Luciferase Cell Culture Lysis 5× Reagent, cat. #E1531) and luciferase substrate solution (Promega, Luciferase Assay, cat.# E4550) was added to each well of the plate with Multidrop. The plate was incubated for 30 minutes at room temperature before the luminescence signal was measured with a TopCount plate-reader.
b) for the $CC_{50}$ assay, a volume of 100 μL of pre-mixed CellTiter-Glo (Promega, cat.# G7572) solution is added directly to the cell culture in each well of the plate and the luminescence signal is measured with a TopCount plate-reader after 10 minutes of incubation at room temperature.

Table 1 below shows $EC_{50}$ and $CC_{50}$ ranges of derivatives tested in this assay. Results in table 1 are expressed by the following data:
the 50% effective concentration ($EC_{50}$), i.e. the concentration that protects 50% of the cell monolayer from virus-induced cythopathic effect, is valued by "A" when below 0.1 μM, by "B" when between 0.1 and 0.25 μM, and indicated by "C" when between 0.25 and 2 μM; and
the 50% cytostatic concentration ($CC_{50}$), i.e. the concentration that results in 50% inhibition of cell growth, is valued by "A" when below 10 μM, by "B" when between 10 and 25 μM, and by "C" when higher than 25 μM.

TABLE 1

| Example | $EC_{50}$ (A <0.1 μM; <0.1 μM < B <0.25 μM; 0.25 μM < C <2 μM) | $CC_{50}$ (A <10 μM; B 10-25 μM; C >25 μM) |
|---|---|---|
| 1 | B | C |
| 2 | A | C |
| 3 | C | C |
| 4 | C | C |
| 5 | A | C |
| 6 | B | C |
| 7 | A | B |
| 8 | C | C |
| 9 | C | C |
| 10 | B | A |
| 11 | C | C |
| 12 | C | B |
| 13 | B | B |
| 14 | A | B |
| 15 | A | C |
| 16 | A | C |
| 17 | A | B |
| 18 | A | C |
| 19 | A | B |
| 20 | A | C |
| 21 | A | C |
| 22 | A | C |

Table 2 below shows $EC_{50}$ and $CC_{50}$ ranges of derivatives tested in this assay. Results in Table 2 are expressed by the following data:
the 50% effective concentration ($EC_{50}$), i.e. the concentration that protects 50% of the cell monolayer from virus-induced cythopathic effect, is valued by "A" when below 0.1 μM, by "B" when between 0.1 and 0.25 μM, and indicated by "C" when between 0.25 and 2 μM; and
the 50% cytostatic concentration ($CC_{50}$), i.e. the concentration that results in 50% inhibition of cell growth, is valued by "A" when below 1 μM, by "B" when between 1 and 10 μM, and by "C" when higher than 10 μM.

TABLE 2

| Example | $EC_{50}$ (A <0.1 μM; <0.1 μM < B <0.25 μM; 0.25 μM < C <2 μM) | $CC_{50}$ (A <1 μM; B 1-10 μM; C >10 μM) |
|---|---|---|
| 23 | A | B |
| 24 | A | C |

TABLE 2-continued

| | | |
|---|---|---|
| 25 | A | C |
| 26 | B | C |
| 27 | B | C |
| 28 | A | B |
| 29 | A | B |
| 30 | A | C |
| 31 | A | C |
| 32 | A | C |

| Ex | EC$_{50}$ | CC$_{50}$ |
|---|---|---|
| 34 | A | B |
| 35 | A | B |
| 36 | A | B |
| 37 | A | B |
| 38 | A | C |
| 39 | A | C |
| 40 | A | B |
| 41 | B | B |
| 42 | A | B |
| 43 | C | C |
| 44 | A | B |
| 45 | A | B |
| 46 | A | C |
| 47 | A | B |
| 48 | A | B |
| 49 | A | C |
| 50 | A | B |
| 51 | C | B |
| 52 | A | B |
| 53 | C | B |
| 54 | C | B |
| 55 | A | B |
| 56 | C | C |
| 57 | A | A |
| 58 | A | A |
| 59 | B | B |
| 61 | A | B |
| 62 | A | C |
| 63 | A | C |
| 65 | A | B |
| 66 | B | C |
| 67 | C | C |
| 68 | C | B |
| 69 | A | C |
| 70 | A | C |
| 71 | C | C |
| 72 | C | C |
| 73 | A | B |
| 75 | C | C |
| 77 | A | C |
| 78 | B | C |
| 79 | A | C |
| 80 | C | B |
| 81 | C | B |
| 82 | A | C |
| 83 | B | C |
| 84 | A | B |
| 86 | A | C |
| 87 | B | C |
| 88 | B | C |
| 90 | A | C |
| 91 | A | C |
| 92 | A | B |
| 93 | A | B |
| 94 | A | B |
| 95 | A | B |
| 96 | A | B |
| 97 | A | C |
| 98 | A | B |
| 99 | A | B |
| 100 | A | B |
| 104 | B | C |
| 105 | A | C |
| 106 | A | C |
| 107 | C | C |
| 108 | C | C |
| 111 | A | B |
| 112 | A | B |
| 113 | B | C |

TABLE 2-continued

| | | |
|---|---|---|
| 114 | A | C |
| 115 | A | B |
| 116 | A | C |
| 117 | A | C |
| 118 | C | C |
| 119 | C | C |
| 120 | A | B |
| 121 | A | C |
| 122 | A | B |
| 123 | C | B |
| 124 | A | B |
| 125 | C | B |
| 126 | C | B |
| 127 | A | B |
| 128 | C | C |
| 129 | A | A |
| 130 | A | A |
| 131 | B | B |
| 132 | A | C |
| 133 | B | C |
| 134 | C | C |
| 136 | A | C |
| 137 | B | C |
| 138 | B | C |
| 139 | A | C |
| 140 | A | B |
| 141 | A | C |
| 142 | C | C |
| 143 | A | C |
| 144 | A | B |
| 145 | B | B |
| 146 | A | C |
| 147 | A | C |
| 149 | A | C |
| 150 | A | B |
| 151 | A | B |
| 152 | A | C |
| 153 | A | C |
| 154 | B | C |
| 155 | A | B |
| 156 | C | C |
| 157 | A | C |
| 158 | C | C |
| 159 | B | C |
| 161 | A | C |
| 162 | C | C |
| 163 | A | C |
| 164 | A | C |
| 165 | A | B |
| 166 | A | B |
| 167 | A | C |
| 168 | B | C |
| 169 | C | C |
| 170 | A | B |
| 172 | B | C |
| 173 | A | B |
| 174 | A | A |
| 175 | A | C |
| 176 | A | B |
| 177 | A | B |
| 178 | A | B |
| 179 | A | C |
| 180 | B | B |
| 181 | A | C |
| 182 | A | B |
| 183 | A | B |
| 184 | A | B |
| 185 | B | C |
| 186 | A | B |
| 187 | A | C |
| 188 | A | C |
| 189 | A | B |
| 190 | A | C |
| 191 | A | C |
| 192 | A | B |
| 193 | A | C |
| 194 | A | B |
| 195 | A | B |
| 196 | A | C |
| 197 | A | C |

TABLE 2-continued

| | | |
|---|---|---|
| 198 | A | C |
| 199 | A | C |
| 200 | B | C |
| 202 | A | C |
| 203 | A | C |
| 204 | A | B |
| 205 | A | C |
| 206 | C | C |
| 225 | A | C |
| 226 | A | — |
| 227 | A | B |
| 228 | C | C |
| 229 | A | C |
| 230 | A | C |
| 232 | A | B |
| 233 | A | B |
| 234 | A | C |
| 235 | B | B |
| 236 | A | B |
| 237 | A | C |
| 239 | A | B |
| 240 | A | C |
| 241 | A | C |
| 242 | A | B |
| 243 | A | C |
| 244 | B | C |
| 245 | A | C |
| 246 | A | C |
| 247 | A | B |
| 248 | A | B |
| 249 | A | B |
| 250 | A | B |
| 251 | B | B |
| 252 | A | B |
| 253 | A | C |
| 254 | A | C |
| 255 | A | B |
| 256 | A | C |
| 257 | A | B |
| 258 | A | C |
| 259 | A | C |
| 260 | A | C |
| 261 | A | C |
| 262 | A | B |
| 263 | A | B |
| 264 | A | B |
| 265 | A | B |
| 266 | A | B |
| 267 | B | C |
| 275 | A | C |
| 276 | C | C |
| 277 | A | C |
| 278 | B | C |
| 279 | B | C |
| 280 | A | C |
| 281 | C | C |
| 282 | C | C |
| 283 | B | C |
| 284 | A | C |
| 285 | C | C |
| 286 | B | C |
| 287 | B | C |
| 288 | A | B |
| 289 | A | B |
| 290 | A | B |
| 291 | A | C |
| 292 | C | C |
| 294 | A | B |
| 295 | A | B |
| 296 | A | C |
| 297 | C | C |
| 298 | A | C |
| 299 | A | B |
| 300 | C | B |
| 301 | A | B |
| 302 | A | C |
| 303 | B | C |
| 304 | A | C |
| 305 | A | C |
| 306 | C | A |
| 307 | C | B |
| 308 | C | C |
| 309 | A | C |
| 310 | A | C |
| 311 | A | C |
| 312 | B | C |
| 313 | A | C |
| 314 | A | C |
| 315 | C | C |
| 316 | B | C |

The present invention teaches compounds which provide increased efficacy, potency and/or pharmacodynamic/kinetic properties compared to known compounds. It was surprising to the inventors that the inventive compounds possessed significantly improved properties over known pyrido(3,2-d)pyrimidine derivatives, such as those disclosed in the applications cited in the above background of the invention. In particular, the inventive compounds are unpredictably much better than the compound of Example 303 (4-position cyano substituted cyclopropylamino) disclosed in PCT/EP2007/011496. The present invention teaches compounds which surprisingly provide increased efficacy, potency and/or pharmacodynamic/kinetic properties over Example 303, as well as over other compounds taught in that application.

What is claimed is:

1. A compound represented by the structural formula (Ia):

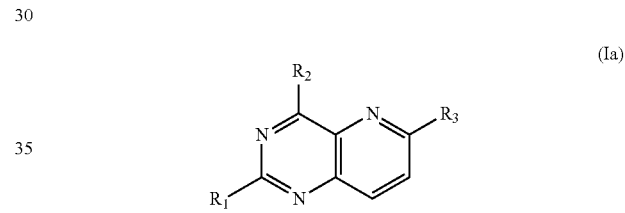

(Ia)

wherein:
$R_1$ is —NH—CHR$_5$R$_6$ or —NH—R$_8$;
$R_5$ and $R_6$ are each independently selected from the group consisting of hydrogen, $C_{1-6}$ alkyl, $C_{3-10}$ cycloalkyl, aryl and heterocyclyl, wherein said aryl is substituted with one or more substituents independently selected from the group consisting of halogen, hydroxy, nitro, cyano, trifluoromethyl, trifluoromethoxy, $C_{1-4}$ alkyl, $C_{1-4}$ alkoxy, carboxamido, sulfamoyl, carbamoyl, sulfonamido, heterocyclyl, —CON(R$_{13}$)$_2$, —COR$_{10}$, —NR$_{12}$COR$_{10}$, —NR$_{11}$R$_{11}$, —SO$_2$R$_9$, —NHSO$_2$R$_9$ and phenoxy, and wherein said $C_{1-6}$ alkyl or heterocyclyl is optionally substituted with one or more substituents independently selected from the group consisting of halogen, —CON(R$_{13}$)$_2$, —SO$_2$R$_9$, hydroxy, $C_{1-4}$ alkoxy and —NR$_{11}$R$_{11}$;
$R_8$ is selected from the group consisting of $C_{3-10}$ cycloalkyl, heteroaryl and aryl, wherein said heteroaryl or aryl is optionally substituted with one or more substituents independently selected from the group consisting of halogen and $C_{1-4}$ alkyl, and wherein said $C_{3-10}$ cycloalkyl is optionally substituted at the carbon position adjacent to the N atom of $R_1$ with aryl or heteroaryl, wherein said aryl is optionally substituted with halogen;
$R_2$ is —NHR$_4$ or XR$_7$ or is selected from the group consisting of N-morpholinyl, N-thiomorpholinyl and N-thiomorpholinyl dioxide;
X is selected from the group consisting of O, S, NR$_{13}$ and CH$_2$;

$R_7$ is selected from the group consisting of $C_{1-20}$ alkyl, $C_{3-10}$ cycloalkyl, aryl, heterocyclyl and aryl-$C_{1-4}$ alkyl; wherein said heterocyclyl is optionally substituted with $C_{1-4}$ alkyl when X is NH; and wherein said $C_{1-20}$ alkyl is optionally substituted with methylsulfonyl, heterocyclyl, one to six halogen atoms or $C_{1-4}$ alkyl when X is $NR_{13}$ or said $C_{1-20}$ alkyl is optionally substituted with $C_{1-4}$ alkoxy, halo-$C_{1-4}$ alkoxy or heterocyclyl-oxy $C_{1-4}$ alkoxy when X is O; wherein said $C_{3-10}$ cycloalkyl is optionally substituted with one or more substituents independently selected from the group consisting of halogen, hydroxy, nitro, cyano, $C_{1-4}$ alkyl optionally substituted with one or more halogen, $C_{1-4}$ alkoxy optionally substituted with one or more halogen, mono-$C_{1-4}$ alkylamino, di-$C_{1-4}$ alkylamino, carboxamido, sulfamoyl, carbamoyl, sulfonamido, —$CON(R_{13})_2$, —$NR_{12}COR_{10}$, —$SO_2R_9$, —$NHSO_2R_9$ and phenoxy;

$R_4$ is $C_{3-10}$ cycloalkyl substituted with one or more substituents independently selected from the group consisting of halogen, hydroxy, nitro, $C_{1-4}$ alkyl optionally substituted with one or more halogen, $C_{1-4}$ alkoxy optionally substituted with one or more halogen, mono-$C_{1-4}$ alkylamino, di-$C_{1-4}$ alkylamino, carboxamido, sulfamoyl, carbamoyl, sulfonamido, —$CON(R_{13})_2$, —$NR_{12}COR_{10}$, —$SO_2R_9$, —$NHSO_2R_9$ and phenoxy;

wherein when $R_2$ is —$NHR_4$, $R_3$ is selected from the group consisting of optionally substituted $C_{1-6}$ alkynyl, optionally substituted $C_{1-6}$ alkenyl, mono-substituted or di-substituted aryl, mono-substituted or di-substituted heteroaryl and mono-substituted or di-substituted heterocyclyl; wherein the substituents of said aryl, heteroaryl or heterocyclyl are independently selected from the group consisting of oxo, halogen, hydroxy, cyano, —$CON(R_{13})_2$, —$NR_{12}COR_{10}$, —$NR_{11}R_{11}$, —$SO_2R_9$, —$NHSO_2R_9$, $C_{3-6}$ cycloalkyl, phenoxy, $C_{1-6}$ alkoxy and $C_{1-6}$ alkyl wherein said $C_{1-6}$ alkoxy and $C_{1-6}$ alkyl is optionally substituted with one or more substituents selected from halogen, hydroxy, alkoxy, cyano, amino, di-$C_{1-4}$ alkylamino, mono-$C_{1-4}$ alkylamino and heterocyclyl; or wherein when $R_2$ is $XR_7$ or is selected from the group consisting of N-morpholinyl, N-thiomorpholinyl and N-thiomorpholinyl dioxide; $R_3$ is selected from:

optionally substituted $C_{2-6}$ alkynyl or optionally substituted $C_{2-6}$ alkenyl;

an at least para-substituted phenyl group wherein the para-substituent of said phenyl group is $C_{1-6}$ alkoxy optionally substituted with 1-6 halogens;

a pyridine-3-yl or pyrimidin-5-yl group wherein the 6-position of said pyridine-3-yl or 2-position of said pyrimidiin-5-yl group is substituted with a $C_{2-6}$ alkoxy group optionally substituted with 2-5 deuteriums; a $C_1$ alkoxy group substituted with 1-3 halogens; or a $C_{3-7}$ cycloalkoxy group; or a mono-substituted or di-substituted phenyl or heteroaryl, wherein at least one substituent of said phenyl or heteroaryl is —$SO_2(C_{1-3}$ alkyl) wherein said $C_{1-3}$ alkyl is optionally substituted with one to three halogens; —$SO_2(C_{3-6}$ cycloalkyl) or —$SO_2(CH_2OCH_3)$ and the remaining substituents of said phenyl or heteroaryl are independently selected from the group consisting of H, halogen, hydroxyl, cyano, —$CON(R_{13})_2$, —$NR_{12}COR_{10}$, —$NR_{11}R_{11}$, —$SO_2R_9$, —$NHSO_2R_9$, $C_{3-6}$ cycloalkyl, phenoxy, $C_{1-6}$ alkoxy and $C_{1-6}$ alkyl wherein said $C_{1-6}$ alkyl or $C_{1-6}$ alkoxy is optionally substituted with one or more substituents selected from halogen, hydroxy, $C_{1-4}$ alkoxy, cyano, amino, di-$C_{1-4}$ alkylamino, mono-$C_{1-4}$ alkylamino or heterocyclyl;

$R_9$ is selected from the group consisting of $C_{1-6}$ alkyl, $C_{3-6}$ cycloalkyl and —$NR_{11}R_{11}$;

each $R_{11}$ is independently selected from the group consisting of hydrogen, $C_{1-6}$ alkyl, $C_{3-6}$ cycloalkyl, —$COR_{10}$, heterocyclyl, aryl and heteroaryl; or each $R_{11}$, together with the nitrogen atom to which they are attached, form a 5-7 membered heterocyclyl or heteroaryl ring;

$R_{10}$ is selected from the group consisting of $C_{1-6}$ alkyl optionally substituted with one or more substituents independently selected from the group consisting of amino, cyano, halogen and hydroxy; hydroxy, $C_{1-6}$ alkoxy optionally substituted with one or more substituents independently selected from the group consisting of amino, mono-$C_{1-4}$ alkylamino, di-$C_{1-4}$ alkylamino, cyano, halogen, and heterocyclyl; heterocyclyl optionally substituted with one or more substituents independently selected from the group consisting of $C_{1-6}$ alkyl, acylamino and oxo; $C_{3-10}$ cycloalkyl optionally substituted with one or more substituents independently selected from the group consisting of halogen, hydroxy, nitro, $C_{1-4}$ alkyl optionally substituted with one or more halogen, $C_{1-4}$ alkoxy optionally substituted with one or more halogen, mono-$C_{1-4}$ alkylamino, di-$C_{1-4}$ alkylamino, carboxamido, sulfamoyl, carbamoyl, sulfonamido, —$CON(R_{13})_2$, —$SO_2R_9$, and —$NHSO_2R_9$; and amino optionally substituted with one or more substituents independently selected from the group consisting of $C_{1-6}$ alkyl, wherein said $C_{1-6}$ alkyl is optionally substituted with one or more substituents independently selected from the group consisting of amino, mono-$C_{1-4}$ alkylamino, di-$C_{1-4}$ alkylamino, cyano, halogen and heterocyclyl;

$R_{12}$ is selected from the group consisting of hydrogen and $C_{1-6}$ alkyl, wherein said $C_{1-6}$ alkyl is optionally substituted with one or more substituents independently selected from the group consisting of cyano, halogen and hydroxy;

each $R_{13}$ is independently selected from the group consisting of hydrogen, $C_{1-20}$ alkyl or $C_{3-10}$ cycloalkyl optionally substituted with one or more substituents independently selected from the group consisting of halogen, hydroxy, nitro, $C_{1-4}$ alkyl optionally substituted with one or more halogen, $C_{1-4}$ alkoxy optionally substituted with one or more halogen, mono-$C_{1-4}$ alkylamino, di-$C_{1-4}$ alkylamino, carboxamido, sulfamoyl, carbamoyl, sulfonamido, —$SO_2R_9$, and —$NHSO_2R_9$;

wherein the substituents of said optionally substituted $C_{2-6}$ alkynyl or optionally substituted $C_{2-6}$ alkenyl are independently selected from the group consisting of oxo, halogen, hydroxyl, cyano, —$CON(R_{13})_2$, —$NR_{12}COR_{10}$, —$NR_{11}R_{11}$, —$SO_2R_9$, —$NHSO_2R_9$, $C_{3-6}$ cycloalkyl, optionally substituted phenyl, optionally substituted heteroaryl, $C_{1-6}$ alkoxy and $C_{1-6}$ alkyl wherein said $C_{1-6}$ alkoxy and $C_{1-6}$ alkyl is optionally substituted with one or more substituents selected from halogen, hydroxyl, alkoxy, cyano, amino, di-$C_{1-4}$ alkylamino, mono-$C_{1-4}$ alkylamino or heterocyclyl;

or a pharmaceutical acceptable addition salt-thereof.

2. A compound according to claim 1, wherein $R_2$ is $NHR_4$.

3. A compound according to claim 2, wherein $R_4$ is $C_{3-6}$ cycloalkyl substituted with one or more substituents independently selected from $C_{1-4}$ alkyl optionally substituted with one or more halogens, or —$CON(R_{13})_2$.

4. A compound according claim 3, wherein $R_4$ is cyclopropyl.

5. A compound according to claim 3, wherein $R_4$ is substituted with $CF_3$.

237

6. A compound according claim 1, wherein $R_3$ is optionally substituted $C_{2-6}$ alkynyl.

7. A compound according to claim 1, wherein $R_3$ is mono-substituted or disubstituted phenyl.

8. A compound according to claim 1, wherein $R_3$ is mono-substituted or di-substituted heteroaryl.

9. A compound according to claim 1, wherein $R_2$ is $XR_7$.

10. A compound according to claim 9, wherein X is O or NH.

11. A compound according to claim 10, wherein $R_7$ is $C_{1-6}$ alkyl wherein said $C_{1-6}$ alkyl is optionally substituted independently with one to six fluorine or chlorine atoms, or $C_{3-6}$ cycloalkyl, wherein said $C_{3-6}$ cycloalkyl is optionally substituted with one or more substituents independently selected from $C_{1-4}$ alkyl optionally substituted with one or more halogen or $C_{1-4}$ alkoxy optionally substituted with one or more halogen.

12. A compound according to claim 11, wherein $R_7$ is 2,2,2-trifluoroethyl or cyclopropyl optionally substituted with one or more $C_{1-4}$ alkyl optionally substituted with one or more fluorine atoms.

13. A compound according to claim 9, wherein $R_3$ is optionally substituted ethynyl wherein the substitutents of said optionally substituted ethynyl are independently selected from the group consisting of optionally substituted phenyl, optionally substituted heteroaryl, $C_{1-6}$ alkoxy, $C_{1-6}$ alkyl, and $C_{3-6}$ cycloalkyl.

14. A compound according to claim 9, wherein $R_3$ is an at least para-substituted phenyl group wherein the para-substituent of said phenyl group is $C_{1-6}$ alkoxy optionally substituted with 1-6 halogens.

15. A compound according to claim 9, wherein $R_3$ is a pyridin-3-yl or pyrimidin-5-yl group wherein the 6-position of said pyridin-3-yl or 2-position of said pyrimidiin-5-yl group is substituted with a $C_{2-6}$ alkoxy group optionally substituted with 2-5 deuteriums; a $C_1$ alkoxy group substituted with 1-3 halogens; or a $C_{3-7}$ cycloalkoxy group.

16. A compound according to claim 9, wherein $R_3$ is a mono-substituted or di-substituted phenyl or heteroaryl, wherein at least one substituent of said phenyl or heteroaryl is —$SO_2(C_{1-3}$ alkyl) wherein said $C_{1-3}$ alkyl is optionally substituted with one to three halogens; —$SO_2(C_{3-6}$cycloalkyl) or —$SO_2(CH_2OCH_3)$ and the remaining substituents of said phenyl or heteroaryl are independently selected from the group consisting of H, halogen, hydroxyl, cyano, —CON$(R_{13})_2$, —$NR_{12}COR_{10}$, —$NR_{11}R_{11}$, —$SO_2R_9$, —$NHSO_2R_9$, $C_{3-6}$ cycloalkyl, phenoxy, $C_{1-6}$ alkoxy and $C_{1-6}$ alkyl wherein said $C_{1-6}$ alkyl or $C_{1-6}$ alkoxy is optionally substituted with one or more substituents selected from halogen, hydroxyl, $C_{1-4}$ alkoxy, cyano, amino, di-$C_{1-4}$ alkylamino, mono-$C_{1-4}$ alkylamino or heterocyclyl.

17. A compound according to claim 1, wherein $R_1$ is NH—$CH_2R_6$,CH($CH_3)R_6$, or NH—CH($CH_2CH_3)R_6$.

18. A compound according to claim 17, wherein $R_6$ is phenyl substituted with at least one substiutent that is —$NR_{11}R_{11}$ or —$SO_2R_9$.

19. A compound of claim 1 selected from the group consisting of:
- 4-{[6-(4-fluoro-phenyl)-4-(1-trifluoromethyl-cyclopropylamino)-pyrido[3,2-d]pyrimidin-2-ylamino]-methyl}-benzenesulfonamide,
- (R)-4-{1-[6-(4-fluorophenyl)-4-(1-trifluoromethyl-cyclopropylamino)-pyrido[3,2-d]pyrimidin-2-ylamino]-ethyl}-benzenesulfonamide,
- 2-fluoro-5-{[6-(4-fluorophenyl)-4-(1-trifluoromethyl-cyclopropylamino)-pyrido[3,2-d]pyrimidin-2-ylamino]-methyl}-benzenesulfonamide,
- 3-{[6-(4-fluorophenyl)-4-(1-trifluoromethyl-cyclopropylamino)-pyrido[3,2-d]pyrimidin-2-ylamino]-methyl}-5-trifluoromethyl-benzenesulfonamide,

238

- 3-chloro-5-{[6-(4-fluorophenyl)-4-(1-trifluoromethyl-cyclopropylamino)-pyrido[3,2-d]pyrimidin-2-ylamino]-methyl}-benzenesulfonamide,
- 4-{[6-(3-Methanesulfonyl-4-methoxy-phenyl)-4-(1-trifluoromethyl-cyclopropylamino)-pyrido[3,2-d]pyrimidin-2-ylamino]-methyl}-benzenesulfonamide,
- 4-{[6-(3-methanesulfonyl-4-methylphenyl)-4-(1-trifluoromethyl-cyclopropylamino)-pyrido[3,2-d]pyrimidin-2-ylamino]-methyl}-benzenesulfonamide,
- 4-{[6-(3-methanesulfonyl-4-methoxymethylphenyl)-4-(1-trifluoromethyl-cyclopropylamino)-pyrido[3,2-d]pyrimidin-2-ylamino]-methyl}-benzenesulfonamide,
- 6-(6-amino-pyridin-3-yl)-N2-(1-methyl-2-[1,2,4]triazol-1-yl-ethyl)-N4-(1-trifluoromethyl-cyclopropyl)-pyrido[3,2-d]pyrimidine-2,4-diamine,
- $N^2$-(3-(methylsulfonyl)benzyl)-6-(4-methyl-3-(methylsulfonyl)phenyl)-$N^4$-(1-(trifluoromethyl)cyclopropyl)pyrido[3,2-d]pyrimidine-2,4-diamine,
- $N^2$-(3-(methylsulfonyl)benzyl)-6-(4-methoxy-3-(methylsulfonyl)phenyl)-$N^4$-(1-(trifluoromethyl)cyclopropyl)pyrido[3,2-d]pyrimidine-2,4-diamine,
- 3-((6-(4-chloro-3-(methylsulfonyl)phenyl)-4-(1-(trifluoromethyl)cyclopropylamino)pyrido[3,2-d]pyrimidin-2-ylamino)methyl)-5-fluorobenzenesulfonamide,
- 5-(2-(4-(1H-1,2,4-triazol-1-yl)benzylamino)-4-(1-(trifluoromethyl)cyclopropylamino)pyrido[3,2-d]pyrimidin-6-yl)-2-chlorobenzenesulfonamide,
- N-tert-butyl-3-((6-(4-chloro-3-(methylsulfonyl)phenyl)-4-(1-(trifluoromethyl)cyclopropylamino)pyrido[3,2-d]pyrimidin-2-ylamino)methyl)-5-fluorobenzenesulfonamide,
- $N^2$-(3-(1H-1,2,4-triazol-1-yl)benzyl)-6-(4-methoxy-3-(methylsulfonyl)phenyl)-$N^4$-(1-(trifluoromethyl)cyclopropyl)pyrido[3,2-d]pyrimidine-2,4-diamine,
- $N^2$-(3,5-difluorobenzyl)-6-(4-methoxy-3-(methylsulfonyl)phenyl)-$N^4$-(1-(trifluoromethyl)cyclopropyl)pyrido[3,2-d]pyrimidine-2,4-diamine,
- 4-chloro-3-((6-(4-fluorophenyl)-4-(1-(trifluoromethyl)cyclopropylamino)pyrido[3,2-d]pyrimidin-2-ylamino)methyl)benzenesulfonamide,
- 5-(2-(4-(1H-1,2,4-triazol-1-yl)benzylamino)-4-(1-(trifluoromethyl)cyclopropylamino)pyrido[3,2-d]pyrimidin-6-yl)-2-methylbenzenesulfonamide,
- 3-chloro-4-((6-(4-fluorophenyl)-4-(1-(trifluoromethyl)cyclopropylamino)pyrido[3,2-d]pyrimidin-2-ylamino)methyl)benzenesulfonamide,
- $N^2$-(3,4-difluorobenzyl)-6-(4-methoxy-3-(methylsulfonyl)phenyl)-$N^4$-(1-(trifluoromethyl)cyclopropyl)pyrido[3,2-d]pyrimidine-2,4-diamine,
- 3-chloro-5-((6-(4-(5-oxoimidazolidin-1-yl)phenyl)-4-(1-(trifluoromethyl)cyclopropylamino)pyrido[3,2-d]pyrimidin-2-ylamino)methyl)benzenesulfonamide,
- 3-chloro-5-((6-(3-methoxyprop-1-ynyl)-4-(1-(trifluoromethyl)cyclopropylamino)pyrido[3,2-d]pyrimidin-2-ylamino)methyl)benzenesulfonamide,
- $N^2$-((R)-1-(4-(1H-1,2,4-triazol-1-yl)phenyl)ethyl)-6-(3-(methylsulfonyl)phenyl)-$N^4$-(1-(trifluoromethyl)cyclopropyl)pyrido[3,2-d]pyrimidine-2,4-diamine,
- 3-chloro-5-((6-(4-(1-(trifluoromethyl)cyclopropylcarboxamido)phenyl)-4-(1-(trifluoromethyl)cyclopropylamino)pyrido[3,2-d]pyrimidin-2-ylamino)methyl)benzenesulfonamide,
- 3-cyano-5-((6-(4-fluorophenyl)-4-(1-(trifluoromethyl)cyclopropylamino)pyrido[3,2-d]pyrimidin-2-ylamino)methyl)benzenesulfonamide,
- 1-(4-(2-(3-(methylsulfonyl)benzylamino)-4-(1-(trifluoromethyl)cyclopropylamino)pyrido[3,2-d]pyrimidin-6-yl)phenyl)-3-methylimidazolidin-2-one, 4-((6-(3-(1,1-dioxo-isothiazolidin-2-yl)phenyl)-4-(1-(trifluoromethyl)cyclopropylamino)pyrido[3,2-d]pyrimidin-2-ylamino)methyl)benzenesulfonamide, $N^2$-(4-(1H-1,2,4-triazol-1-yl)benzyl)-6-(6-ethoxypyridin-3-yl)-$N^4$-(1-(trifluoromethyl)cyclopropyl)pyrido[3,2-d]pyrimidine-2,4-diamine, $N^2$-(3-(2-methyl-1H-imidazol-1-yl)benzyl)-6-(4-fluorophenyl)-$N^4$-(1-(trifluoromethyl)cyclopropyl)pyrido[3,2-d]pyrimidine-2,4-diamine, $N^2$-(4-(1H-imidazol-1-yl)benzyl)-6-(4-fluorophenyl)-$N^4$-(1-(trifluoromethyl)cyclopropyl)pyrido[3,2-d]pyrimidine-2,4-diamine, $N^2$-(4-(1H-1,2,4-triazol-1-yl)benzyl)-6-(6-(cyclopropylamino)pyridin-3-yl)-$N^4$-(1-(trifluoromethyl)cyclopropyl)pyrido[3,2-d]pyrimidine-2,4-diamine, $N^2$-(3-fluoro-5-(1H-1,2,4-triazol-1-yl)benzyl)-6-(4-fluorophenyl)-$N^4$-(1-(trifluoromethyl)cyclopropyl)pyrido[3,2-d]pyrimidine-2,4-diamine, 1-(4-(2-(4-(1H-1,2,4-triazol-1-yl)benzylamino)-4-(1-(trifluoromethyl)cyclopropylamino)pyrido[3,2-d]pyrimidin-6-yl)phenyl)imidazolidin-2-one, 4-((6-(4-(1,1-dioxo-isothiazolidin-2-yl)phenyl)-4-(1-(trifluoromethyl)cyclopropylamino)pyrido[3,2-d]pyrimidin-2-ylamino)methyl)benzenesulfonamide, $N^2$-((R)-1-(4-(1H-1,2,4-triazol-1-yl)phenyl)ethyl)-6-(6-(cyclopropylamino)-5-fluoropyridin-3-yl)-$N^4$-(1-(trifluoromethyl)cyclopropyl)pyrido[3,2-d]pyrimidine-2,4-diamine, 3-cyano-4-((6-(4-fluorophenyl)-4-(1-(trifluoromethyl)cyclopropylamino)pyrido[3,2-d]pyrimidin-2-ylamino)methyl)benzenesulfonamide, 4-((6-(4-(difluoromethoxy)phenyl)-4-(1-(trifluoromethyl)cyclopropylamino)pyrido[3,2-d]pyrimidin-2-ylamino)methyl)benzenesulfonamide, $N^2$-(3-(1H-1,2,4-triazol-1-yl)benzyl)-6-(6-(cyclopropylamino)-5-fluoropyridin-3-yl)-$N^4$-(1-(trifluoromethyl)cyclopropyl)pyrido[3,2-d]pyrimidine-2,4-diamine, 3-((6-(2-cyclopropylethynyl)-4-(1-(trifluoromethyl)cyclopropylamino)pyrido[3,2-d]pyrimidin-2-ylamino)methyl)-5-fluorobenzenesulfonamide, $N^2$-(4-(1H-1,2,4-triazol-1-yl)benzyl)-6-(6-(cyclopropylamino)-5-fluoropyridin-3-yl)-$N^4$-(1-(trifluoromethyl)cyclopropyl)pyrido[3,2-d]pyrimidine-2,4-diamine, 3-((6-(4-fluorophenyl)-4-(1-(trifluoromethyl)cyclohexylamino)pyrido[3,2-d]pyrimidin-2-ylamino)methyl)benzenesulfonamide, (R)-4-(1-(6-(4-fluorophenyl)-4-(1-(trifluoromethyl)cyclohexylamino)pyrido[3,2-d]pyrimidin-2-ylamino)ethyl)benzenesulfonamide, 3-ethyl-4-((6-(4-fluorophenyl)-4-(1-(trifluoromethyl)cyclopropylamino)pyrido[3,2-d]pyrimidin-2-ylamino)methyl)benzenesulfonamide, (R)-4-(1-(6-(2-cyclopropylethynyl)-4-(1-(trifluoromethyl)cyclopropylamino)pyrido[3,2-d]pyrimidin-2-ylamino)ethyl)benzenesulfonamide, $N^2$-(3-(1H-1,2,4-triazol-1-yl)benzyl)-6-(6-(cyclopropylamino)pyridin-3-yl)-$N^4$-(1-(trifluoromethyl)cyclopropyl)pyrido[3,2-d]pyrimidine-2,4-diamine, (R)-4-(1-(6-(4-fluorophenyl)-4-(1-(trifluoromethyl)cyclopentylamino)pyrido[3,2-d]pyrimidin-2-ylamino)ethyl)benzenesulfonamide, (R)-4-(1-(6-(4-fluorophenyl)-4-(1-(trifluoromethyl)cyclobutylamino)pyrido[3,2-d]pyrimidin-2-ylamino)ethyl)benzenesulfonamide, $N^2$-(3-(1H-1,2,4-triazol-1-yl)benzyl)-6-(6-aminopyridin-3-yl)-$N^4$-(1-(trifluoromethyl)cyclopropyl)pyrido[3,2-d]pyrimidine-2,4-diamine, 4-((6-(4-fluorophenyl)-4-(1-(trifluoromethyl)cyclopropylamino)pyrido[3,2-d]pyrimidin-2-ylamino)methyl)-3-isopropylbenzenesulfonamide, 4-((6-(4-methoxy-3-(trifluoromethyl)phenyl)-4-(1-(trifluoromethyl)cyclopropylamino)pyrido[3,2-d]pyrimidin-2-ylamino)methyl)benzenesulfonamide, 2-((6-(4-fluorophenyl)-4-(1-(trifluoromethyl)cyclopropylamino)pyrido[3,2-d]pyrimidin-2-ylamino)methyl)-5-methylbenzenesulfonamide, 3-fluoro-5-((6-(6-fluoropyridin-3-yl)-4-(1-(trifluoromethyl)cyclopropylamino)pyrido[3,2-d]pyrimidin-2-ylamino)methyl)benzenesulfonamide, N-tert-butyl-3-fluoro-5-((6-(6-fluoropyridin-3-yl)-4-(1-(trifluoromethyl)cyclopropylamino)pyrido[3,2-d]pyrimidin-2-ylamino)methyl)benzenesulfonamide, 4-((R)-1-(6-(6-fluoropyridin-3-yl)-4-(1-(trifluoromethyl)cyclopropylamino)pyrido[3,2-d]pyrimidin-2-ylamino)ethyl)benzenesulfonamide, 4-((4-(1-(trifluoromethyl)cyclopropylamino)-6-(3-(trifluoromethyl)phenyl)pyrido[3,2-d]pyrimidin-2-ylamino)methyl)benzenesulfonamide, $N^2$-(4-(1H-1,2,4-triazol-1-yl)benzyl)-6-(4-fluorophenyl)-$N^4$-(1-(trifluoromethyl)cyclopropyl)pyrido[3,2-d]pyrimidine-2,4-diamine, 3-((6-(4-fluorophenyl)-4-(1-(trifluoromethyl)cyclopropylamino)pyrido[3,2-d]pyrimidin-2-ylamino)methyl)-5-methylbenzenesulfonamide, 4-((6-(4-fluorophenyl)-4-(1-(trifluoromethyl)cyclopropylamino)pyrido[3,2-d]pyrimidin-2-ylamino)methyl)-2,5-dimethylbenzenesulfonamide, $N^2$-((R)-1-(4-(1H-1,2,4-triazol-1-yl)phenyl)ethyl)-6-(6-aminopyridin-3-yl)-$N^4$-(1-(trifluoromethyl)cyclopropyl)pyrido[3,2-d]pyrimidine-2,4-diamine, $N^2$-(3-(methylsulfonyl)benzyl)-6-(4-fluorophenyl)-$N^4$-(1-(trifluoromethyl)cyclopropyl)pyrido[3,2-d]pyrimidine-2,4-diamine, N-(3-((6-(4-fluorophenyl)-4-(1-(trifluoromethyl)cyclopropylamino)pyrido[3,2-d]pyrimidin-2-ylamino)methyl)phenyl)methanesulfonamide, 2-chloro-5-((6-(4-fluorophenyl)-4-(1-(trifluoromethyl)cyclopropylamino)pyrido[3,2-d]pyrimidin-2-ylamino)methyl)benzenesulfonamide, (R)-4-(1-(6-(4-fluorophenyl)-4-(1-(trifluoromethyl)cyclopropylamino)pyrido[3,2-d]pyrimidin-2-ylamino)ethyl)-3-(trifluoromethyl)benzenesulfonamide, 3-chloro-5-((6-(6-fluoropyridin-3-yl)-4-(1-(trifluoromethyl)cyclopropylamino)pyrido[3,2-d]pyrimidin-2-ylamino)methyl)benzenesulfonamide, 3-chloro-5-((6-(2-cyclopropylethynyl)-4-(1-(trifluoromethyl)cyclopropylamino)pyrido[3,2-d]pyrimidin-2-ylamino)methyl)benzenesulfonamide, 4-((6-(2-cyclopropylethynyl)-4-(1-(trifluoromethyl)cyclopropylamino)pyrido[3,2-d]pyrimidin-2-ylamino)methyl)benzenesulfonamide, 2-(6-(4-methoxy-3-(methylsulfonyl)phenyl)-4-(1-(trifluoromethyl)cyclopropylamino)pyrido[3,2-d]pyrimidin-2-ylamino)ethanesulfonamide, $N^2$-((R)-1-(4-(1H-1,2,4-triazol-1-yl)phenyl)ethyl)-6-(4-methoxy-3-(methylsulfonyl)phenyl)-$N^4$-(1-(trifluoromethyl)cyclopropyl)pyrido[3,2-d]pyrimidine-2,4-diamine, 3-chloro-5-((6-(4-(1-(trifluoromethyl)cyclopropylaminocarbonyl)phenyl)-4-(1-(trifluoromethyl)cyclopropylamino)pyrido[3,2-d]pyrimidin-2-ylamino)methyl)benzenesulfonamide, 4-((6-(6-fluoropyridin-3-yl)-4-(1-(trifluoromethyl)cyclopropylamino)pyrido[3,2-d]pyrimidin-2-ylamino)methyl)benzenesulfonamide, $N^2$-(1-(4-(1H-1,2,4-triazol-1-yl)phenyl)ethyl)-6-(4-methoxy-3-(methylsulfonyl)phenyl)-$N^4$-(1-(trifluoromethyl)cyclopropyl)pyrido[3,2-d]pyrimidine-2,4-diamine, 3-((6-(2-cyano-4-fluorophenyl)-4-(1-(trifluoromethyl)cyclopropylamino)pyrido[3,2-d]pyrimidin-2-ylamino)methyl)benzenesulfonamide,
3-((6-(2-cyano-4-fluorophenyl)-4-(1-(trifluoromethyl)cyclopropylamino)pyrido[3,2-d]pyrimidin-2-ylamino)methyl)-5-(trifluoromethyl)benzenesulfonamide,
3-chloro-5-((6-(2-cyano-4-fluorophenyl)-4-(1-(trifluoromethyl)cyclopropylamino)pyrido[3,2-d]pyrimidin-2-ylamino)methyl)benzenesulfonamide,
3-chloro-5-((6-(4-fluoro-2-aminocarbonylphenyl)-4-(1-(trifluoromethyl)cyclopropylamino)pyrido[3,2-d]pyrimidin-2-ylamino)methyl)benzenesulfonamide,
3-((6-(4-fluoro-2-aminocarbonylphenyl)-4-(1-(trifluoromethyl)cyclopropylamino)pyrido[3,2-d]pyrimidin-2-ylamino)methyl)-5-(trifluoromethyl)benzenesulfonamide,
(S)-N-(4-(1-(6-(4-fluorophenyl)-4-(1-(trifluoromethyl)cyclopropylamino)pyrido[3,2-d]pyrimidin-2-ylamino)ethyl)-3-methylphenylsulfonyl)propionamide,
2-(2-(3-(methylsulfonyl)benzylamino)-4-(1-(trifluoromethyl)cyclopropylamino)pyrido[3,2-d]pyrimidin-6-yl)-5-fluorobenzonitrile,
$N^2$-(3-fluorobenzyl)-6-(4-methoxy-3-(methylsulfonyl)phenyl)-$N^4$-(1-(trifluoromethyl)cyclopropyl)pyrido[3,2-d]pyrimidine-2,4-diamine,
3-((6-(2-cyclopropylethynyl)-4-(1-(trifluoromethyl)cyclopropylamino)pyrido[3,2-d]pyrimidin-2-ylamino)methyl)-5-(trifluoromethyl)benzenesulfonamide,
N-(3-fluoro-5-((6-(4-fluorophenyl)-4-(1-(trifluoromethyl)cyclopropylamino)pyrido[3,2-d]pyrimidin-2-ylamino)methyl)phenyl)methanesulfonamide,
(S)-4-(1-(6-(4-fluorophenyl)-4-(1-(trifluoromethyl)cyclopropylamino)pyrido[3,2-d]pyrimidin-2-ylamino)ethyl)-3-methylbenzenesulfonamide,
(S)-$N^2$-(1-(1H-1,2,4-triazol-1-yl)butan-2-yl)-6-(4-fluorophenyl)-$N^4$-(1-(trifluoromethyl)cyclopropyl)pyrido[3,2-d]pyrimidine-2,4-diamine,
(R)-$N^2$-(1-(1H-1,2,4-triazol-1-yl)butan-2-yl)-6-(4-fluorophenyl)-$N^4$-(1-(trifluoromethyl)cyclopropyl)pyrido[3,2-d]pyrimidine-2,4-diamine,
1-(4-(2-(3-(methylsulfonyl)benzylamino)-4-(1-(trifluoromethyl)cyclopropylamino)pyrido[3,2-c]pyrimidin-6-yl)phenyl)imidazolidin-2-one,
$N^2$-(4-(1H-1,2,4-triazol-1-yl)benzyl)-6-(6-aminopyridin-3-yl)-$N^4$-(1-(trifluoromethyl)cyclopropyl)pyrido[3,2-d]pyrimidine-2,4-diamine,
$N^2$-(3-(trifluoromethyl)benzyl)-6-(4-methoxy-3-(methylsulfonyl)phenyl)-$N^4$-(1-(trifluoromethyl)cyclopropyl)pyrido[3,2-d]pyrimidine-2,4-diamine,
$N^2$-(1-(1H-1,2,4-triazol-1-yl)propan-2-yl)-6-(6-(cyclopropylamino)pyridin-3-yl)-$N^4$-(1-(trifluoromethyl)cyclopropyl)pyrido[3,2-d]pyrimidine-2,4-diamine,
3-fluoro-5-((6-(4-fluorophenyl)-4-(1-(trifluoromethyl)cyclopropylamino)pyrido[3,2-d]pyrimidin-2-ylamino)methyl)benzenesulfonamide,
3-((6-(4-fluorophenyl)-4-(1-(trifluoromethyl)cyclopropylamino)pyrido[3,2-d]pyrimidin-2-ylamino)methyl)benzenesulfonamide,
(R)-4-(1-(6-(4-fluorophenyl)-4-(1-(trifluoromethyl)cyclopropylamino)pyrido[3,2-d]pyrimidin-2-ylamino)ethyl)-3-methylbenzenesulfonamide,
5-((6-(4-fluorophenyl)-4-(1-(trifluoromethyl)cyclopropylamino)pyrido[3,2-d]pyrimidin-2-ylamino)methyl)-2-(trifluoromethyl)benzenesulfonamide,
(R)-4-(1-(6-(4-fluorophenyl)-4-(1-(trifluoromethyl)cyclopropylamino)pyrido[3,2-d]pyrimidin-2-ylamino)ethyl)-2-(trifluoromethyl)benzenesulfonamide,
3-chloro-5-((6-(4-(1-(trifluoromethyl)cyclopropylcarboxamido)phenyl)-4-(1-(trifluoromethyl)cyclopropylamino)pyrido[3,2-d]pyrimidin-2-ylamino)methyl)benzenesulfonamide,
3-cyano-5-((6-(4-fluorophenyl)-4-(1-(trifluoromethyl)cyclopropylamino)pyrido[3,2-d]pyrimidin-2-ylamino)methyl)benzenesulfonamide,
1-(4-(2-(3-(methylsulfonyl)benzylamino)-4-(1-(trifluoromethyl)cyclopropylamino)pyrido[3,2-d]pyrimidin-6-yl)phenyl)-3-methylimidazolidin-2-one,
4-((6-(3-(1,1-dioxo-isothiazolidin-2-yl)phenyl)-4-(1-(trifluoromethyl)cyclopropylamino)pyrido[3,2-d]pyrimidin-2-ylamino)methyl)benzenesulfonamide,
$N^2$-(4-(1H-1,2,4-triazol-1-yl)benzyl)-6-(6-ethoxypyridin-3-yl)-$N^4$-(1-(trifluoromethyl)cyclopropyl)pyrido[3,2-d]pyrimidine-2,4-diamine,
$N^2$-(3-(2-methyl-1H-imidazol-1-yl)benzyl)-6-(4-fluorophenyl)-$N^4$-(1-(trifluoromethyl)cyclopropyl)pyrido[3,2-d]pyrimidine-2,4-diamine,
$N^2$-(4-(1H-imidazol-1-yl)benzyl)-6-(4-fluorophenyl)-$N^4$-(1-(trifluoromethyl)cyclopropyl)pyrido[3,2-d]pyrimidine-2,4-diamine,
$N^2$-(4-(1H-1,2,4-triazol-1-yl)benzyl)-6-(6-(cyclopropylamino)pyridin-3-yl)-$N^4$-(1-(trifluoromethyl)cyclopropyl)pyrido[3,2-d]pyrimidine-2,4-diamine,
$N^2$-(3-fluoro-5-(1H-1,2,4-triazol-1-yl)benzyl)-6-(4-fluorophenyl)-$N^4$-(1-(trifluoromethyl)cyclopropyl)pyrido[3,2-d]pyrimidine-2,4-diamine,
1-(4-(2-(4-(1H-1,2,4-triazol-1-yl)benzylamino)-4-(1-(trifluoromethyl)cyclopropylamino)pyrido[3,2-d]pyrimidin-6-yl)phenyl)imidazolidin-2-one,
4-((6-(4-(1,1-dioxo-isothiazolidin-2-yl)phenyl)-4-(1-(trifluoromethyl)cyclopropylamino)pyrido[3,2-d]pyrimidin-2-ylamino)methyl)benzenesulfonamide,
$N^2$-((R)-1-(4-(1H-1,2,4-triazol-1-yl)phenyl)ethyl)-6-(6-(cyclopropylamino)-5-fluoropyridin-3-yl)-$N^4$-(1-(trifluoromethyl)cyclopropyl)pyrido[3,2-d]pyrimidine-2,4-diamine,
4-((4-(1-cyanocyclopropylamino)-6-(6-methoxypyridin-3-yl)pyrido[3,2-d]pyrimidin-2-ylamino)methyl)benzenesulfonamide,
5-((4-(1-carbamoylcyclopropylamino)-6-(4-fluorophenyl)pyrido[3,2-d]pyrimidin-2-ylamino)methyl)picolinamide,
N-(5-((6-(4-fluorophenyl)-4-(1-(trifluoromethyl)cyclopropylamino)pyrido[3,2-d]pyrimidin-2-ylamino)methyl)pyridin-3-yl)methanesulfonamide,
4-((6-(4-(methylsulfonyl)phenyl)-4-(2,2,2-trifluoroethylamino)pyrido[3,2-d]pyrimidin-2-ylamino)methyl)benzenesulfonamide,
N-tert-butyl-4-((R)-1-(6-(3-(methylsulfonyl)phenyl)-4-(2,2,2-trifluoroethylamino)pyrido[3,2-d]pyrimidin-2-ylamino)ethyl)benzenesulfonamide,
2-(6-(3-(methylsulfonyl)phenyl)-4-(2,2,2-trifluoroethylamino)pyrido[3,2-d]pyrimidin-2-ylamino)ethanesulfonamide,
$N^2$-cyclopropyl-6-(3-(methylsulfonyl)phenyl)-$N^4$-(2,2,2-trifluoroethyl)pyrido[3,2-d]pyrimidine-2,4-diamine,
$N^2$-(2-methoxyethyl)-6-(3-(methylsulfonyl)phenyl)-$N^4$-(2,2,2-trifluoroethyl)pyrido[3,2-d]pyrimidine-2,4-diamine,
$N^2$-(3-(1H-pyrazol-1-yl)benzyl)-6-(4-methoxy-3-(methylsulfonyl)phenyl)-$N^4$-(2,2,2-trifluoroethyl)pyrido[3,2-d]pyrimidine-2,4-diamine,
3-((6-(4-methoxy-3-(methylsulfonyl)phenyl)-4-(2,2,2-trifluoroethylamino)pyrido[3,2-d]pyrimidin-2-ylamino)methyl)-5-(trifluoromethyl)benzenesulfonamide,
N-(4-((6-(4-methoxy-3-(methylsulfonyl)phenyl)-4-(2,2,2-trifluoroethylamino)pyrido[3,2-d]pyrimidin-2-ylamino)methyl)phenylsulfonyl)propionamide, 4-((6-(4-methyl-3-(methylsulfonyl)phenyl)-4-(2,2,2-trifluoroethylamino)pyrido[3,2-d]pyrimidin-2-ylamino)methyl)benzenesulfonamide, 3-((6-(4-methoxy-3-(methylsulfonyl)phenyl)-4-(2,2,2-trifluoroethylamino)pyrido[3,2-d]pyrimidin-2-ylamino)methyl)benzenesulfonamide, 4-((R)-1-(6-(4-methoxy-3-(methylsulfonyl)phenyl)-4-(2,2,2-trifluoroethylamino)pyrido[3,2-d]pyrimidin-2-ylamino)ethyl)benzenesulfonamide, 4-((6-(4-(methoxymethyl)-3-(methylsulfonyl)phenyl)-4-(2,2,2-trifluoroethylamino)pyrido[3,2-d]pyrimidin-2-ylamino)methyl)benzenesulfonamide, 2-chloro-4-((6-(4-methoxy-3-(methylsulfonyl)phenyl)-4-(2,2,2-trifluoroethylamino)pyrido[3,2-d]pyrimidin-2-ylamino)methyl)benzenesulfonamide, N-(3-((6-(4-methoxy-3-(methylsulfonyl)phenyl)-4-(2,2,2-trifluoroethylamino)pyrido[3,2-d]pyrimidin-2-ylamino)methyl)-5-(trifluoromethyl)phenylsulfonyl)propionamide, 4-((6-(3-(ethylsulfonyl)-4-methoxyphenyl)-4-(2,2,2-trifluoroethylamino)pyrido[3,2-d]pyrimidin-2-ylamino)methyl)benzenesulfonamide, $N^2$-((R)-1-(4-(1H-1,2,4-triazol-1-yl)phenyl)ethyl)-6-(4-methoxy-3-(methylsulfonyl)phenyl)-$N^4$-(2,2,2-trifluoroethyl)pyrido[3,2-d]pyrimidine-2,4-diamine, 4-((4-(1,1,1,3,3,3-hexafluoropropan-2-ylamino)-6-(4-methoxy-3-(methylsulfonyl)phenyl)pyrido[3,2-d]pyrimidin-2-ylamino)methyl)benzenesulfonamide, 4-((R)-1-(6-(4-methyl-3-(methylsulfonyl)phenyl)-4-(2,2,2-trifluoroethylamino)pyrido[3,2-d]pyrimidin-2-ylamino)ethyl)benzenesulfonamide, 6-(4-methoxy-3-(methylsulfonyl)phenyl)-$N^2$-(2-methoxyethyl)-$N^4$-(2,2,2-trifluoroethyl)pyrido[3,2-d]pyrimidine-2,4-diamine, 4-((R)-1-(6-(4-methoxy-3-(methylsulfonyl)phenyl)-4-(2,2,2-trifluoroethylamino)pyrido[3,2-d]pyrimidin-2-ylamino)propyl)benzenesulfonamide, 4-((R)-1-(6-(4-chloro-3-(methylsulfonyl)phenyl)-4-(2,2,2-trifluoroethylamino)pyrido[3,2-d]pyrimidin-2-ylamino)ethyl)benzenesulfonamide, 4-((R)-1-(6-(5-(methylsulfonyl)pyridin-3-yl)-4-(2,2,2-trifluoroethylamino)pyrido[3,2-d]pyrimidin-2-ylamino)ethyl)benzenesulfonamide, 4-((6-(3-(cyclopropylsulfonyl)-4-methoxyphenyl)-4-(2,2,2-trifluoroethylamino)pyrido[3,2-d]pyrimidin-2-ylamino)methyl)benzenesulfonamide, 3-(6-(3-(methylsulfonyl)phenyl)-4-(2,2,2-trifluoroethylamino)pyrido[3,2-d]pyrimidin-2-ylamino)propane-1,2-diol, 2-methyl-1-(6-(3-(methylsulfonyl)phenyl)-4-(2,2,2-trifluoroethylamino)pyrido[3,2-d]pyrimidin-2-ylamino)propan-2-ol, (2R)-2-(6-(3-(methylsulfonyl)phenyl)-4-(2,2,2-trifluoroethylamino)pyrido[3,2-d]pyrimidin-2-ylamino)propanoic acid, $N^2$-(3,4-difluorobenzyl)-6-(4-methoxy-3-(methylsulfonyl)phenyl)-$N^4$-(2,2,2-trifluoroethyl)pyrido[3,2-d]pyrimidine-2,4-diamine, 2-(6-(3-(methylsulfonyl)phenyl)-4-(2,2,2-trifluoroethylamino)pyrido[3,2-d]pyrimidin-2-ylamino)ethanol, $N^2$-(4-(1H-1,2,4-triazol-1-yl)benzyl)-6-(3-(methylsulfonyl)phenyl)-$N^4$-(2,2,2-trifluoroethyl)pyrido[3,2-d]pyrimidine-2,4-diamine, 4-((6-(4-(difluoromethoxy)-3-(methylsulfonyl)phenyl)-4-(2,2,2-trifluoroethylamino)pyrido[3,2-d]pyrimidin-2-ylamino)methyl)benzenesulfonamide, 4-((6-(4-methoxy-3-(trifluoromethylsulfonyl)phenyl)-4-(2,2,2-trifluoroethylamino)pyrido[3,2-d]pyrimidin-2-ylamino)methyl)benzenesulfonamide, 6-(4-methoxy-3-(methylsulfonyl)phenyl)-$N^2$-(pyridin-3-ylmethyl)-$N^4$-(2,2,2-trifluoroethyl)pyrido[3,2-d]pyrimidine-2,4-diamine, $N^2$-(4-(1H-pyrazol-1-yl)benzyl)-6-(3-(methylsulfonyl)phenyl)-$N^4$-(2,2,2-trifluoroethyl)pyrido[3,2-d]pyrimidine-2,4-diamine, $N^2$-((R)-1-(1H-1,2,4-triazol-1-yl)propan-2-yl)-6-(3-(methylsulfonyl)phenyl)-$N^4$-(2,2,2-trifluoroethyl)pyrido[3,2-d]pyrimidine-2,4-diamine, $N^2$-((S)-1-(1H-1,2,4-triazol-1-yl)propan-2-yl)-6-(3-(methylsulfonyl)phenyl)-$N^4$-(2,2,2-trifluoroethyl)pyrido[3,2-d]pyrimidine-2,4-diamine, $N^2$-((R)-1-(4-(1H-1,2,4-triazol-1-yl)phenyl)ethyl)-6-(3-(methylsulfonyl)phenyl)-$N^4$-(2,2,2-trifluoroethyl)pyrido[3,2-d]pyrimidine-2,4-diamine, $N^2$-(3-(methylsulfonyl)benzyl)-6-(4-methoxy-3-(trifluoromethylsulfonyl)phenyl)-$N^4$-(2,2,2-trifluoroethyl)pyrido[3,2-d]pyrimidine-2,4-diamine, 2-(6-(4-methoxy-3-(methylsulfonyl)phenyl)-4-(2,2,2-trifluoroethylamino)pyrido[3,2-d]pyrimidin-2-ylamino)ethanesulfonamide, $N^2$-(3-(methylsulfonyl)benzyl)-6-(4-methyl-3-(methylsulfonyl)phenyl)-$N^4$-(2,2,2-trifluoroethyl)pyrido[3,2-d]pyrimidine-2,4-diamine, $N^2$-(3-(methylsulfonyl)benzyl)-6-(4-(difluoromethoxy)-3-(methylsulfonyl)phenyl)-$N^4$-(2,2,2-trifluoroethyl)pyrido[3,2-d]pyrimidine-2,4-diamine, $N^2$-(4-(1H-1,2,4-triazol-1-yl)benzyl)-6-(4-(difluoromethoxy)-3-(methylsulfonyl)phenyl)-$N^4$-(2,2,2-trifluoroethyl)pyrido[3,2-d]pyrimidine-2,4-diamine, $N^2$-(3-fluoro-4-methylbenzyl)-6-(4-methoxy-3-(methylsulfonyl)phenyl)-$N^4$-(2,2,2-trifluoroethyl)pyrido[3,2-d]pyrimidine-2,4-diamine, $N^2$-(3-(methylsulfonyl)benzyl)-6-(4-methoxy-3-(methylsulfonyl)phenyl)-$N^4$-(2,2,2-trifluoroethyl)pyrido[3,2-d]pyrimidine-2,4-diamine, 6-(4-(difluoromethoxy)-3-(methylsulfonyl)phenyl)-$N^2$-(pyridin-3-ylmethyl)-$N^4$-(2,2,2-trifluoroethyl)pyrido[3,2-d]pyrimidine-2,4-diamine, $N^2$-(4-(1H-1,2,4-triazol-1-yl)benzyl)-6-(4-methyl-3-(methylsulfonyl)phenyl)-$N^4$-(2,2,2-trifluoroethyl)pyrido[3,2-d]pyrimidine-2,4-diamine, $N^2$-(1-(3,5-difluorophenyl)ethyl)-6-(4-methoxy-3-(methylsulfonyl)phenyl)-$N^4$-(2,2,2-trifluoroethyl)pyrido[3,2-d]pyrimidine-2,4-diamine, $N^2$-(4-(1H-1,2,4-triazol-1-yl)benzyl)-6-(3-(ethylsulfonyl)phenyl)-$N^4$-(2,2,2-trifluoroethyl)pyrido[3,2-d]pyrimidine-2,4-diamine, $N^2$-((R)-1-(4-(1H-1,2,4-triazol-1-yl)phenyl)ethyl)-6-(3-(ethylsulfonyl)phenyl)-$N^4$-(2,2,2-trifluoroethyl)pyrido[3,2-d]pyrimidine-2,4-diamine, $N^2$-(4-(1H-1,2,4-triazol-1-yl)benzyl)-6-(4-ethoxy-3-(methylsulfonyl)phenyl)-$N^4$-(2,2,2-trifluoroethyl)pyrido[3,2-d]pyrimidine-2,4-diamine, $N^2$-((6-(1H-1,2,4-triazol-1-yl)pyridin-3-yl)methyl)-6-(3-(methylsulfonyl)phenyl)-$N^4$-(2,2,2-trifluoroethyl)pyrido[3,2-d]pyrimidine-2,4-diamine, 4-((R)-1-(4-cyclopropoxy-6-(4-(difluoromethoxy)-3-(methylsulfonyl)phenyl)pyrido[3,2-d]pyrimidin-2-ylamino)ethyl)benzenesulfonamide, $N^2$-((R)-1-(4-(1H-1,2,4-triazol-1-yl)phenyl)ethyl)-6-(4-(difluoromethoxy)-3-(methylsulfonyl)phenyl)-$N^4$-(2,2,2-trifluoroethyl)pyrido[3,2-d]pyrimidine-2,4-diamine, $N^2$-(4-(1H-1,2,4-triazol-1-yl)benzyl)-6-(3-(methylsulfonyl)phenyl)-$N^4$-((S)-1,1,1-trifluoropropan-2-yl)pyrido[3,2-d]pyrimidine-2,4-diamine, N-(4-(1H-1,2,4-triazol-1-yl)benzyl)-4-cyclopropoxy-6-(3-(methylsulfonyl)phenyl)pyrido[3,2-d]pyrimidin-2-amine, N-(4-(1H-1,2,4-triazol-1-yl)benzyl)-4-(1-methylcyclopropoxy)-6-(3-(methylsulfonyl)phenyl)pyrido[3,2-d]pyrimidin-2-amine,
N-(4-(1H-1,2,4-triazol-1-yl)benzyl)-4-ethoxy-6-(3-(methylsulfonyl)phenyl)pyrido[3,2-d]pyrimidin-2-amine,
N-(4-(1H-1,2,4-triazol-1-yl)benzyl)-6-(4-(difluoromethoxy)-3-(methylsulfonyl)phenyl)-4-(1-methylcyclopropoxy)pyrido[3,2-d]pyrimidin-2-amine,
N-(4-(1H-1,2,4-triazol-1-yl)benzyl)-4-cyclopropoxy-6-(4-(difluoromethoxy)-3-(methylsulfonyl)phenyl)pyrido[3,2-d]pyrimidin-2-amine,
$N^2$-(4-(1H-imidazol-1-yl)benzyl)-6-(3-(methylsulfonyl)phenyl)-$N^4$-(2,2,2-trifluoroethyl)pyrido[3,2-d]pyrimidine-2,4-diamine,
N-(4-(1H-1,2,4-triazol-1-yl)benzyl)-4-((1S,3r,5R)-bicyclo[3.1.0]hexan-3-yloxy)-6-(3-(methylsulfonyl)phenyl)pyrido[3,2-d]pyrimidin-2-amine,
N-(4-(1H-1,2,4-triazol-1-yl)benzyl)-4-((1S,3r,5R)-bicyclo[3.1.0]hexan-3-yloxy)-6-(4-(difluoromethoxy)-3-(methylsulfonyl)phenyl)pyrido[3,2-d]pyrimidin-2-amine,
$N^2$-(4-(1H-1,2,4-triazol-1-yl)benzyl)-$N^4$-(2-chloro-2,2-difluoroethyl)-6-(3-(methylsulfonyl)phenyl)pyrido[3,2-d]pyrimidine-2,4-diamine,
N-(4-(1H-1,2,4-triazol-1-yl)benzyl)-4-tert-butoxy-6-(3-(methylsulfonyl)phenyl)pyrido[3,2-d]pyrimidin-2-amine,
N-(4-(1H-1,2,4-triazol-1-yl)benzyl)-4-isopropoxy-6-(3-(methylsulfonyl)phenyl)pyrido[3,2-d]pyrimidin-2-amine,
N-(4-(1H-1,2,4-triazol-1-yl)benzyl)-6-(4-(difluoromethoxy)-3-(methylsulfonyl)phenyl)-4-isopropoxypyrido[3,2-d]pyrimidin-2-amine,
4-((R)-1-(4-cyclobutoxy-6-(3-(methylsulfonyl)phenyl)pyrido[3,2-d]pyrimidin-2-ylamino)ethyl)benzenesulfonamide,
N-(4-(1H-1,2,4-triazol-1-yl)benzyl)-4-cyclobutoxy-6-(3-(methylsulfonyl)phenyl)pyrido[3,2-d]pyrimidin-2-amine,
N-(4-(3,5-dimethyl-1H-1,2,4-triazol-1-yl)benzyl)-4-(1-methylcyclopropoxy)-6-(3-(methylsulfonyl)phenyl)pyrido[3,2-d]pyrimidin-2-amine,
N-(4-(1H-1,2,4-triazol-1-yl)benzyl)-4-cyclobutoxy-6-(4-(difluoromethoxy)-3-(methylsulfonyl)phenyl)pyrido[3,2-d]pyrimidin-2-amine,
N-(4-(3,5-dimethyl-1H-1,2,4-triazol-1-yl)benzyl)-6-(4-(difluoromethoxy)-3-(methylsulfonyl)phenyl)-4-(1-methylcyclopropoxy)pyrido[3,2-d]pyrimidin-2-amine,
$N^2$-((R)-1-(1H-1,2,4-triazol-1-yl)propan-2-yl)-6-(4-(difluoromethoxy)-3-(methylsulfonyl)phenyl)-$N^4$-(2,2,2-trifluoroethyl)pyrido[3,2-d]pyrimidine-2,4-diamine,
N-(4-(pyrimidin-5-yl)benzyl)-4-(1-methylcyclopropoxy)-6-(3-(methylsulfonyl)phenyl)pyrido[3,2-d]pyrimidin-2-amine,
N-(4-(thiazol-5-yl)benzyl)-4-(1-methylcyclopropoxy)-6-(3-(methylsulfonyl)phenyl)pyrido[3,2-d]pyrimidin-2-amine,
N-(4-(1H-imidazol-5-yl)benzyl)-4-(1-methylcyclopropoxy)-6-(3-(methylsulfonyl)phenyl)pyrido[3,2-d]pyrimidin-2-amine,
4-((4-(1-methylcyclopropoxy)-6-(3-(methylsulfonyl)phenyl)pyrido[3,2-d]pyrimidin-2-ylamino)methyl)phenol,
methyl (R)-1-((S)-3-(6-(4-(difluoromethoxy)-3-(methylsulfonyl)phenyl)-4-(2,2,2-trifluoroethylamino)pyrido[3,2-d]pyrimidin-2-ylamino)pyrrolidin-1-yl)-3-methyl-1-oxobutan-2-ylcarbamate,
methyl (R)-3-methyl-1-((S)-3-(6-(3-(methylsulfonyl)phenyl)-4-(2,2,2-trifluoroethylamino)pyrido[3,2-d]pyrimidin-2-ylamino)pyrrolidin-1-yl)-1-oxobutan-2-ylcarbamate,
N-((R)-1-(1H-1,2,4-triazol-1-yl)propan-2-yl)-4-(1-methylcyclopropoxy)-6-(3-(methylsulfonyl)phenyl)pyrido[3,2-d]pyrimidin-2-amine,
$N^2$-(4-(3,5-dimethyl-1H-1,2,4-triazol-1-yl)benzyl)-6-(3-(methylsulfonyl)phenyl)-$N^4$-(2,2,2-trifluoroethyl)pyrido[3,2-d]pyrimidine-2,4-diamine,
N-(4-(2-methylpyridin-3-yl)benzyl)-4-(1-methylcyclopropoxy)-6-(3-(methylsulfonyl)phenyl)pyrido[3,2-d]pyrimidin-2-amine,
N-(4-(thiophen-3-yl)benzyl)-4-(1-methylcyclopropoxy)-6-(3-(methylsulfonyl)phenyl)pyrido[3,2-d]pyrimidin-2-amine,
N-(4-(5-ethyl-1,3,4-thiadiazol-2-yl)benzyl)-4-(1-methylcyclopropoxy)-6-(3-(methylsulfonyl)phenyl)pyrido[3,2-d]pyrimidin-2-amine,
N-(4-(1-methyl-1H-imidazol-5-yl)benzyl)-4-(1-methylcyclopropoxy)-6-(3-(methylsulfonyl)phenyl)pyrido[3,2-d]pyrimidin-2-amine,
N-(4-(1-methyl-1H-imidazol-4-yl)benzyl)-4-(1-methylcyclopropoxy)-6-(3-(methylsulfonyl)phenyl)pyrido[3,2-d]pyrimidin-2-amine,
N-(4-(furan-3-yl)benzyl)-4-(1-methylcyclopropoxy)-6-(3-(methylsulfonyl)phenyl)pyrido[3,2-d]pyrimidin-2-amine,
N-(4-(6-methylpyridin-2-yl)benzyl)-4-(1-methylcyclopropoxy)-6-(3-(methylsulfonyl)phenyl)pyrido[3,2-d]pyrimidin-2-amine,
N-(4-(pyrimidin-2-yl)benzyl)-4-(1-methylcyclopropoxy)-6-(3-(methylsulfonyl)phenyl)pyrido[3,2-d]pyrimidin-2-amine,
N-(4-(3,5-dimethyl-1H-1,2,4-triazol-1-yl)benzyl)-4-cyclopropoxy-6-(3-(methylsulfonyl)phenyl)pyrido[3,2-d]pyrimidin-2-amine,
4-((6-(4-methoxy-3-(aminosulfonyl)phenyl)-4-(2,2,2-trifluoroethylamino)pyrido[3,2-d]pyrimidin-2-ylamino)methyl)benzenesulfonamide,
4-((6-(aminocarbonyl)-4-methoxyphenyl)-4-(2,2,2-trifluoroethylamino)pyrido[3,2-d]pyrimidin-2-ylamino)methyl)benzenesulfonamide,
4-((6-(4-methoxy-3-(morpholinosulfonyl)phenyl)-4-(2,2,2-trifluoroethylamino)pyrido[3,2-d]pyrimidin-2-ylamino)methyl)benzenesulfonamide,
4-((6-(4-methoxy-3-(trifluoromethyl)phenyl)-4-(2,2,2-trifluoroethylamino)pyrido[3,2-d]pyrimidin-2-ylamino)methyl)benzenesulfonamide,
$N^2$-(4-(1H-1,2,4-triazol-1-yl)benzyl)-6-(6-ethoxypyridin-3-yl)-$N^4$-(2,2,2-trifluoroethyl)pyrido[3,2-d]pyrimidine-2,4-diamine,
$N^2$-(3-(methylsulfonyl)benzyl)-6-(6-ethoxypyridin-3-yl)-$N^4$-(2,2,2-trifluoroethyl)pyrido[3,2-d]pyrimidine-2,4-diamine,
3-chloro-5-((4-(2,2,2-trifluoroethylamino)-6-(4-(trifluoromethoxy)phenyl)pyrido[3,2-d]pyrimidin-2-ylamino)methyl)benzenesulfonamide,
$N^2$-((R)-1-(1H-1,2,4-triazol-1-yl)propan-2-yl)-6-(6-ethoxypyridin-3-yl)-$N^4$-(2,2,2-trifluoroethyl)pyrido[3,2-d]pyrimidine-2,4-diamine,
3-chloro-5-((6-(6-ethoxypyridin-3-yl)-4-(2,2,2-trifluoroethylamino)pyrido[3,2-d]pyrimidin-2-ylamino)methyl)benzenesulfonamide,
5-(2-(3,4-difluorobenzylamino)-4-(2,2,2-trifluoroethylamino)pyrido[3,2-d]pyrimidin-6-yl)-2-methoxybenzenesulfonamide,
5-(2-(1-(3,5-difluorophenyl)ethylamino)-4-(2,2,2-trifluoroethylamino)pyrido[3,2-d]pyrimidin-6-yl)-2-methoxybenzenesulfonamide,
5-(2-(4-(1H-pyrazol-1-yl)benzylamino)-4-(2,2,2-trifluoroethylamino)pyrido[3,2-d]pyrimidin-6-yl)-2-methoxybenzenesulfonamide, 5-(2-(4-(1H-1,2,4-triazol-1-yl)benzylamino)-4-(2,2,2-trifluoroethylamino)pyrido[3,2-d]pyrimidin-6-yl)-2-methoxybenzenesulfonamide, 5-(2-(4-(1H-1,2,4-triazol-1-yl)benzylamino)-4-(2,2,2-trifluoroethylamino)pyrido[3,2-d]pyrimidin-6-yl)-2-methoxybenzonitrile, 5-(2-(4-cyclopropylbut-3-yn-2-ylamino)-4-(2,2,2-trifluoroethylamino)pyrido[3,2-d]pyrimidin-6-yl)-2-methoxybenzenesulfonamide, $N^2$-(4-(1H-1,2,4-triazol-1-yl)benzyl)-6-(6-isopropoxypyridin-3-yl)-$N^4$-(2,2,2-trifluoroethyl)pyrido[3,2-d]pyrimidine-2,4-diamine, $N^2$-((R)-1-(1H-1,2,4-triazol-1-yl)propan-2-yl)-6-(6-isopropoxypyridin-3-yl)-$N^4$-(2,2,2-trifluoroethyl)pyrido[3,2-d]pyrimidine-2,4-diamine, $N^2$-(4-(1H-pyrazol-1-yl)benzyl)-6-(6-isopropoxypyridin-3-yl)-$N^4$-(2,2,2-trifluoroethyl)pyrido[3,2-d]pyrimidine-2,4-diamine, 5-(2-(4-(1H-1,2,4-triazol-1-yl)benzylamino)-4-(2,2,2-trifluoroethylamino)pyrido[3,2-d]pyrimidin-6-yl)-2-ethoxybenzenesulfonamide, 4-((6-(6-(difluoromethoxy)pyridin-3-yl)-4-(2,2,2-trifluoroethylamino)pyrido[3,2-d]pyrimidin-2-ylamino)methyl)benzenesulfonamide, $N^2$-(4-(1H-1,2,4-triazol-1-yl)benzyl)-6-(6-(difluoromethoxy)pyridin-3-yl)-$N^4$-(2,2,2-trifluoroethyl)pyrido[3,2-d]pyrimidine-2,4-diamine, $N^2$-(4-(1H-1,2,4-triazol-1-yl)benzyl)-6-(6-cyclopropoxypyridin-3-yl)-$N^4$-(2,2,2-trifluoroethyl)pyrido[3,2-d]pyrimidine-2,4-diamine, N-(4-(1H-1,2,4-triazol-1-yl)benzyl)-6-(6-cyclopropoxypyridin-3-yl)-4-(1-methylcyclopropoxy)pyrido[3,2-d]pyrimidin-2-amine, N-(4-(1H-1,2,4-triazol-1-yl)benzyl)-4-cyclopropoxy-6-(6-cyclopropoxypyridin-3-yl)pyrido[3,2-d]pyrimidin-2-amine, N-(4-(1H-1,2,4-triazol-1-yl)benzyl)-6-(6-cyclobutoxypyridin-3-yl)-4-(1-methylcyclopropoxy)pyrido[3,2-d]pyrimidin-2-amine, $N^2$-(4-(1H-1,2,4-triazol-1-yl)benzyl)-6-(6-cyclobutoxypyridin-3-yl)-$N^4$-(2,2,2-trifluoroethyl)pyrido[3,2-d]pyrimidine-2,4-diamine, N-(4-(1H-1,2,4-triazol-1-yl)benzyl)-6-(6-cyclobutoxypyridin-3-yl)-4-cyclopropoxypyrido[3,2-d]pyrimidin-2-amine, 4-((R)-1-(4-cyclobutoxy-6-(6-cyclopropoxypyridin-3-yl)pyrido[3,2-d]pyrimidin-2-ylamino)ethyl)benzenesulfonamide, $N^2$-(4-(1H-1,2,4-triazol-1-yl)benzyl)-6-(2-cyclopropoxypyrimidin-5-yl)-$N^4$-(2,2,2-trifluoroethyl)pyrido[3,2-d]pyrimidine-2,4-diamine, N-(4-(1H-1,2,4-triazol-1-yl)benzyl)-4-cyclopropoxy-6-(2-cyclopropoxypyrimidin-5-yl)pyrido[3,2-d]pyrimidin-2-amine, $N^2$-((R)-1-(4-(1H-1,2,4-triazol-1-yl)phenyl)ethyl)-6-(6-pentadeuteroethoxypyridin-3-yl)-$N^4$-(2,2,2-trifluoroethyl)pyrido[3,2-d]pyrimidine-2,4-diamine, $N^2$-(4-(1H-1,2,4-triazol-1-yl)benzyl)-6-(6-pentadeuteroethoxypyridin-3-yl)-$N^4$-(2,2,2-trifluoroethyl)pyrido[3,2-d]pyrimidine-2,4-diamine, N-(4-(1H-1,2,4-triazol-1-yl)benzyl)-6-(2-cyclopropoxypyrimidin-5-yl)-4-(1-methylcyclopropoxy)pyrido[3,2-d]pyrimidin-2-amine, $N^2$-((R)-1-(1H-1,2,4-triazol-1-yl)propan-2-yl)-6-(6-cyclopropoxypyridin-3-yl)-$N^4$-(2,2,2-trifluoroethyl)pyrido[3,2-d]pyrimidine-2,4-diamine, $N^2$-(4-(1H-1,2,4-triazol-1-yl)benzyl)-6-(6-ethoxypyridin-3-yl)-$N^4$-(2,2,2-trifluoroethyl)pyrido[3,2-d]pyrimidine-2,4-diamine, $N^2$-(4-(1H-1,2,4-triazol-1-yl)benzyl)-6-(6-pentadeuteroethoxypyridin-3-yl)-$N^4$-(2,2,2-trifluoroethyl)pyrido[3,2-d]pyrimidine-2,4-diamine, 4-((R)-1-(6-(4-ethoxy-3-(aminosulfonyl)phenyl)-4-(2,2,2-trifluoroethylamino)pyrido[3,2-d]pyrimidin-2-ylamino)ethyl)benzenesulfonamide, 5-(2-(4-(1H-imidazol-1-yl)benzylamino)-4-(2,2,2-trifluoroethylamino)pyrido[3,2-d]pyrimidin-6-yl)-2-ethoxybenzenesulfonamide, 5-(2-(4-(1H-1,2,4-triazol-1-yl)benzylamino)-4-(1-methylcyclopropoxy)pyrido[3,2-d]pyrimidin-6-yl)-2-ethoxybenzenesulfonamide, 4-((R)-1-(6-(4-ethoxy-3-(aminosulfonyl)phenyl)-4-(1-methylcyclopropoxy)pyrido[3,2-d]pyrimidin-2-ylamino)ethyl)benzenesulfonamide, 5-(2-((R)-1-(4-(1H-1,2,4-triazol-1-yl)phenyl)ethylamino)-4-(2,2,2-trifluoroethylamino)pyrido[3,2-d]pyrimidin-6-yl)-2-ethoxybenzenesulfonamide, methyl (R)-1-((S)-3-(6-(4-ethoxy-3-(aminosulfonyl)phenyl)-4-(2,2,2-trifluoroethylamino)pyrido[3,2-d]pyrimidin-2-ylamino)pyrrolidin-1-yl)-3-methyl-1-oxobutan-2-ylcarbamate, N-(4-(1H-1,2,4-triazol-1-yl)benzyl)-6-(6-cyclopropoxypyridin-3-yl)-4-cyclopropylpyrido[3,2-d]pyrimidin-2-amine, N-(4-(3,5-dimethyl-1H-1,2,4-triazol-1-yl)benzyl)-6-(6-cyclopropoxypyridin-3-yl)-4-(1-methylcyclopropoxy)pyrido[3,2-d]pyrimidin-2-amine, 5-(2-(4-(3,5-dimethyl-1H-1,2,4-triazol-1-yl)benzylamino)-4-(1-methylcyclopropoxy)pyrido[3,2-d]pyrimidin-6-yl)-2-ethoxybenzenesulfonamide, N-((R)-1-(1H-1,2,4-triazol-1-yl)propan-2-yl)-6-(6-cyclopropoxypyridin-3-yl)-4-(1-methylcyclopropoxy)pyrido[3,2-d]pyrimidin-2-amine, $N^2$-(4-(1H-1,2,4-triazol-1-yl)benzyl)-$N^4$-(2-chloro-2,2-difluoroethyl)-6-(6-cyclopropoxypyridin-3-yl)pyrido[3,2-d]pyrimidine-2,4-diamine, 5-(2-(4-(3,5-dimethyl-1H-1,2,4-triazol-1-yl)benzylamino)-4-cyclopropoxypyrido[3,2-d]pyrimidin-6-yl)-2-ethoxybenzenesulfonamide, 4-((4-ethoxy-6-(1-(4-fluorophenyl)vinyl)pyrido[3,2-d]pyrimidin-2-ylamino)methyl)benzenesulfonamide, (R)-N-tert-butyl-4-(1-(6-(2-cyclopropylethynyl)-4-(2,2,2-trifluoroethylamino)pyrido[3,2-d]pyrimidin-2-ylamino)ethyl)benzenesulfonamide, (R)-4-(1-(6-(2-cyclopropylethynyl)-4-(2,2,2-trifluoroethylamino)pyrido[3,2-d]pyrimidin-2-ylamino)ethyl)benzenesulfonamide, (R)-4-(1-(6-(3-hydroxy-3-methylbut-1-ynyl)-4-(2,2,2-trifluoroethylamino)pyrido[3,2-d]pyrimidin-2-ylamino)ethyl)benzenesulfonamide, (R)-4-(1-(6-(3-methoxyprop-1-ynyl)-4-(2,2,2-trifluoroethylamino)pyrido[3,2-d]pyrimidin-2-ylamino)ethyl)benzenesulfonamide, 3-((6-(2-cyclopropylethynyl)-4-(2,2,2-trifluoroethylamino)pyrido[3,2-d]pyrimidin-2-ylamino)methyl)-5-(trifluoromethyl)benzenesulfonamide, 4-((6-(2-cyclopropylethynyl)-4-(2,2,2-trifluoroethylamino)pyrido[3,2-d]pyrimidin-2-ylamino)methyl)benzenesulfonamide, 3-chloro-5-((6-(2-cyclopropylethynyl)-4-(2,2,2-trifluoroethylamino)pyrido[3,2-d]pyrimidin-2-ylamino)methyl)benzenesulfonamide, (R)-$N^2$-(1-(1H-1,2,4-triazol-1-yl)propan-2-yl)-6-(2-cyclopropylethynyl)-$N^4$-(2,2,2-trifluoroethyl)pyrido[3,2-d]pyrimidine-2,4-diamine, 3-((6-(3-methoxyprop-1-ynyl)-4-(2,2,2-trifluoroethylamino)pyrido[3,2-d]pyrimidin-2-ylamino)methyl)-5-(trifluoromethyl)benzenesulfonamide, 4-((6-(3-methoxyprop-1-ynyl)-4-(2,2,2-trifluoroethylamino)pyrido[3,2-d]pyrimidin-2-ylamino)methyl)benzenesulfonamide,
(R)-4-(1-(6-ethynyl-4-(2,2,2-trifluoroethylamino)pyrido[3,2-d]pyrimidin-2-ylamino)ethyl)benzenesulfonamide,
(R)-4-(1-(6-(3,3-dimethylbut-1-ynyl)-4-(2,2,2-trifluoroethylamino)pyrido[3,2-d]pyrimidin-2-ylamino)ethyl)benzenesulfonamide,
4-((4-cyclopropoxy-6-(2-cyclopropylethynyl)pyrido[3,2-d]pyrimidin-2-ylamino)methyl)benzenesulfonamide,
$N^2$-(4-(1H-1,2,4-triazol-1-yl)benzyl)-6-(2-cyclopropylethynyl)-$N^4$-(2,2,2-trifluoroethyl)pyrido[3,2-d]pyrimidine-2,4-diamine,
4-((6-ethynyl-4-(2,2,2-trifluoroethylamino)pyrido[3,2-d]pyrimidin-2-ylamino)methyl)benzenesulfonamide,
(S)-4-((6-ethynyl-4-(1,1,1-trifluoropropan-2-ylamino)pyrido[3,2-d]pyrimidin-2-ylamino)methyl)benzenesulfonamide,
(S)-4-((6-(2-cyclopropylethynyl)-4-(1,1,1-trifluoropropan-2-ylamino)pyrido[3,2-d]pyrimidin-2-ylamino)methyl)benzenesulfonamide,
(S)-$N^2$-(4-(1H-1,2,4-triazol-1-yl)benzyl)-6-ethynyl-$N^4$-(1,1,1-trifluoropropan-2-yl)pyrido[3,2-d]pyrimidine-2,4-diamine,
(S)-$N^2$-(4-(1H-1,2,4-triazol-1-yl)benzyl)-6-(2-cyclopropylethynyl)-$N^4$-(1,1,1-trifluoropropan-2-yl)pyrido[3,2-d]pyrimidine-2,4-diamine,
$N^2$-((6-(1H-1,2,4-triazol-1-yl)pyridin-3-yl)methyl)-6-(2-cyclopropylethynyl)-$N^4$-(2,2,2-trifluoroethyl)pyrido[3,2-d]pyrimidine-2,4-diamine,
(R)-4-(1-(4-cyclopropoxy-6-ethynylpyrido[3,2-d]pyrimidin-2-ylamino)ethyl)benzenesulfonamide,
(R)-4-(1-(6-ethynyl-4-(1-methylcyclopropoxy)pyrido[3,2-d]pyrimidin-2-ylamino)ethyl)benzenesulfonamide,
(R)-4-(1-(6-(2-cyclopropylethynyl)-4-(1-methylcyclopropoxy)pyrido[3,2-d]pyrimidin-2-ylamino)ethyl)benzenesulfonamide,
(R)-4-(1-(6-(2-(thiazol-5-yl)ethynyl)-4-(2,2,2-trifluoroethylamino)pyrido[3,2-d]pyrimidin-2-ylamino)ethyl)benzenesulfonamide,
(R)-4-(1-(6-(prop-1-ynyl)-4-(2,2,2-trifluoroethylamino)pyrido[3,2-d]pyrimidin-2-ylamino)ethyl)benzenesulfonamide,
4-((R)-1-(4-((1S,3r, 5R)-bicyclo[3.1.0]hexan-3-yloxy)-6-(2-cyclopropylethynyl)pyrido[3,2-d]pyrimidin-2-ylamino)ethyl)benzenesulfonamide,
4-((4-cyclopropoxy-6-ethynylpyrido[3,2-d]pyrimidin-2-ylamino)methyl)benzenesulfonamide,
3-chloro-5-((6-(2-cyclopropylethynyl)-4-(1-methylcyclopropoxy)pyrido[3,2-d]pyrimidin-2-ylamino)methyl)benzenesulfonamide,
(R)-4-(1-(4-(1-methylcyclopropoxy)-6-(prop-1-ynyl)pyrido[3,2-d]pyrimidin-2-ylamino)ethyl)benzenesulfonamide,
3-chloro-5-((4-(1-methylcyclopropoxy)-6-vinylpyrido[3,2-d]pyrimidin-2-ylamino)methyl)benzenesulfonamide,
(R)-4-(1-(6-(2-cyclopropylethynyl)-4-isopropoxypyrido[3,2-d]pyrimidin-2-ylamino)ethyl)benzenesulfonamide,
(R)-4-(1-(4-cyclobutoxy-6-(2-cyclopropylethynyl)pyrido[3,2-d]pyrimidin-2-ylamino)ethyl)benzenesulfonamide,
(R)-4-(1-(6-ethynyl-4-isopropoxypyrido[3,2-d]pyrimidin-2-ylamino)ethyl)benzenesulfonamide,
(R)-4-(1-(4-cyclobutoxy-6-ethynylpyrido[3,2-d]pyrimidin-2-ylamino)ethyl)benzenesulfonamide,
N-(4-(1H-1,2,4-triazol-1-yl)benzyl)-6-(2-cyclopropylethynyl)-4-isopropoxypyrido[3,2-d]pyrimidin-2-amine,
(R)-4-(1-(4-cyclopropoxy-6-(prop-1-ynyl)pyrido[3,2-d]pyrimidin-2-ylamino)ethyl)benzenesulfonamide,
(R)-4-(1-(4-cyclobutoxy-6-(prop-1-ynyl)pyrido[3,2-d]pyrimidin-2-ylamino)ethyl)benzenesulfonamide,
3-chloro-5-((4-(1-methylcyclopropoxy)-6-(prop-1-ynyl)pyrido[3,2-d]pyrimidin-2-ylamino)methyl)benzenesulfonamide,
(R)-4-(1-(4-(2,2,2-trifluoroethylamino)-6-vinylpyrido[3,2-d]pyrimidin-2-ylamino)ethyl)benzenesulfonamide,
4-((R)-1-(4-((1S,3r,5R)-bicyclo[3.1.0]hexan-3-yloxy)-6-(prop-1-ynyl)pyrido[3,2-d]pyrimidin-2-ylamino)ethyl)benzenesulfonamide,
4-((R)-1-(4-((1S,3r,5R)-bicyclo[3.1.0]hexan-3-yloxy)-6-ethynylpyrido[3,2-d]pyrimidin-2-ylamino)ethyl)benzenesulfonamide,
(R)-4-(1-(6-(2-cyclopropylethynyl)-4-methoxypyrido[3,2-d]pyrimidin-2-ylamino)ethyl)benzenesulfonamide,
(R)-4-(1-(6-(2-cyclopropylethynyl)-4-ethoxypyrido[3,2-d]pyrimidin-2-ylamino)ethyl)benzenesulfonamide,
(R)-4-(1-(6-(2-(1H-imidazol-4-yl)ethynyl)-4-(2,2,2-trifluoroethylamino)pyrido[3,2-d]pyrimidin-2-ylamino)ethyl)benzenesulfonamide,
(R)-4-(1-(6-(2-(1H-imidazol-4-yl)ethynyl)-4-(1-methylcyclopropoxy)pyrido[3,2-d]pyrimidin-2-ylamino)ethyl)benzenesulfonamide,
(R)-4-(1-(6-(2-(1H-imidazol-2-yl)ethynyl)-4-(2,2,2-trifluoroethylamino)pyrido[3,2-d]pyrimidin-2-ylamino)ethyl)benzenesulfonamide, and
4-((R)-1-(6-(2-(1H-imidazol-4-yl)ethynyl)-4-((1S,3r,5R)-bicyclo[3.1.0]hexan-3-yloxy)pyrido[3,2-d]pyrimidin-2-ylamino)ethyl)benzenesulfonamide; or
a pharmaceutically acceptable salt thereof.

20. A compound of claim 1 selected from the group consisting of:
4-{1-[6-(4-Fluoro-phenyl)-4-(1-trifluoromethyl-cyclopropylamino)-pyrido[3,2-d]pyrimidin-2-ylamino]-ethyl}-3-methyl-benzenesulfonamide,
4-{1-[6-(4-Fluoro-phenyl)-4-(1-trifluoromethyl-cyclopropylamino)-pyrido[3,2-d]pyrimidin-2-ylamino]-ethyl}-3-trifluoromethyl-benzenesulfonamide,
4-{[6-(4-Fluoro-phenyl)-4-(1-trifluoromethyl-cyclopropylamino)-pyrido[3,2-d]pyrimidin-2-ylamino]-methyl}-3-methyl-benzenesulfonamide,
4-{[6-(4-Fluoro-phenyl)-4-(1-trifluoromethyl-cyclopropylamino)-pyrido[3,2-d]pyrimidin-2-ylamino]-methyl}-3-trifluoromethyl-benzenesulfonamide,
2-Chloro-4-{[6-(4-fluoro-phenyl)-4-(1-trifluoromethyl-cyclopropylamino)-pyrido[3,2-d]pyrimidin-2-ylamino]-methyl}-benzenesulfonamide,
2-Fluoro-4-{[6-(4-fluoro-phenyl)-4-(1-trifluoromethyl-cyclopropylamino)-pyrido[3,2-d]pyrimidin-2-ylamino]-methyl}-benzenesulfonamide,
2-Chloro-4-{1-[6-(4-fluoro-phenyl)-4-(1-trifluoromethyl-cyclopropylamino)-pyrido[3,2-d]pyrimidin-2-ylamino]-methyl}-benzenesulfonamide,
2-Fluoro-4-{1-[6-(4-fluoro-phenyl)-4-(1-trifluoromethyl-cyclopropylamino)-pyrido[3,2-d]pyrimidin-2-ylamino]-ethyl}-benzenesulfonamide,
2-Chloro-5-{[6-(4-fluoro-phenyl)-4-(1-trifluoromethyl-cyclopropylamino)-pyrido[3,2-d]pyrimidin-2-ylamino]-methyl}-benzenesulfonamide,
3-Fluoro-5-{[6-(4-fluoro-phenyl)-4-(1-trifluoromethyl-cyclopropylamino)-pyrido[3,2-d]pyrimidin-2-ylamino]-methyl}-benzenesulfonamide,
4-{[6-(4-Fluoro-phenyl)-4-(1-trifluoromethyl-cyclopropylamino)-pyrido[3,2-d]pyrimidin-2-ylamino]-methyl}-2-trifluoromethyl-benzenesulfonamide,
4-{1-[6-(4-Fluoro-phenyl)-4-(1-trifluoromethyl-cyclopropylamino)-pyrido[3,2-d]pyrimidin-2-ylamino]-ethyl}-2-trifluoromethyl-benzenesulfonamide, N-(3-{[6-(4-Fluoro-phenyl)-4-(1-trifluoromethyl-cyclopropylamino)-pyrido[3,2-d]pyrimidin-2-ylamino]-methyl}-phenyl)-methanesulfonamide, N-(2-Fluoro-5-{[6-(4-fluoro-phenyl)-4-(1-trifluoromethyl-cyclopropylamino)-pyrido[3,2-d]pyrimidin-2-ylamino]-methyl}-phenyl)-methanesulfonamide, N-(5-{[6-(4-Fluoro-phenyl)-4-(1-trifluoromethyl-cyclopropylamino)-pyrido[3,2-d]pyrimidin-2-ylamino]-methyl}-2-trifluoromethyl-phenyl)-methanesulfonamide, N-(2-Chloro-5-{[6-(4-fluoro-phenyl)-4-(1-trifluoromethyl-cyclopropylamino)-pyrido[3,2-d]pyrimidin-2-ylamino]-methyl}-phenyl)-methanesulfonamide, N-(3-Chloro-5-{[6-(4-fluoro-phenyl)-4-(1-trifluoromethyl-cyclopropylamino)-pyrido[3,2-d]pyrimidin-2-ylamino]-methyl}-phenyl)-methanesulfonamide, N-(3-Fluoro-5-{[6-(4-fluoro-phenyl)-4-(1-trifluoromethyl-cyclopropylamino)-pyrido[3,2-d]pyrimidin-2-ylamino]-methyl}-phenyl)-methanesulfonamide, N-(3-{[6-(4-Fluoro-phenyl)-4-(1-trifluoromethyl-cyclopropylamino)-pyrido[3,2-d]pyrimidin-2-ylamino]-methyl}-5-trifluoromethyl-phenyl)-methanesulfonamide, 4-{[6-(4-Fluoro-phenyl)-4-(1-trifluoromethyl-cyclobutylamino)-pyrido[3,2-d]pyrimidin-2-ylamino]-methyl}-benzenesulfonamide, 4-{[6-(4-Fluoro-phenyl)-4-(1-trifluoromethyl-cyclopentylamino)-pyrido[3,2-d]pyrimidin-2-ylamino]-methyl}-benzenesulfonamide, 4-{[6-(4-Fluoro-phenyl)-4-(1-trifluoromethyl-cyclohexylamino)-pyrido[3,2-d]pyrimidin-2-ylamino]-methyl}-benzenesulfonamide, 6-(6-Cyclopropylamino-pyridin-3-yl)-N2-(1-methyl-2-[1,2,4]triazol-1-yl-ethyl)-N4-(1-trifluoromethyl-cyclopropyl)-pyrido[3,2-d]pyrimidine-2,4-diamine, 4-{[6-(4-Fluoro-3-methanesulfonyl-phenyl)-4-(1-trifluoromethyl-cyclopropylamino)-pyrido[3,2-d]pyrimidin-2-ylamino]-methyl}-benzenesulfonamide, 4-{[6-(3-Methanesulfonyl-4-methyl-phenyl)-4-(1-trifluoromethyl-cyclopropylamino)-pyrido[3,2-d]pyrimidin-2-ylamino]-methyl}-benzenesulfonamide, 4-{[6-(3-Methanesulfonyl-4-methoxy-phenyl)-4-(1-trifluoromethyl-cyclopropylamino)-pyrido[3,2-d]pyrimidin-2-ylamino]-methyl}-benzenesulfonamide, 4-{[6-(4-Chloro-3-methanesulfonyl-phenyl)-4-(1-trifluoromethyl-cyclopropylamino)-pyrido[3,2-d]pyrimidin-2-ylamino]-methyl}-benzenesulfonamide, 4-{[6-(3-Cyclopropanesulfonyl-4-methoxy-phenyl)-4-(1-trifluoromethyl-cyclopropylamino)-pyrido[3,2-d]pyrimidin-2-ylamino]-methyl}-benzenesulfonamide, 6-(3-Methanesulfonyl-4-methoxy-phenyl)-N2-[1-(4-[1,2,4]triazol-1-yl-phenyl)-ethyl]-N4-(1-trifluoromethyl-cyclopropyl)-pyrido[3,2-d]pyrimidine-2,4-diamine, and 6-(3-Methanesulfonyl-4-methoxy-phenyl)-N2-[1-(4-[1,2,4]triazol-1-yl-phenyl)-ethyl]-N4-(1-trifluoromethyl-cyclopropyl)-pyrido[3,2-d]pyrimidine-2,4-diamine; or a pharmaceutically acceptable salt thereof.

21. A compound of claim 1 selected from the group consisting of:

3-{1-[6-(4-fluorophenyl)-4-(2,2,2-trifluoroethylamino)-pyrido[3,2-d]pyrimidin-2-ylamino]-ethyl}-5-trifluoromethyl-benzenesulfonamide, 2-fluoro-5-{1-[6-(4-fluorophenyl)-4-(2,2,2-trifluoroethylamino)-pyrido[3,2-d]pyrimidin-2-ylamino]-ethyl}-benzenesulfonamide, 5-{[6-(4-fluorophenyl)-4-(2,2,2-trifluoroethylamino)-pyrido[3,2-d]pyrimidin-2-ylamino]-methyl}-2-trifluoromethyl-benzenesulfonamide, 4-{1-[6-(4-fluorophenyl)-4-(2,2,2-trifluoroethylamino)-pyrido[3,2-d]pyrimidin-2-ylamino]-ethyl}-2-trifluoromethyl-benzenesulfonamide, 3-fluoro-5-{[6-(4-fluorophenyl)-4-(2,2,2-trifluoroethylamino)-pyrido[3,2-d]pyrimidin-2-ylamino]-methyl}-benzenesulfonamide, 3-cyano-5-{[6-(4-fluorophenyl)-4-(2,2,2-trifluoroethylamino)-pyrido[3,2-d]pyrimidin-2-ylamino]-methyl}-benzenesulfonamide, 3-chloro-5-{[6-(4-fluorophenyl)-4-(2,2,2-trifluoroethylamino)-pyrido[3,2-d]pyrimidin-2-ylamino]-methyl}-benzenesulfonamide, 3-{[6-(4-fluorophenyl)-4-(2,2,2-trifluoroethylamino)-pyrido[3,2-d]pyrimidin-2-ylamino]-methyl}-5-[1,2,4]triazol-1-yl-benzenesulfonamide, 2-fluoro-4-{[6-(4-fluorophenyl)-4-(2,2,2-trifluoroethylamino)-pyrido[3,2-d]pyrimidin-2-ylamino]-ethyl}-benzenesulfonamide, 4-{1-[6-(4-fluorophenyl)-4-(2,2,2-trifluoroethylamino)-pyrido[3,2-d]pyrimidin-2-ylamino]-2-methyl-propyl}-benzenesulfonamide, 4-{1-[6-(4-fluorophenyl)-4-(2,2,2-trifluoroethylamino)-pyrido[3,2-d]pyrimidin-2-ylamino]-butyl}-benzenesulfonamide, 2-chloro-4-{[6-(4-fluorophenyl)-4-(2,2,2-trifluoroethylamino)-pyrido[3,2-d]pyrimidin-2-ylamino]-ethyl}-benzenesulfonamide, 2-chloro-5-{[6-(4-fluorophenyl)-4-(2,2,2-trifluoroethylamino)-pyrido[3,2-d]pyrimidin-2-ylamino]-methyl}-benzenesulfonamide, 6-(4-fluorophenyl)-N2-(3-fluoro-5-[1,2,4]triazol-1-yl-benzyl)-N4-(2,2,2-trifluoroethyl)-pyrido[3,2-d]pyrimidine-2,4-diamine, 2-chloro-5-{[6-(4-fluorophenyl)-4-(2,2,2-trifluoroethylamino)-pyrido[3,2-d]pyrimidin-2-ylamino]-ethyl}-benzenesulfonamide, 6-(4-fluorophenyl)-N2-[1-(3-fluoro-5-[1,2,4]triazol-1-yl-phenyl)-ethyl]-N4-(2,2,2-trifluoroethyl)-pyrido[3,2-d]pyrimidine-2,4-diamine, 3-chloro-5-{1-[6-(4-fluorophenyl)-4-(2,2,2-trifluoroethylamino)-pyrido[3,2-d]pyrimidin-2-ylamino]-ethyl}-benzenesulfonamide, 3-fluoro-5-{1-[6-(4-fluorophenyl)-4-(2,2,2-trifluoroethylamino)-pyrido[3,2-d]pyrimidin-2-ylamino]-ethyl}-benzenesulfonamide, 3-{1-[6-(4-fluorophenyl)-4-(2,2,2-trifluoroethylamino)-pyrido[3,2-d]pyrimidin-2-ylamino]-ethyl}-benzenesulfonamide, (R)-4-{1-[6-(4-fluorophenyl)-4-cyclopropoxy-pyrido[3,2-d]pyrimidin-2-ylamino]-ethyl}-benzenesulfonamide, (R)-4-{1-[6-(4-fluorophenyl)-4-cyclobutoxy-pyrido[3,2-d]pyrimidin-2-ylamino]-ethyl}-benzenesulfonamide, (R)-4-{[6-(4-fluorophenyl)-4-cyclopentoxy-pyrido[3,2-d]pyrimidin-2-ylamino]-ethyl}-benzenesulfonamide, (R)-4-{[6-(4-fluorophenyl)-4-cyclohexyloxy-pyrido[3,2-d]pyrimidin-2-ylamino]-ethyl}-benzenesulfonamide, (R)-4-{[6-(4-fluorophenyl)-4-cycloheptyloxy-pyrido[3,2-d]pyrimidin-2-ylamino]-ethyl}-benzenesulfonamide, and (R)-4-{1-[6-(4-fluorophenyl)-4-cyclooctyloxy-pyrido[3,2-d]pyrimidin-2-ylamino]-ethyl}-benzenesulfonamide; or a pharmaceutically acceptable salt thereof.

22. A compound of claim 1 selected from the group consisting of:

6-(4-Fluoro-phenyl)-N2-(3-[1,2,4]triazol-1-yl-benzyl)-N4-(2,2,2-trifluoro-ethyl)-pyrido[3,2-d]pyrimidine-2,4-diamine, 6-(4-Fluoro-phenyl)-N2-(3-pyrazol-1-yl-benzyl)-N4-(2,2,2-trifluoro-ethyl)-pyrido[3,2-d]pyrimidine-2,4-diamine, 2-Fluoro-4-{[6-(4-fluoro-phenyl)-4-(2,2,2-trifluoro-ethylamino)-pyrido[3,2-d]pyrimidin-2-ylamino]-methyl}-benzenesulfonamide,
4-{[6-(4-Fluoro-phenyl)-4-(2,2,2-trifluoro-ethylamino)-pyrido[3,2-d]pyrimidin-2-ylamino]-methyl}-3-methyl-benzenesulfonamide,
2-Chloro-4-{[6-(4-fluoro-phenyl)-4-(2,2,2-trifluoro-ethylamino)-pyrido[3,2-d]pyrimidin-2-ylamino]-methyl}-benzenesulfonamide,
5-{[6-(4-Fluoro-phenyl)-4-(2,2,2-trifluoro-ethylamino)-pyrido[3,2-d]pyrimidin-2-ylamino]-methyl}-2-methoxy-benzenesulfonamide,
2-Fluoro-5-{[6-(4-fluoro-phenyl)-4-(2,2,2-trifluoro-ethylamino)-pyrido[3,2-d]pyrimidin-2-ylamino]-methyl}-benzenesulfonamide,
3-{[6-(4-Fluoro-phenyl)-4-(2,2,2-trifluoro-ethylamino)-pyrido[3,2-d]pyrimidin-2-ylamino]-methyl}-5-trifluoromethyl-benzenesulfonamide,
4-{[6-(4-Fluoro-phenyl)-4-(2,2,2-trifluoro-ethylamino)-pyrido[3,2-d]pyrimidin-2-ylamino]-methyl}-2-trifluoromethyl-benzenesulfonamide,
4-{[6-(4-Fluoro-phenyl)-4-(2,2,2-trifluoro-ethylamino)-pyrido[3,2-d]pyrimidin-2-ylamino]-ethyl}-3-methyl-benzenesulfonamide,
(R)-2-{[6-(4-Fluoro-phenyl)-4-(2,2,2-trifluoro-ethylamino)-pyrido[3,2-d]pyrimidin-2-ylamino]-propyl}-benzenesulfonamide,
(R)-4-{[6-(4-Fluoro-phenyl)-4-(2,2,2-trifluoro-ethylamino)-pyrido[3,2-d]pyrimidin-2-ylamino]-propyl}-benzenesulfonamide,
(R)-4-{1-[6-(4-Fluoro-phenyl)-4-cyclopropoxy-pyrido[3,2-d]pyrimidin-2-ylamino]-ethyl}-benzenesulfonamide,
3-{[6-(3-Methanesulfonyl-phenyl)-4-(2,2,2-trifluoro-ethylamino)-pyrido[3,2-d]pyrimidin-2-ylamino]-methyl}-benzenesulfonamide,
4-{[6-(3-Methanesulfonyl-phenyl)-4-(2,2,2-trifluoro-ethylamino)-pyrido[3,2-d]pyrimidin-2-ylamino]-methyl}-benzenesulfonamide,
6-(3-Methanesulfonyl-phenyl)-N2-(3-[1,2,4]triazol-1-yl-benzyl)-N4-(2,2,2-trifluoro-ethyl)-pyrido[3,2-d]pyrimidine-2,4-diamine,
4-{[6-(3-Methanesulfonyl-4-methoxy-phenyl)-4-(2,2,2-trifluoro-ethylamino)-pyrido[3,2-d]pyrimidin-2-ylamino]-methyl}-benzenesulfonamide,
6-(3-Methanesulfonyl-phenyl)-N2-[1-(4-[1,2,4]triazol-1-yl-phenyl)-ethyl]-N4-(2,2,2-trifluoro-ethyl)-pyrido[3,2-d]pyrimidine-2,4-diamine,
6-(3-Methanesulfonyl-phenyl)-N2-(3-[1,2,4]triazol-1-yl-benzyl)-N4-(2,2,2-trifluoro-ethyl)-pyrido[3,2-d]pyrimidine-2,4-diamine,
4-{[6-(4-Fluoro-3-methanesulfonyl-phenyl)-4-(2,2,2-trifluoro-ethylamino)-pyrido[3,2-d]pyrimidin-2-ylamino]-methyl}-benzenesulfonamide, and
4-{[4-Cyclopropoxy-6-(3-methanesulfonyl-phenyl)-pyrido[3,2-d]pyrimidin-2-ylamino]-methyl}-benzenesulfonamide; or
a pharmaceutically acceptable salt thereof.

23. A pharmaceutical composition comprising one or more pharmaceutically acceptable carriers and the pyrido(3,2-d) pyrimidine derivative according to- claim 1, or a pharmaceutical acceptable addition salt thereof and optionally one or more antiviral agents.

* * * * *